US012642792B2

(12) United States Patent
Elpek et al.

(10) Patent No.: US 12,642,792 B2
(45) **Date of Patent: \*Jun. 2, 2026**

(54) CA2-IL15 FUSION PROTEINS FOR TUNABLE REGULATION

(71) Applicant: Obsidian Therapeutics, Inc., Cambridge, MA (US)

(72) Inventors: Kutlu Goksu Elpek, Arlington, MA (US); Dhruv Kam Sethi, Cambridge, MA (US); Meghan C. Langley, Cambridge, MA (US); Tucker Read Ezell, Cambridge, MA (US); Dexue Sun, Cambridge, MA (US); Jennifer Leah Gori, Jamaica Plain, MA (US); Geetha Hanna Mylvaganam, Boston, MA (US); Michelle Ols, Northborough, MA (US); Michelle Fleury, Cambridge, MA (US); Celeste Richardson, Brookline, MA (US); James A. Storer, Medford, MA (US); Vipin Suri, Belmont, MA (US); Shyamsundar Subramanian, Downingtown, PA (US); Colleen Foley, Cambridge, MA (US); Molly Reed Perkins, Milton, MA (US); Jeremy Hatem Tchaicha, Belmont, MA (US); Scott Francis Heller, Stoughton, MA (US)

(73) Assignee: OBSIDIAN THERAPEUTICS, INC., Cambridge, MA (US)

( * ) Notice: Subject to any disclaimer, the term of this patent is extended or adjusted under 35 U.S.C. 154(b) by 1020 days.

This patent is subject to a terminal disclaimer.

(21) Appl. No.: 17/753,594

(22) PCT Filed: Sep. 10, 2020

(86) PCT No.: PCT/US2020/050273
§ 371 (c)(1),
(2) Date: Mar. 9, 2022

(87) PCT Pub. No.: WO2021/050789
PCT Pub. Date: Mar. 18, 2021

(65) Prior Publication Data
US 2022/0332780 A1 Oct. 20, 2022

Related U.S. Application Data

(60) Provisional application No. 62/898,520, filed on Sep. 10, 2019.

(51) Int. Cl.
| | |
|---|---|
| *C07K 14/54* | (2006.01) |
| *A61K 31/427* | (2006.01) |
| *A61K 31/433* | (2006.01) |
| *A61K 35/17* | (2025.01) |
| *A61K 40/11* | (2025.01) |
| *A61K 40/15* | (2025.01) |
| *A61K 40/31* | (2025.01) |
| *A61K 40/35* | (2025.01) |
| *A61K 40/42* | (2025.01) |

(Continued)

(52) U.S. Cl.
CPC .......... *A61K 31/433* (2013.01); *A61K 31/427* (2013.01); *A61K 40/11* (2025.01); *A61K 40/15* (2025.01); *A61K 40/31* (2025.01); *A61K 40/35* (2025.01); *A61K 40/4211* (2025.01); *A61P 35/00* (2018.01); *C07K 14/5443* (2013.01); *C07K 14/7051* (2013.01); *C12N 5/0636* (2013.01); *C12N 9/88* (2013.01); *C12N 15/625* (2013.01); *C12N 15/86* (2013.01); *C12N 15/861* (2013.01); *C12N 15/8645* (2013.01); *C12N 15/867* (2013.01); *C12N 15/869* (2013.01); *A61K 2239/31* (2023.05); *A61K 2239/38* (2023.05); *A61K 2239/48* (2023.05); *C07K 2319/00* (2013.01); *C07K 2319/02* (2013.01); *C07K 2319/03* (2013.01); *C12N 2740/15043* (2013.01); *C12Y 402/01001* (2013.01)

(58) Field of Classification Search
CPC ...... A61K 31/433; A61K 40/35; A61K 40/15; A61P 35/00; C07K 14/5443; C12N 5/0636; C12N 9/88
See application file for complete search history.

(56) References Cited

U.S. PATENT DOCUMENTS

| | | | |
|---|---|---|---|
| 4,690,915 | A | 9/1987 | Rosenberg |
| 5,532,123 | A | 7/1996 | Schlessinger |

(Continued)

FOREIGN PATENT DOCUMENTS

| | | |
|---|---|---|
| CA | 3055202 | 9/2018 |
| EP | 0930892 | 7/1999 |

(Continued)

OTHER PUBLICATIONS

Hurton et al., Tethered IL-15 augments antitumor activity and promotes a stem-cell memory subset in tumor-specific T cells, PNAS, E7788-E7792. (Year: 2016).*

(Continued)

*Primary Examiner* — James D Schultz
*Assistant Examiner* — Joseph Paul Miano
(74) *Attorney, Agent, or Firm* — Kilpatrick Townsend & Stockton LLP

(57) ABSTRACT

The present disclosure provides drug responsive domains derived from human carbonic anhydrase 2 that can modulate protein stability for human interleukin 15 (IL15) payloads, as well as compositions and methods of use thereof.

15 Claims, 12 Drawing Sheets
Specification includes a Sequence Listing.

(51) Int. Cl.

| | |
|---|---|
| *A61P 35/00* | (2006.01) |
| *C07K 14/725* | (2006.01) |
| *C12N 5/0783* | (2010.01) |
| *C12N 9/88* | (2006.01) |
| *C12N 15/62* | (2006.01) |
| *C12N 15/86* | (2006.01) |
| *C12N 15/861* | (2006.01) |
| *C12N 15/864* | (2006.01) |
| *C12N 15/867* | (2006.01) |
| *C12N 15/869* | (2006.01) |

(56) References Cited

U.S. PATENT DOCUMENTS

| | | | |
|---|---|---|---|
| 5,540,926 | A | 7/1996 | Aruffo et al. |
| 6,083,477 | A | 7/2000 | Goldenberg |
| 6,475,784 | B1 | 11/2002 | Papkoff |
| 6,531,451 | B1 | 3/2003 | Chaux et al. |
| 6,548,249 | B1 | 4/2003 | Anderson et al. |
| 6,548,632 | B1 | 4/2003 | Anderson et al. |
| 6,562,617 | B1 | 5/2003 | Anderson et al. |
| 6,797,263 | B2 | 9/2004 | Strom et al. |
| 6,805,861 | B2 | 10/2004 | Stauss |
| 6,808,905 | B2 | 10/2004 | McArthur et al. |
| 7,179,903 | B2 | 2/2007 | McArthur et al. |
| 7,323,450 | B2 | 1/2008 | Chu et al. |
| 7,347,995 | B2 | 3/2008 | Strom et al. |
| 7,435,596 | B2 | 10/2008 | Campana et al. |
| 7,569,670 | B2 | 8/2009 | Novak et al. |
| 7,575,924 | B2 | 8/2009 | Trono et al. |
| 7,579,439 | B2 | 8/2009 | Strom et al. |
| 7,605,139 | B2 | 10/2009 | Yu et al. |
| 7,629,153 | B2 | 12/2009 | Trono et al. |
| 7,745,179 | B2 | 6/2010 | McArthur et al. |
| 8,013,114 | B2 | 9/2011 | Kundra |
| 8,173,792 | B2 | 5/2012 | Wandless et al. |
| 8,278,066 | B2 | 10/2012 | Kundra |
| 8,450,470 | B2 | 5/2013 | Bookbinder et al. |
| 8,530,636 | B2 | 9/2013 | Wandless et al. |
| 8,722,618 | B2 | 5/2014 | Jacobs et al. |
| 8,846,385 | B2 | 9/2014 | Naldini et al. |
| 8,871,191 | B2 | 10/2014 | Pavlakis et al. |
| 9,006,400 | B2 | 4/2015 | Boettcher et al. |
| 9,290,746 | B2 | 3/2016 | Ciani et al. |
| 9,458,214 | B2 | 10/2016 | Boettcher et al. |
| 9,475,862 | B2 | 10/2016 | Connors et al. |
| 9,487,787 | B2 | 11/2016 | Wandless et al. |
| 9,487,800 | B2 | 11/2016 | Schonfeld et al. |
| 9,586,996 | B2 | 3/2017 | Alila et al. |
| 9,631,218 | B2 | 4/2017 | Tsourkas et al. |
| 9,677,061 | B2 | 6/2017 | Bookbinder et al. |
| 9,725,492 | B2 | 8/2017 | Felber et al. |
| 9,944,910 | B2 | 4/2018 | Ciani et al. |
| 9,963,495 | B2 | 5/2018 | Liu et al. |
| 10,040,835 | B2 | 8/2018 | Luo |
| 10,125,193 | B2 | 11/2018 | Cooper et al. |
| 10,137,180 | B2 | 11/2018 | Wandless et al. |
| 10,202,433 | B2 | 2/2019 | Jacques et al. |
| 10,351,612 | B2 | 7/2019 | Schonfeld et al. |
| 10,415,017 | B2 | 9/2019 | O'neill |
| 10,428,305 | B2 | 10/2019 | Campana et al. |
| 10,472,637 | B2 | 11/2019 | Wang et al. |
| 10,570,186 | B2 | 2/2020 | Cooper et al. |
| 10,675,305 | B2 | 6/2020 | Wang et al. |
| 10,688,132 | B2 | 6/2020 | Wang et al. |
| 10,774,311 | B2 | 9/2020 | Campana et al. |
| 11,058,725 | B2 | 7/2021 | Elpek et al. |
| 2002/0100068 | A1 | 7/2002 | Chambon et al. |
| 2003/0170238 | A1 | 9/2003 | Gruenberg et al. |
| 2004/0038373 | A1 | 2/2004 | Platz et al. |
| 2004/0063912 | A1 | 4/2004 | Blumberg et al. |
| 2004/0102370 | A1 | 5/2004 | Saffell |
| 2005/0048573 | A1 | 3/2005 | Artis et al. |
| 2005/0175582 | A1 | 8/2005 | Goldenberg |
| 2006/0160104 | A1 | 7/2006 | Johnson et al. |

| | | | |
|---|---|---|---|
| 2006/0257361 | A1 | 11/2006 | Watanabe et al. |
| 2007/0009483 | A1 | 1/2007 | Yoon et al. |
| 2007/0048845 | A1 | 3/2007 | Novak et al. |
| 2007/0098683 | A1 | 5/2007 | Novak et al. |
| 2008/0280830 | A1 | 11/2008 | Choi et al. |
| 2009/0087871 | A1 | 4/2009 | Kanacher et al. |
| 2009/0105455 | A1 | 4/2009 | Herrmann |
| 2009/0117618 | A1 | 5/2009 | Herrmann et al. |
| 2009/0215169 | A1 | 8/2009 | Wandless et al. |
| 2010/0021997 | A1 | 1/2010 | Koochekpour et al. |
| 2010/0034777 | A1 | 2/2010 | Wandless et al. |
| 2010/0196370 | A1 | 8/2010 | Yu et al. |
| 2010/0292089 | A1 | 11/2010 | Bachmann et al. |
| 2010/0297063 | A1 | 11/2010 | Novak et al. |
| 2011/0150861 | A1 | 6/2011 | Carson et al. |
| 2011/0312872 | A1 | 12/2011 | Tamm et al. |
| 2012/0076732 | A1 | 3/2012 | Feng et al. |
| 2012/0178168 | A1 | 7/2012 | Wandless et al. |
| 2012/0276142 | A1 | 11/2012 | Weiner et al. |
| 2013/0266551 | A1 | 10/2013 | Campana et al. |
| 2013/0302276 | A1 | 11/2013 | Cantor et al. |
| 2014/0010791 | A1 | 1/2014 | Wandless et al. |
| 2014/0206599 | A1 | 7/2014 | Baumann et al. |
| 2014/0255361 | A1 | 9/2014 | Wandless et al. |
| 2014/0255363 | A1 | 9/2014 | Metelitsa et al. |
| 2014/0271635 | A1 | 9/2014 | Brogdon et al. |
| 2015/0152387 | A1 | 6/2015 | Lee et al. |
| 2015/0190471 | A1 | 7/2015 | Copik et al. |
| 2015/0191711 | A1 | 7/2015 | Carlsson et al. |
| 2015/0307564 | A1 | 10/2015 | Young et al. |
| 2016/0017012 | A1 | 1/2016 | Ildefonso et al. |
| 2016/0017017 | A1 | 1/2016 | Zhao et al. |
| 2016/0108105 | A1 | 4/2016 | Yang et al. |
| 2016/0145337 | A1 | 5/2016 | Galetto et al. |
| 2016/0152686 | A1 | 6/2016 | Camphausen et al. |
| 2016/0348072 | A1 | 12/2016 | June et al. |
| 2017/0002060 | A1 | 1/2017 | Bolen et al. |
| 2017/0088597 | A1 | 3/2017 | Wong et al. |
| 2017/0119874 | A1 | 5/2017 | Lanzavecchia et al. |
| 2017/0157176 | A1 | 6/2017 | Wang et al. |
| 2017/0216275 | A1 | 8/2017 | Feng et al. |
| 2017/0224732 | A1 | 8/2017 | Cantor et al. |
| 2017/0224798 | A1 | 8/2017 | Cooper et al. |
| 2018/0134761 | A1 | 5/2018 | Lindhout et al. |
| 2018/0155439 | A1 | 6/2018 | Galipeau et al. |
| 2018/0200299 | A1 | 7/2018 | Cooper et al. |
| 2018/0256644 | A1 | 9/2018 | Swanson et al. |
| 2018/0282386 | A1 | 10/2018 | Vallera et al. |
| 2018/0327725 | A1 | 11/2018 | Ciani et al. |
| 2018/0353544 | A1 | 12/2018 | Rezvani et al. |
| 2018/0355013 | A1 | 12/2018 | Dranoff et al. |
| 2018/0369334 | A1 | 12/2018 | Cochran et al. |
| 2019/0060440 | A1 | 2/2019 | Zhu et al. |
| 2019/0070264 | A1 | 3/2019 | Qu et al. |
| 2019/0106472 | A1 | 4/2019 | Jacques et al. |
| 2019/0119343 | A1 | 4/2019 | Chung et al. |
| 2019/0151359 | A1 | 5/2019 | Sullivan et al. |
| 2019/0192691 | A1 | 6/2019 | Barrett et al. |
| 2019/0256818 | A1 | 8/2019 | Swee et al. |
| 2019/0281797 | A1 | 9/2019 | Lee et al. |
| 2019/0321403 | A1 | 10/2019 | Levitsky |
| 2019/0330277 | A1 | 10/2019 | Chen et al. |
| 2019/0345222 | A1 | 11/2019 | Hirano et al. |
| 2019/0359655 | A1 | 11/2019 | Zhu et al. |
| 2019/0375854 | A1 | 12/2019 | Sabzevari et al. |
| 2020/0085872 | A1 | 3/2020 | Rezvani et al. |
| 2020/0085929 | A1 | 3/2020 | Cooper et al. |
| 2020/0101142 | A1 | 4/2020 | Suri et al. |
| 2020/0102366 | A1 | 4/2020 | Cooper et al. |
| 2020/0123514 | A1 | 4/2020 | Wandless et al. |
| 2020/0131244 | A1 | 4/2020 | Leong et al. |
| 2020/0179447 | A1 | 6/2020 | Gaensler |
| 2020/0216826 | A1 | 7/2020 | Cooper et al. |
| 2020/0283778 | A1 | 9/2020 | Shah et al. |

FOREIGN PATENT DOCUMENTS

| | | |
|---|---|---|
| EP | 0932417 | 3/2003 |
| EP | 1550457 | 12/2008 |

(56)                References Cited

FOREIGN PATENT DOCUMENTS

| EP | 1809321 | 3/2012 |
| EP | 2388266 | 4/2014 |
| EP | 1638987 | 11/2014 |
| EP | 2177620 | 11/2014 |
| EP | 2776463 | 9/2017 |
| EP | 3013356 | 10/2018 |
| EP | 2755487 | 12/2018 |
| EP | 3110837 | 6/2019 |
| EP | 2614151 | 7/2019 |
| EP | 2968613 | 9/2019 |
| EP | 3105335 | 10/2019 |
| EP | 3215534 | 4/2020 |
| EP | 3235830 | 9/2020 |
| WO | 0023091 | 4/2000 |
| WO | 0136460 | 5/2001 |
| WO | 03030946 | 4/2003 |
| WO | 2004101751 | 11/2004 |
| WO | 2005012493 | 2/2005 |
| WO | 2007142929 | 12/2007 |
| WO | 2009002562 | 12/2008 |
| WO | 2011064758 | 6/2011 |
| WO | 2012079000 | 6/2012 |
| WO | 2012175222 | 12/2012 |
| WO | 2013041487 | 3/2013 |
| WO | 2013059593 | 4/2013 |
| WO | 2014028311 | 2/2014 |
| WO | 2014066527 | 5/2014 |
| WO | 2014134165 | 9/2014 |
| WO | 2015018528 | 2/2015 |
| WO | 2015142675 | 9/2015 |
| WO | 2015150771 | 10/2015 |
| WO | 2015174928 | 11/2015 |
| WO | 2016012623 | 1/2016 |
| WO | 2016018920 | 2/2016 |
| WO | 2016040393 | 3/2016 |
| WO | 2016040395 | 3/2016 |
| WO | 2016113203 | 7/2016 |
| WO | 2016134284 | 8/2016 |
| WO | 2016168595 | 10/2016 |
| WO | 2016210293 | 12/2016 |
| WO | 2017015427 | 1/2017 |
| WO | 2017024318 | 2/2017 |
| WO | 2017062953 | 4/2017 |
| WO | 2017106937 | 6/2017 |
| WO | 2017178562 | 10/2017 |
| WO | 2017180587 | 10/2017 |
| WO | 2017205810 | 11/2017 |
| WO | 2017210617 | 12/2017 |
| WO | 2018005617 | 1/2018 |
| WO | 2018023025 | 2/2018 |
| WO | 2018102795 | 6/2018 |
| WO | 2018132494 A1 | 7/2018 |
| WO | 2018140733 | 8/2018 |
| WO | 2018160993 | 9/2018 |
| WO | 2018161000 | 9/2018 |
| WO | 2018161017 | 9/2018 |
| WO | 2018161026 | 9/2018 |
| WO | 2018161038 | 9/2018 |
| WO | 2018183385 | 10/2018 |
| WO | 2018212770 | 11/2018 |
| WO | 2018213731 | 11/2018 |
| WO | 2018213747 | 11/2018 |
| WO | 2018213828 | 11/2018 |
| WO | 2018231759 | 12/2018 |
| WO | 2018237323 | 12/2018 |
| WO | 2019111194 | 6/2019 |
| WO | 2019135879 | 7/2019 |
| WO | 2019154986 | 8/2019 |
| WO | 2019155286 | 8/2019 |
| WO | 2019155288 | 8/2019 |
| WO | 2019157130 | 8/2019 |
| WO | 2019162521 | 8/2019 |
| WO | 2019166617 | 9/2019 |
| WO | 2019180279 | 9/2019 |
| WO | 2019185828 | 10/2019 |
| WO | 2019202035 | 10/2019 |
| WO | 2019213517 | 11/2019 |
| WO | 2019241315 | 12/2019 |
| WO | 2020014366 | 1/2020 |
| WO | 2020056045 | 3/2020 |
| WO | 2020072546 | 4/2020 |
| WO | 2020086742 | 4/2020 |
| WO | 2020123716 | 6/2020 |
| WO | 2020180882 | 9/2020 |
| WO | 2020185628 | 9/2020 |
| WO | 2020185632 | 9/2020 |
| WO | 2020185698 | 9/2020 |
| WO | 2020190902 | 9/2020 |
| WO | 2020252404 | 12/2020 |
| WO | 2020252405 | 12/2020 |

OTHER PUBLICATIONS

Shum et al., Strategies for enhancing adoptive T-cell immunotherapy against solid tumors using engineered cytokine signaling and other modalities, Expert Opin Biol Ther, 18(6): 653-664. (Year: 2018).*

Chen et al., A Self-Activating IL-15 Chimeric Cytokine Receptor to Empower Cancer Immunotherapy, ImmunoTargets and Therapy, 13: 513-524. (Year: 2024).*

Burga et al., IL-2-independent expansion, persistence, and antitumor activity in TIL expressing regulatable membrane-bound IL-15, Molecular Therapy, 33(8): 1-19. (Year: 2025).*

Innis et al., Carbonic anhydrase 2-derived drug responsive domain regulates membrane bound cytokine expression and function in engineered T cells, Communications Biology, 8:28: 1-15. (Year: 2025).*

Singapore Patent Application No. SG11202202204U, Office Action, mailed Jun. 4, 2024, 10 pages.

"33rd Annual Meeting & Pre-Conference Programs of the Society for Immunotherapy of Cancer (SITC 2018)", Journal for ImmunoTherapy of Cancer, vol. 6, Nov. 6, 2018, pp. 1-205.

"Company Overview", Oral Presentation Presented at: MaidStone Life Science/William Blair 9th Annual Cancer Immunotherapy Conference, Mar. 21, 2019, 17 pages.

"Corporate Presentation", Obsidian Therapeutics, Oral Presentation Presented, Sep. 11, 2019, 18 pages.

"Corporate Presentation", Obsidian Therapeutics, Oral Presentation Presented, Nov. 2019, 20 pages.

"Corporate Presentation", Obsidian Therapeutics, Oral Presentation Presented, Sep. 23, 2020, 24 pages.

U.S. Appl. No. 12/069,235 , Final Office Action, Mailed on Nov. 4, 2011, 20 pages.

U.S. Appl. No. 12/069,235 , Non-Final Office Action, Mailed on Jul. 6, 2011, 13 pages.

U.S. Appl. No. 12/069,235 , Non-Final Office Action, Mailed on Jun. 3, 2010, 16 pages.

U.S. Appl. No. 12/437,279 , Final Office Action, Mailed on Apr. 1, 2011, 10 pages.

U.S. Appl. No. 12/437,279 , Final Office Action, Mailed on Jan. 22, 2013, 13 pages.

U.S. Appl. No. 12/437,279 , Non-Final Office Action, Mailed on May 10, 2012, 13 pages.

U.S. Appl. No. 12/437,279 , Non-Final Office Action, Mailed on Oct. 7, 2010, 14 pages.

U.S. Appl. No. 17/017,670 , Non-Final Office Action, Mailed on Nov. 16, 2020, 12 pages.

U.S. Appl. No. 17/017,670 , Notice of Allowance, Mailed on Mar. 12, 2021, 11 pages.

Ahlskog et al., "In Vivo Targeting of Tumor-Associated Carbonic Anhydrases Using Acetazolamide Derivatives", Bioorganic & Medicinal Chemistry Letters, vol. 19, No. 16, Aug. 15, 2009, pp. 4851-4856.

Anguille et al., "Interleukin-15 Dendritic Cells Harness NK Cell Cytotoxic Effector Function in a Contact- and IL-15-Dependent Manner", PLoS One, vol. 10, No. 5, May 7, 2015, 18 pages.

Banaszynski et al., "A Rapid, Reversible, and Tunable Method to Regulate Protein Function in Living Cells Using Synthetic Small Molecules", Cell, vol. 126, No. 5, Sep. 8, 2006, pp. 995-1004.

(56)         References Cited

OTHER PUBLICATIONS

Bessard et al., "High Antitumor Activity of RLI, an Interleukin-15 (IL-15)—IL-15 Receptor a Fusion Protein, in Metastatic Melanoma and Colorectal Cancer", Molecular Cancer Therapeutics, vol. 8, No. 9, Sep. 2009, pp. 2736-2745.

Chen et al., "Regulating Cytokine Function Enhances Safety and Activity of Genetic Cancer Therapies", Molecular Therapy, vol. 21, No. 1, Jan. 2013, pp. 167-174.

Cheng et al., "Membrane-Tethered Proteins for Basic Research, Imaging, and Therapy", Medicinal Research Reviews, vol. 28, No. 6, Nov. 2008, pp. 885-928.

Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression", Cancer Research, vol. 71, No. 17, Sep. 1, 2011, pp. 5697-5706.

Chu et al., "CS1-Specific Chimeric Antigen Receptor (CAR)-Engineered Natural Killer Cells Enhance in Vitro and in Vivo Antitumor Activity Against Human Multiple Myeloma", Leukemia, vol. 28, No. 4, Apr. 2014, pp. 917-927.

Chu et al., "Recent Progress with FKBP-Derived Destabilizing Domains", Bioorganic & Medicinal Chemistry Letters, vol. 18, No. 22, Nov. 15, 2008, pp. 5941-5944.

Clackson et al., "Redesigning an FKBP-Ligand Interface to Generate Chemical Dimerizers with Novel Specificity", Proceedings of the National Academy of Sciences of the U.S.A., vol. 95, No. 18, Sep. 1, 1998, pp. 10437-10442.

Dai et al., "Prediction of the Tissue-Specificity of Selective Estrogen Receptor Modulators by Using a Single Biochemical Method", Proceedings of the National Academy of Sciences of the United States of America, vol. 105, No. 20, May 20, 2008, pp. 7171-7176.

Davila et al., "CD19 Car-Targeted T Cells Induce Long-Term Remission and B Cell Aplasia in an Immunocompetent Mouse Model of B Cell Acute Lymphoblastic Leukemia", PLoS One, vol. 8, No. 4, Apr. 9, 2013, pp. 1-14.

Desbois et al., "IL-15 Trans-Signaling with the Superagonist RLI Promotes Effector/Memory CD8+ T Cell Responses and Enhances Antitumor Activity of PD-1 Antagonists", Journal of Immunology, vol. 197, No. 1, Jul. 1, 2016, pp. 168-178.

Dolinski et al., "Enhancing Adoptive Cell Therapies Through Exogenous Regulation", Poster Presented at: AACR Annual Meeting 2018, Apr. 14-18, 2018, 1 page.

Dolinski et al., "Enhancing Adoptive Cell Therapies Through Exogenous Regulation", Poster Presented at: Keystone Symposium: Emerging Cellular Therapies: T Cells and Beyond (Joint meeting with Lymphocytes and their Roles in Cancer), Feb. 11-15, 2018, 1 page.

Dolinski et al., "Regulation of In Vivo Anti-Tumor Activity of Adoptively Transferred CAR-T Cells Using FDA Approved Small Molecule Drugs", Poster Presented at: The Society for Immunotherapy of Cancer (SITC) 33rd Annual Meeting, Nov. 7-11, 2018, 1 page.

Dolinski et al., "Titratable and Reversible Regulation of IL12 or IL15 with FDA-Approved Drugs for Enhanced CAR-T Therapy", Poster Presented at: The Society for Immunotherapy of Cancer (SITC) 33rd Annual Meeting, Nov. 7-11, 2018, 1 page.

Doty et al., "Two Regions in the CD80 Cytoplasmic Tail Regulate CD80 Redistribution and T Cell Costimulation", Journal of Immunology, vol. 161, No. 6, Sep. 15, 1998, pp. 2700-2707.

Elpek et al., "Mature Natural Killer Cells with Phenotypic and Functional Alterations Accumulate Upon Sustained Stimulation With IL-15/IL-15Rα Complexes", Proceedings of the National Academy of Sciences of the United States of America, vol. 107, No. 50, Dec. 14, 2010, pp. 21647-21652.

Epardaud et al., "Interleukin-15/Interleukin-15Rα Complexes Promote Destruction of Established Tumors by Reviving Tumor-Resident CD8+ T Cells", Cancer Research, vol. 68, No. 8, Apr. 15, 2008, pp. 2972-2983.

Fanning et al., "The SERM/SERD Bazedoxifene Disrupts ESR1 Helix 12 to Overcome Acquired Hormone Resistance in Breast Cancer Cells", eLife, vol. 7, e37161, Nov. 29, 2018, 26 pages.

Felices et al., "Continuous Treatment with IL-15 Exhausts Human NK Cells via a Metabolic Defect", JCI Insight, vol. 3, No. 3, Feb. 8, 2018, 14 pages.

Fleury, "Regulation of CD40L Transgene Expression in Human CAR-T cells using FDA Approved Ligands", Oral Presentation Presented at: AACR Immune Cell Therapies for Cancer, Jul. 19-22, 2019, 12 pages.

Foa et al., "IL2 Treatment for Cancer: From Biology to Gene Therapy", British Journal of Cancer, vol. 66, No. 6, Dec. 1992, pp. 992-998.

Geller et al., "Use of Allogeneic NK Cells for Cancer Immunotherapy", Immunotherapy, vol. 3, No. 12, Dec. 2011, pp. 1445-1459.

Gennaro, "Remington's Pharmaceutical Sciences, 17th Ed.", Mack Publishing Company, 1985, 2 pages.

Giron-Michel et al., "Membrane-Bound and Soluble IL-15/IL-15Rα Complexes Display Differential Signaling and Functions on Human Hematopoietic Progenitors", Blood, vol. 106, No. 7, Oct. 1, 2005, pp. 2302-2310.

Gori, "Enhancing Adoptive Cell Therapies Through Exogenous Regulation", Oral Presentation Presented at: Genome Writers Guild Annual Conference, Jul. 19-21, 2018, 23 pages.

Gori et al., "Regulation of In Vivo Anti-Tumor Activity of Adoptively Transferred CAR-T Cells Using FDA Approved Small Molecule Drugs", Journal for ImmunoTherapy of Cancer, vol. 6, Nov. 6, 2018, p. 121.

Hernandez et al., "Novel Kidney Cancer Immunotherapy Based on the Granulocyte-Macrophage Colony-Stimulating Factor and Carbonic Anhydrase IX Fusion Gene", Clinical Cancer Research, vol. 9, May 2003, pp. 1906-1916.

Hoyos et al., "Engineering CD19-Specific T Lymphocytes with Interleukin-15 and a Suicide Gene to Enhance Their Anti-Lymphoma/Leukemia Effects and Safety", Leukemia, vol. 24, No. 6, Jun. 2010, pp. 1160-1170.

Hurton et al., "Tethered IL-15 Augments Antitumor Activity and Promotes a Stem-Cell Memory Subset in Tumor-Specific T Cells", Proceedings of the National Academy of Sciences of the United States of America, vol. 113, No. 48, Nov. 14, 2016, pp. E7788-E7797.

Hurton, "Tethered IL-15 to Augment the Therapeutic Potential of T Cells Expressing Chimeric Antigen Receptor: Maintaining Memory Potential, Persistence, and Antitumor Activity", UT GSBS Dissertation and Thesis, May 2014, 173 pages.

Imamura et al., "Autonomous Growth and Increased Cytotoxicity of Natural Killer Cells Expressing Membrane-Bound Interleukin-15", Blood, vol. 124, No. 7, Aug. 14, 2014, pp. 1081-1088.

Iwamoto et al., "A General Chemical Method to Regulate Protein Stability in the Mammalian Central Nervous System", Chemistry & Biology, vol. 17, No. 9, Sep. 24, 2010, pp. 981-988.

Juillerat et al., "Design of Chimeric Antigen Receptors with Integrated Controllable Transient Functions", Scientific Reports, vol. 6, No. 18950, Jan. 11, 2016, pp. 1-7.

Kassum, "Company Overview", Obsidian, Oral Presentation Presented at: Boston Cancer Summit, Apr. 16, 2019, 16 pages.

Kaufman et al., "Brief Report: Local Delivery of Vaccinia Virus Expressing Multiple Costimulatory Molecules for the Treatment of Established Tumors", Human Gene Therapy, vol. 17, No. 2, Feb. 2006, pp. 239-244.

Kermer et al., "An Antibody Fusion Protein for Cancer Immunotherapy Mimicking IL-15 Trans-Presentation at the Tumor Site", Molecular Cancer Therapeutics, vol. 11, No. 6, Jun. 2012, pp. 1279-1288.

Khawam et al., "Human Renal Cancer Cells Express a Novel Membrane-Bound Interleukin-15 that Induces, in Response to the Soluble Interleukin-15 Receptor α Chain, Epithelial-to-Mesenchymal Transition", Cancer Research, vol. 69, No. 4, Feb. 15, 2009, pp. 1561-1569.

Kochenderfer et al., "Lymphoma Remissions Caused by Anti-CD19 Chimeric Antigen Receptor T Cells are Associated with High Serum Interleukin-15 Levels", Journal of Clinical Oncology, vol. 35, No. 16, Jun. 1, 2017, pp. 1803-1813.

Lee et al., "Construction of Stable Producer Cells to Make High-Titer Lentiviral Vectors for Dendritic Cell-Based Vaccination", Biotechnology and Bioengineering, vol. 109, No. 6, Jun. 2012, pp. 1551-1560.

(56)        References Cited

OTHER PUBLICATIONS

Lusty et al., "IL-18/IL-15/IL-12 Synergy Induces Elevated and Prolonged IFN-γ Production by Ex Vivo Expanded NK Cells Which is Not Due to Enhanced STAT4 Activation", Molecular Immunology, vol. 88, Aug. 2017, pp. 138-147.

Machado Diaz et al., "Proinflammatory Soluble Interleukin-15 Receptor Alpha Is Increased in Rheumatoid Arthritis", Arthritis, vol. 2012, Jul. 25, 2012, 7 pages.

Malhotra, "Deducing the Essentiality of a Putative Apicoplast Deubiquitinating Protease: The OTU-Like Cysteine Protease PF10_0308 in Plasmodium Falciparum", Research Thesis, Available Online at: https://kb.osu.edu/bitstream/handle/1811/51570/Thesis_Project_Report.pdf?sequence=1&isAllowed=y, Feb. 2012, 33 pages.

Mesen-Ramirez et al., "Stable Translocation Intermediates Jam Global Protein Export in Plasmodium Falciparum Parasites and Link the PTEX Component EXP2 with Translocation Activity", PLoS Pathogens, vol. 12, No. 5, May 11, 2016, pp. 1-28.

Miyazaki et al., "Destabilizing Domains Derived from the Human Estrogen Receptor", Journal of the American Chemical Society, vol. 134, No. 9, Mar. 7, 2012, pp. 3942-3945.

Mortier et al., "Soluble Interleukin-15 Receptor α (IL-15Rα)-Sushi as a Selective and Potent Agonist of IL-15 Action Through IL-15Rβ/γ. Hyperagonist IL-15-IL-15Rα Fusion Proteins", The Journal of Biological Chemistry, vol. 281, No. 3, Jan. 20, 2006, pp. 1612-1619.

Musso et al., "Human Monocytes Constitutively Express Membrane-Bound, Biologically Active, and Interferon-γ-Upregulated Interleukin-15", Blood, vol. 93, No. 10, May 15, 1999, pp. 3531-3539.

Naldini, "Lentiviruses as Gene Transfer Agents for Delivery to Non-Dividing Cells", Current Opinion in Biotechnology, vol. 9, No. 5, Oct. 1998, pp. 457-463.

Neely et al., "Monocyte Surface-Bound IL-15 Can Function as an Activating Receptor and Participate in Reverse Signaling", Journal of Immunology, vol. 172, No. 7, Apr. 1, 2004, pp. 4225-4234.

Nishimura et al., "A Novel Autoregulatory Mechanism for Transcriptional Activation of the IL-15 Gene by a Nonsecretable Isoform of IL-15 Generated by Alternative Splicing", The FASEB Journal, vol. 19, No. 1, Jan. 2005, pp. 19-28.

Ochoa et al., "Antitumor Immunotherapeutic and Toxic Properties of an HDL-Conjugated Chimeric IL-15 Fusion Protein", Cancer Research, vol. 73, No. 1, Jan. 1, 2013, pp. 139-149.

Olinger, "Fine Tuning of CD19 CAR T Cell Activity Using Drug Responsive Domains", Oral Presentation Presented at: American Society of Gene & Cell Therapy (ASGCT) 22nd Annual Meeting, Apr. 29-May 2, 2019, 14 pages.

Olinger, "Pharmacological Control of In Vivo Tumor Regression by T Cells Engineered with CD19-Car Regulated with PDE5 Derived Destabilizing Domains", Molecular Therapy, vol. 27, No. 4S1, Apr. 2019, p. 173.

Ols et al., "Abstract LB-013: CAR-Ts Armored with Small Molecule-Regulated IL 12 or CD40L Cassettes for Enhanced Activity Against Solid Tumors", Cancer Research, vol. 79, Jul. 1, 2019, 4 pages.

Ols et al., "Car-Ts Armored with Small Molecule-Regulated IL12 or CD40L Cassettes for Enhanced Activity Against Solid Tumors", Proceedings: AACR Annual Meeting 2019, Abstract LB-013, Mar. 29, 2019, 1 page.

Ols et al., "Enhancing Adoptive Cell Therapies Through Regulation of IL2", Poster Presented at: Keystone Symposium Cancer Immunotherapy: Mechanistic Insights to Improve Clinical Benefit, Mar. 10-14, 2019, 1 page.

Ols, "Enhancing Adoptive Immunotherapy with Pharmacologic Operating Systems", Oral Presentation Presented at: Medical University of South Carolina, Oct. 15, 2018, 25 pages.

Oyer et al., "Natural Killer Cells Stimulated with PM21 Particles Expand and Biodistribute in Vivo: Clinical Implications for Cancer Treatment", Cytotherapy, vol. 18, No. 5, May 2016, pp. 653-663.

Pacheco et al., "Despite an Impaired Response to IL-7, CD4+EM T Cells from HIV-Positive Patients Proliferate Normally in Response to IL-15 and its Superagonist, RLI", AIDS, vol. 25, No. 14, Sep. 10, 2011, pp. 1701-1710.

Application No. PCT/US2020/050273, International Preliminary Report on Patentability, Mailed on Mar. 24, 2022, 9 pages.

Application No. PCT/US2020/050273, International Search Report and Written Opinion, Mailed on Nov. 27, 2020, 12 pages.

Qian et al., "Construction of a Plasmid for Co-Expression of Mouse Membrane-Bound Form of IL-15 and RAE-1ε and Its Biological Activity", Plasmid, vol. 65, No. 3, May 2011, pp. 239-245.

Reardon et al., "Dose-Dependent Exogenous Regulation of Membrane Bound Interleukin 15-Interleukin 15 Receptor Alpha Fusion Protein for Adoptive T-Cell Therapy", Poster Presented at: ASGCT 21st Annual Meeting, May 16-19, 2018, 1 page.

Reardon et al., "Kinetics of Lentiviral Copy Numbers and Transgene Expression in Primary Human T Cells Transduced with VSV-G Pseudotyped 3rd Generation Lentivirus", Poster Presented at: American Society of Gene & Cell therapy (ASGCT) 22nd Annual Meeting, Apr. 29-May 2, 2019, 1 page.

Reardon et al., "Kinetics of Lentiviral Integration and Transgene Expression, in Cell Lines and Primary Human T-Cells, Transduced with VSV-G Pseudotyped 3rd Generation Lentivirus", Molecular Therapy, vol. 27, No. 4S1, Apr. 2019, p. 211.

Relander et al., "Gene Transfer to Repopulating Human CD34+ Cells Using Amphotropic-, GALV-, or RD114-Pseudotyped HIV-1-Based Vectors from Stable Producer Cells", Molecular Therapy, vol. 11, No. 3, Mar. 2005, pp. 452-459.

Richardson et al., "Abstract 3580: Enhancing Adoptive Cell Therapies Through Exogenous Regulation", Cancer Research, vol. 78, Jul. 2018, 4 pages.

Rosenberg, "Cell Transfer Immunotherapy for Metastatic Solid Cancer—What Clinicians Need to Know", Nature Reviews Clinical Oncology, vol. 8, No. 10, Aug. 2, 2011, pp. 577-585.

Ruggeri et al., "Effectiveness of Donor Natural Killer Cell Alloreactivity in Mismatched Hematopoietic Transplants", Science, vol. 295, No. 5562, Mar. 15, 2002, pp. 2097-2100.

Saeterdal et al., "Frameshift-Mutation-Derived Peptides as Tumor-Specific Antigens in Inherited and Spontaneous Colorectal Cancer", Proceedings of the National Academy of Sciences of the United States of America (PNAS), vol. 98, No. 23, Nov. 6, 2001, pp. 13255-13260.

Schebesta et al., "Enhancing Adoptive Cell Therapies Through Regulation of CD40 Ligand", Poster Presented at: Keystone Symposium Cancer Immunotherapy: Mechanistic Insights to Improve Clinical Benefit, Mar. 10-14, 2019, 1 page.

Schebesta, "Enhancing Adoptive Cell Therapies Through Regulation of CD40 Ligand", Oral Presentation Presented at: Keystone Symposium Cancer Immunotherapy: Mechanistic Insights to Improve Clinical Benefit, Mar. 10-14, 2019, 11 pages.

Shamah, "Development of a Novel System for Exogenous Regulation of Adoptive Cell Therapy", Oral Presentation Presented at: CAR-TCR Summit, Sep. 5-8, 2017, 22 pages.

Shamah, "Enhancing Adoptive Cell Therapies Through Exogenous Regulation", Oral Presentation Presented at: Summit for Cancer Immunotherapy, Oct. 27-30, 2018, 25 pages.

Shamah, "Enhancing CAR-T Therapies with Regulated Immunomodulatory Factors", Oral Presentation Presented at: CAR-TCR Summit, Sep. 10-13, 2019, 18 pages.

Shamah et al., "P271: Titratable and Reversible Regulation of IL12 or IL15 with FDA-Approved Drugs Enhances CAR-T Therapy", Journal for ImmunoTherapy of Cancer, vol. 6, Nov. 6, 2018, p. 139.

Stewart et al., "A Stable Producer Cell Line for the Manufacture of a Lentiviral Vector for Gene Therapy of Parkinson's Disease", Human Gene Therapy, vol. 22, No. 3, Mar. 2011, pp. 357-369.

Stone et al., "Design and Characterization of a Protein Superagonist of IL-15 Fused with IL-15Rα and a High-Affinity T Cell Receptor", Biotechnology Progress, vol. 28, No. 6, Nov. 2012, pp. 1588-1597.

Sun et al., "Exogenous In Vitro and In Vivo Regulation of Interleukin-12 Secretion From T Cells Using Destabilizing Domain Technology", Poster Presented at: ASGCT 21st Annual Meeting, May 16-19, 2018, 1 page.

Suri et al., "Small Molecule Regulated Cytokine Expression Enables Potent and Durable Responses to Engineered T-Cell Therapy", Poster Presented at: 60th American Society of Hematology Annual Meeting and Exposition, Dec. 1-4, 2018, 1 page.

(56)                    References Cited

OTHER PUBLICATIONS

Suri et al., "Small Molecule Regulated Cytokine Expression Enables Potent and Durable Responses to Engineered T-Cell Therapy", Blood: American Society of Hematology, vol. 132, Nov. 29, 2018, p. 2045.

Suri et al., "Titratable and Reversible Regulation of Therapeutic Proteins in Cell and Gene Therapies Using FDA Approved Drugs and a Modular Protein Stabilization Platform", Molecular Therapy, vol. 27, No. 4S1, Apr. 2019, pp. 40-41.

Suri, "Titratable Therapeutic Protein Expression Using FDA Approved Drugs", Oral Presentation Presented at: American Society of Gene & Cell therapy (ASGCT) 22nd Annual Meeting, Apr. 29-May 2, 2019, 22 pages.

Tagaya et al., "Generation of Secretable and Nonsecretable Interleukin 15 Isoforms Through Alternate Usage of Signal Peptides", Proceedings of the National Academy of Sciences of the United States of America, vol. 94, No. 26, Dec. 23, 1997, pp. 14444-14449.

Themeli et al., "Generation of Tumor-Targeted Human T Lymphocytes from Induced Pluripotent Stem Cells for Cancer Therapy", Nature Biotechnology, vol. 31, No. 10, Oct. 2013, pp. 928-935.

Throm et al., "Efficient Construction of Producer Cell Lines for a Sin Lentiviral Vector for Scid-x1 Gene Therapy by Concatemeric Array Transfection", Blood, vol. 113, No. 21, May 21, 2009, pp. 5104-5110.

Topfer et al., "DAP12-Based Activating Chimeric Antigen Receptor for NK Cell Tumor Immunotherapy", The Journal of Immunology, vol. 194, No. 7, Apr. 1, 2015, pp. 3201-3212.

Tran et al., "Abstract A220: Destabilizing Domain Technology Facilitates Exogenous Regulation of IL15 and IL12 for Adaptive T-Cell Therapy", Cancer Immunology Research, vol. 7, No. 2, Feb. 1, 2019, 2 pages.

Tran et al., "Destabilizing Domain Technology Facilitates Exogenous Regulation of IL12 and IL15 for Adoptive T-Cell Therapy", Poster Presented at: Fourth CRI-CIMT-EATI-AACR International Cancer Immunotherapy Conference: Translating Science into Survival, Sep. 30-Oct. 3, 2018, 1 page.

Tsukahara et al., "CD19 Target-Engineered T-Cells Accumulate at Tumor Lesions in Human B-Cell Lymphoma Xenograft Mouse Models", Biochemical and Biophysical Research Communications, vol. 438, No. 1, Aug. 16, 2013, pp. 84-89.

Turko et al., "Potential Roles of Conserved Amino Acids in the Catalytic Domain of the cGMP-Binding cGMP-Specific Phosphodiesterase (PDE5)", The Journal of Biological Chemistry, vol. 273, No. 11, Mar. 13, 1998, pp. 6460-6466.

Vincent et al., "Tumor Targeting of the IL-15 Superagonist RLI by an Anti-GD2 Antibody Strongly Enhances its Antitumor Potency", International Journal of Cancer, vol. 133, No. 3, Aug. 1, 2013, pp. 757-766.

Wang et al., "Conformational Variations of Both Phosphodiesterase-5 and Inhibitors Provide the Structural Basis for the Physiological Effects of Vardenafil and Sildenafil", Molecular Pharmacology, vol. 73, No. 1, Jan. 2008, pp. 104-110.

Wang et al., "Overcoming Intrinsic Inhibitory Pathways to Augment the Antineoplastic Activity of Adoptively Transferred T Cells: Re-Tuning Your CAR Before Hitting a Rocky Road", Oncolmmunology, vol. 2, No. 11, Nov. 1, 2013, pp. e26492-1-e26492-3.

Weisman et al., "Regulation of CD40 Ligand Transgene Expression in Human CAR-T Cells Using FDA Approved Drugs", Poster Presented at: American Society of Gene & Cell therapy (ASGCT) 22nd Annual Meeting, Apr. 29-May 2, 2019, 1 page.

Weisman et al., "Regulation of CD40L Transgene Expression in Human CAR-T Cells Using FDA Approved Ligands", Molecular Therapy, vol. 27, No. 4S1, Apr. 2019, p. 266.

Wittnebel et al., "Membrane-Bound Interleukin (IL)-15 on Renal Tumor Cells Rescues Natural Killer Cells from IL-2 Starvation-Induced Apoptosis", Cancer Research, vol. 67, No. 12, Jun. 15, 2007, pp. 5594-5599.

Wu et al., "Genetic Engineering in Primary Human B Cells with CRISPR-Cas9 Ribonucleoproteins", Journal of Immunological Methods, vol. 457, Jun. 2018, pp. 33-40.

Yuan et al., "Transmembrane-Bound IL-15-Promoted Epithelial-Mesenchymal Transition in Renal Cancer Cells Requires the Src-Dependent Akt/GSK-3β/β-Catenin Pathway", Neoplasia, vol. 17, No. 5, May 2015, pp. 410-420.

Zhang et al., "Improving Adoptive T Cell Therapy by Targeting and Controlling IL-12 Expression to the Tumor Environment", Molecular Therapy, vol. 19, No. 4, Apr. 2011, pp. 751-759.

CN Application No. 202080078243.0 , Office Action, mailed Mar. 20, 2025, 15 pages, with English translation.

Canadian Patent Application No. 3150224, Office Action mailed Oct. 16, 2023, 7 pages.

European Patent Application No. 20780498.0, Communication pursuant to Article 94(3) EPC, mailed Sep. 26, 2023, 6 pages.

CN Patent Application No. 202080078243.0, Office Action, mailed Jan. 4, 2025, 13 pages with English translation.

JP Patent Application No. 2022-515112 , Office Action, mailed Dec. 11, 2024, 8 pages with English translation.

European Patent Application No. 20780498.0, Office Action, mailed Sep. 5, 2024, 5 pages.

Japanese Patent Application No. 2022-515112, Office Action, mailed Aug. 28, 2024, 8 pages.

Chinese Patent Application No. 202080078243.0, "Office Action", mailed Mar. 9, 2024, 11 pages with translation.

Canadian Patent Application No. 3150224, "Office Action", mailed Apr. 16, 2025, 5 pages.

Japanese Patent Application No. 2022-515112, "Notice of Allowance", mailed May 26, 2025, 2 pages.

Australian Patent Application No. 2020345943, "First Examination Report", mailed Jul. 24, 2025, 3 pages.

European Patent Application No. 20780498.0, "Office Action", mailed Nov. 13, 2025, 5 pages.

* cited by examiner

Measure IL15 Expression
Measure Antigen-Independent Cell Expansion

Measure IL15 Expression
Measure Antigen-Independent Cell Expansion

CA2-IL15 FUSION PROTEINS FOR TUNABLE REGULATION

CROSS REFERENCE TO RELATED APPLICATIONS

This application claims benefit of priority to U.S. Provisional Application No. 62/898,520, filed Sep. 10, 2019. The entire contents of the aforementioned application are incorporated herein by reference in their entireties.

REFERENCE TO THE SEQUENCE LISTING

The instant application contains a Sequence Listing which has been submitted electronically in ASCII format and is hereby incorporated by reference in its entirety. Said ASCII copy, created on Sep. 10, 2020, is named 268052_473951_SL.txt and is 178,693 bytes in size.

FIELD

The present disclosure relates to drug responsive domains (DRDs) derived from human carbonic anhydrase 2 (CA2) which can modulate protein stability for at least one payload comprising human interleukin 15 (IL15), compositions and methods of use thereof. Provided in the present disclosure are polypeptides of CA2 biocircuit systems, CA2 effector modules, stimulus response elements (SREs), polynucleotides encoding the same, vectors and cells containing the polypeptides and/or polynucleotides for use in augmenting responses from immune cells.

BACKGROUND

Utilization of the DRD technology described herein with methods of regulating cytokine function and/or expression represent a significant improvement on existing immunotherapy strategies, and can expand the universe of protein therapeutics that can be safely and effectively incorporated into gene transfer and adoptive T cell transfer (ACT) therapies, including applications that have previously been considered unsuitable for therapeutic use. Improved Natural Killer cells (NK cells), Tumor Infiltrating Lymphocytes (TIL) and T cell-based immunotherapies are needed to enhance and improve the functionality of the treatments, for example, by improving the persistence and/or survival of engineered immune cells, for use in various immunotherapies upon administration to subjects. Provided are CA2 DRDs linked to human IL15, modified cells comprising such DRDs, compositions, and methods that meet such needs.

SUMMARY

The present disclosure provides novel protein domains derived from human carbonic anhydrase 2 (CA2) displaying small molecule-dependent stability. Such protein domains are called drug responsive domains (DRDs). In the absence of its binding (i.e., stabilizing) ligand, the DRD is destabilizing and causes degradation of a payload operably linked to the DRD (e.g., a protein of interest (POI)), while in the presence of its binding ligand, the DRD and its operably linked payload are stabilized. The stability of the DRD and its operably linked payload is dependent on the dose of the binding ligand.

In some embodiments, the present disclosure provides a stimulus response element (SRE), which may comprise a drug responsive domain (DRD) derived from human carbonic anhydrase 2 (CA2, having the amino acid sequence of SEQ ID NO: 1) in whole or in part. In one embodiment, the DRD may be derived from the full-length CA2 polypeptide (SEQ ID NO: 1). In some embodiments, the DRD may be derived from a portion or region of the human carbonic anhydrase. The portion or region of CA2 may be selected from amino acids 2-260 of CA2 (SEQ ID NO: 2).

In some embodiments, the SRE may include a DRD comprising one, two, three, four or more mutations in CA2 relative to SEQ ID NO:1 or SEQ ID NO: 2. In some embodiments, the SRE may include a DRD comprising one, two, three, four or more amino acid substitutions in CA2 relative to SEQ ID NO:1 or SEQ ID NO: 2.

In some embodiments, the SRE may include a DRD comprising one, two, three, four or more mutations in a portion of CA2. In some embodiments, the SRE may include a DRD comprising one, two, three, four or more mutations in CA2 or portion thereof, and may further comprise additional amino acids. In some embodiments, the SRE may include a DRD comprising one, two, three, four or more amino acid substitutions in a portion of CA2. In some embodiments, the SRE may include a DRD comprising one, two, three, four or more amino acid substitutions in CA2 or portion thereof, and may further comprise additional amino acids.

Also provided herein are isolated polypeptide variants comprising at least one mutation relative to SEQ ID NO: 1. Non-limiting examples of CA2 mutations relative to SEQ ID NO: 1 include M1del and L156H. In another aspect, a DRD is a polypeptide comprising or consisting of the amino acid sequence of SEQ ID NO:4, wherein the CA2 mutation comprises Mdel1 and L156H relative to SEQ ID NO: 1. In another aspect, the DRD is a polypeptide containing the amino acid deletion M1del and amino acid substitution L156H relative to SEQ ID NO: 1 and may further comprise additional amino acids. In another aspect, the DRD is a polypeptide consisting of the amino acid sequence of SEQ ID NO:4.

Also provided herein are biocircuit systems that include at least one effector module. The effector module of the biocircuit may include a stimulus response element (SRE), and the SRE may include a DRD derived from a human carbonic anhydrase 2 (CA2; SEQ ID NO: 1) or a mutant thereof comprising one, two, three, four or more mutations of CA2 relative to the amino acid sequence of SEQ ID NO: 1 or SEQ ID NO: 2. In some embodiments, the effector module of the biocircuit includes an SRE including a DRD comprising one, two, three, four or more amino acid substitutions in CA2 relative to SEQ ID NO:1 or SEQ ID NO: 2. The biocircuits may also include at least one payload, which may be attached, appended or associated with the SRE. The payload may include but is not limited to (i) a human IL15 comprising the amino acid sequence of SEQ ID NO: 8.

The SRE of the biocircuit system may include one, two, three or more mutations of CA2 (SEQ ID NO: 1 or SEQ ID NO: 2) such as, but not limited to, Medl1 and L156H. The SRE of the biocircuit system may include one, two, three or more amino acid substitutions in CA2 (SEQ ID NO: 1 or SEQ ID NO: 2), such as, but not limited to L156H.

In some embodiments, the SRE in the CA2 biocircuit system may be CA2 having the mutations M1del and L156H, wherein the numbering is relative to the amino acid sequence of SEQ ID NO:1 (SEQ ID NO: 4). In some embodiments, the SRE is a polypeptide comprising or consisting of the amino acid sequence of SEQ ID NO:4. In some embodiments, the SRE is a polypeptide consisting of the amino acid sequence of SEQ ID NO:4.

The biocircuit system described herein may include SREs that are responsive to one or more stimuli.

In some embodiments, the stimulus may be a small molecule, wherein the small molecule is acetazolamide (ACZ).

In another aspect, the present disclosure provides an effector module comprising at least one payload. In some embodiments, the effector module comprises an SRE comprising a CA2 DRD operably linked to an IL15 payload. In some embodiments, the IL15 payload comprises the amino acid sequence of SEQ ID NO: 8. In some embodiments, the IL15 payload may be encoded in part by a nucleic acid sequence comprising the nucleotide sequence of SEQ ID NO: 9. In some embodiments, the IL15 payload is a membrane-bound form of IL15. In some embodiments, the IL15 payload is a membrane-bound form of IL15 comprising a functional IL15 component or domain, a transmembrane domain and an intracellular tail. In some embodiments, the IL15 payload is a membrane-bound form of IL15 comprising a functional IL15 component or domain, a transmembrane domain, an intracellular tail and a leader sequence. In some embodiments, the present disclosure provides an SRE comprising a CA2 DRD operably linked to a membrane-bound IL15 polypeptide. In some embodiments, the present disclosure provides an SRE comprising a CA2 DRD operably linked to a membrane-bound IL15 polypeptide, wherein the membrane-bound IL15 polypeptide comprises, from N-terminal to C-terminal, a leader sequence, an IL15 polypeptide comprising the amino acid sequence of SEQ ID NO: 8, a peptide linker, a transmembrane domain, and an intracellular tail.

In another aspect, the present disclosure provides a method of making a modified or genetically engineered cell comprising introducing a polynucleotide encoding an effector module into the cell. In some embodiments, the modified or engineered cell is an immune cell. In some embodiments, the immune cell is a T cell, a natural killer (NK) cell or a tumor infiltrating lymphocyte (TIL). In some embodiments, the polynucleotide encodes a CA2 DRD operably linked to an IL15 payload. In some embodiments, the polynucleotide encodes a CA2 DRD operably linked to a membrane-bound IL15 payload. In some embodiments, the polynucleotide is introduced into the cell by a non-viral vector delivery method. In some embodiments, the polynucleotide is introduced into the cell by viral transduction. In some embodiments, the polynucleotide in introduced into the cell by lentiviral transduction. In some embodiments, the polynucleotide is introduced into the cell by lentiviral transduction into a T cell, an NK cell or a TIL. In some embodiments, the present disclosure provides a method of making a modified or genetically engineered T cell, NK cell or TIL comprising introducing a polynucleotide encoding a CA2 DRD operably linked to a membrane-bound IL15 payload into the T cell, NK cell or TIL by a viral vector, such as a lentiviral vector.

In another aspect, the present disclosure provides a method of treatment, comprising (a) administering a modified cell comprising a recombinant construct comprising an SRE linked to a payload of the present disclosure or a composition comprising a plurality of such modified cells to a subject having a disease or condition, and (b) administering to the subject a therapeutically effective amount of a stimulus to which the SRE responds. In some embodiments of this aspect, the disease or condition is a cancer, a neoplasm or a tumor. In some embodiments, the SRE is a CA2 DRD. In some embodiments, the payload is IL15 or membrane-bound IL15. In some embodiments, the modified cells comprise a CA2 SRE operably linked to an IL15 payload. In some embodiments, the modified cells comprise a CA2 SRE operably linked to a membrane-bound IL15 payload. In some embodiments, the stimulus is acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the modified cells comprise a CA2 SRE operably linked to a membrane-bound IL15 payload and the stimulus is acetazolamide. In some related aspects, the modified cells are engineered or modified immune cells, for example, CA2-IL15 biocircuits and systems may be used with immune cells including T cells such as CD8+ T cells and CD4+ T cells, natural killer (NK) cells, NK T cells, cytotoxic T lymphocytes (CTLs), tumor infiltrating lymphocytes (TIL), lymphokine-activated killer (LAK) cells, memory T cells, regulatory T cells (Tregs), helper T cells, cytokine-induced killer (CIK) cells, and any combination thereof. In other embodiments, immune stimulatory cells for ACT may be generated from embryonic stem cell (ESC) and induced pluripotent stem cell (iPSC). In some embodiments, autologous or allogeneic immune cells are used for ACT. In some embodiments, the immune cells are T cells, TIL or NK cells. In some embodiments, the immune cells are NK cells derived from iPSCs, cord blood, or peripheral blood mononuclear cells, wherein the modified immune cells exhibit increased or longer expansion and/or persistence in the subject than in a subject administered the same or about the same dosage amount of a reference cell composition lacking the SRE linked to a payload.

In another aspect, the present disclosure provides a method of treating a malignant tumor in a subject, comprising (a) administering a modified T cell, modified NK cell or a modified TIL, wherein the T cell, NK cell or TIL comprises a recombinant construct comprising an SRE linked to a payload of the present disclosure or a composition comprising a plurality of such modified cells to the subject, and (b) administering to the subject a therapeutically effective amount of a stimulus to which the SRE responds. In some embodiments, the tumor expresses a tumor-associated antigen. In some embodiments, the modified T cell or modified NK cell further comprises a chimeric antigen receptor (CAR) or T cell receptor (TCR) that comprises an antigen-binding domain specific to the tumor-associated antigen. In some embodiments, the modified T cell or modified NK cell comprises a CAR comprising an antigen-binding domain specific to the tumor-associated antigen. In some embodiments, the modified T cell, modified NK cell or modified TIL comprise an SRE that is a CA2 DRD. In some embodiments, the modified T cell, modified NK cell or modified TIL comprise a payload that is IL15 or membrane-bound IL15. In some embodiments, the modified the modified T cell, modified NK cell or modified TIL comprise a CA2 SRE operably linked to an IL15 payload. In some embodiments, the modified the modified T cell, modified NK cell or modified TIL comprise a CA2 SRE operably linked to a membrane-bound IL15 payload. In some embodiments, the stimulus is acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the modified cells comprise a CA2 SRE operably linked to a membrane-bound IL15 payload and the stimulus is acetazolamide.

In another aspect, the present disclosure provides polynucleotides and vectors encoding the biocircuit system, and a pharmaceutical composition that includes the biocircuit system and a pharmaceutically acceptable excipient.

In another aspect, the present disclosure provides recombinant proteins encoded by the polynucleotides of the disclosure. In some embodiments, the recombinant proteins comprise an effector module comprising a CA2 DRD operably linked to an IL15 payload.

BRIEF DESCRIPTION OF THE DRAWINGS

The foregoing and other objects, features, and advantages will be apparent from the following description of particular embodiments of the present disclosure, as illustrated in the accompanying drawings. The drawings are not necessarily to scale; emphasis instead being placed upon illustrating the principles of various embodiments of the present disclosure.

FIG. 5A shows in vivo expansion of T cells expressing constitutive IL15 (IL15-292 and IL15-294) and regulated IL15 (IL15-293 and IL15-295) constructs. FIG. 5B shows in vivo expansion of bystander NK cells under the same conditions. T cell and NK cell frequencies in blood was determined by flow cytometry. FIG. 5C shows expression of IL15 on T cells on day 25, analyzed by flow cytometry. Empty vector (EV) transduced cells were used as controls.

FIG. 7A shows flow cytometry analyses for expression of mbIL15 and CAR in peripheral blood T cells. FIG. 7B shows tumor growth curves of individual mice implanted with CD19+

Nalm6-Luc tumors and infused with T cells that were transduced with lentiviral vectors expressing CD19 CAR with or without constitutive or regulated mbIL15. FIG. 7C shows tumor growth curves with group averages and standard error. FIG. 7D shows frequency of T cells in blood collected from animals on days 7, 14 and 21 post T cell infusion. FIG. 7E shows frequency of T cells in bone marrow harvested from animals on day 14 post T cell infusion.

FIG. 8 shows analyses of TILs from patient tumor samples after a culturing process and after transduction with mbIL15-expressing constructs.

DETAILED DESCRIPTION

Figure 1:
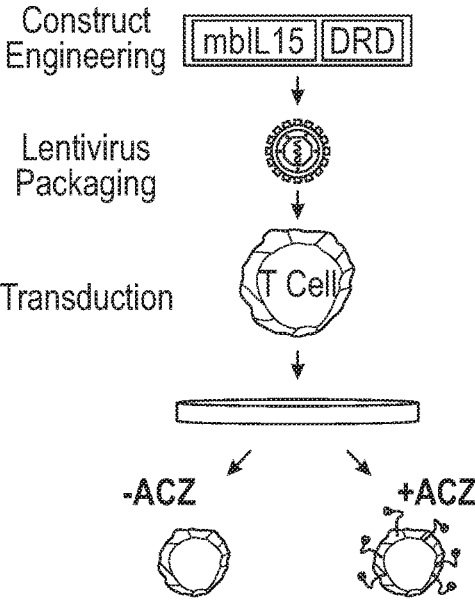
FIG. 1 depicts a representative procedure for in vitro characterization and/or validation of ACZ-regulated membrane-bound IL15 (mbIL15) expression in T cells.

The details of one or more embodiments of the present disclosure are set forth in the accompanying description below. Although any materials and methods similar or equivalent to those described herein can be used in the practice or testing of the present disclosure, the preferred materials and methods are now described. Other features, objects and advantages of the present disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which the present disclosure belongs. In the case of conflict, the present description will control.

Cancer immunotherapy aims to induce or restore the reactivity of the immune system towards cancer. Significant advances in immunotherapy research have led to the development of various strategies which may broadly be classified into active immunotherapy and passive immunotherapy. In general, these strategies may be utilized to directly kill cancer cells or to counter the immunosuppressive tumor microenvironment. Active immunotherapy aims at induction of an endogenous, long-lasting tumor-antigen specific immune response. The response can further be enhanced by non-specific stimulation of immune response modifiers such as cytokines. In contrast, passive immunotherapy includes approaches where immune effector molecules such as tumor-antigen specific cytotoxic T cells or antibodies are administered to the host. This approach is short lived and requires multiple applications.

Efficient T cell activation requires three signals, T cell receptor (TCR) signaling (Signal 1), activation by co-stimulatory molecules (Signal 2), and immune-stimulatory cytokines (Signal 3). So far, the majority of the CAR-based immunotherapies designed and discussed possess Signal 1 and Signal 2; however, Signal 3, generally provided by homeostatic cytokines, is typically absent in conventional CAR T cells and is also less abundant in the tumor microenvironment.

Therefore, there exists a need to engineer T cells (including for example, CAR T cells) that are capable of supplying additional cytokine signaling to satisfy the need for Signal 3 for optimal T cell activation. The major cytokines involved in T cell activation, which encompass Signal 3 cytokines, belong to γc class like IL-2, IL-7, IL-15, IL-21, and IL-9. These cytokines control T cell survival and proliferation, which ultimately has significant roles in T cell persistence and efficacy. These cytokines are currently employed in ex vivo expansion of CAR T cells prior to therapy in combinations or alone.

Supporting T cell longevity via continuous exposure to IL15 however may have risk, because chronic high exposure to IL-15 may cause aberrant T cell proliferation or toxicities. In humans, dysregulated IL15 production, elevated serum levels, or abnormal IL15 signaling has been associated with autoimmune disease and may be involved in the pathogenesis of large granular lymphocytic leukemia and cutaneous T cell lymphoma.

Natural killer (NK) cells are members of the innate lymphoid cell family and characterized in humans by expression of the phenotypic marker CD56 (neural cell adhesion molecule) in the absence of CD3 (T cell co-receptor). NK cells are potent effector cells of the innate immune system which mediate cytotoxic attack without the requirement of prior antigen priming, forming the first line of defense against diseases including cancer malignancies and viral infection.

Several pre-clinical and clinical trials have demonstrated that adoptive transfer of NK cells is a promising treatment approach against cancers such as acute myeloid leukemia (Ruggeri et al., Science; 2002, 295: 2097-2100; and Geller et al., Immunotherapy, 2011, 3: 1445-1459). Adoptive transfer of NK cells expressing CAR such as DAP12-Based Activating CAR revealed improved eradication of tumor cells (Topfer et al., J Immunol. 2015; 194:3201-3212). NK cell engineered to express a CS-1 specific CAR also displayed enhanced cytolysis and interferon-γ (IFN-γ) production in multiple myeloma (Chu et al., Leukemia, 2014, 28(4): 917-927).

NK cell activation is characterized by an array of receptors with activating and inhibitory functions. The important activation receptors on NK cells include CD94/NKG2C and NKG2D (the C-type lectin-like receptors), and the natural cytotoxicity receptors (NCR) NKp30, NKp44 and NKp46, which recognize ligands on tumor cells or virally infected cells. NK cell inhibition is essentially mediated by interactions of the polymorphic inhibitory killer cell immunoglobulin-like receptors (KIRs) with their cognate human-leukocyte-antigen (HLA) ligands via the alpha-1 helix of the HLA molecule. The balance between signals that are generated from activating receptors and inhibitory receptors mainly determines the immediate cytotoxic activation.

NK cells may be isolated from peripheral blood mononuclear cells (PBMCs) and cord blood, or derived from human embryonic stem (ES) cells and induced pluripotent stem cells (iPSCs). NK cells may be further expanded for adoptive immunotherapy. Strategies and protocols useful for the expansion of NK cells may include interleukin 2 (IL2) stimulation and the use of autologous feeder cells, or the use of genetically modified allogeneic feeder cells. In some aspects, NK cells can be selectively expanded with a combination of stimulating ligands including IL15, IL21, IL2, 41BBL, IL12, IL18, MICA, 2B4, LFA-1, and BCM1/SLAMF2 (e.g., US patent publication NO. US20150190471).

NK cell-based immunotherapy is rapidly evolving due to the ability of NK cells to directly lyse tumor targets, the emergence of antibodies and molecules that mediate NK cell-driven antibody-dependent cell-mediated cytotoxicity (ADCC), and the ability of NK cells to induce inflammatory responses. NK cells are being exploited in clinical trials using autologous and allogeneic NK cell infusion strategies alone or with hematopoietic stem cell transplantation. In addition, other modalities of NK cell therapy, such as use of NK cell line products and NK cells transduced with chimeric antigen receptors (CARs) are on the horizon. Others have shown that in vivo persistence and expansion of NK cells correlate with antitumor efficacy in patients with advanced AML. Among the strategies being evaluated preclinically to address this issue, utilization of cytokines to induce NK cell persistence and expansion seems to dominate current clinical trials. IL15 has a known physiologic role on NK cell development and homeostasis without stimulating regulatory T cells but experimental findings indicate that continuous treatment with IL-15 results in a functional NK cell changes consistent with exhaustion. For example, continuously IL15-treated NK cells have been experimentally shown in at least one study to initially display better proliferation and expansion during a 9-day experimental continuous treatment with IL15 but were more susceptible to cell death. In addition, cell cycle gene expression data show that NK cells continuously dosed with IL15 are enriched for expression of cell cycle checkpoint and arrest genes, indicating that at day 9 of culture these cells transition to an arrested state due to cellular stress.

Tumor infiltrating lymphocytes (TIL) consist of all lymphocytic cell populations that have invaded the tumor tissue. The cellular constituents of tumors include TIL, NK cells, macrophages, dendritic cells, and myeloid lineage cells, suggesting a productive immune response. However, most of the immune cells residing in the tumor microenvironment are functionally impaired in some manner because many of the immune cell populations are converted to phenotypes that further impair immune system responses. Tumors are able to recruit Treg lymphocytes, TAMs, myeloid-derived suppressor cells (MDSCs), and cancer-associated fibroblasts (CAFs) to aid them in escape from immune recognition. Tregs and MDSCs have both been shown to immunosuppressing functions, limiting response by TIL and other cells. Depletion of CD4+ Tregs improves clinical responses in patients during immune reconstitution treated with autologous TIL during TIL therapy. In mouse models, even small numbers of Tregs can abrogate effective CD8+ T cell-mediated adoptive cell therapy.

TIL have been described in a number of solid tumors, including breast cancer and melanoma, and are emerging as an important biomarker in predicting the efficacy and outcome of treatment. In breast cancer, TIL are comprised primarily of cytotoxic (CD8+) and helper (CD4+) T cells, and a smaller proportion of B– and NK cells. Breast cancer patients who had advanced tumors with higher CD8+ T cell infiltrates or a high density of TIL have more favorable outcomes. In melanoma, TIL therapy is improved by including lymphodepleting preparative regimens prior to cell infusion. Investigations in humans and murine models of melanoma suggest that lymphodepletion depletes negative regulatory cells including regulatory T cells (Tregs) and peripheral myeloid-derived suppressor cells, which can suppress T cell proliferation in melanoma patients, both of which aid in the proliferation of adoptively transferred T lymphocytes.

Adoptive cell therapy (ACT) using TIL is a personalized cancer treatment based on the infusion of autologous CD4+ and CD8+ T lymphocytes expanded from tumors in the presence of interleukin-2 (IL-2) alone or in combination with IL-7, IL-15, and/or IL-21. TIL are polyclonal populations enriched for lymphocytes recognizing tumor-specific antigens, including shared tumor-associated antigens as well as individual tumor neoantigens. Studies at the National Cancer Institute (NCI) initiated in 1980 demonstrated tumor regression in selected patients receiving adoptive transfer of lymphokine-activated killer cells in combination with recombinant IL-2. Subsequent methods for large-scale expansion of human TIL, simplified and shortened TIL production processes, and improved patient preconditioning and treatment protocols have resulted in enhanced response rates for patients. However, complete response rates for TIL therapy are still quite low and need improvement.

The present disclosure provides systems, compositions, immunotherapeutic agents and methods that avoid the issues of continuously dosed or expressed IL15 by providing tunable regulation of IL15 gene expression and function for cancer immunotherapy. The present invention also provides biocircuit systems, effector modules, stimulus response elements (SREs) and IL15 payloads, as well as polynucleotides encoding any of the foregoing. In one aspect, the systems, compositions, immunotherapeutic agents and other components of the invention can be controlled by a separately added stimulus, which provides a significant flexibility to regulate cancer immunotherapy.

The tunable nature of the systems and compositions of the invention has the potential to improve the potency and duration of the efficacy of immunotherapies. The ability to reversibly increase, decrease or silence the biological activity of adoptively transferred cells using compositions of the present invention allows maximizing the potential of cell therapy, which is not available using a "kill switch" that will terminate the therapy. Without being bound by any particular theory, it is believed that the long-term engraftment of T cells can be achieved through temporal, intermittent exposure of IL15 in NK cells, TIL and T cell groups used in various therapies, including cancer immunotherapies, without dysregulated proliferation or activation and no phenotypic, functional, or chromosomal anomalies.

The present invention provides methods for fine tuning of immunotherapy after administration to patients. This in turn improves the safety and efficacy of immunotherapy and increases the subject population that may benefit from immunotherapy. Effector module(s) as described and disclosed in the present disclosure are independently associated, or integral therewith, one or more stimulus response elements (SREs), which may be operably linked to an IL15, to form an effector module comprising mbIL15. The biocircuits, SRE, DRDs of the present disclosure can be employed with immune cells and may provide a desired signaling enabling adoptively transferred NK cells and T cells, including TIL, to prolong persistence, thereby providing durable immune surveillance and therapeutic potential.

As used herein, a "biocircuit" or "biocircuit system" is defined as a circuit within or useful in biologic systems comprising a stimulus and at least one effector module responsive to a stimulus, where the response to the stimulus produces at least one signal or outcome within, between, as an indicator of, or on a biologic system. Biologic systems are generally understood to be any cell, tissue, organ, organ system or organism, whether animal, plant, fungi, bacterial, or viral. It is also understood that biocircuits may be artificial circuits which employ the stimuli or effector modules taught by the present disclosure and effect signals or outcomes in acellular environments such as with diagnostic, reporter systems, devices, assays or kits.

The biocircuits of the present disclosure include at least one effector module. As used herein, an "effector module" is a single or multi-component construct or complex comprising at least (a) one or more stimulus response elements (SREs) and (b) one or more payloads (e.g., proteins of interest (POIs)). In some embodiments, the effector module comprises one SRE and one payload.

Effector modules may be designed to include one or more payloads, one or more SREs, one or more cleavage sites, one or more signal sequences and one or more additional features including the presence or absence of one or more linkers.

In one embodiment, the effector module comprises at least one immunotherapeutic agent, for example, IL15.

Effector modules, including their SREs and payloads, may be nucleic acid-based, protein-based or a combination thereof. They may be in the form of DNA, RNA, mRNA, proteins, fusion proteins, or any combination of the foregoing. In one embodiment, the effector module is a fusion protein. In one embodiment, the effector module is encoded by nucleic acid, such as DNA.

Effector modules, including their SREs and payloads may individually, collectively or independently comprise peptides, polypeptides or proteins. At the protein level, such payload may be any natural or artificial peptide or polypeptide or fragment thereof. Natural peptides or polypeptide components of the payload may be derived from any known protein of any species.

Effector modules may be designed to operate in groups of one, two, three, four or more modules. When more than one effector module is utilized in a biocircuit, it is known as an effector module system of that biocircuit.

As used herein a "stimulus response element" (SRE) is a component of an effector module which is joined, attached, linked to or associated with one or more payloads and in some instances, is responsible for the responsive nature of the effector module to one or more stimuli. As used herein, the "responsive" nature of an SRE to a stimulus may be characterized by a covalent or non-covalent interaction, a direct or indirect association or a structural or chemical reaction to the stimulus. Further, the response of any SRE to a stimulus may be a matter of degree or kind. The response may be a partial response. The response may be a reversible response. The response may ultimately lead to a regulated signal or output. Such output signal may be of a relative nature to the stimulus, e.g., producing a modulatory effect of between 1% and 100% or a factored increase or decrease such as 2-fold, 3-fold, 4-fold, 5-fold, 10-fold or more. In some embodiments, the SRE is a polypeptide operably linked to a polypeptide payload. In some embodiments, the SRE is a polypeptide fused to a polypeptide payload.

In some embodiments, the present disclosure provides methods for modulating protein expression, function or level. In some aspects, the modulation of protein expression, function or level refers to modulation of expression, function or level by at least about 20%, such as by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

Drug responsive domains (DRDs) are small protein domains that can be appended to a target protein of interest. In some embodiments, a DRD is operably linked to a target protein of interest. DRDs render the attached protein of interest unstable in the absence of a DRD-binding ligand. However, when a specific small molecule ligand binds its intended DRD as a ligand binding partner, the instability is reversed, and protein function is restored. The conditional nature of DRD stability allows a rapid and non-perturbing switch from stable protein to unstable substrate for degradation. Moreover, its dependency on the concentration of its ligand further provides tunable control of degradation rates. The term drug responsive domain (DRD) is interchangeable with the term destabilizing domain (DD).

In one embodiment, the SRE is a drug responsive domain (DRD). In some embodiments, the CA2 drug responsive domains described herein may be used as SREs in the biocircuit systems of the present disclosure in association with any of the IL15 payloads taught herein.

Regions or portions or domains of wild type proteins (e.g., CA2) may be utilized as SREs/DRDs in whole or in part. In one embodiment, the SRE is derived from parent protein CA2 or from a mutant CA2 protein. In various embodiments, the DRD comprises one, two, three, or four or more mutations compared to the parent CA2 protein, for example, a human CA2

```
SEQ ID NO: 1 having the amino acid sequence:
MSHHWGYGKH NGPEHWHKDF PIAKGERQSP VDIDTHTAKY

DPSLKPLSVS YDQATSLRIL NNGHAFNVEF DDSQDKAVLK

GGPLDGTYRL IQFHFHWGSL DGQGSEHTVD KKKYAAELHL

VHWNTKYGDF GKAVQQPDGL AVLGIFLKVG SAKPGLQKVV

DVLDSIKTKG KSADFTNFDP RGLLPESLDY WTYPGSLTTP

PLLECVTWIV LKEPISVSSE QVLKFRKLNF NGEGEPEELM

VDNWRPAQPL

KNRQIKASFK or SEQ ID NO: 2 having the amino
acid sequence:
SHHWGYGKH NGPEHWHKDF PIAKGERQSP VDIDTHTAKY

DPSLKPLSVS YDQATSLRIL NNGHAFNVEF DDSQDKAVLK

GGPLDGTYRL IQFHFHWGSL DGQGSEHTVD KKKYAAELHL

VHWNTKYGDF GKAVQQPDGL AVLGIFLKVG SAKPGLQKVV

DVLDSIKTKG KSADFTNFDP RGLLPESLDY WTYPGSLTTP

PLLECVTWIV LKEPISVSSE QVLKFRKLNF NGEGEPEELM

VDNWRPAQPL KNRQIKASFK.
```

Human CA2 having the amino acid sequence of SEQ ID NO: 1 is encoded by the polynucleotide having a nucleic acid sequence of SEQ ID NO: 3:

```
atgtcccatcactggggggtacggcaaacacaacggacctgagcact ggcataaggacttccccattgccaagggagagcgccagtccctgt tgacatcgacactcatacagccaagtatgacccttcctgaagccc ctgtctgtttcctatgatcaagcaacttccctgaggatcctcaaca
```

```
                    -continued
atggtcatgctttcaacgtggagtttgatgactctcaggacaaagc agtgctcaagggaggaccctggatggcacttacagattgattcag tttcactttcactggggttcacttgatggacaaggttcagagcata ctgtggataaaaagaaatatgctgcagaacttcacttggttcactg gaacaccaaatatggggattttgggaaagctgtgcagcaacctgat ggactggccgttctaggtattttttttgaaggttggcagcgctaaac cgggccttcagaaagttgttgatgtgctggattccattaaaacaaa gggcaagagtgctgacttcactaacttcgatcctcgtggcctcctt cctgaatccctggattactggacctacccaggctcactgaccaccc ctcctcttctggaatgtgtgacctggattgtgctcaaggaacccat cagcgtcagcagcgagcaggtgttgaaattccgtaaacttaacttc aatggggagggtgaacccgaagaactgatggtggacaactggcgcc cagctcagccactgaagaacaggcaaatcaaagcttccttcaaa
```

As used herein, the phrase "derived from" as it relates to effector modules, SREs or payloads means that the effector module, SRE or payload originates at least in part from the stated parent molecule or sequence. For example, in designing an SRE, such SRE may be derived from an epitope or region of a naturally occurring protein but then have been modified in any of the ways taught herein to optimize the SRE function.

In some embodiments, the DRDs of the present disclosure may be derived from CA2 (SEQ ID NO: 1; Uniprot ID: P00918) which may be stabilized by ligands such as small molecule inhibitors of CA2. As used herein, the term "CA2 WT", refers to the human wildtype CA2 protein sequence, which is defined as SEQ ID NO: 1, with the GenBank Access NO. P00918. In some aspects, the DRDs may be derived from CA2 of SEQ ID NO: 2.

In some embodiments, DRDs may be derived from CA2 having amino acids 2-260 of the parent CA2 sequence. This is referred to herein as an M1del mutation. The M1del mutation may also be referred herein as an amino acid deletion. In some embodiments, human DRD constructs disclosed herein may not comprise an N-terminal methionine corresponding to the N-terminal methionine of SEQ ID NO: 1. Regardless of the presence or absence of the N-terminal methionine in a disclosed CA2 DRD, the present disclosure identifies positions of the CA2 DRD relative to the wildtype human CA2 (Uniprot ID: P00918) of SEQ ID NO: 1, wherein reference position 1 is the N-terminal methionine of SEQ ID NO: 1. For example, a hypothetical CA2 DRD comprising a G12A mutation, refers herein to a CA2 DRD construct wherein glycine (G) is mutated to alanine (A) at a position in the CA2 DRD construct that corresponds to the twelfth amino acid of SEQ ID NO: 1, regardless of whether the CA2 DRD construct itself comprises an N-terminal methionine corresponding to the N-terminal methionine of SEQ ID NO: 1. In this hypothetical CA2 DRD comprising a G12A mutation example, the glycine (G) to alanine (A) change may also be referred to as an amino acid substitution.

In some embodiments, DRDs may be derived from human CA2 having amino acids 2-260 of the wild type human CA2 sequence of SEQ ID NO: 1. This may be referred to as an M1del mutation and has an amino acid sequence of SEQ ID NO: 2. In some embodiments, the DRD of the present disclosure has an amino acid sequence as set forth in SEQ ID NO: 4.

Table 1 provides a CA2 DRD. The position of the mutated amino acids listed in Table 1 is relative to the full length CA2 of SEQ ID NO: 1.

TABLE 1

CA2 DRD amino acid and nucleotide sequences.

| Description | AA SEQUENCE | Nucleic Acid Sequence | AA SEQ ID NO | NA SEQ ID NO |
|---|---|---|---|---|
| CA2 mutant (M1del, L156H) relative to SEQ ID NO: 1 | SHHWGYGKHNG PEHWHKDFPIA KGERQSPVDID THTAKYDPSLK PLSVSYDQATS LRILNNGHAFN VEFDDSQDKAV LKGGPLDGTYR LIQFHFHWGSL DGQGSEHTVDK KKYAAELHLVH WNTKYGDFGKA VQQPDGLAVLG IFLKVGSAKPG HQKVVDVLDSI KTKGKSADFTN FDPRGLLPESL DYWTYPGSLTT PPLLECVTWIV LKEPISVSSEQ VLKFRKLNFNG EGEPEELMVDN WRPAQPLKNRQ IKASFK | TCCCATCACTGGGGGT ACGGCAAACACAACGG ACCTGAGCACTGGCAT AAGGACTTCCCCATTG CCAAGGGAGAGCGCCA GTCCCCTGTTGACATC GACACTCATACAGCCA AGTATGACCCTTCCCT GAAGCCCCTGTCTGTT TCCTATGATCAAGCAA CTTCCCTGAGAATCCT CAACAATGGTCATGCT TTCAACGTGGAGTTTG ATGACTCTCAGGACAA AGCAGTGCTCAAGGGA GGACCCCTGGATGGCA CTTACAGATTGATTCA GTTTCACTTTCACTGG GGTTCACTTGATGGAC AAGGTTCAGAGCATAC TGTGGATAAAAAGAAA TATGCTGCAGAACTTC ACTTGGTTCACTGGAA CACCAAATATGGGGAT TTTGGGAAAGCTGTGC AGCAACCTGATGGACT GGCCGTTCTAGGTATT TTTTTGAAGGTTGGCA GCGCTAAACCGGGCCA TCAGAAAGTTGTTGAT GTGCTGGATTCCATTA AAACAAAGGGCAAGAG TGCTGACTTCACTAAC TTCGATCCTCGTGGCC TCCTTCCTGAATCCCT GGATTACTGGACCTAC CCAGGCTCACTGACCA CCCCTCCTCTTCTGGA ATGTGTGACCTGGATT GTGCTCAAGGAACCCA TCAGCGTCAGCAGCGA GCAGGTGTTGAAATTC CGTAAACTTAACTTCA ATGGGGAGGGTGAACC CGAAGAACTGATGGTG GACAACTGGCGCCCAG CTCAGCCACTGAAGAA TCAGGCAAATCAAAGC TCCTTCAAA | 4 | 5 |

In some embodiments, an exemplary DRD derived from CA2 that regulates an operably linked IL15 payload comprises or consists of the amino acid sequence of SEQ ID NO: 4 or is encoded by the nucleotide sequence of SEQ ID NO: 5.

In some embodiments, the CA2 DRD useful for the regulated and tunable expression of IL15 as described herein may include one or more mutations that are relative to Uniprot ID: P00918 (SEQ ID NO: 1) and include but are not limited to (M1del, L156H) relative to the amino acid sequence of SEQ ID NO: 1. In some embodiments, the CA2 DRD useful for the regulated and tunable expression of IL15 as described herein may include one mutation relative to (SEQ ID NO: 2) (L156H). In some embodiments, the CA2 DRD useful for the regulated and tunable expression of IL15 as described herein may include one amino acid substitution relative to (SEQ ID NO: 2) (L156H). In some embodiments, the CA2 DRD comprises the amino acid sequence of SEQ ID NO: 4. In some embodiments, the CA2 DRD consists of the amino acid sequence of SEQ ID NO: 4.

The SRE described herein may include CA2 DRDs which include but are not limited to one or two mutations such as, but not limited to, M1del, and L156H relative to the CA2 WT of SEQ ID NO: 1. In some embodiments, the CA2 DRD comprises the L156H mutation relative to SEQ ID NO: 1 and further comprises one or more additional mutations. In some embodiments, the CA2 DRD comprises the M1del and L156H mutation relative to SEQ ID NO: 1 and further comprises one or more additional mutations. In some embodiments, the CA2 DRD comprises the M1del amino acid deletion and L156H amino acid substitution relative to SEQ ID NO: 1 and further comprises one or more additional amino acid substitutions.

Also provided herein are biocircuit systems that include at least one effector module. The effector module of the biocircuit may include a stimulus response element (SRE) derived from CA2 (SEQ ID NO: 1 or SEQ ID NO: 2). In one embodiment, the SRE comprises or consists of the amino acid sequence of SEQ ID NO: 4. The biocircuits may also include at least one payload, which may be attached, appended or associated with the SRE. The payload may include a human IL15, comprising the amino acid sequence of SEQ ID NO: 8; the payload may be encoded by a nucleic acid sequence comprising the nucleotide sequence of SEQ ID NO: 9.

TABLE 2

An IL15 payload of the present disclosure.

| Description | AA SEQUENCE | Nucleic Acid Sequence | AA SEQ ID NO | NA SEQ ID NO |
|---|---|---|---|---|
| IL15 | NWVNVISDLKK IEDLIQSMHID ATLYTESDVHP SCKVTAMKCFL LELQVISLESG DASIHDTVENL IILANNSLSSN GNVTESGCKEC EELEEKNIKEF LQSFVHIVQMF INTS | AATTGGGTAAATGT TATCAGTGATCTCA AGAAGATAGAGGAT CTCATCCAGTCCAT GCATATTGATGCCA CGCTGTACACAGAA AGCGATGTGCATCC TAGCTGTAAGGTGA CAGCGATGAAGTGT TTTCTTTTGGAGCT GCAGGTAATTAGTC TTGAGTCCGGCGAT GCCAGCATTCATGA TACCGTAGAAAACT TGATTATCCTGGCC AACAATTCTCTGTC CTCAAACGGAAACG TAACCGAGAGCGGT TGTAAAGAATGTGA AGAACTGGAAGAAA AGAACATCAAGGAG TTTCTGCAATCATT CGTTCACATCGTAC AAATGTTCATAAAT ACGTCA | 8 | 9 |

In some embodiments, the present disclosure provides methods for modulating protein, expression, function or level by measuring the stabilization ratio and destabilization ratio. As used herein, the stabilization ratio may be defined as the ratio of expression, function or level of a protein of interest in response to the stimulus to the expression, function or level of the protein of interest in the absence of the stimulus specific to the SRE. As used herein, the destabilization ratio may be defined as the ratio of expression, function or level of a protein of interest in the absence of the stimulus specific to the effector module to the expression, function or level of the protein of interest, that is expressed constitutively and in the absence of the stimulus specific to the SRE. As used herein "constitutively" refers to the expression, function or level of a protein of interest that is not linked to an SRE and is therefore expressed both in the presence and absence of the stimulus.

As used herein a "payload" or "target payload" or "payload of interest (POI)" is defined as any protein whose function is to be altered. Payloads may include any protein or fragment thereof.

In some embodiments, payloads of the present disclosure include IL15. It is understood in the art that certain gene and/or protein nomenclature for the same gene or protein may be inclusive or exclusive of punctuation such as a dash "-" or symbolic such as Greek letters. Whether these are included or excluded herein, the meaning is not meant to be changed as would be understood by one of skill in the art. For example, IL15, IL 15 and IL-15 refer to the same interleukin. In some embodiments, payloads of the present disclosure may be an IL15 interleukin cytokine that stimulate certain immune responses.

Payloads of the present disclosure may comprise amino acid sequences similar to the amino acid sequence of human IL15, for example, UniProtKB-P40933 (IL15_HUMAN). In one embodiment, the IL15 payload comprises the amino acid sequence provided in Table 2 (SEQ ID NO. 8).

In some embodiments, payloads of the present disclosure may be utilized to improve expansion, survival, persistence, and potency of immune cells such as CD8+TEM, natural killer (NK) cells and tumor infiltrating lymphocytes (TIL), and CAR T cells used for immunotherapy. In one aspect, the present disclosure provides biocircuits and compositions to minimize toxicity related to cytokine therapy.

In some embodiments, the effector module may be a CA2 DRD-IL15 fusion polypeptide. In some embodiments, the IL15-containing constructs of the disclosure may be placed under the transcriptional control of the human cytomegalovirus (CMV) promoter, an Elongation Factor 1α (EF1α) promoter, HIV LTR promoter, 3-phosphoglycerate kinase (PGK) promoter, Rous sarcoma virus long terminal repeat (RSV) promoter, spleen focus forming virus (SFFV) promoter, synthetic MND promoter, murine stem cell virus (MSCV) promoter, synthetic RPBSA promoter or a ubiquitin promoter.

A unique feature of IL15 mediated activation is the mechanism of trans-presentation in which IL15 is presented as a complex with the alpha subunit of IL15 receptor (IL15Ra) that binds to and activates membrane bound IL15 beta/gamma receptor, either on the same cell or a different cell. In various embodiments, the payload of the present disclosure is a membrane bound IL15, wherein the amino acid sequence of said membrane bound IL15 comprises the amino acid sequence of SEQ ID NO: 8.

Payloads of the present disclosure may comprise nucleic acid sequences as disclosed herein but the payload may comprise additional or fewer nucleotides than those listed. Such nucleic acid sequences may comprise about 1 more or fewer nucleotides, about 2 more or fewer nucleotides, about 3 more or fewer nucleotides, about 4 more or nucleotides acids, about 5 more or fewer nucleotides, about 6 more or fewer nucleotides, about 7 more or fewer nucleotides, about 8 more or fewer nucleotides, about 9 more or fewer nucleotides, about 10 more or fewer nucleotides or greater than 10 nucleotides.

Biocircuit components including effector modules, their SREs and payloads, may be nucleic acid-based. The term "nucleic acid," in its broadest sense, includes any compound and/or substance that comprise a polymer of nucleotides, e.g., linked nucleosides. These polymers are often referred to as polynucleotides. Exemplary nucleic acids or polynucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

In some embodiments, the nucleic acid molecule is DNA. In some embodiments, the nucleic acid molecule is a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo. Polynucleotides of the disclosure may be mRNA or any nucleic acid molecule and may or may not be chemically modified.

In some embodiments, polynucleotides of the present disclosure may harbor 5'UTR sequences which play a role in translation initiation. 5'UTR sequences may include features such as Kozak sequences which are commonly known to be involved in the process by which the ribosome initiates translation of genes, Kozak sequences have the consensus XCCR(A/G) CCAUG, where R is a purine (adenine or guanine) three bases upstream of the start codon (AUG) and X is any nucleotide. In one embodiment, the Kozak sequence is ACCGCC. By engineering the features that are typically found in abundantly expressed genes of target cells or tissues, the stability and protein production of the polynucleotides of the disclosure can be enhanced.

In one embodiment, polynucleotides of the present disclosure may encode variant polypeptides which have a certain identity with a reference polypeptide sequence. As used herein, a "reference polypeptide sequence" refers to a starting polypeptide sequence. Reference sequences may be wild type sequences or any sequence to which reference is made in the design of another sequence.

The term "identity" as known in the art, refers to a relationship between two or more sequences, as determined by comparing the sequences. In the art, identity also means the degree of sequence relatedness between sequences, as determined by the number of matches between strings of two or more residues (amino acid or nucleic acid). Identity measures the percent of identical matches between two or more sequences with gap alignments (if any) aDRDressed by a particular mathematical model or computer program (i.e., "algorithms"). Identity of related sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the variant sequence may have the same or a similar activity as the reference sequence. Alternatively, the variant may have an altered activity (e.g., increased or decreased) relative to a reference sequence. Generally, variants of a particular polynucleotide or polypeptide of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. MaDRDen, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.)

The effector module of the present disclosure may further comprise a signal sequence which regulates the distribution of the payload of interest, a cleavage and/or processing feature which facilitate cleavage of the payload from the effector module construct, a targeting and/or penetrating signal which can regulate the cellular localization of the effector module, a tag, and/or one or more linker sequences which link different components of the effector module.

In addition to the SRE and payload region, effector modules of the disclosure may further comprise one or more additional features such as one or more signal sequences.

Signal sequences (sometimes referred to as signal peptides, targeting signals, target peptides, localization sequences, transit peptides, leader sequences or leader peptides) direct proteins (e.g., the effector module of the present disclosure) to their designated cellular and/or extracellular locations. Protein signal sequences play a central role in the targeting and translocation of nearly all secreted proteins and many integral membrane proteins.

A signal sequence is a short (5-30 amino acids long) peptide present at the N-terminus of the majority of newly synthesized proteins that are destined towards a particular location. Signal sequences can be recognized by signal recognition particles (SRPs) and cleaved using type I and type II signal peptide peptidases. Signal sequences derived from human proteins can be incorporated as a regulatory module of the effector module to direct the effector module to a particular cellular and/or extracellular location.

In some embodiments, a signal sequence may be, although not necessarily, located at the N-terminus or C-terminus of the effector module, and may be, although not necessarily, cleaved off the desired effector module to yield a "mature" payload.

In some embodiments, the signal sequence used herein may exclude the methionine at the position 1 of amino acid sequence of the signal sequence. This may be referred to as an M1del mutation.

In addition to signal sequences naturally occurring such as from a secreted protein, a signal sequence may be a variant modified from a known signal sequence of a protein.

In some instances, signal sequences directing the payload of interest to the surface membrane of the target cell may be used. Expression of the payload on the surface of the target cell may be useful to limit the diffusion of the payload to non-target in vivo environments, thereby potentially improving the safety profile of the payloads. Additionally, the membrane presentation of the payload may allow for physiologically and qualitative signaling as well as stabilization and recycling of the payload for a longer half-life. Membrane sequences may be the endogenous signal sequence of the N terminal component of the payload of interest. Optionally, it may be desirable to exchange this sequence for a different signal sequence. Signal sequences may be selected based on their compatibility with the secretory pathway of the cell type of interest so that the payload is presented on the surface of the T cell. In some embodiments, the signal sequence may be IgE signal sequence, CD8a signal sequence (also referred to as CD8a leader), or IL15Ra signal sequence (also referred to as IL15Ra leader) or M1del CD8a signal sequence (also referred to as M1del CD8 leader sequence).

In some embodiments, the effector module comprises a cleavage and/or processing feature. In some embodiments, the effector module of the present disclosure may include at least one protein cleavage signal/site. The protein cleavage signal/site may be located at the N-terminus, the C-terminus, at any space between the N- and the C-termini such as, but not limited to, half-way between the N- and C-termini, between the N-terminus and the half-way point, between the half-way point and the C-terminus, and combinations thereof.

In some embodiments, the effector module comprises a linker.

In some embodiments, the effector module of the disclosure may further comprise a linker sequence. The linker region serves primarily as a spacer between two or more polypeptides within the effector module. The "linker" or "spacer", as used herein, refers to a molecule or group of molecules that connects two molecules, or two parts of a molecule such as two domains of a recombinant protein.

In some embodiments, "Linker" (L) or "linker domain" or "linker region" or "linker module" or "peptide linker" as used herein refers to an oligo- or polypeptide region of from about 1 to 100 amino acids in length, which links together any of the domains/regions of the effector module (also called peptide linker).

In some embodiments, an artificially designed peptide linker may be composed of a polymer of flexible residues such as Glycine (G) and Serine (S) so that the adjacent protein domains are free to move relative to one another. Longer linkers may be used when it is desirable to ensure that two adjacent domains do not interfere with one another. The choice of a particular linker sequence may be of concern if it affects biological activity, stability, folding, targeting and/or pharmacokinetic features of the fusion construct.

A linker sequence may be a natural linker derived from a multi-domain protein. A natural linker is a short peptide sequence that separates two different domains or motifs within a protein.

In one embodiment, the linker may be a BamHI site. As a non-limiting example, the BamHI site has the amino acid sequence GS and/or the DNA sequence GGATCC.

Biocircuits of the present disclosure are triggered by one or more stimuli. In some embodiments, the stimulus is a small molecule. In some embodiments, the small molecules are cell permeable. In some embodiments, the small molecules are FDA-approved, safe and orally administered.

In some embodiments, the ligands bind to carbonic anhydrases. In some embodiments, the ligand binds to and inhibits carbonic anhydrase function and is herein referred to as carbonic anhydrase inhibitor.

In some embodiments, the ligand is a small molecule that binds to carbonic anhydrase 2. In one embodiment, the small molecule is CA2 inhibitor. In some embodiments, the ligand is a small molecule selected from acetazolamide, celecoxib, valdecoxib, rofecoxib, methazolamide, dorzolamide, brinzolamide, diclofenamide, ethoxzolamide, zonisamide, dansylamide, and dichlorphenamide. In some embodiments, the ligand is a small molecule selected from acetazolamide, brinzolamide, dorzolamide hydrochloride, dichlorphenamide, chlorthalidone, methazolamide, topiramate, indapamide, ambroxol hydrochloride, glimepiride, tetracaine hydrochloride and celecoxib. In some embodiments, the ligand is a small molecule selected from acetazolamide, brinzolamide, dorzolamide hydrochloride, dichlorphenamide, chlorthalidone, methazolamide or topiramate. In some embodiments, the ligand is a CA2 inhibitor selected from acetazolamide, brinzolamide, dorzolamide hydrochloride, dichlorphenamide or methazolamide. In some embodiments, the ligand is acetazolamide (ACZ).

In some embodiments, ligands that do not affect the activity of the immune cell, and/or the chimeric antigen receptor, in the absence of the SREs may be preferably selected.

In some embodiments, compositions of the disclosure comprise a promoter.

As used herein a promoter is defined as a DNA sequence recognized by transcription machinery of the cell, required to initiate specific transcription of the polynucleotide sequence of the present disclosure. Vectors can comprise native or non-native promoters operably linked to the polynucleotides of the disclosure. The promoters selected may be strong, weak, constitutive, inducible, tissue specific, development stage-specific, and/or organism specific. A strong constitutive promoter sequence is capable of driving high levels of expression of polynucleotide sequence that is operatively linked to it. Examples of strong constitutive promoters include, without limitation, immediate early cytomegalovirus (CMV) promoter and Elongation Growth Factor-1 Alpha (EF-1 alpha). Other constitutive promoters that may be used, include, but are not limited to, simian virus 40 (SV40), mouse mammary tumor virus (MMTV) promoter, human immunodeficiency virus (HIV) long terminal repeat (LTR) promoter, an avian leukemia virus promoter, a spleen focus forming virus (SFFV) promoter, a murine stem cell virus (MSCV) promoter, an Epstein-Barr virus immediate early promoter, a Rous sarcoma virus promoter, human gene promoters including, but not limited to, the phosphoglycerate kinase (PGK) promoter, an actin promoter, a myosin promoter, the hemoglobin promoter, the Ubiquitin C (Ubc) promoter, the human U6 small nuclear protein promoter and a creatine kinase promoter. Synthetic promoters include a MND promoter and a RPBSA promoter. In some instances, inducible promoters such as, but not limited to, metallothionine promoter, glucocorticoid promoter, a progesterone promoter, and a tetracycline promoter may be used.

In some embodiments, the optimal promoter may be selected based on its ability to achieve minimal expression of the SREs and payloads of the disclosure in the absence of the ligand and detectable expression in the presence of the ligand.

Additional promoter elements, e.g., enhancers may be used to regulate the frequency of transcriptional initiation. Such regions may be located 10-100 base pairs upstream or downstream of the start site. In some instances, two or more promoter elements may be used to cooperatively or independently activate transcription.

Biocircuits of the present disclosure may comprise at least one effector module which may comprise at least one SRE derived from CA2 (referred to as "CA2 SREs") which may be operably linked to at least one payload of interest. These types of biocircuits and effector modules are referred to as "CA2 biocircuits" and "CA2 effector modules". Additionally, the CA2 effector module may comprise additional features including, but not limited to, signal sequences, linker, spacers, tags, flags, cleavage sites, and IRES. Any of the exemplary SREs (e.g., DRDs), payloads of interest, signal sequences, linker, spacers, hinges, tags, flags, cleavage sites, and IRES taught herein or known in the art may be combined to create the CA2 effector modules of the present disclosure.

In one embodiment, the CA2 effector module comprises a payload of interest. The payload of interest may be a wild-type sequence, a fragment of a wild-type sequence and/or comprise one or more mutations. In one embodiment, the CA2 effector module produces regulated interleukin-15 (IL15). In some embodiments, an IL15 payload is N-terminal to the DRD. The CA2 effector module may include or be derived from any of the IL15-related sequences in Table 3. In some embodiments, at least one payload in the CA2 effector module is an IL15 (e.g. an IL15 payload) comprising an amino acid sequence that is at least 95%, or at least 96%, or at least 97%, or at least 98%, or at least 99%, or 100% identical to the amino acid sequence of SEQ ID NO: 8; the payload may be encoded by a nucleic acid sequence comprising the nucleotide sequence of SEQ ID NO: 9). In some embodiments, the payload is a membrane-bound form of IL15. In some embodiments, the payload is a membrane-bound form of IL15 comprising a transmembrane domain and an intracellular tail. In some embodiments, the payload is a membrane-bound form of IL15 comprising an IL15 polypeptide component comprising the amino acid sequence of SEQ ID NO: 8, a transmembrane domain and an intracellular tail, wherein the transmembrane domain is C-terminal to the IL15 polypeptide component and the intracellular tail is C-terminal to the transmembrane domain. In some embodiments, the payload is a membrane-bound form of IL15 comprising a transmembrane domain, intracellular tail and one or more linkers. In some embodiments, linkers are peptide domains that may be placed between the SRE or DRD and the payload, or between different domains within the payload. In some embodiments, linkers are peptide domains comprising glycine and serine amino acid residues. In some embodiments, peptide linkers comprising glycine and serine amino acid residues may be from 2-36 amino acids in length. In one embodiment, at least one payload in the CA2 effector module is a membrane-bound form of IL15 which further includes a linker (GS)15, a B7.1 Hinge, a B7.1 transmembrane domain, a B7.1 intracellular tail, and a linker (GS). The CA2 effector module may include a payload component of a transmembrane domain and/or cytoplasmic domain from another parent protein as well as the IL15 payload component. In one embodiment, at least one payload in the CA2 effector module includes at least one mutation as compared to the wild-type sequence. In one embodiment, at least one payload in the CA2 effector module includes at least one amino acid substitution as compared to the wild-type sequence.

Non-limiting examples of constructs and construct components are shown in Table 3.

TABLE 3

| | | | Amino Acid SEQ ID NO | Nucleic Acid SEQ ID NO |
|---|---|---|---|---|
| Constructs and construct components of interest. | | | | |
| Description | Amino Acid Sequence (AA) | Nucleic Acid Sequence (NA) | | |
| Leader sequence | MDMRVPAQLLGLLLLWL SGARC | ATGGACATGCGGGTGCCTGCACAACTTCTGGGCCTG CTGTTGTTGTGGCTGTCTGGAGCCCGGTGT | 6 | 7 |
| Interleu-kin-15 (IL15) | NWVNVISDLKKIEDLIQ SMHIDATLYTESDVHPS CKVTAMKCFLLELQVIS LESGDASIHDTVENLII LANNSLSSNGNVTESGC KECEELEEKNIKEFLQS FVHIVQMFINTS | AATTGGGTAAATGTTATCAGTGATCTCAAGAAGATA GAGGATCTCATCCAGTCCATGCATATTGATGCCACG CTGTACACAGAAAGCGATGTGCATCCTAGCTGTAAG GTGACAGCGATGAAGTGTTTTCTTTTGGAGCTGCAG GTAATTAGTCTTGAGTCCGGCGATGCCAGCATTCAT GATACCGTAGAAAACTTGATTATCCTGGCCAACAAT TCTCTGTCCTCAAACGGAAACGTAACCGAGAGCGGT TGTAAAGAATGTGAAGAACTGGAAGAAAGAACATC AAGGAGTTTCTGCAATCATTCGTTCACATCGTACAA ATGTTCATAAATACGTCA | 8 | 9 |
| Linker (GS)15 | GSGSGSGSGSGSGSGSG SGSGSGSGSGSGSGS | GGATCTGGTTCTGGTTCCGGAAGTGGATCTGGTTCA GGGTCCGGTAGTGGATCTGGGTCAGGAAGTGGAAGC GGTAGTGGGTCTGGATCT | 10 | 11 |
| Hinge | KQEHFPDN | AAACAAGAGCACTTTCCTGATAAC | 12 | 13 |
| Transmem-brane | LLPSWAITLISVNGIFV ICCL | CTGTTGCCGAGCTGGGCGATTACGCTTATCAGTGTA AACGGCATCTTTGTAATATGCTGTCTG | 14 | 15 |
| Intracel-lular tail | TYCFAPRCRERRRNERL RRESVRPV | ACCTACTGCTTCGCACCAAGGTGCCGGGAGAGAAGG AGAAATGAAAGACTGAGAAGGGAGAGCGTGAGACCT GTG | 16 | 17 |
| Intracel-lular tail | TYCFAPRCRERARNERL RRETVRPV | ACCTACTGCTTCGCACCAAGGTGCCGGGAGAGAGCA AGAAATGAAAGACTGAGAAGGGAGACCGTGAGACCT GTG | 18 | 19 |
| Linker (GS) | GS | GGATCC | 20 | 21 |
| CA2 (M1del, L156H) | SHHWGYGKHNGPEHWHK DFPIAKGERQSPVDIDT HTAKYDPSLKPLSVSYD QATSLRILNNGHAFNVE FDDSQDKAVLKGGPLDG TYRLIQFHFHWGSLDGQ GSEHTVDKKKYAAELHL VHWNTKYGDFGKAVQQP DGLAVLGIFLKVGSAKP GHQKVVDVLDSIKTKGK SADFTNFDPRGLLPESL DYWTYPGSLTTPPLLEC VTWIVLKEPISVSSEQV LKFRKLNFNGEGEPEEL MVDNWRPAQPLKNRQIK ASFK | TCCCATCACTGGGGGTACGGCAAACACAACGGACCT GAGCACTGGCATAAGGACTTCCCCATTGCCAAGGGA GAGCGCCAGTCCCCTGTTGACATCGACACTCATACA GCCAAGTATGACCCTTCCCTGAAGCCCCTGTCTGTT TCCTATGATCAAGCAACTTCCCTGAGAATCCTCAAC AATGGTCATGCTTTCAACGTGGAGTTTGATGACTCT CAGGACAAAGCAGTGCTCAAGGGAGGACCCCTGGAT GGCACTTACAGATTGATTCAGTTTCACTTTCACTGG GGTTCACTTGATGGACAAGGTTCAGAGCATACTGTG GATAAAAAGAAATATGCTGCAGAACTTCACTTGGTT CACTGGAACACCAAATATGGGGATTTTGGGAAAGCT GTGCAGCAACCTGATGGACTGGCCGTTCTAGGTATT TTTTTGAAGGTTGGCAGCGCTAAACCGGGCCATCAG AAAGTTGTTGATGTGCTGGATTCCATTAAAACAAAG GGCAAGAGTGCTGACTTCACTAACTTCGATCCTCGT GGCCTCCTTCCTGAATCCCTGGATTACTGGACCTAC CCAGGCTCACTGACCACCCCTCCTCTTCTGGAATGT GTGACCTGGATTGTGCTCAAGGAACCCATCAGCGTC AGCAGCGAGCAGGTGTTGAAATTCCGTAAACTTAAC TTCAATGGGGAGGGTGAACCCGAAGAACTGATGGTG GACAACTGGCGCCCAGCTCAGCCACTGAAGAACAGG CAAATCAAAGCTTCCTTCAAA | 4 | 5 |
| IL15-292 | MDMRVPAQLLGLLLLWL SGARCNWVNVISDLKKI EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERRRNERLRRESVRPVG S | ATGGACATGCGGGTGCCTGCACAACTTCTGGGCCTG CTGTTGTTGTGGCTGTCTGGAGCCCGGTGTAATTGG GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA | 22 | 23 |

TABLE 3-continued

| | | | Amino Acid SEQ ID NO | Nucleic Acid SEQ ID NO |
|---|---|---|---|---|
| Description | Amino Acid Sequence (AA) | Nucleic Acid Sequence (NA) | | |
| | | GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAAGGAGAAATGAAAGACTGAGAAGGGAGAGC GTGAGACCTGTGGGATCC | | |
| OT-IL15-293 | MDMRVPAQLLGLLLLWL SGARCNWVNVISDLKKI EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERRRNERLRRESVRPVG SSHHWGYGKHNGPEHWH KDFPIAKGERQSPVDID THTAKYDPSLKPLSVSY DQATSLRILNNGHAFNV EFDDSQDKAVLKGGPLD GTYRLIQFHFHWGSLDG QGSEHTVDKKKYAAELH LVHWNTKYGDFGKAVQQ PDGLAVLGIFLKVGSAK PGHQKVVDVLDSIKTKG KSADFTNFDPRGLLPES LDYWTYPGSLTTPPLLE CVTWIVLKEPISVSSEQ VLKFRKLNFNGEGEPEE LMVDNWRPAQPLKNRQI KASFK | ATGGACATGCGGGTGCCTGCACAACTTCTGGGCCTG CTGTTGTTGTGGCTGTCTGGAGCCCGGTGTAATTGG GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAAGGAGAAATGAAAGACTGAGAAGGGAGAGC GTGAGACCTGTGGGATCCTCCCATCACTGGGGGTAC GGCAAACACAACGGACCTGAGCACTGGCATAAGGAC TTCCCCATTGCCAAGGGAGAGCGCCAGTCCCCTGTT GACATCGACACTCATACAGCCAAGTATGACCCTTCC CTGAAGCCCCTGTCTGTTTCCTATGATCAAGCAACT TCCCTGAGAATCCTCAACAATGGTCATGCTTTCAAC GTGGAGTTTGATGACTCTCAGGACAAAGCAGTGCTC AAGGGAGGACCCCTGGATGGCACTTACAGATTGATT CAGTTTCACTTTCACTGGGGTTCACTTGATGGACAA GGTTCAGAGCATACTGTGGATAAAAAGAAATATGCT GCAGAACTTCACTTGGTTCACTGGAACACCAAATAT GGGGATTTTGGGAAAGCTGTGCAGCAACCTGATGGA CTGGCCGTTCTAGGTATTTTTTTTGAAGGTTGGCAGC GCTAAACCGGGCCATCAGAAAGTTGTTGATGTGCTG GATTCCATTAAAACAAAGGGCAAGAGTGCTGACTTC ACTAACTTCGATCCTCGTGGCCTCCTTCCTGAATCC CTGGATTACTGGACCTACCCAGGCTCACTGACCACC CCTCCTCTTCTGGAATGTGTGACCTGGATTGTGCTC AAGGAACCCATCAGCGTCAGCAGCGAGCAGGTGTTG AAATTCCGTAAACTTAACTTCAATGGGGAGGGTGAA CCCGAAGAACTGATGGTGGACAACTGGCGCCCAGCT CAGCCACTGAAGAACAGGCAAATCAAAGCTTCCTTC AAA | 24 | 25 |
| OT-IL15-294 | MDMRVPAQLLGLLLLWL SGARCNWVNVISDLKKI EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERRRNERLRRETVRPVG S | ATGGACATGCGGGTGCCTGCACAACTTCTGGGCCTG CTGTTGTTGTGGCTGTCTGGAGCCCGGTGTAATTGG GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAGCAAGAAATGAAAGACTGAGAAGGGAGACC GTGAGACCTGTGGGATCC | 26 | 27 |

TABLE 3-continued

| | Constructs and construct components of interest. | | | |
|---|---|---|---|---|
| Descrip-<br>tion | Amino Acid<br>Sequence (AA) | Nucleic Acid Sequence (NA) | Amino<br>Acid<br>SEQ<br>ID<br>NO | Nu-<br>cleic<br>Acid<br>SEQ<br>ID<br>NO |
| OT-IL15-<br>295 | MDMRVPAQLLGLLLLWL<br>SGARCNWVNVISDLKKI<br>EDLIQSMHIDATLYTES<br>DVHPSCKVTAMKCFLLE<br>LQVISLESGDASIHDTV<br>ENLIILANNSLSSNGNV<br>TESGCKECEELEEKNIK<br>EFLQSFVHIVQMFINTS<br>GSGSGSGSGSGSGSGSG<br>SGSGSGSGSGSGSKQEH<br>FPDNLLPSWAITLISVN<br>GIFVICCLTYCFAPRCR<br>ERARNERLRRETVRPVG<br>SSHHWGYGKHNGPEHWH<br>KDFPIAKGERQSPVDID<br>THTAKYDPSLKPLSVSY<br>DQATSLRILNNGHAFNV<br>EFDDSQDKAVLKGGPLD<br>GTYRLIQFHFHWGSLDG<br>QGSEHTVDKKKYAAELH<br>LVHWNTKYGDFGKAVQQ<br>PDGLAVLGIFLKVGSAK<br>PGHQKVVDVLDSIKTKG<br>KSADFTNFDPRGLLPES<br>LDYWTYPGSLTTPPLLE<br>CVTWIVLKEPISVSSEQ<br>VLKFRKLNFNGEGEPEE<br>LMVDNWRPAQPLKNRQI<br>KASFK | ATGGACATGCGGGTGCCTGCACAACTTCTGGGCCTG<br>CTGTTGTTGTGGCTGTCTGGAGCCCGGTGTAATTGG<br>GTAAATGTTATCAGTGATCTCAAGAAGATAGAGGAT<br>CTCATCCAGTCCATGCATATTGATGCCACGCTGTAC<br>ACAGAAAGCGATGTGCATCCTAGCTGTAAGGTGACA<br>GCGATGAAGTGTTTTCTTTTGGAGCTGCAGGTAATT<br>AGTCTTGAGTCCGGCGATGCCAGCATTCATGATACC<br>GTAGAAAACTTGATTATCCTGGCCAACAATTCTCTG<br>TCCTCAAACGGAAACGTAACCGAGAGCGGTTGTAAA<br>GAATGTGAAGAACTGGAAGAAAAGAACATCAAGGAG<br>TTTCTGCAATCATTCGTTCACATCGTACAAATGTTC<br>ATAAATACGTCAGGATCTGGTTCTGGTTCCGGAAGT<br>GGATCTGGTTCAGGGTCCGGTAGTGGATCTGGGTCA<br>GGAAGTGGAAGCGGTAGTGGGTCTGGATCTAAACAA<br>GAGCACTTTCCTGATAACCTGTTGCCGAGCTGGGCG<br>ATTACGCTTATCAGTGTAAACGGCATCTTTGTAATA<br>TGCTGTCTGACCTACTGCTTCGCACCAAGGTGCCGG<br>GAGAGAGCAAGAAATGAAAGACTGAGAAGGGAGACC<br>GTGAGACCTGTGGGATCCTCCCATCACTGGGGGTAC<br>GGCAAACACAACGGACCTGAGCACTGGCATAAGGAC<br>TTCCCCATTGCCAAGGGAGAGCGCCAGTCCCCTGTT<br>GACATCGACACTCATACAGCCAAGTATGACCCTTCC<br>CTGAAGCCCCTGTCTGTTTCCTATGATCAAGCAACT<br>TCCCTGAGAATCCTCAACAATGGTCATGCTTTCAAC<br>GTGGAGTTTGATGACTCTCAGGACAAAGCAGTGCTC<br>AAGGGAGGACCCCTGGATGGCACTTACAGATTGATT<br>CAGTTTCACTTTCACTGGGGTTCACTTGATGGACAA<br>GGTTCAGAGCATACTGTGGATAAAAAGAAATATGCT<br>GCAGAACTTCACTTGGTTCACTGGAACACCAAATAT<br>GGGGATTTTGGGAAAGCTGTGCAGCAACCTGATGGA<br>CTGGCCGTTCTAGGTATTTTTTTGAAGGTTGGCAGC<br>GCTAAACCGGGCCATCAGAAAGTTGTTGATGTGCTG<br>GATTCCATTAAAACAAAGGGCAAGAGTGCTGACTTC<br>ACTAACTTCGATCCTCGTGGCCTCCTTCCTGAATCC<br>CTGGATTACTGGACCTACCCAGGCTCACTGACCACC<br>CCTCCTCTTCTGGAATGTGTGACCTGGATTGTGCTC<br>AAGGAACCCATCAGCGTCAGCAGCGAGCAGGTGTTG<br>AAATTCCGTAAACTTAACTTCAATGGGGAGGGTGAA<br>CCCGAAGAACTGATGGTGGACAACTGGCGCCCAGCT<br>CAGCCACTGAAGAACAGGCAAATCAAAGCTTCCTTC<br>AAA | 28 | 29 |

In various embodiments, the effector module produces regulated membrane-bound interleukin-15 (IL15). In some embodiments, the effector module is IL15-293 or IL15-295 as described in Table 3. In various embodiments, the IL15 payload is expressed as a CA2 DRD fusion protein comprising a membrane-bound form of IL15.

The CA2 biocircuits and/or CA2 effector modules of the present disclosure may be monocistronic or multicistronic meaning one (monocistronic) or more than one (multicistronic) message (e.g., payload of interest) is produced. If two messages are produced, the CA2 biocircuit or CA2 effector module is considered bicistronic. In one embodiment, at least one CA2 effector module of the present disclosure is monocistronic.

Various embodiments of the present disclosure provide nucleic acid molecules comprising one or more of the polynucleotides described. In some embodiments, the nucleic acid molecule comprises a polynucleotide encoding a recombinant protein comprising a drug responsive domain (DRD) operably linked to an IL15 payload, wherein said DRD is derived from human carbonic anhydrase II (CA2) and comprises one, two, three, four or more mutations relative to SEQ ID NO:1 or SEQ ID NO:2. In some embodiments, the nucleic acid molecule further comprises a second polynucleotide encoding a chimeric antigen receptor (CAR) or T cell receptor (TCR), wherein the CAR or TCR comprises an antigen-binding domain specific to an antigen of interest. In some embodiments, the CAR or TCR comprises an antigen-binding domain specific to an antigen of interest for example, the CAR comprises an antigen-binding domain specific to CD19.

The present teachings further comprise pharmaceutical compositions comprising one or more of CA2 biocircuits, CA2 effector modules or systems of the present disclosure, and optionally at least one pharmaceutically acceptable excipient or inert ingredient.

As used herein the term "pharmaceutical composition" refers to a preparation of one or more of the CA2 biocircuits or components described herein, or pharmaceutically acceptable salts thereof, optionally with other chemical components such as physiologically suitable carriers and excipients.

The term "excipient" or "inactive ingredient" refers to an inert or inactive substance added to a pharmaceutical composition to further facilitate administration of a compound. Non-limiting examples of such inert ingredients are disclosed herein.

In some embodiments, compositions are administered to humans, such as human patients or subjects. For the purposes of the present disclosure, the phrase "active ingredient" generally refers to any one or more CA2 biocircuit components to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including agricultural animals such as cattle, horses, chickens and pigs, domestic animals such as cats, dogs, or research animals such as mice, rats, rabbits, dogs and non-human primates.

A pharmaceutical composition in accordance with the disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or inert ingredient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of compositions of the present disclosure, "effective against" for example a cancer, indicates that administration in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating the particular type of cancer.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given composition or formulation of the present disclosure can also be judged using an experimental animal model for the given disease as known in the art. When using an experimental animal model, efficacy of treatment is evidenced when a statistically significant change is observed.

The compositions of the present disclosure may be formulated in any manner suitable for delivery. The formulation may be, but is not limited to, nanoparticles, poly (lactic-co-glycolic acid) (PLGA) microspheres, lipidoids, lipoplex, liposome, polymers, carbohydrates (including simple sugars), cationic lipids and combinations thereof.

In some embodiments, pharmaceutical or other formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present disclosure may be approved by the US Food and Drug Administration (FDA). The compositions of the disclosure may be delivered to a cell or a subject through one or more routes and modalities. The viral vectors containing one or more CA2 biocircuits, CA2 effector modules, SREs, payloads and other components described herein may be used to deliver them to a cell and/or a subject. Other modalities may also be used such as mRNAs, plasmids, and as recombinant proteins.

Pharmaceutical compositions, CA2 biocircuits, CA2 biocircuit components, CA2 effector modules including their SREs or payloads of the present disclosure may be delivered to cells, tissues, organs and/or organisms in naked form. As used herein in, the term "naked" refers to pharmaceutical compositions, CA2 biocircuits, CA2 biocircuit components, CA2 effector modules including their SREs or payloads delivered free from agents or modifications which promote transfection or permeability. The naked pharmaceutical compositions, CA2 biocircuits, CA2 biocircuit components, CA2 effector modules including their SREs or payloads may be delivered to the cells, tissues, organs and/or organisms using routes of administration known in the art and described herein. In some embodiments, naked delivery may include formulation in a simple buffer such as saline or PBS.

In some embodiments, pharmaceutical compositions, CA2 biocircuits, CA2 biocircuit components, CA2 effector modules including their SREs or payloads of the present disclosure may be formulated, using methods described herein. Formulations may comprise pharmaceutical compositions, CA2 biocircuits, CA2 biocircuit components, CA2 effector modules including their SREs or payloads which may be modified and/or unmodified. Formulations may further include, but are not limited to, cell penetration agents, pharmaceutically acceptable carriers, delivery agents, bioerodible or biocompatible polymers, solvents, and/or sustained-release delivery depots. Formulations of the present disclosure may be delivered to cells using routes of administration known in the art and described herein.

Pharmaceutical compositions, CA2 biocircuits, CA2 biocircuit components, CA2 effector modules including their SREs or payloads may also be formulated for direct delivery to organs or tissues in any of several ways in the art including, but not limited to, direct soaking or bathing, via a catheter, by gels, powder, ointments, creams, gels, lotions, and/or drops, by using substrates such as fabric or biodegradable materials coated or impregnated with compositions, and the like.

In another aspect of the disclosure, polynucleotides encoding CA2 biocircuits, CA2 effector modules, SREs (e.g., CA2 DRDs), payloads of interest (e.g., IL15) and compositions of the disclosure and vectors comprising said polynucleotides may be introduced into cells. As a non-limiting example, the cells may be effector immune cells.

In various embodiments, the present disclosure provides a cell comprising one or more nucleic acid molecules, one or more vectors or one or more recombinant proteins of the disclosure. In some embodiments, a method of modulating the expression, function, and/or level of an IL15 payload in the cell are provided, said method comprising administering to the cell a stimulus to which the DRD is responsive, wherein the stimulus is administered in an amount sufficient to modulate the expression, function and/or level of the IL15 payload. In some embodiments, the cell is isolated. In some embodiments, the cell is a bacterial cell. In some embodiments, the cell is a mammalian cell. The mammalian cell may be a human cell. The human cell may be a T cell, natural killer (NK) cell, or tumor infiltrating lymphocyte (TIL). In some embodiments, the cell is a CD4+ or CD8+ T cell. In some embodiments, the human T cell or the human NK cell further comprises a polynucleotide encoding a chimeric antigen receptor (CAR) or T cell receptor (TCR), wherein the CAR or TCR comprises an antigen-binding domain specific to an antigen of interest. In some embodiments, the CAR comprises antigen-binding domain specific to CD19.

In one aspect of the disclosure, polynucleotides encoding CA2 biocircuits, CA2 effector modules, SREs (e.g., CA2 DRDs), payloads of interest (e.g., IL15) and compositions of the disclosure, may be packaged into viral vectors or integrated into viral genomes allowing transient or stable expression of the polynucleotides. Preferable viral vectors are retroviral vectors including lentiviral vectors and gamma retroviral vectors. In order to construct a retroviral vector, a polynucleotide molecule encoding a CA2 biocircuit, a CA2 effector module, a CA2 DRD or a payload of interest (e.g., an immunotherapeutic agent) is inserted into the viral genome in the place of certain viral sequences to produce a virus that is replication-defective. The recombinant viral vector is then introduced into a packaging cell line containing the gag, pol, and env genes, but without the LTR (for lentiviral vectors) and packaging components. The recombinant retroviral particles are secreted into the culture media, then collected, optionally concentrated, and used for gene transfer. Lentiviral vectors are especially preferred as they are capable of infecting both dividing and non-dividing cells.

Vectors may also be transferred to cells by non-viral methods by physical methods such as needles, electroporation, sonoporation, hyrdoporation; chemical carriers such as inorganic particles (e.g. calcium phosphate, silica, gold) and/or chemical methods. In some embodiments, synthetic or natural biodegradable agents may be used for delivery such as cationic lipids, lipid nano emulsions, nanoparticles, peptide-based vectors, or polymer-based vectors.

The CA2 biocircuit systems, CA2 effector modules, SREs and/or payloads of the present disclosure may be delivered using one or more modalities. The present disclosure also provides vectors that package polynucleotides of the disclosure encoding CA2 biocircuits, CA2 effector modules, SREs (e.g., CA2 DRDs) and IL15 payloads of interest, and combinations thereof. Vectors of the present disclosure may also be used to deliver the packaged polynucleotides to a cell, a local tissue site or a subject. These vectors may be of any kind, including DNA vectors, RNA vectors, plasmids, viral vectors and particles. Viral vector technology is well known and described in Sambrook et al. (2001, Molecular Cloning: A Laboratory Manual, Cold Spring Harbor Laboratory, New York). Viruses, which are useful as vectors include, but are not limited to lentiviral vectors, adenoviral vectors, adeno-associated viral (AAV) vectors, herpes simplex viral vectors, retroviral vectors, oncolytic viruses, and the like. In some embodiments, a viral vector useful for introducing one or more nucleic acid molecules encoding a DRD and IL15 payload exemplified herein into a cell may be derived from an adenovirus, adeno-associated virus (AAV), alphavirus, flavivirus, herpes virus, measles virus, rhabdovirus, retrovirus, lentivirus, Newcastle disease virus (NDV), poxvirus, or picornavirus.

In general, vectors contain an origin of replication functional in at least one organism, a promoter sequence and convenient restriction endonuclease site, and one or more selectable markers e.g. a drug resistance gene.

In some embodiments, the recombinant expression vector may comprise regulatory sequences, such as transcription and translation initiation and termination codons, which are specific to the type of host cell into which the vector is to be introduced.

In some embodiments, the vector of the disclosure may comprise one or more payloads taught herein, wherein the two or more payloads may be included in one CA2 effector module. In this case, the two or more payloads are tuned by the same stimulus simultaneously. In other embodiments, the vector of the disclosure may comprise two or more CA2 effector modules, wherein each CA2 effector module comprises a different payload. In this case, the two or more CA2 effector modules and payloads are tuned by different stimuli, providing separately independent regulation of the two or more components. In other embodiments, the vector of the disclosure may comprise one or more CA2 effector modules and one or more non-CA2 effector modules, wherein each CA2 effector module comprises a different payload. In this case, the CA2 effector modules and payloads are tuned by different stimuli, providing separately independent regulation of the two or more components.

In some embodiments, lentiviral vehicles/particles may be used as delivery modalities. Lentiviruses are subgroup of the Retroviridae family of viruses, named because reverse transcription of viral RNA genomes to DNA is required before integration into the host genome. As such, the most important features of lentiviral vehicles/particles are the integration of their genetic material into the genome of a target/host cell. Some examples of lentivirus include the Human Immunodeficiency Viruses: HIV-1 and HIV-2, the Simian Immunodeficiency Virus (SIV), feline immunodeficiency virus (Hy), bovine immunodeficiency virus (BIV), Jembrana Disease Virus (JDV), equine infectious anemia virus (EIAV), equine infectious anemia virus, visna-maedi and caprine arthritis encephalitis virus (CAEV).

Typically, lentiviral particles making up the gene delivery vehicle are replication defective on their own (also referred to as "self-inactivating"). Lentiviruses are able to infect both dividing and non-dividing cells by virtue of the entry mechanism through the intact host nuclear envelope (Naldini L et al., Curr. Opin. Biotechnol, 1998, 9: 457-463). Recombinant lentiviral vehicles/particles have been generated by multiply attenuating the HIV virulence genes, for example, the genes Env, Vif, Vpr, Vpu, Nef and Tat are deleted making the vector biologically safe. Correspondingly, lentiviral vehicles, for example, derived from HIV-1/HIV-2 can mediate the efficient delivery, integration and long-term expression of transgenes into non-dividing cells. As used herein, the term "recombinant" refers to a vector or other nucleic acid containing both lentiviral sequences and non-lentiviral retroviral sequences.

Lentiviral particles may be generated by co-expressing the virus packaging elements and the vector genome itself in a producer cell such as human HEK293T cells. These elements are usually provided in three or four separate plasmids. The producer cells are co-transfected with plasmids that encode lentiviral components including the core (i.e. structural proteins) and enzymatic components of the virus, and the envelope protein(s) (referred to as the packaging systems), and a plasmid that encodes the genome including a foreign transgene, to be transferred to the target cell, the vehicle itself (also referred to as the transfer vector). In general, the plasmids or vectors are included in a producer cell line. The plasmids/vectors are introduced via transfection, transduction or infection into the producer cell line. Methods for transfection, transduction or infection are well known by those of skill in the art. As non-limiting example, the packaging and transfer constructs can be introduced into producer cell lines by calcium phosphate transfection, lipofection or electroporation, generally together with a dominant selectable marker, such as neo, DHFR, Gln synthetase or ADA, followed by selection in the presence of the appropriate drug and isolation of clones.

The producer cell produces recombinant viral particles that contain the foreign gene, for example, the CA2 effector module of the present disclosure. The recombinant viral particles are recovered from the culture media and titrated by standard methods used by those of skill in the art. The recombinant lentiviral vehicles can be used to infect target cells.

Cells that can be used to produce high-titer lentiviral particles may include, but are not limited to, HEK293T cells, 293G cells, STAR cells (Relander et al., Mol. Ther., 2005, 11: 452-459), FreeStyle™ 293 Expression System (ThermoFisher, Waltham, MA), and other HEK293T-based producer cell lines (e.g., Stewart et al., Hum Gene Ther. 2011, 22(3):357-369; Lee et al., Biotechnol Bioeng, 2012, 10996): 1551-1560; Throm et al., Blood. 2009, 113(21): 5104-5110; the contents of each of which are incorporated herein by reference in their entirety).

In some aspects, the envelope proteins may be heterologous envelop proteins from other viruses, such as the G protein of vesicular stomatitis virus (VSV G) or baculoviral gp64 envelop proteins. The VSV-G glycoprotein may especially be chosen among species classified in the vesiculovirus genus: Carajas virus (CJSV), Chandipura virus (CHPV), Cocal virus (COCV), Isfahan virus (ISFV), Maraba virus (MARAV), Piry virus (PIRYV), Vesicular stomatitis Alagoas virus (VSAV), Vesicular stomatitis Indiana virus (VSIV) and Vesicular stomatitis New Jersey virus (VSNJV) and/or stains provisionally classified in the vesiculovirus genus as Grass carp rhabdovirus, BeAn 157575 virus (BeAn 157575), Boteke virus (BTKV), Calchaqui virus (CQIV), Eel virus American (EVA), Gray Lodge virus (GLOV), Jurona virus (JURY), Klamath virus (KLAV), Kwatta virus (KWAV), La Joya virus (LJV), Malpais Spring virus (MSPV), Mount Elgon bat virus (MEBV), Perinet virus (PERV), Pike fry rhabdovirus (PFRV), Porton virus (PORV), Radi virus (RADIV), Spring viremia of carp virus (SVCV), Tupaia virus (TUPV), Ulcerative disease rhabdovirus (UDRV) and Yug Bogdanovac virus (YBV). The gp64 or other baculoviral env protein can be derived from Autographa californica nucleopolyhedrovirus (AcMNPV), Anagrapha falcifera nuclear polyhedrosis virus, Bombyx mori nuclear polyhedrosis virus, Choristoneura fumiferana nucleopolyhedrovirus, Orgyia pseudotsugata single capsid nuclear polyhedrosis virus, Epiphyas postvittana nucleopolyhedrovirus, Hyphantria cunea nucleopolyhedrovirus, Galleria mellonella nuclear polyhedrosis virus, Dhori virus, Thogoto virus, Antheraea pemyi nucleopolyhedrovirus or Batken virus.

Other elements provided in lentiviral particles may comprise retroviral LTR (long-terminal repeat) at either 5' or 3' terminus, a retroviral export element, optionally a lentiviral reverse response element (RRE), a promoter or active portion thereof, and a locus control region (LCR) or active portion thereof. The CA2 effector module is linked to the vector.

Methods for generating recombinant lentiviral particles are discussed in the art, for example, U.S. Pat. Nos. 8,846, 385; 7,745,179; 7,629,153; 7,575,924; 7,179,903; and 6,808,905; the contents of each of which are incorporated herein by reference in their entirety.

Lentivirus vectors used may be selected from, but are not limited to pLVX, pLenti, pLenti6, pLJM1, FUGW, pWPXL, pWPI, pLenti CMV puro DEST, pLJM1-EGFP, pULTRA, pInducer20, pHIV-EGFP, pCW57.1, pTRPE, pELPS, pRRL, and pLionII.

Lentiviral vectors are used for introducing transgenes into T cells (e.g., primary human T cells or Jurkat cells) for preclinical research and clinical applications, including recently approved products such as Tisagenlecleucel (KYMRIAH®) for relapsed/refractory B-cell lymphoma. VSV-G pseudotyped 3rd generation lentiviral vectors offer high titers, high transduction efficiency and safety, and have become the vectors of choice for T cell engineering. While not wishing to be bound by theory, T cell engineering usually involves T cell activation by CD3/CD28 antibodies, followed by lentivirus transduction, and then cell expansion which can last from 5 to 30 days (e.g., 9 to 14 days or 9 to 15 days). In general, lentivirus transgene integration may take over 7 days to fully stabilize in T cells (e.g., primary human T cells or Jurkat cells).

In some embodiments, to determine the transgene expression kinetics CD3/CD28 activated primary human T cells can be transduced with lentivirus carrying a transgene (e.g., IL15). The cells may be analyzed by methods described herein and/or known in the art for viability, viral genomic integration (e.g., by using quantitative PCR), transcript levels (e.g., by using quantitative RT-PCR), and cell surface expression of the transgene. The cells may be analyzed prior to transduction and/or after transduction such as 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, the cells may be analyzed at various time points between 3 to 14 days after transduction (e.g., 3 days, 4 days, 5 days, 6 days, 7 days, 8 days, 9 days, 10 days, 11 days, 12 days, 13 days, and/or 14 days). As a non-limiting example, the cells may be analyzed 3 to 15 days after transduction. As a non-limiting example, the cells may be analyzed 9 to 15 days after transduction.

In some embodiments, the CD3/CD28 activated primary human T cells can be reactivated with CD3/CD28 beads after transduction. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. The cells may be analyzed by methods described herein and/or known in the art for viability, viral genomic integration (e.g., by using quantitative PCR), transcript levels (e.g., by using quantitative RT-PCR), cell surface expression of the transgene, copy number, and/or mRNA levels.

In some embodiments, the cell viability of activated primary human T cells transduced with lentivirus carrying a transgene is greater than 65%, 70%, 75%, 80%, 85%, 90%, 95%, 97%, or 99%. As a non-limiting example, the cell viability is greater than 90%. As a non-limiting example, the cell viability is greater than 85%.

In some embodiments, the cell viability of Jurkat cells transduced with lentivirus carrying a transgene is greater than 65%, 70%, 75%, 80%, 85%, 90%, 95%, 97%, or 99%. As a non-limiting example, the cell viability is greater than 90%. As a non-limiting example, the cell viability is greater than 85%.

In some embodiments, the integration of the transgene into the genome of the cell may be at or above the saturation point. As a non-limiting example, the saturation point may be 3 copies per cell.

In some embodiments, the integration of the transgene into the genome may be high in the initial timepoints evaluated and then decline to a lower integration value before becoming stable for the remainder of the culture. As a non-limiting example, the integration may be up to 20 copies per cell of the transgene into the genome during the early timepoints before declining to 2 copies per cell and being stable throughout the remainder of the culture.

In some embodiments, the transduction of ability of T cells may be evaluated. T cells from at least one donor may be transduced with a lentivirus containing a transgene at a dose that is predicted to reach the saturating levels (e.g., enough virus that each cell should contain a copy if a Poisson distribution is expected) and a higher lentivirus dose that exceeds saturation 5 times. Copies per cell, percentage and MFI of cells (or concentration in media of transgene) may be detected in order to determine if all cells are expressing transgene. As a non-limiting example, T cells from two distinct donors may be transduced with lentivirus which includes a transgene. The transduction may be at two doses, saturation and 5× saturation, and show that 5-10 days after transduction that all groups may reach or exceed a predicted saturating level of integrated transgene and similar expression intensity across groups but not all cells are expressing the transgene. Not all T cells may have equal transduction susceptibility, even when sourced from the same donor. The fraction of total cells that express GFP (above the detection threshold) may vary between donors, lots and/or viral dose.

In some embodiments, a percentage of the cultured T cells (e.g., primary human T cells and/or Jurkat cells) may express the transgene. The percentage of culture T cells expressing the transgene may be, but is not limited to, 5%, 10%, 15%, 20%, 25%, 30%, 35%, 40%, 45%, 50%, 55%, 60%, 65%, 70%, 75%, 80%, 85%, 90%, 95%, 97%, 99% or greater than 99%. As a non-limiting example, the percentage may be greater than 70%. As a non-limiting example, the percentage may be greater than 75%. As a non-limiting example, the percentage may be greater than 80%. As a non-limiting example, the percentage may be greater than 85%. As a non-limiting example, the percentage may be greater than 90%. As a non-limiting example, the percentage may be greater than 95%.

In some embodiments, the mRNA levels from the culture may decline over the duration of the study. The decline may not be limited to a specific transgene and the trend may be seen across multiple classes of expressed proteins. In order to increase the mRNA levels, the cells may be reactivated after the mRNA levels decrease from the initial levels. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, in order to increase mRNA levels in the culture, the cells may be reactivated with CD3/CD28 beads 13 days after transduction. As a non-limiting example, in order to increase mRNA levels in the culture, the cells may be reactivated with CD3/CD28 beads 14 days after transduction. As a non-limiting example, in order to increase mRNA levels in the culture, the cells may be reactivated with CD3/CD28 beads 15 days after transduction In some embodiments, the surface expression from the culture may decline over the duration of the study. For example, the surface expression may decline between days 3 to 13 days, 3 to 14 days, or 3 to 15 days after transduction. In order to increase the surface expression, the cells may be reactivated after the surface expression decrease from the initial levels. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, in order to increase surface expression in the culture, the cells may be reactivated with CD3/CD28 beads 13 days after transduction. As a non-limiting example, in order to increase surface expression in the culture, the cells may be reactivated with CD3/CD28 beads 14 days after transduction. As a non-limiting example, in order to increase surface expression in the culture, the cells may be reactivated with CD3/CD28 beads 15 days after transduction.

In some embodiments, the transgene is IL15 (e.g., a membrane bound IL15 payload when combined with the other effector module components described in Table 3). The cell viability may be greater than 90% in cells transduced with IL15. The cell viability may be greater than 85% in cells transduced with IL15. If the cells are primary T cells transduced with IL15, the number of viable cells may increase over the initial timepoints before decreasing. If the cells are Jurkat cells transduced with IL15, the number of viable cells may increase for at least 10 days. The number of copies per cell for IL15 transduced cells may be higher for the initial timepoints before decreasing by 50% or more for the later timepoints. For IL15 transduced primary human T cells, the level of soluble IL15 in the media may drop steadily over the time course of the study with a slight increase visible in the restimulated group. For IL15 transduced Jurkat cells, the level of soluble IL15 in the media may have a drop in IL15 secretion in the first half of the culture with the levels remaining low through the second half of the culture time.

In some embodiments, lentivirally engineered cells described herein have genomic DNA integration that stabilizes after an initial decline of copy number, decreasing RNA and surface expression levels over time, and an increase in RNA and surface expression after restimulation.

In some embodiments, lentivirally engineering cells may be evaluated using the following 14-day method where samples are collected 5 times throughout the culture. On day −1 the T cells (e.g., primary human T cells or Jurkat cells) may be thawed and the CD3/CD28 beads are added. On day 0, the lentivirus for each of the conditions is added (e.g., 4 mL of cells at 0.5e6/mL) and there is a control of non-transduced cells. Double media to 8 mL on day 1 and then double the media to 16 mL on day 2. On day 3, harvest 4 mL and then double media to 24 mL on day 4. Harvest 4 mL on day 6 before doubling media to 40 mL. The cells can be split (e.g., 14 mL 0.5e6 cells/mL) on day 8 and then on day 6 harvest 4 mL before doubling media to 40 mL. 4 mL may be harvested on day 10 before the media is doubled to 20 mL. On day 13, 4 mL are harvested before doubling the media to 32 mL. The culture is split in half and half of the culture is activated (CD3/CD28 activation beads 1:1) and stimulated overnight. On day 14, 4 mL of each stimulated and non-stimulated cells are harvested and the culture is ended. Transgene copy number per cell are assayed by harvesting cells and extracting genomic DNA then quantifying with standard curve qPCR against the endogenous genome and against the transgene sequence, then converting the detected quantities to a ratio. Mean Fluorescence Intensity (MFI) is assayed by FLO on an Attune with appropriate staining for each group. Percent expressing may also be assayed by FLO on an attune quantifying the percent of cells fluorescing above threshold. Soluble payloads can be quantified by harvesting culture supernatant at each marked timepoint and running MesoScale Discovery plate assay (MSD) then normalizing for cell density.

In some embodiments, the CA2 effector modules of the disclosure may be designed as a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo.

The present disclosure provides methods comprising administering any one or more or components of a CA2 biocircuit system to a subject in need thereof. These may be administered to a subject using any amount and any route of administration effective for preventing or treating or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like.

In some embodiments, the present disclosure provides a method of treating a disease or disorder responsive to regulated IL15 in a subject in need thereof, said method comprising: (a) administering to the subject a therapeutically effective amount of a nucleic acid molecule, vector, recombinant protein, cell, or pharmaceutical composition of the disclosure; and administering a therapeutically effective amount of a stimulus to the subject, wherein the DRD is responsive to the stimulus and wherein expression of the IL15 payload is modulated in response to the stimulus. In some embodiments, the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the stimulus is acetazolamide.

In some embodiments, the present disclosure provides a method of treating a malignant tumor in a subject in need thereof, wherein said tumor expresses a tumor-associated antigen, said method comprising: (a) administering to the subject a therapeutically effective amount of a human T cell or a human NK cell of the disclosure, which further comprises a polynucleotide encoding a CAR or TCR, or a pharmaceutical composition thereof, wherein the CAR or TCR comprises an antigen-binding domain specific to the tumor-associated antigen; and (b) administering a therapeutically effective amount of a stimulus to the subject, wherein the CA2 DRD is responsive to the stimulus and wherein expression of the IL15 payload is modulated in response to the stimulus. In some embodiments, the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the stimulus administered to the subject is acetazolamide.

In some embodiments, the present disclosure provides a method of treating a malignant tumor in a subject in need thereof, said method comprising: (a) administering to the subject a therapeutically effective amount of a human TIL of the disclosure; and (b) administering a therapeutically effective amount of a stimulus to the subject, wherein the CA2 DRD is responsive to the stimulus and wherein expression of the IL15 payload is modulated in response to the stimulus. In some embodiments, the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the stimulus administered to the subject is acetazolamide.

Compositions in accordance with the disclosure are typically formulated in dosage unit form for ease of administration and uniformity of dosage. It will be understood, however, that the total daily usage of the compositions of the present disclosure may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Compositions of the disclosure may be used in varying doses to avoid T cell anergy, prevent cytokine release syndrome and minimize toxicity associated with immunotherapy. For example, low doses of the compositions of the present disclosure may be used to initially treat patients with high tumor burden, while patients with low tumor burden may be treated with high and repeated doses of the compositions of the disclosure to ensure recognition of a minimal tumor antigen load. In another instance, the compositions of the present disclosure may be delivered in a pulsatile fashion to reduce tonic T cell signaling and enhance persistence in vivo. In some aspects, toxicity may be minimized by initially using low doses of the compositions of the disclosure, prior to administering high doses. Dosing may be modified if serum markers such as ferritin, serum C-reactive protein, IL6, IFN-$\gamma$, and TNF-$\alpha$ are elevated.

Also provided herein are methods of administering ligands in accordance with the disclosure to a subject in need thereof. The ligand may be administered to a subject or to cells, using any amount and any route of administration effective for tuning the CA2 biocircuits of the present disclosure. The exact amount required will vary from subject to subject, depending on the species, age, and general condition of the subject, the severity of the disease, the particular composition, its mode of administration, its mode of activity, and the like. The subject may be a human, a mammal, or an animal. Compositions in accordance with the present disclosure are typically formulated in unit dosage form for ease of administration and uniformity of dosage. It will be understood, however, that the total daily usage of the compositions of the present disclosure may be decided by the attending physician within the scope of sound medical judgment. In certain embodiments, the ligands in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, from about 10 mg/kg to about 100 mg/kg, from about 50 mg/kg to about 500 mg/kg, from about 100 mg/kg to about 1000 mg/kg, of subject body weight per day, one or more times a day, to obtain the desired effect. In some embodiments, the dosage levels may be 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg or mg/kg of subject body weight per day, or more times a day, to obtain the desired effect.

The present disclosure provides methods for delivering to a cell or tissue any of the ligands described herein, comprising contacting the cell or tissue with said ligand and can be accomplished in vitro, ex vivo, or in vivo. In certain embodiments, the ligands in accordance with the present disclosure may be administered to cells at dosage levels sufficient to deliver from about 1 nM to about 10 nM, from about 5 nM to about 50 nM, from about 10 nM to about 100 nM, from about 50 nM to about 500 nM, from about 100 nM to about 1000 nM, from about 1 µM to about 10µM from about 5 µM to about 50 µM from about 1004 to about 10004 from about 25 µM to about 250 µM from about 50 µM to about 500 µM. In some embodiments, the ligand may be administered to cells at doses selected from but not limited to 0.00064 µM, 0.0032 µM, 0.016 µM, 0.08 µM, 0.4 µM, 1 µM 2 µM, 10 µM, 50 µM, 75, µM, 100 µM, 150 µM, 175 µM, 200 µM, 250 µM.

The desired dosage of the ligands of the present disclosure may be delivered only once, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event. The desired dosage of the ligand of the present disclosure may be administered as a "pulse dose" or as a "continuous flow". As used herein, a "pulse dose" is a series of single unit doses of any therapeutic administered with a set frequency over a period of time. As used herein, a "continuous flow" is a dose of therapeutic administered continuously for a period of time in a single route/single point of contact, i.e., continuous administration event. A total daily dose, an amount given or prescribed in 24-hour period, may be administered by any of these methods, or as a combination of these methods, or by any other methods suitable for a pharmaceutical administration.

In some embodiments, the compositions for immunotherapy may be administered to cells ex vivo and subsequently administered to the subject. Immune cells can be isolated and expanded ex vivo using a variety of methods known in the art. For example, methods of isolating cytotoxic T cells are described in U.S. Pat. Nos. 6,805,861 and 6,531,451; the contents of each of which are incorporated herein by reference in their entirety. Isolation of NK cells is described in U.S. Pat. No. 7,435,596; the contents of which are incorporated by reference herein in its entirety.

In some embodiments, depending upon the nature of the cells, the cells may be introduced into a host organism e.g. a mammal, in a wide variety of ways including by injection, transfusion, infusion, local instillation or implantation. In some aspects, the cells described herein may be introduced at the site of the tumor. The number of cells that are employed will depend upon a number of circumstances, the purpose for the introduction, the lifetime of the cells, the protocol to be used, for example, the number of administrations, the ability of the cells to multiply, or the like. The cells may be in a physiologically-acceptable medium.

In some embodiments, the cells described herein may be administrated in multiple doses to subjects having a disease or condition. The administrations generally effect an improvement in one or more symptoms of cancer or a clinical condition and/or treat or prevent cancer or clinical condition or symptom thereof.

In some embodiments, the compositions for immunotherapy may be administered in vivo. In some embodiments, polypeptides of the present disclosure comprising CA2 biocircuits, CA2 effector molecules, SREs, payloads of interest (IL15) and compositions of the disclosure may be delivered in vivo to the subject. In vivo delivery of immunotherapeutic agents is well described in the art. For example, methods of delivery of cytokines are described in the EP Pat. No. EP0930892 A1, the contents of which are incorporated herein by reference.

The pharmaceutical compositions, CA2 biocircuits, CA2 biocircuit components, CA2 effector modules including their SREs (e.g., CA2 DRDs), payloads (e.g., IL15), vectors and cells of the present disclosure may be administered by any route to achieve a therapeutically effective outcome.

The pharmaceutical compositions, CA2 biocircuits, CA2 biocircuit components, CA2 effector modules including their SREs or payloads of the present disclosure may be administered by any route to achieve a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intra-epidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In some embodiments, pharmaceutical compositions, CA2 biocircuits, CA2 biocircuit components, CA2 effector modules including their SREs or payloads of the present disclosure may be administered parenterally. Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile intravenous preparations or injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

The CA2 biocircuits, CA2 effector modules, SREs, stimuli, compositions or systems comprising one or more of the stimuli, CA2 biocircuits, CA2 effector modules of the present disclosure may be utilized in a large variety of applications including, but not limited to, therapeutics, diagnosis and prognosis, bioengineers, bioprocessing, biofactory, research agents, metabolomics, gene expression, enzyme replacement, etc.

According to the present disclosure, the CA2-IL15 biocircuits and systems may be used in the development and implementation of cell therapies such as adoptive cell therapy. The CA2-IL15 biocircuits and systems may be used to effect CAR T cell therapy, T cell receptor (TCR) cell therapy, CAR NK cell therapy, TCR NK cell therapy, TIL therapy, any of which may be used in combination therapy with other treatment lines (e.g. radiation, cytokines).

In some embodiments, CA2-IL15 biocircuits and systems may be used to engineer immune cells including T cells such as CD8$^+$ T cells and CD4$^+$ T cells, natural killer (NK) cells, NK T cells, Cytotoxic T lymphocytes (CTLs), tumor infiltrating lymphocytes (TIL), lymphokine activated killer (LAK) cells, memory T cells, regulatory T cells (Tregs), helper T cells, cytokine-induced killer (CIK) cells, and any combination thereof. In other embodiments, CA2-IL15 biocircuits and systems may be used to engineer immune stimulatory cells generated from embryonic stem cell (ESC) and induced pluripotent stem cell (iPSC) that may be used for ACT. In some embodiments, CA2-IL15 biocircuits and systems may be used to engineer autologous or allogeneic immune cells that may be used for ACT. In some embodiments, CA2-IL15 biocircuits and systems may be used to engineer T cells, TIL or NK cells. In some embodiments, the immune cells are NK cells derived from cord blood, iPSCs or peripheral blood mononuclear cells.

In some embodiments, CA2-IL15-engineered cells used for ACT may be T cells that also have been engineered to express a CAR or TCR comprising an antigen-binding domain specific to an antigen on tumor cells of interest. In other embodiments, CA2-IL15-engineered cells used for ACT may be NK cells engineered to express a CAR or TCR comprising an antigen-binding domain specific to an antigen on tumor cells of interest. In some embodiments, CA2-IL15-engineered cells used for ACT may be a mixture of T cells and NK cells, either or both of which may be expressing a CAR or TCR.

A chimeric antigen receptor (CAR), when transduced into immune cells (e.g., T cells and NK cells), can re-direct the immune cells against a target (e.g., a tumor cell) which expresses a molecule recognized by the extracellular target moiety of the CAR. As used herein, the term "chimeric antigen receptor (CAR)" refers to a synthetic receptor that mimics TCR on the surface of T cells. In general, a CAR is composed of an extracellular targeting domain, a transmembrane domain/region and an intracellular signaling/activation domain. In a standard CAR receptor, the extracellular targeting domain, transmembrane domain and intracellular signaling/activation domain, are linearly constructed as a single fusion protein. The extracellular region comprises a targeting domain/moiety (e.g., a scFv) that recognizes a specific tumor antigen (e.g., a tumor neoantigen) or other tumor cell-surface molecules. The intracellular region may contain a intracellular signaling domain (the immunoreceptor tyrosine-based activation motifs) of TCR complex (e.g., the signaling region of CD3ζ), and/or one or more costimulatory signaling domains, such as those from CD28, 4-1BB (CD137) and OX-40 (CD134). A CAR, when expressed by a T cell or NK cell, endows the T cell or NK cell with antigen specificity determined by the extracellular targeting moiety of the CAR.

In some embodiments, the extracellular targeting domain is joined through the hinge (also called space domain or spacer) and transmembrane regions to an intracellular signaling domain. The hinge connects the extracellular targeting domain to the transmembrane domain which transverses the cell membrane and connects to the intracellular signaling domain. The hinge may need to be varied to optimize the potency of CAR transformed cells toward cancer cells due to the size of the target protein where the targeting moiety binds, and the size and affinity of the targeting domain itself. Upon recognition and binding of the targeting moiety to the target cell, the intracellular signaling domain leads to an activation signal to the CAR T cell or CAR NK cell, which is further amplified by the "second signal" from one or more intracellular costimulatory domains. The CAR T cell or CAR NK cell, once activated, can destroy the target cell.

In some embodiments, the present disclosure provides an immune cell comprising a CA2-IL15 effector module and further comprising a chimeric antigen receptor (CAR). The CAR may be regulated by a DRD or may be constitutively expressed. In some embodiments, the CAR is constitutively expressed.

In some embodiments, the constitutively expressed or regulated CAR and the CA2-IL15 effector module are encoded on different vectors. In some embodiments, a single vector comprises both the CA2-IL15 effector module and the constitutively expressed or regulated CAR to form a tandem construct. The CA2-IL15 effector module and the CAR may be separated from one another by an internal ribosome entry site (IRES); a ribosomal skipping sequence 2A peptide selected from foot-and-mouth disease virus (FMDV) 2A (F2A), equine rhinitis A virus (ERAV) 2A (E2A), porcine teschovirus-1 2A (P2A) or Thosea asigna virus 2A (T2A); or other ribosomal skipping sequence or ribosomal entry sequence, giving rise to a bicistronic construct. In some embodiments, the 2A sequence is a P2A sequence. The IRES, 2A sequence, or other ribosomal skipping sequence or ribosomal entry sequence leads to the expression of the upstream and downstream sequences expressed as two independent polypeptides. In some embodiments, a single vector comprises, in order, a sequence encoding a CAR, a P2A sequence, and a sequence encoding the CA2-IL15 effector module. The sequence encoding the CAR may be either 5' or 3' to the sequence encoding the CA2-IL15 effector module.

A T cell receptor (TCR) when transduced into immune cells (e.g., T cells and NK cells), can re-direct the immune cells against a target (e.g., a tumor cell) which expresses a molecule recognized by the TCR. A TCR is a molecule that contains a variable α and β chains (also known as TCRα and TCRβ, respectively) or a variable γ and δ chains (also known as TCRγ and TCRδ, respectively), or antigen-binding portions or fragments thereof, which is capable of specifically binding to a peptide bound to an WIC molecule. In some embodiments, the TCR is TCRαβ. Generally, a TCR is found on the surface of T cells where it is generally responsible for recognizing antigens bound to major histocompatibility complex (MHC) molecules.

As used herein, the term TCR encompasses full TCRs as well as antigen-binding portions or antigen-binding fragments thereof. In some embodiments, the TCR is a full-length TCR comprising both the α chain and β chain. In some embodiments, the TCR is an antigen-binding portion or fragment of a TCR, for example a portion of each of the α chain and β chain, that binds to a specific peptide bound in an WIC molecule. In some embodiments, the antigen-binding portion or fragment comprises the variable domains of a TCR, such as the variable α (Vα) chain and variable β (Vβ) chain, sufficient to bind to a specific WIC-peptide complex.

The variable domains of the TCR contain complementarity determining regions (CDRs), which primarily contribute to MHC-peptide antigen recognition, binding and specificity. The CDRs within a variable region of a TCR chain are separated by framework regions (FRs), which typically display less variability than the CDRs. In some embodiments, one or more CDRs of a TCR form all or substantially all of the antigen-binding site of a given TCR molecule. In some embodiments, CDR3 is the main CDR responsible for antigen binding or specificity and for interaction with the processed peptide portion of the peptide-MHC complex.

The α-chain and β-chain of a TCR also may contain a constant domain, a transmembrane domain and a short cytoplasmic tail. The cytoplasmic tail of a TCR, anchors the protein in the cell membrane, where it associates with invariant subunits of the CD3 complex, which are involved in the signaling capacity of the TCR complex.

In some embodiments, the present disclosure provides a CAR T cell or TCR T cell that is "armed" with a CA2-IL15 effector module to improve the engineered cells' efficacy and persistence.

In some embodiments, the present disclosure provides CAR NK cell or TCR NK cell that is "armed" with a CA2-IL15 effector module to improve the engineered cells' efficacy and persistence or prevent immune exhaustion and senescence.

In some embodiments, the present disclosure provides TIL engineered with a CA2-IL15 effector module to improve the engineered cells' efficacy and persistence.

In some embodiments, cells of the present disclosure may be autologous, allogeneic, syngeneic, or xenogeneic in relation to a particular individual subject. In some embodiments, cells of the present disclosure may be mammalian cells, particularly human cells. Cells described herein may be primary cells or immortalized cell lines.

Cancer immunotherapy aims at the induction or restoration of the reactivity of the immune system towards cancer. Adoptive cell therapy is a form of active immunotherapy that aims at induction of an endogenous, long-lasting tumor-antigen specific immune response. The response may be enhanced by non-specific stimulation of immune response modifiers such as cytokines but cytokine stimulation can cause toxicity or immune exhaustion.

Despite significant advances, the efficacy of current immunotherapy strategies is limited by associated toxicities. These are often related to the narrow therapeutic window associated with immunotherapy, which in part, emerges from the need to push therapy dose to the edge of potentially fatal toxicity to get a clinically meaningful treatment effect. Further, dose expands in vivo since adoptively transferred immune cells continue to proliferate within the patient, often unpredictably.

A major risk involved in immunotherapy is the on-target but off tumor side effects resulting from T cell activation in response to normal tissue expression of the tumor associated antigen (TAA).

Immunotherapy may also produce on target, on-tumor toxicities that emerge when tumor cells are killed in response to the immunotherapy. The adverse effects include tumor lysis syndrome, cytokine release syndrome and the related macrophage activation syndrome. Importantly, these adverse effects may occur during the destruction of tumors, and thus even a successful on-tumor immunotherapy might result in toxicity. Approaches to regulatably control immunotherapy are thus highly desirable since they have the potential to reduce toxicity and maximize efficacy.

The present disclosure provides systems, compositions, immunotherapeutic agents and methods for cancer immunotherapy. These compositions provide tunable regulation of gene expression and function in immunotherapy. The present disclosure also provides CA2 biocircuits, CA2 effector modules, stimulus response elements (SREs) and payloads, as well as polynucleotides encoding any of the foregoing. In one aspect, the systems, compositions, immunotherapeutic agents and other components of the disclosure can be controlled by a separately added stimulus, which provides a significant flexibility to regulate cancer immunotherapy. Further, the systems, compositions and the methods of the present disclosure may also be combined with therapeutic agents such as chemotherapeutic agents, small molecules, gene therapy, and antibodies.

The tunable nature of the systems and compositions of the disclosure has the potential to improve the potency and duration of the efficacy of immunotherapies. Reversibly silencing the biological activity of adoptively transferred cells using compositions of the present disclosure allows maximizing the potential of cell therapy without irretrievably killing and terminating the therapy.

The present disclosure provides methods for fine tuning of immunotherapy after administration to patients. This in turn improves the safety and efficacy of immunotherapy and increases the subject population that may benefit from immunotherapy.

In one embodiment, the CA2 biocircuits, CA2 effector modules, SREs, and components that tune expression levels and activities of any agents may be used for immunotherapy. As non-limiting examples, the immunotherapeutic agent used in the constructs of the present disclosure is IL15 that induces an immune response in a cell and a subject.

In some embodiments, the composition for inducing an immune response may comprise a CA2 effector module. In some embodiments, the CA2 effector module may comprise a stimulus response element (SRE) operably linked to a human IL15 comprising the amino acid sequence of SEQ ID NO: 8.

In some embodiments, CA2 biocircuits, CA2 effector modules, and compositions of the present disclosure relate to post-translational regulation of protein (payload) function anti-tumor immune responses of immunotherapeutic agents.

In some embodiments, cells which are genetically modified to express at least one CA2 biocircuit, CA2 effector module, SRE (e.g., CA2 DRD), and/or payload of interest (immunotherapeutic agent) may be used for adoptive cell therapy (ACT). As used herein, adoptive cell transfer refers to the administration of immune cells (from autologous, allogenic or genetically modified hosts) with direct anticancer activity. ACT has shown promise in clinical application against malignant and infectious disease.

According to the present disclosure, the CA2 biocircuits and systems may be used in the development and implementation of cell therapies such as adoptive cell therapy. The CA2 biocircuits, CA2 effector modules and their SREs and payloads may be used in cell therapies to effect immune cell therapies alone or in combination with other treatment lines (e.g. radiation, cytokines).

Provided herein are methods for use in adoptive cell therapy. In one embodiment, the method involves preconditioning a subject in need thereof, removing a portion of the subject's T cells, engineering the subject's T cells with a CA2 effector module of the present disclosure, and administering to the subject the engineered T cells expressing the CA2 effector module, wherein the engineered cells successfully engraft within the subject.

In another embodiment, the method involves preconditioning a subject in need thereof and administering to the subject allogeneic engineered T cells expressing the CA2 effector module, wherein the engineered cells successfully engraft within the subject.

In some embodiments, the method involves removing a malignant tumor from a subject, isolating TIL from the tumor, engineering the TIL with the CA2 effector module of the present disclosure, and administering to the subject the engineered TIL, wherein the TIL successfully infiltrate any remaining tumor or metastases in the subject.

In some embodiments, SREs, CA2 biocircuits and compositions of the present disclosure may be used to minimize preconditioning regimens associated with adoptive cell therapy. As used herein "preconditioning" refers to any therapeutic regimen administered to a subject to improve the outcome of adoptive cell therapy. Preconditioning strategies include but are not limited to total body irradiation and/or lymphodepleting chemotherapy. Adoptive therapy clinical trials without preconditioning have failed to demonstrate any clinical benefit, indicating its importance in ACT. Yet, preconditioning is associated with significant toxicity and limits the subject cohort that is suitable for ACT. In some instances, immune cells for ACT may be engineered to express cytokines such as IL15 as payload using SREs of the present disclosure to reduce the need for preconditioning.

In some embodiments, NK cells engineered to express the present compositions may be used for ACT. NK cell activation induces perforin/granzyme-dependent apoptosis in target cells. NK cell activation also induces cytokine secretion such as IFN γ, TNF-α and GM-CSF. These cytokines enhance the phagocytic function of macrophages and their antimicrobial activity and augment the adaptive immune response via up-regulation of antigen presentation by antigen presenting cells such as dendritic cells (DCs).

Immune cells can be isolated and expanded ex vivo using a variety of methods known in the art. For example, methods of isolating and expanding cytotoxic T cells are described in U.S. Pat. Nos. 6,805,861 and 6,531,451; US Patent Publication NO. US20160348072A1 and International Patent Publication NO. WO2016168595A1; the contents of each of which are incorporated herein by reference in their entirety. Isolation and expansion of NK cells is described in US Patent Publication NO. US20150152387A1, U.S. Pat. No. 7,435,596; and Oyer, J. L. (2016). Cytotherapy. 18(5):653-63; the contents of each of which are incorporated by reference herein in its entirety. Specifically, human primary NK cells may be expanded in the presence of feeder cells e.g. a myeloid cell line that has been genetically modified to express membrane bound IL15 and 4-1BBL.

In some embodiments, activation and expansion of T cells for ACT is achieved by antigenic stimulation of a transiently expressed Chimeric Antigen Receptor (CAR) on the cell surface. Such activation methods are taught in International Patent NO. WO2017015427, the content of which are incorporated herein by reference in their entirety.

In some embodiments, immune cells may be activated by antigens associated with antigen presenting cells (APCs). In some embodiments, the APCs may be dendritic cells, macrophages or B cells that antigen specific or nonspecific. The APCs may autologous or homologous in their organ. In some embodiments, the APCs may be artificial antigen presenting cells (aAPCs) such as cell based aAPCs or acellular aAPCs. Cell based aAPCs are may be selected from either genetically modified allogeneic cells such as human erythroleukemia cells or xenogeneic cells such as murine fibroblasts and Drosophila cells. Alternatively, the APCs maybe be acellular wherein the antigens or costimulatory domains are presented on synthetic surfaces such as latex beads, polystyrene beads, lipid vesicles or exosomes.

In some embodiments, adoptive cell therapy is carried out by autologous transfer, wherein the cells are derived from a subject in need of a treatment and the cells, following isolation and processing are administered to the same subject. In other instances, ACT may involve allogenic transfer wherein the cells are isolated and/or prepared from a donor subject other than the recipient subject who ultimately receives cell therapy. The donor and recipient subject may be genetically identical, or similar or may express the same HLA class or subtype.

Following genetic modulation using SREs, CA2 biocircuits and compositions of the disclosure, cells are administered to the subject in need thereof. Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338; the contents of each of which are incorporated herein by reference in their entirety.

In some embodiments, immune cells engineered with CA2-IL15 for ACT may be further modified to express one or more immunotherapeutic agents which facilitate immune cells activation, infiltration, expansion, survival and anti-tumor functions. The immunotherapeutic agents may be a CAR or TCR specific to a target molecule on a tumor cell; a second cytokine or a cytokine receptor; a chimeric switch receptor that converts an inhibitory signal to a stimulatory signal; a homing receptor that guides adoptively transferred cells to a target site such as the tumor tissue; an agent that optimizes the metabolism of the immune cell; or a safety switch gene (e.g., a suicide gene) that kills activated T cells when a severe event is observed after adoptive cell transfer or when the transferred immune cells are no-longer needed.

In some embodiments, immune cells used for adoptive cell transfer can be genetically manipulated to improve their persistence, cytotoxicity, tumor targeting capacity, and ability to home to disease sites in vivo, with the overall aim of further improving upon their capacity to kill tumors in cancer patients. One example is to introduce CA2 effector modules of the disclosure comprising IL15 into immune cells to promote immune cell proliferation and survival. Transduction of IL15 into cells will permit immune cells to propagate without addition of exogenous cytokines and cytokine-expressing NK cells may have enhanced tumor cytotoxicity.

In some embodiments, CA2 biocircuits, SREs or CA2 effector modules may be utilized to prevent T cell exhaustion. As used herein, "T cell exhaustion" refers to the stepwise and progressive loss of T cell function caused by chronic T cell activation. T cell exhaustion is a major factor limiting the efficacy of antiviral and antitumor immunotherapies. Exhausted T cells have low proliferative and cytokine producing capabilities concurrent with high rates of apoptosis and high surface expression of multiple inhibitory receptors. T cell activation leading to exhaustion may occur either in the presence or absence of the antigen.

In some embodiments, the CA2 biocircuits and their components may be utilized to prevent T cell exhaustion in the context of Chimeric Antigen Receptor-T cell therapy (CAR-T). In this context, exhaustion in some instances, may be caused by the oligomerization of the scFvs of the CAR on the cell surface which leads to continuous activation of the intracellular domains of the CAR. As a non-limiting example, CARs of the present disclosure may include scFvs that are unable to oligomerize. As another non-limiting example, CARs that are rapidly internalized and re-expressed following antigen exposure may also be selected to prevent chronic scFv oligomerization on cell surface. In one embodiment, the framework region of the scFvs may be modified to prevent constitutive CAR signaling.

Tunable CA2 biocircuits of the present disclosure may also be used to regulate the surface expression of the CAR on the T cell surface to prevent chronic T cell activation. The CARs of the disclosure may also be engineered to minimize exhaustion. As a non-limiting example, the 4-1-BB signaling domain may be incorporated into CAR design together with membrane bound IL15 expression regulated by CA2 biocircuits, SREs or CA2 effector modules, exemplified in Table 3 of the present disclosure, to ameliorate T cell exhaustion.

In some embodiments, the tunable nature of the CA2-IL15 biocircuits of the present disclosure may be utilized to reverse human T cell exhaustion observed with tonic CAR signaling. Reversibly silencing the biological activity of adoptively transferred cells using compositions of the present disclosure may be used to reverse tonic signaling which, in turn, may reinvigorate the T cells. Reversal of exhaustion may be measured by the downregulation of multiple inhibitory receptors associated with exhaustion.

In some embodiments, the compositions of the present disclosure may be utilized to alter TIL (tumor infiltrating lymphocyte) populations in a subject. In one embodiment, any of the payloads described herein may be utilized to change the ratio of CD4 positive cells to CD8 positive populations. In some embodiments, TIL may be sorted ex vivo and engineered to express any of the cytokines described herein. Payloads of the disclosure may be used to expand CD4 and/or CD8 populations of TIL to enhance TIL mediated immune response.

Provided in the present disclosure is a method of reducing a tumor volume or burden in a subject in need, the method comprising introducing into the subject a composition of the disclosure.

The present disclosure also provides methods for treating a cancer in a subject, comprising administering to the subject an effective amount of an effector immune cell genetically modified to express at least one CA2 effector module of the disclosure.

Various cancers may be treated with pharmaceutical compositions, CA2 biocircuits, CA2 biocircuit components, CA2 effector modules including their SREs and IL15 payloads of the present disclosure. As used herein, the term "cancer" refers to any of various malignant neoplasms characterized by the proliferation of anaplastic cells that tend to invade surrounding tissue and metastasize to new body sites and also refers to the pathological condition characterized by such malignant neoplastic growths. Cancers may be tumors or hematological malignancies, and include but are not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

Types of carcinomas which may be treated with the compositions of the present disclosure include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

Types of carcinomas which may be treated with the compositions of the present disclosure include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

As a non-limiting example, the carcinoma which may be treated may be Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, GallblaDRDer cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

In some embodiments, pharmaceutical compositions, CA2 biocircuits, CA2 biocircuit components, CA2 effector modules including their SREs or payloads of the present disclosure may be used in the modulation or alteration or exploitation of the immune system to target one or more cancers. This approach may also be considered with other such biological approaches, e.g., immune response modifying therapies such as the administration of interferons, interleukins, colony-stimulating factors, other monoclonal antibodies, vaccines, gene therapy, and nonspecific immunomodulating agents are also envisioned as anti-cancer therapies to be combined with the pharmaceutical compositions, CA2 biocircuits, CA2 biocircuit components, CA2 effector modules including their SREs or payloads of the present disclosure.

Cancer immunotherapy refers to a diverse set of therapeutic strategies designed to induce the patient's own immune system to fight the cancer. In some embodiments, pharmaceutical compositions, CA2 biocircuits, CA2 biocircuit components, CA2 effector modules including their SREs or payloads of the present disclosure are designed as immune-oncology therapeutics.

There are several types of cellular immunotherapies, including NK cells, tumor infiltrating lymphocyte (TIL) therapy, and genetically engineered T cells bearing chimeric antigen receptors (CARs) or recombinant TCR technology.

In one embodiment, the CAR T cell or TCR T cell of the present disclosure may be an "armed" T cell which is transformed with a CA2-IL15 effector module to improve efficacy and persistence.

In one embodiment, patients may also be stratified according to the immunogenic peptides presented by their immune cells and may be utilized as a parameter to determine suitable patient cohorts that may therapeutically benefit for the compositions of the disclosure.

In some embodiments, cells of the disclosure may be autologous, allogeneic, syngeneic, or xenogeneic in relation to a particular individual subject.

In some embodiments, cells of the disclosure may be mammalian cells, particularly human cells. Cells of the disclosure may be primary cells or immortalized cell lines.

Engineered immune cells can be accomplished by transducing a cell composition with one or more polynucleotides encoding a polypeptide of a CA2 biocircuit, a CA2 effector module, an SRE and an IL15 payload, or a vector comprising said polynucleotide. The vector may be a viral vector such as a lentiviral vector or gamma retroviral vector. In some embodiments, immune cells of the disclosure are genetically modified to express at least one immunotherapeutic agent of the disclosure which is tunable using a stimulus.

DEFINITIONS

At various places in the present specification, features or functions of the compositions of the present disclosure are disclosed in groups or in ranges. It is specifically intended that the present disclosure include each and every individual sub combination of the members of such groups and ranges. The following is a non-limiting list of term definitions.

Activity: As used herein, the term "activity" refers to the condition in which things are happening or being done. Compositions of the disclosure may have activity and this activity may involve one or more biological events. In some embodiments, biological events may include cell signaling events. In some embodiments, biological events may include cell signaling events associated protein interactions with one or more corresponding proteins, receptors, small molecules or any of the biocircuit components described herein.

Adoptive cell therapy (ACT): The terms "Adoptive cell therapy" or "Adoptive cell transfer", as used herein, refer to a cell therapy involving in the transfer of cells into a patient, wherein cells may have originated from the patient, or from another individual, and are engineered (altered) before being transferred back into the patient. The therapeutic cells may be derived from the immune system, such as effector immune cells: CD4+ T cell; CD8+ T cell, Natural Killer cell (NK cell); and B cells and tumor infiltrating lymphocytes (TIL) derived from the resected tumors. Most commonly transferred cells are autologous anti-tumor T cells after ex vivo expansion or manipulation. For example, autologous peripheral blood lymphocytes can be genetically engineered to recognize specific tumor antigens by expressing T cell receptors (TCR) or chimeric antigen receptor (CAR).

Agent: As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a receptor, and soluble factor.

Antigen: the term "antigen" as used herein is defined as a molecule that provokes an immune response when it is introduced into a subject or produced by a subject such as tumor antigens which arise by the cancer development itself. This immune response may involve either antibody production, or the activation of specific immunologically-competent cells such as cytotoxic T lymphocytes and T helper cells, or both. An antigen can be derived from organisms, subunits of proteins/antigens, killed or inactivated whole cells or lysates. In the context of the disclosure, the terms "antigens of interest" or "desired antigens" refers to those proteins and/or other biomolecules provided herein that are immunospecifically bound or interact with antibodies of the present disclosure and/or fragments, mutants, variants, and/or alterations thereof described herein. In some embodiments, antigens of interest may comprise any of the polypeptides or payloads or proteins described herein, or fragments or portions thereof.

Associated with: As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

Autologous: the term "autologous" as used herein is meant to refer to any material derived from the same individual to which it is later to be re-introduced into the individual.

Cancer: the term "cancer" as used herein refers a broad group of various diseases characterized by the uncontrolled growth of abnormal cells in the body. Unregulated cell division and growth results in the formation of malignant tumors that invade neighboring tissues ultimately metastasize to distant parts of the body through the lymphatic system or bloodstream.

Co-stimulatory molecule: As used herein, in accordance with its meaning in immune T cell activation, refers to a group of immune cell surface receptor/ligands which engage between T cells and APCs and generate a stimulatory signal in T cells which combines with the stimulatory signal in T cells that results from T cell receptor (TCR) recognition of antigen/MHC complex (pMHC) on APCs Cytokines: the term "cytokines", as used herein, refers to a family of small soluble factors with pleiotropic functions that are produced by many cell types that can influence and regulate the function of the immune system.

Delivery: the term "delivery" as used herein refers to the act or manner of delivering a compound, substance, entity, moiety, cargo or payload. A "delivery agent" refers to any agent which facilitates, at least in part, the in vivo delivery of one or more substances (including, but not limited to a compound and/or composition of the present disclosure) to a cell, subject or other biological system cells.

Destabilized: As used herein, the term "destable," "destabilize," or "destabilizing region" means a region or molecule that is less stable than a starting, reference, wild-type or native form of the same region or molecule.

Engineered: As used herein, embodiments of the disclosure are "engineered" when they are designed to have a feature or property, whether structural or chemical, that varies from a starting point, wild type or native molecule.

Formulation: As used herein, a "formulation" includes at least a compound and/or composition of the present disclosure and a delivery agent.

Fragment: A "fragment," as used herein, refers to a portion of a molecule that is less than the entire molecule. For example, fragments of proteins may comprise polypeptides obtained by digesting full-length protein. In some embodiments, fragments of an antibody include portions of an antibody.

Functional: As used herein, a "functional" biological molecule is a biological entity with a structure and in a form in which it exhibits a property and/or activity by which it is characterized.

Immune cells: the term "an immune cell", as used herein, refers to any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a T γδ cell, a Tαβ cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

Immunotherapy: the term "immunotherapy" as used herein, refers to a type of treatment of a disease by the induction or restoration of the reactivity of the immune system towards the disease.

Immunotherapeutic agent: the term "immunotherapeutic agent" as used herein, refers to the treatment of disease by the induction or restoration of the reactivity of the immune system towards the disease with a biological, pharmaceutical, or chemical compound.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Linker: As used herein, a linker refers to a moiety that connects two or more domains, moieties or entities. In one embodiment, a linker may comprise 10 or more atoms. In a further embodiment, a linker may comprise a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. In some embodiments, a linker may comprise one or more nucleic acids comprising one or more nucleotides. In some embodiments, the linker may comprise an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent). or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bonds include an amido bond which may be cleaved for example by the use of tris(2-carboxyethyl) phosphine (TCEP), or other reducing agents, and/or photolysis, as well as an ester bond which may be cleaved for example by acidic or basic hydrolysis.

Modified: As used herein, the term "modified" refers to a changed state or structure of a molecule or entity as compared with a parent or reference molecule or entity. Molecules may be modified in many ways including chemically, structurally, and functionally. In some embodiments, compounds and/or compositions of the present disclosure are modified by the introduction of non-natural amino acids.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids e.g., polynucleotides). In some embodiments, wherein mutations comprise the addition and/or substitution of amino acids and/or nucleotides, such additions and/or substitutions may comprise 1 or more amino acid and/or nucleotide residues and may include modified amino acids and/or nucleotides. The resulting construct, molecule or sequence of a mutation, change or alteration may be referred to herein as a mutant.

Neoantigen: the term "neoantigen", as used herein, refers to a tumor antigen that is present in tumor cells but not normal cells and do not induce deletion of their cognate antigen specific T cells in thymus (i.e., central tolerance). These tumor neoantigens may provide a "foreign" signal, similar to pathogens, to induce an effective immune response needed for cancer immunotherapy. A neoantigen may be restricted to a specific tumor. A neoantigen be a peptide/protein with a missense mutation (missense neoantigen), or a new peptide with long, completely novel stretches of amino acids from novel open reading frames (neoORFs). The neoORFs can be generated in some tumors by out-of-frame insertions or deletions (due to defects in DNA mismatch repair causing microsatellite instability), gene-fusion, read-through mutations in stop codons, or translation of improperly spliced RNA (e.g., Saeterdal et al., Proc Natl Acad Sci USA, 2001, 98: 13255-13260).

Off-target: As used herein, "off target" refers to any unintended effect on any one or more target, gene, cellular transcript, cell, and/or tissue.

Operably linked: As used herein, the phrase "operably linked" refers to a functional connection between two or more molecules, constructs, transcripts, entities, moieties or the like.

Payload or payload of interest (POI): the terms "payload" and "payload of interest (POI)", as used herein, are used interchangeable. A payload of interest (POI) refers to any protein or compound whose function is to be altered. In the context of the present disclosure, the POI is a component in the immune system, including both innate and adaptive immune systems. Payloads of interest may be a protein, a fusion construct encoding a fusion protein, or non-coding gene, or variant and fragment thereof. Payload of interest may, when amino acid based, may be referred to as a protein of interest.

Pharmaceutically acceptable excipients: the term "pharmaceutically acceptable excipient," as used herein, refers to any ingredient other than active agents (e.g., as described herein) present in pharmaceutical compositions and having the properties of being substantially nontoxic and non-inflammatory in subjects. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments, a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-V C H, 2008, and Berge et al., Journal of Pharmaceutical Science, 66, 1-19 (1977), each of which is incorporated herein by reference in its entirety. Pharmaceutically acceptable solvate: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N, N'-dimethylformamide (DMF), N, N'-dimethyl acetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a secondary status or state or to a reference compound or entity.

Standard CAR: As used herein, the term "standard CAR" refers to the standard design of a chimeric antigen receptor. The components of a CAR fusion protein including the extracellular scFv fragment, transmembrane domain and one or more intracellular domains are linearly constructed as a single fusion protein.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

T cell: A T cell is an immune cell that produces T cell receptors (TCRs). T cells can be naïve (not exposed to antigen; increased expression of CD62L, CCR7, CD28, CD3, CD127, and CD45RA, and decreased expression of CD45RO as compared to TCM), memory T cells (TM) (antigen-experienced and long-lived), and effector cells (antigen-experienced, cytotoxic). TM can be further divided into subsets of central memory T cells (TCM, increased expression of CD62L, CCR7, CD28, CD127, CD45RO, and CD95, and decreased expression of CD54RA as compared to naïve T cell and effector memory T cells (TEM, decreased expression of CD62L, CCR7, CD28, CD45RA, and increased expression of CD127 as compared to naïve T cells or TCM). Effector T cells (TE) refers to antigen-experienced CD8+ cytotoxic T lymphocytes that have decreased expression of CD62L, CCR7, CD28, and are positive for granzyme and perforin as compared to TCM. Other exemplary T cells include regulatory T cells, such as CD4+ CD25+ (Foxp3+) regulatory T cells and Treg17 cells, as well as Tr1, Th3, CD8+ CD28−, and Qa-1 restricted T cells.

T cell receptor: T cell receptor (TCR) refers to an immunoglobulin superfamily member having a variable antigen binding domain, a constant domain, a transmembrane region, and a short cytoplasmic tail, which is capable of specifically binding to an antigen peptide bound to a WIC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). The extracellular portion of TCR chains (e.g., α-chain, β-chain) contains two immunoglobulin domains, a variable domain (e.g., α-chain variable domain or Vα, β-chain variable domain or Vβ) at the N terminus, and one constant domain (e.g., α-chain constant domain or Cα and β-chain constant domain or Cβ,) adjacent to the cell membrane. Similar to immunoglobulin, the variable domains contain complementary determining regions (CDRs) separated by framework regions (FRs). A TCR is usually associated with the CD3 complex to form a TCR complex. As used herein, the term "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain. A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Treatment or treating: As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

Tune: As used herein, the term "tune" means to adjust, balance or adapt one thing in response to a stimulus or toward a particular outcome. In one non-limiting example, the SREs and/or DRDs of the present disclosure adjust, balance or adapt the function or structure of compositions to which they are appended, attached or associated with in response to particular stimuli and/or environments.

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure. The present disclosure is further illustrated by the following nonlimiting examples.

EXAMPLES

FIG. 1 depicts a representative procedure for in vitro characterization and/or validation of ACZ-regulated mbIL15 expression in T cells. As shown in FIG. 1, T cells may be transduced with an mbIL15 construct, for example, by following the procedures described in Example 1. Following transduction, T cells may be treated with control condition or ACZ and assayed for IL15 expression and/or antigen-independent cell expansion in vitro, for example, by following the procedures described in Example 2.

Figure 2:
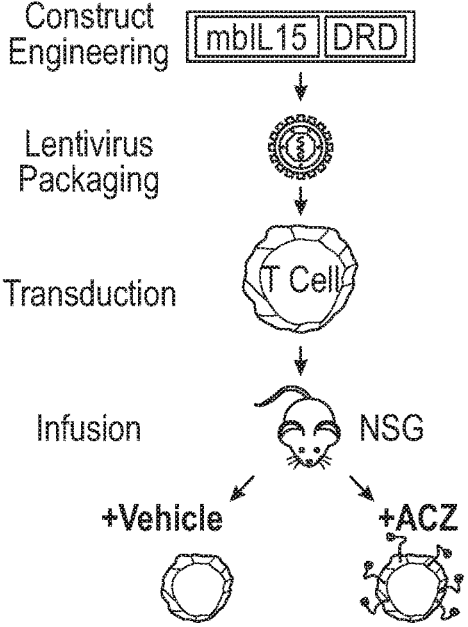
FIG. 2 depicts a representative procedure for in vivo characterization and/or validation of ACZ-regulated mbIL15 expression in T cells.

FIG. 2 depicts a representative procedure for in vivo characterization and/or validation of ACZ-regulated mbIL15 expression in T cells. As shown in FIG. 2, T cells may be transduced with an mbIL15 construct, for example, by following the procedures described in Example 1. Following transduction, T cells may be infused into a murine subject (e.g., an NSG mouse) and samples from mice treated with vehicle or ACZ may be assayed for IL15 expression and/or antigen-independent cell expansion, for example, by following the procedures described in Example 3.

Example 1. T Cell Transduction with Acetazolamide (ACZ)-Regulated mbIL15 Construct The present example demonstrates methods that may be used for preparing ACZ-regulated mbIL15 constructs and methods that may be used for transduction of T cells with ACZ-regulated mbIL15 constructs.

IL15 Construct Assembly

OT-IL15-292, OT-IL15-293, OT-IL15-294, and OT-IL15-295 were each constructed in a pELNS vector (a third-generation self-inactivating lentiviral expression vector) using standard molecular biology techniques. Gene fragments (Gblocks) encoding codon-optimized IL15, GS linker, B7-1 hinge, transmembrane domain and cytoplasmic tails were purchased from Integrated DNA Technologies, Inc. (IDT, Coralville, Iowa). The gene fragments were inserted into the pELNS vector and placed under the control of the EF1a promoter using Gibson assembly (NEBuilder Hifi). The assembled plasmid was transformed into E. coli (NEB stable) for amplification and sequence confirmed before proceeding with virus production.

Table 4 presents the nucleic acid and amino acid sequences for components of constitutive IL15 constructs (OT-IL15-292 and OT-IL15-294) and ACZ-regulated IL15 constructs (OT-IL15-293 and OT-IL15-295) disclosed herein. Bold and underlined amino acids in Table 4 indicate differences in the B7-1 cytoplasmic tail between constructs OT-IL15-292/OT-IL15-293 and OT-IL15-294/OT-IL15-295. Constructs OT-IL15-293 and OT-IL15-295 comprise a destabilizing domain labeled as CA2 (M1del, L156H) in Table 4.

TABLE 4

| Description | DNA Sequence | DNA NO. | AA Sequence | AA SEQ ID NO. |
|---|---|---|---|---|
| components of constitutive and ACZ-regulated IL15 constructs | | | | |
| Leader sequence | ATGGACATGCGGGTGCCTGCACAAC TTCTGGGCCTGCTGTTGTTGTGGCTG TCTGGAGCCCGGTGT | 7 | MDMRVPAQLLGLLLLWLSG ARC | 6 |
| IL15 | AATTGGGTAAATGTTATCAGTGATCTC AAGAAGATAGAGGATCTCATCCAGTC CATGCATATTGATGCCACGCTGTACA CAGAAAGCGATGTGCATCCTAGCTGT AAGGTGACAGCGATGAAGTGTTTTCT TTTGGAGCTGCAGGTAATTAGTCTTG AGTCCGGCGATGCCAGCATTCATGAT ACCGTAGAAAACTTGATTATCCTGGC CAACAATTCTCTGTCCTCAAACGGAA ACGTAACCGAGAGCGGTTGTAAAGAA TGTGAAGAACTGGAAGAAAAGAACAT CAAGGAGTTTCTGCAATCATTCGTTC ACATCGTACAAATGTTCATAAATACGT CA | 9 | NWVNVISDLKKIEDLIQSMHI DATLYTESDVHPSCKVTAM KCFLLELQVISLESGDASIHD TVENLIILANNSLSSNGNVTE SGCKECEELEEKNIKEFLQS FVHIVQMFINTS | 8 |
| Linker (GS)15 | GGATCTGGTTCTGGTTCCGGAAGTG GATCTGGTTCAGGGTCCGGTAGTGG ATCTGGGTCAGGAAGTGGAAGCGGT AGTGGGTCTGGATCT | 11 | GSGSGSGSGSGSGSGSGS GSGSGSGSGSGS | 10 |
| Hinge | AAACAAGAGCACTTTCCTGATAAC | 13 | KQEHFPDN | 12 |
| Transmembrane domain | CTGTTGCCGAGCTGGGCGATTACGC TTATCAGTGTAAACGGCATCTTTGTAA TATGCTGTCTG | 15 | LLPSWAITLISVNGIFVICCL | 14 |
| Intracellular tail (OT-IL15-292 and OT-IL15-293) | ACCTACTGCTTCGCACCAAGGTGCCG GGAGAGAAGGAGAAATGAAAGACTG AGAAGGGAGAGCGTGAGACCTGTG | 17 | TYCFAPRCRERRRNERLRR ESVRPV | 16 |
| Intracellular tail (OT-IL15-294 and OT-IL15-295) | ACCTACTGCTTCGCACCAAGGTGCCG GGAGAGAGCAAGAAATGAAAGACTG AGAAGGGAGAGCGTGAGACCTGTG | 19 | TYCFAPRCRER_A_RNERLRR E_T_VRPV | 18 |
| Linker (GS) | GGATCC | 21 | GS | 20 |
| CA2 (M1del, L156H) (OT-IL15-293 and OT-IL15-295) | TCCCATCACTGGGGGTACGGCAAAC ACAACGGACCTGAGCACTGGCATAA GGACTTCCCCATTGCCAAGGGAGAG CGCCAGTCCCCTGTTGACATCGACAC TCATACAGCCAAGTATGACCCTTCCC TGAAGCCCCTGTCTGTTTCCTATGAT CAAGCAACTTCCCTGAGAATCCTCAA CAATGGTCATGCTTTCAACGTGGAGT TTGATGACTCTCAGGACAAAGCAGTG CTCAAGGGAGGACCCCTGGATGGCA CTTACAGATTGATTCAGTTTCACTTTC ACTGGGGTCACTTGATGGACAAGGT TCAGAGCATACTGTGGATAAAAAGAA ATATGCTGCAGAACTTCACTTGGTTC ACTGGAACACCAAATATGGGGATTTT GGGAAAGCTGTGCAGCAACCTGATG GACTGGCCGTTCTAGGTATTTTTTTG AAGGTTGGCAGCGCTAAACCGGGCC ATCAGAAAGTTGTTGATGTGCTGGAT TCCATTAAAACAAAGGGCAAGAGTGC TGACTTCACTAACTTCGATCCTCGTG GCCTCCTTCCTGAATCCCTGGATTAC TGGACCTACCCAGGCTCACTGACCAC CCCTCCTCTTCTGGAATGTGTGACCT GGATTGTGCTCAAGGAACCCATCAGC GTCAGCAGCGAGCAGGTGTTGAAATT CCGTAAACTTAACTTCAATGGGGAGG GTGAACCCGAAGAACTGATGGTGGA CAACTGGCGCCCAGCTCAGCCACTG | 5 | SHHWGYGKHNGPEHWHKD FPIAKGERQSPVDIDTHTAK YDPSLKPLSVSYDQATSLRI LNNGHAFNVEFDDSQDKAV LKGGPLDGTYRLIQFHFHW GSLDGQGSEHTVDKKKYAA ELHLVHWNTKYGDFGKAVQ QPDGLAVLGIFLKVGSAKPG HQKVVDVLDSIKTKGKSADF TNFDPRGLLPESLDYWTYP GSLTTPPLLECVTWIVLKEPI SVSSEQVLKFRKLNFNGEG EPEELMVDNWRPAQPLKNR QIKASFK | 4 |

TABLE 4-continued

| | | | AA SEQ |
| --- | --- | --- | --- |
| | | DNA | ID |
| Description | DNA Sequence | NO.AA Sequence | NO. |
| | AAGAACAGGCAAATCAAAGCTTCCTT CAAA | | |

Table 5 presents the nucleic acid and amino acid sequences of the constitutive IL15 (IL15-292 and IL15-294) and ACZ-regulated IL15 (IL15-293 and IL15-295 constructs disclosed herein.

TABLE 5

Constitutive and ACZ-regulated IL15 constructs

| Descrip-tion | DNA Sequence | DNA SEQ | AA Sequence | AA SEQ |
| --- | --- | --- | --- | --- |
| IL15-292 | ATGGACATGCGGGTGCCTG CACAACTTCTGGGCCTGCTGTTGTT GTGGCTGTCTGGAGCCCGGTGTAAT TGGGTAAATGTTATCAGTGATCTCAA GAAGATAGAGGATCTCATCCAGTCC ATGCATATTGATGCCACGCTGTACA CAGAAAGCGATGTGCATCCTAGCTG TAAGGTGACAGCGATGAAGTGTTTT CTTTTGGAGCTGCAGGTAATTAGTCT TGAGTCCGGCGATGCCAGCATTCAT GATACCGTAGAAAACTTGATTATCCT GGCCAACAATTCTCTGTCCTCAAAC GGAAACGTAACCGAGAGCGGTTGTA AAGAATGTGAAGAACTGGAAGAAAA GAACATCAAGGAGTTTCTGCAATCAT TCGTTCACATCGTACAAATGTTCATA AATACGTCAGGATCTGGTTCTGGTT CCGGAAGTGGATCTGGTTCAGGGTC CGGTAGTGGATCTGGGTCAGGAAGT GGAAGCGGTAGTGGGTCTGGATCTA AACAAGAGCACTTTCCTGATAACCT GTTGCCGAGCTGGGCGATTACGCTT ATCAGTGTAAACGGCATCTTTGTAAT ATGCTGTCTGACCTACTGCTTCGCA CCAAGGTGCCGGGAGAGAAGGAGA AATGAAAGACTGAGAAGGGAGAGCG TGAGACCTGTGGGATCC | 23 | MDMRVPAQLLGLLLLWL SGARCNWVNVISDLKKIEDLIQSM HIDATLYTESDVHPSCKVTAMKCF LLELQVISLESGDASIHDTVENLIIL ANNSLSSNGNVTESGCKECEELE EKNIKEFLQSFVHIVQMFINTSGS GSGSGSGSGSGSGSGSGSGSG SGSGSGSKQEHFPDNLLPSWAIT LISVNGIFVICCLTYCFAPRCRERR RNERLRRESVRPVGS | 22 |
| IL15-293 | ATGGACATGCGGGTGCCTG CACAACTTCTGGGCCTGCTGTTGTT GTGGCTGTCTGGAGCCCGGTGTAAT TGGGTAAATGTTATCAGTGATCTCAA GAAGATAGAGGATCTCATCCAGTCC ATGCATATTGATGCCACGCTGTACA CAGAAAGCGATGTGCATCCTAGCTG TAAGGTGACAGCGATGAAGTGTTTT CTTTTGGAGCTGCAGGTAATTAGTCT TGAGTCCGGCGATGCCAGCATTCAT GATACCGTAGAAAACTTGATTATCCT GGCCAACAATTCTCTGTCCTCAAAC GGAAACGTAACCGAGAGCGGTTGTA AAGAATGTGAAGAACTGGAAGAAAA GAACATCAAGGAGTTTCTGCAATCAT TCGTTCACATCGTACAAATGTTCATA AATACGTCAGGATCTGGTTCTGGTT CCGGAAGTGGATCTGGTTCAGGGTC CGGTAGTGGATCTGGGTCAGGAAGT GGAAGCGGTAGTGGGTCTGGATCTA AACAAGAGCACTTTCCTGATAACCT GTTGCCGAGCTGGGCGATTACGCTT ATCAGTGTAAACGGCATCTTTGTAAT ATGCTGTCTGACCTACTGCTTCGCA CCAAGGTGCCGGGAGAGAAGGAGA AATGAAAGACTGAGAAGGGAGAGCG TGAGACCTGTGGGATCCTCCCATCA | 25 | MDMRVPAQLLGLLLLWL SGARCNWVNVISDLKKIEDLIQSM HIDATLYTESDVHPSCKVTAMKCF LLELQVISLESGDASIHDTVENLIIL ANNSLSSNGNVTESGCKECEELE EKNIKEFLQSFVHIVQMFINTSGS GSGSGSGSGSGSGSGSGSGSG SGSGSGSKQEHFPDNLLPSWAIT LISVNGIFVICCLTYCFAPRCRERR RNERLRRESVRPVGSSHHWGYG KHNGPEHWHKDFPIAKGERQSP VDIDTHTAKYDPSLKPLSVSYDQA TSLRILNNGHAFNVEFDDSQDKA VLKGGPLDGTYRLIQFHFHWGSL DGQGSEHTVDKKKYAAELHLVH WNTKYGDFGKAVQQPDGLAVLGI FLKVGSAKPGHQKVVDVLDSIKTK GKSADFTNFDPRGLLPESLDYWT YPGSLTTPPLLECVTWIVLKEPISV SSEQVLKFRKLNFNGEGEPEELM VDNWRPAQPLKNRQIKASFK | 24 |

TABLE 5-continued

| Description | DNA Sequence | DNA SEQ | AA Sequence | AA SEQ |
|---|---|---|---|---|

Constitutive and ACZ-regulated IL15 constructs

| Description | DNA Sequence | DNA SEQ | AA Sequence | AA SEQ |
|---|---|---|---|---|
| | CTGGGGGTACGGCAAACACAACGG ACCTGAGCACTGGCATAAGGACTTC CCCATTGCCAAGGGAGAGCGCCAG TCCCCTGTTGACATCGACACTCATA CAGCCAAGTATGACCCTTCCCTGAA GCCCCTGTCTGTTTCCTATGATCAA GCAACTTCCCTGAGAATCCTCAACA ATGGTCATGCTTTCAACGTGGAGTTT GATGACTCTCAGGACAAAGCAGTGC TCAAGGGAGGACCCCTGGATGGCA CTTACAGATTGATTCAGTTTCACTTT CACTGGGGTTCACTTGATGGACAAG GTTCAGAGCATACTGTGGATAAAAA GAAATATGCTGCAGAACTTCACTTG GTTCACTGGAACACCAAATATGGGG ATTTTGGGAAAGCTGTGCAGCAACC TGATGGACTGGCCGTTCTAGGTATT TTTTTGAAGGTTGGCAGCGCTAAAC CGGGCCATCAGAAAGTTGTTGATGT GCTGGATTCCATTAAAACAAAGGGC AAGAGTGCTGACTTCACTAACTTCG ATCCTCGTGGCCTCCTTCCTGAATC CCTGGATTACTGGACCTACCCAGGC TCACTGACCACCCCTCCTCTTCTGG AATGTGTGACCTGGATTGTGCTCAA GGAACCCATCAGCGTCAGCAGCGA GCAGGTGTTGAAATTCCGTAAACTTA ACTTCAATGGGGAGGGTGAACCCGA AGAACTGATGGTGGACAACTGGCGC CCAGCTCAGCCACTGAAGAACAGGC AAATCAAAGCTTCCTTCAAA | | | |
| IL15-294 | ATGGACATGCGGGTGCCTG CACAACTTCTGGGCCTGCTGTTGTT GTGGCTGTCTGGAGCCCGGTGTAAT TGGGTAAATGTTATCAGTGATCTCAA GAAGATAGAGGATCTCATCCAGTCC ATGCATATTGATGCCACGCTGTACA CAGAAAGCGATGTGCATCCTAGCTG TAAGGTGACAGCGATGAAGTGTTTT CTTTTGGAGCTGCAGGTAATTAGTCT TGAGTCCGGCGATGCCAGCATTCAT GATACCGTAGAAAACTTGATTATCCT GGCCAACAATTCTCTGTCCTCAAAC GGAAACGTAACCGAGAGCGGTTGTA AGAATGTGAAGAACTGGAAGAAAA GAACATCAAGGAGTTTCTGCAATCAT TCGTTCACATCGTACAAATGTTCATA AATACGTCAGGATCTGGTTCTGGTT CCGGAAGTGGATCTGGTTCAGGGTC CGGTAGTGGATCTGGGTCAGGAAGT GGAAGCGGTAGTGGGTCTGGATCTA AACAAGAGCACTTTCCTGATAACCTT GTTGCCGAGCTGGGCGATTACGCTT ATCAGTGTAAACGGCATCTTTGTAAT ATGCTGTCTGACCTACTGCTTCGCA CCAAGGTGCCGGGAGAGAGCAAGA AATGAAAGACTGAGAAGGGAGACCG TGAGACCTGTGGGATCC | 27 | MDMRVPAQLLGLLLLWL SGARCNWVNVISDLKKIEDLIQSM HIDATLYTESDVHPSCKVTAMKCF LLELQVISLESGDASIHDTVENLIIL ANNSLSSNGNVTESGCKECEELE EKNIKEFLQSFVHIVQMFINTSGS GSGSGSGSGSGSGSGSGSGSGSG SGSGSGSKQEHFPDNLLPSWAIT LISVNGIFVICCLTYCFAPRCRERA RNERLRRETVRPVGS | 26 |
| IL15-295 | ATGGACATGCGGGTGCCTG CACAACTTCTGGGCCTGCTGTTGTT GTGGCTGTCTGGAGCCCGGTGTAAT TGGGTAAATGTTATCAGTGATCTCAA GAAGATAGAGGATCTCATCCAGTCC ATGCATATTGATGCCACGCTGTACA CAGAAAGCGATGTGCATCCTAGCTG TAAGGTGACAGCGATGAAGTGTTTT CTTTTGGAGCTGCAGGTAATTAGTCT TGAGTCCGGCGATGCCAGCATTCAT GATACCGTAGAAAACTTGATTATCCT GGCCAACAATTCTCTGTCCTCAAAC GGAAACGTAACCGAGAGCGGTTGTA AGAATGTGAAGAACTGGAAGAAAA GAACATCAAGGAGTTTCTGCAATCAT | 29 | MDMRVPAQLLGLLLLWL SGARCNWVNVISDLKKIEDLIQSM HIDATLYTESDVHPSCKVTAMKCF LLELQVISLESGDASIHDTVENLIIL ANNSLSSNGNVTESGCKECEELE EKNIKEFLQSFVHIVQMFINTSGS GSGSGSGSGSGSGSGSGSGSGSG SGSGSGSKQEHFPDNLLPSWAIT LISVNGIFVICCLTYCFAPRCRERA RNERLRRETVRPVGSSHHWGYG KHNGPEHWHKDFPIAKGERQSP VDIDTHTAKYDPSLKPLSVSYDQA TSLRILNNGHAFNVEFDDSQDKA VLKGGPLDGTYRLIQFHFHWGSL DGQGSEHTVDKKKYAAELHLVH | 28 |

TABLE 5-continued

Constitutive and ACZ-regulated IL15 constructs

| Descrip-tion | DNA Sequence | DNA SEQ | AA Sequence | AA SEQ |
|---|---|---|---|---|
| | TCGTTCACATCGTACAAATGTTCATA | | WNTKYGDFGKAVQQPDGLAVLGI | |
| | AATACGTCAGGATCTGGTTCTGGTT | | FLKVGSAKPGHQKVVDVLDSIKTK | |
| | CCGGAAGTGGATCTGGTTCAGGGTC | | GKSADFTNFDPRGLLPESLDYWT | |
| | CGGTAGTGGATCTGGGTCAGGAAGT | | YPGSLTTPPLLECVTWIVLKEPISV | |
| | GGAAGCGGTAGTGGGTCTGGATCTA | | SSEQVLKFRKLNFNGEGEPEELM | |
| | AACAAGAGCACTTTCCTGATAACCT | | VDNWRPAQPLKNRQIKASFK | |
| | GTTGCCGAGCTGGGCGATTACGCTT | | | |
| | ATCAGTGTAAACGGCATCTTTGTAAT | | | |
| | ATGCTGTCTGACCTACTGCTTCGCA | | | |
| | CCAAGGTGCCGGGAGAGAGCAAGA | | | |
| | AATGAAAGACTGAGAAGGGAGACCG | | | |
| | TGAGACCTGTGGGATCCTCCCATCA | | | |
| | CTGGGGGTACGGCAAACACAACGG | | | |
| | ACCTGAGCACTGGCATAAGGACTTC | | | |
| | CCCATTGCCAAGGGAGAGCGCCAG | | | |
| | TCCCCTGTTGACATCGACACTCATA | | | |
| | CAGCCAAGTATGACCCTTCCCTGAA | | | |
| | GCCCCTGTCTGTTTCCTATGATCAA | | | |
| | GCAACTTCCCTGAGAATCCTCAACA | | | |
| | ATGGTCATGCTTTCAACGTGGAGTTT | | | |
| | GATGACTCTCAGGACAAAGCAGTGC | | | |
| | TCAAGGGAGGACCCCTGGATGGCA | | | |
| | CTTACAGATTGATTCAGTTTCACTTT | | | |
| | CACTGGGGTTCACTTGATGGACAAG | | | |
| | GTTCAGAGCATACTGTGGATAAAAA | | | |
| | GAAATATGCTGCAGAACTTCACTTG | | | |
| | GTTCACTGGAACACCAAATATGGGG | | | |
| | ATTTTGGGAAAGCTGTGCAGCAACC | | | |
| | TGATGGACTGGCCGTTCTAGGTATT | | | |
| | TTTTTGAAGGTTGGCAGCGCTAAAC | | | |
| | CGGGCCATCAGAAAGTTGTTGATGT | | | |
| | GCTGGATTCCATTAAAACAAAGGGC | | | |
| | AAGAGTGCTGACTTCACTAACTTCG | | | |
| | ATCCTCGTGGCCTCCTTCCTGAATC | | | |
| | CCTGGATTACTGGACCTACCCAGGC | | | |
| | TCACTGACCACCCCTCCTCTTCTGG | | | |
| | AATGTGTGACCTGGATTGTGCTCAA | | | |
| | GGAACCCATCAGCGTCAGCAGCGA | | | |
| | GCAGGTGTTGAAATTCCGTAAACTTA | | | |
| | ACTTCAATGGGGAGGGTGAACCCGA | | | |
| | AGAACTGATGGTGGACAACTGGCGC | | | |
| | CCAGCTCAGCCACTGAAGAACAGGC | | | |
| | AAATCAAAGCTTCCTTCAAA | | | |

Lentivirus Production

HEK293T cells were seeded on collagen coated tissue culture plates until 70% confluent. Cells were transfected with pELNS transfer vector carrying constitutive (IL15-292 or IL15-294) or regulated (IL15-293 or IL15-295) IL15 constructs, as well as packaging plasmids (pRSV.REV, pMDLg/p.RRE and pMD2.G) using Lipofectamine 3000 transfection reagent in Opti-MEM media. Media was replaced 6-8 hrs post-transfection with serum-free media. Supernatants containing virus were harvested 24 hr post-transfection, fresh media was added, and supernatants were harvested again at 48 hr post-transfection. Viral supernatants were filtered to remove debris and concentrated by ultracentrifugation in 20% sucrose gradient. Virus were resuspended, aliquoted and stored at −80 C freezer.

The nucleotide sequences of the pELNS transfer vectors OT-IL15-292, OT-IL15-293, OT-IL15-294 and OT-IL15-295 are SEQ ID NO: 34, SEQ ID NO: 35, SEQ ID NO: 36 and SEQ ID NO: 37, respectively.

As used herein, the lentiviruses used to transduce cells are referred to by their construct name (e.g., IL15-292, IL15-293, IL15-294, IL15-295, CD19-IL15-057, CD19-IL15-058 or CD19-063) or their transfer vector name (e.g., OT-IL15-292, OT-IL15-293, OT-IL15-294, OT-IL15-295, OT-CD19-IL15-057, OT-CD19-IL15-058 or OT-CD19-063).

T Cell Stocks

T cells were isolated from Leukopaks collected from human healthy donors. After PBMC isolation with Ficoll gradients, T cells were isolated using negative selection kit (StemCell Technologies) according to manufacturer's protocol. T cells were resuspended in cell freezing media (Bambanker), aliquoted and stored in liquid nitrogen.

Lentivirus Transduction of T Cells

T cells were thawed, cells were washed and counted. T cells were mixed with CD3/CD28 beads (Invitrogen cat #11141D) at 3:1 bead to T cell ratio. 5×10[5] cells/well were added to 24-well plates in 500 μL media. Cells were activated for 24 hrs. Next day, lentivirus was thawed and added to each well at different volumes. After 24 hrs, 500 μL of fresh media was added to wells, and cells were expanded by adding equal volume of fresh media every 2-3 days to keep cell density at 0.5-1×10[6]/mL. Cells were analyzed by flow cytometry to confirm expression on day 5 or 6. Cells were expanded for 9-10 days.

Example 2. In Vitro Analysis of ACZ-Regulated mbIL15 Expression and ACZ-Regulated T Cell Expansion The present example demonstrates in vitro validation of (i) ACZ-regulated mbIL15 expression in T cells and (ii) ACZ-regulated expansion of T cells expressing ACZ-regulated mbIL15.

Human primary T cells capable of expressing constitutive mbIL15 or ACZ-regulated mbIL15 were prepared in accordance with methods described in Example 1 above. See FIG. 1.

After T cell transduction and expansion, CD3/CD28 beads were removed using magnets, cells were washed twice, resuspended in fresh media and counted. Cells were plated in 12-well plates at $1\times10^6$ in 2 mL. One well of untransduced cells was cultured in the presence of 2 ng/mL IL15 as a control. T cells expressing regulated constructs were cultured in the absence or presence of acetazolamide (ACZ, 30, 10, 3, 1, 0.3 µM). Cell numbers were monitored by flow cytometry every 3-4 days and cells were cultured for 10-12 days. At each time point 100 µL of cells were collected from wells and analyzed by flow cytometry. Cells were split as needed. Cell cultures were maintained in 12-well plates by taking a portion and adding media in a new plate. Volumes for each well were recorded before and after split to calculate final volume in cell number assessment. IL15 or ACZ were replenished at final concentration of the fresh media added during each split. See FIG. 1.

Figure 3A:
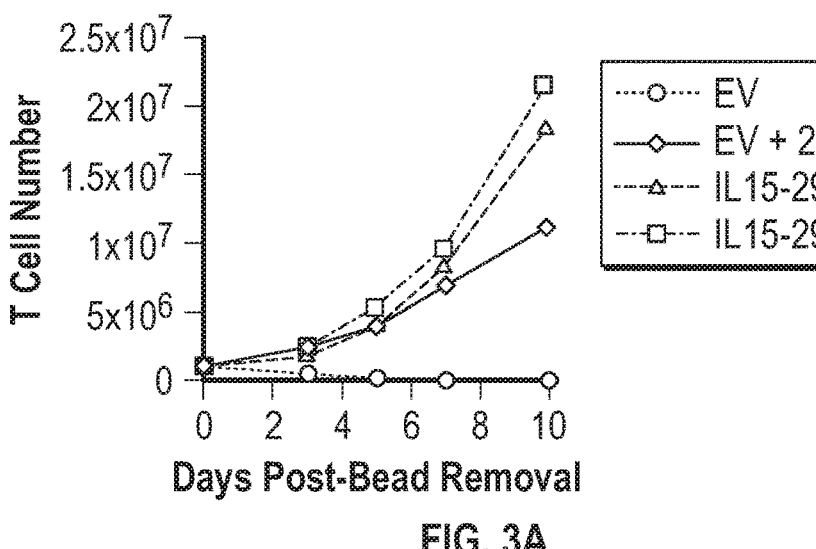
FIG. 3A-FIG. 3C shows in vitro expansion of T cells expressing constitutive IL15-292 and IL15-294 (FIG. 3A), and regulated IL15-293 (FIG. 3B) and IL15-295 (FIG. 3C) constructs in the presence of different concentrations of ACZ. Empty vector (EV) transduced cells cultured in the absence or presence of exogenous IL15 (2 ng/mL) were used as controls.
Figure 3B:
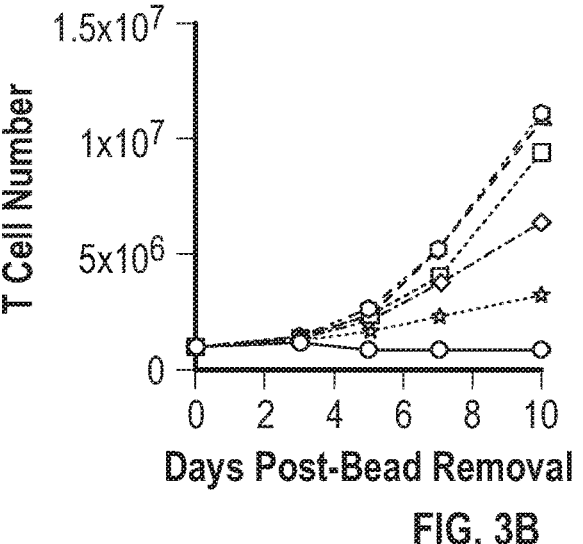
Figure 3C:
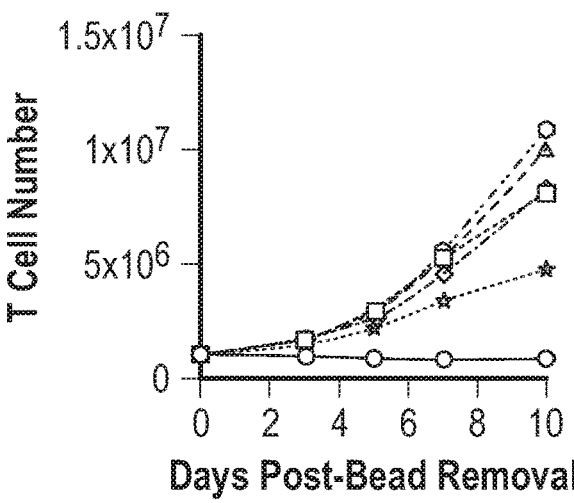
Figure 3C:

T cell numbers were determined by flow cytometry. Empty vector (EV) transduced cell numbers decreased to background levels between 3-5 days in the absence of IL15, and cells expanded 11-fold in the presence of 2 ng/mL exogenous IL15 (FIG. 3A). T cells expressing constitutive IL15-292 and IL15-294 expanded between 18 and 21-fold, respectively, in 10 days (FIG. 3A). In T cells expressing IL15-293, maximum expansion was 9.5-11× with 30, 10, 3 µM (FIG. 3B). At the lowest concentration tested (0.3 µM), cells expanded 3.3×. These cells survived longer (0.8×) compared to EV cells without drug treatment (0.8×). In T cells expressing IL15-295, maximum expansion was 8.2-10× with 30, 10, 3 µM and cells expanded 4.9× at the lowest concentration (0.3 µM) tested (FIG. 3C). Without drug treatment, these cells survived (0.9×) longer compared to EV.

Figure 4A:
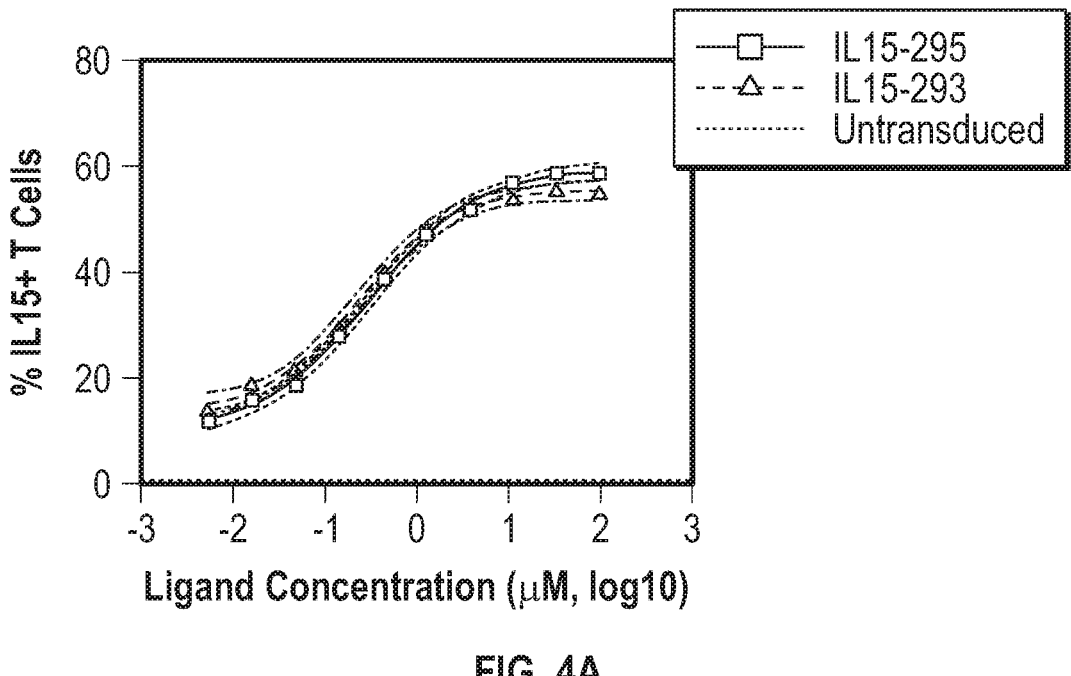
FIG. 4A-FIG. 4B shows acetazolamide dose response and IL15 expression on T cells. Cells were treated with different concentrations of ACZ (ligand) starting at 100 $\mu$M for 24 hrs. Graphs show % IL15+ T Cells (FIG. 4A) and mean fluorescence intensity (MFI) of IL15 (FIG. 4B).
Figure 4B:
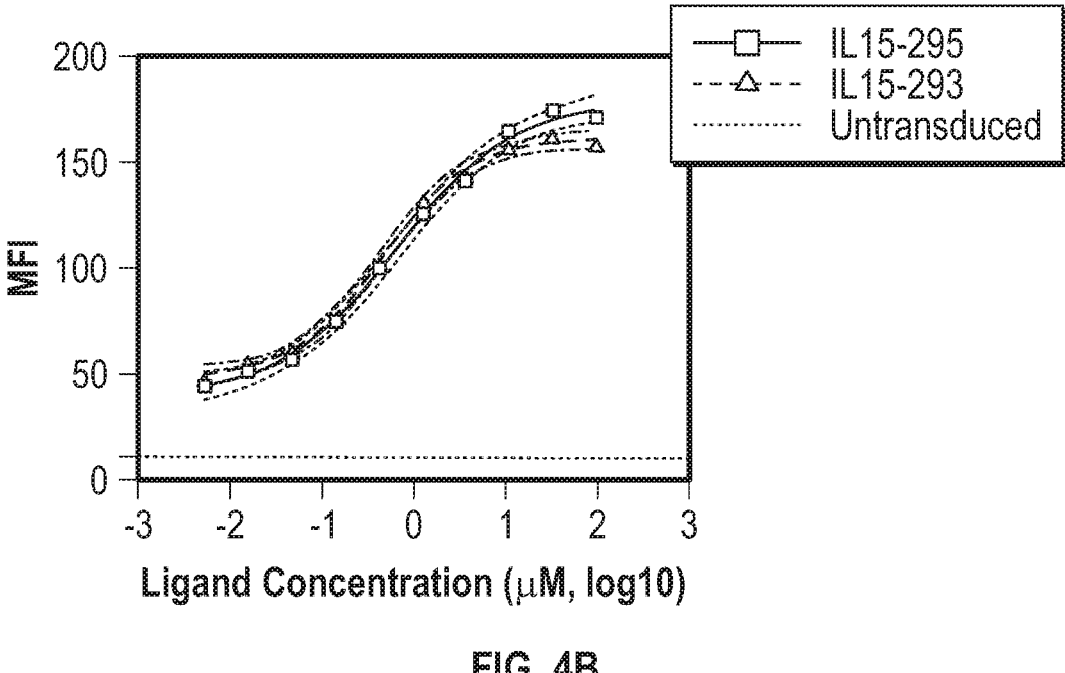

The effect of different concentrations of ACZ on IL15 expression was tested. T cells were treated with ACZ for 24 hrs starting at 100 µM, diluted 3-fold for 9 points. Both % IL15+ T Cells (FIG. 4A) and IL15 Mean Fluorescence Intensity (MFI) (FIG. 4B) analysis indicated similar dose curves for OT-IL15-293 and OT-IL15-295. There was 4-5-fold increase in expression (both % IL15+ T cells and IL15 MFI) between highest and lowest concentrations of ACZ. $EC_{50}$ values were 0.29 µM and 0.22 µM EC50 based on % IL15+ T Cells, 0.65 µM and 0.44 µM based on MFI of IL15 for OT-IL15-293 and OT-IL15-295, respectively.

Example 3. In Vivo Analysis of ACZ-Regulated mbIL15 Expression and ACZ-Regulated T Cell Expansion The present example demonstrates in vivo validation of (i) ACZ-regulated mbIL15 expression in T cells and (ii) ACZ-regulated expansion of T cells expressing ACZ-regulated mbIL15.

NK Cell Expansion

A portion of the PBMCs isolated from Leukopaks were used to enrich NK cells using negative selection kits (StemCell Technologies) according to manufacturer's protocol. Cells were cultured in 1:1 ratio with feeder K562 cells expressing 4-1BB-L and membrane-bound IL21, and recombinant IL2 (100 U/mL) for 7-14 days. Expansion was monitored by cell counts and purity was evaluated by flow cytometry.

In Vivo Analysis

Human primary T cells capable of expressing constitutive mbIL15 or ACZ-regulated mbIL15 were prepared in accordance with methods described in Example 1 above. After T cell transduction and expansion, CD3/CD28 beads were removed using magnets, cells were washed twice, resuspended in fresh media and counted. T cells were mixed with expanded NK cells and each animal received $5\times10^6$ T cells and $2\times10^6$ expanded NK cells. Cells were infused by intravenous injections into NSG mice. Animals infused with T cells expressing regulated constructs were dosed daily with 200 mg/kg ACZ or vehicle by PO injections. Every 3-4 days, 50 µL blood was analyzed by flow cytometry for presence of T cells and NK cells using antibodies against mouse and human CD45, CD3 and CD56. IL15 expression on day 25 was analyzed using IL15Ra-Fc and fluorochrome conjugated anti-human IgG antibody. See FIG. 2.

Figure 5A:
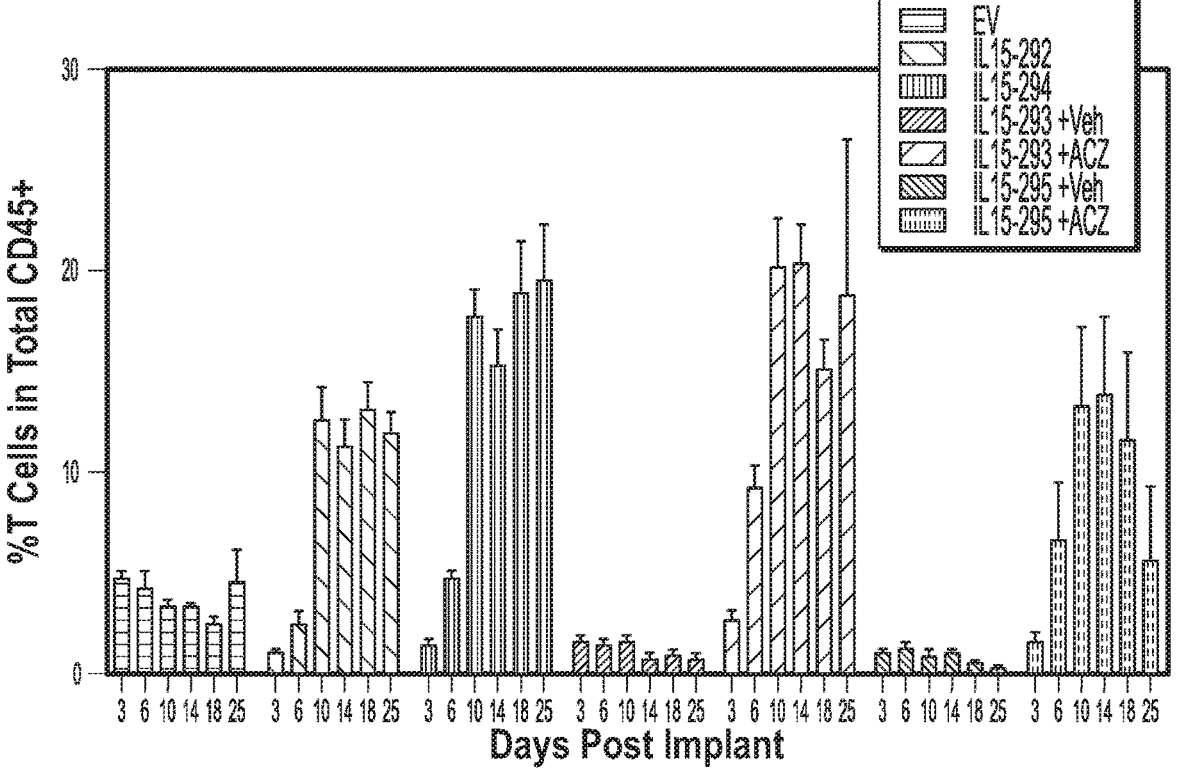
FIG. 5A-FIG. 5C shows in vivo analyses of T cells expressing constitutive and regulated IL15 constructs and their effects on NK cells.
Figure 5B:
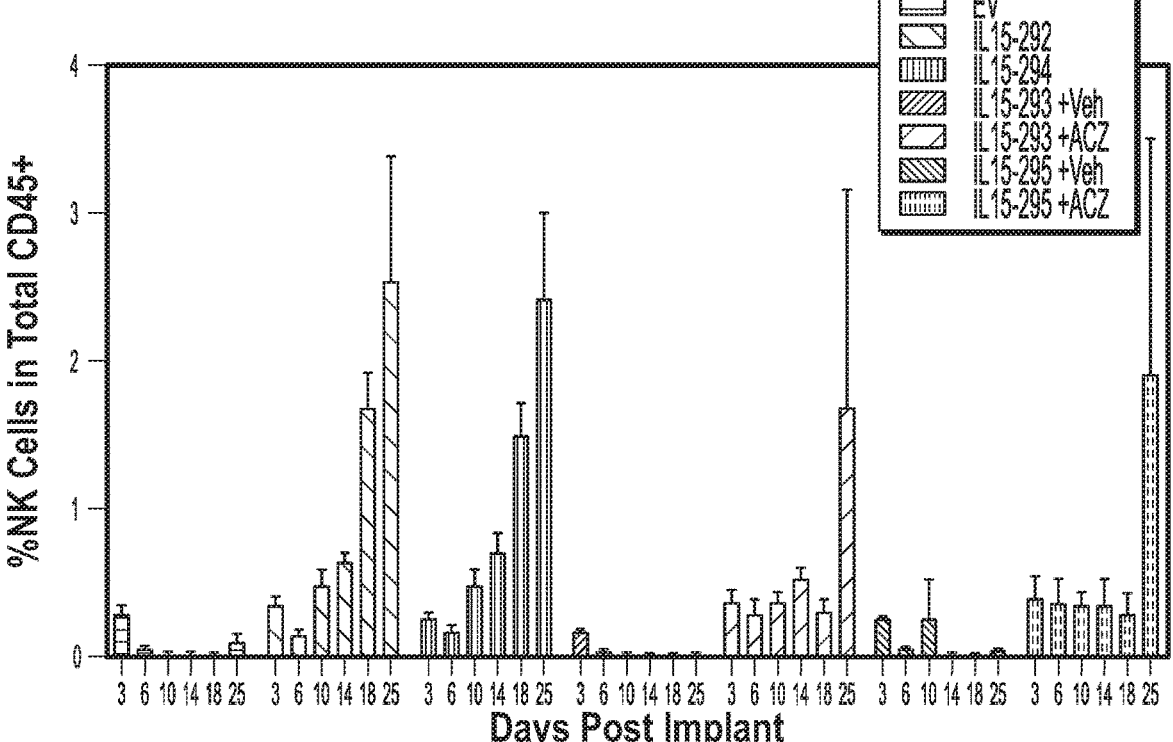

Expansion of T cells expressing constitutive and regulated IL15 constructs, and their effects on bystander NK cells were evaluated in vivo in NSG mice over a course of 25 days (FIG. 5A-FIG. 5B). Empty vector (EV) transduced cell numbers slowly declined over time. T cells expressing constitutive IL15-292 and IL15-294 expanded up to 13× compared to the frequencies on day 3. In mice infused with T cells expressing regulated constructs, cell frequencies decreased in the presence of vehicle treatment. In groups treated with daily ACZ, cells expanded up to 7-8× compared to the frequencies on day 3. Bystander NK cells survived and expanded in the presence of T cells expressing constitutive IL15 constructs, or in the presence of T cells expressing regulated IL15 constructs treated daily with ACZ.

Figures 5C, 6:
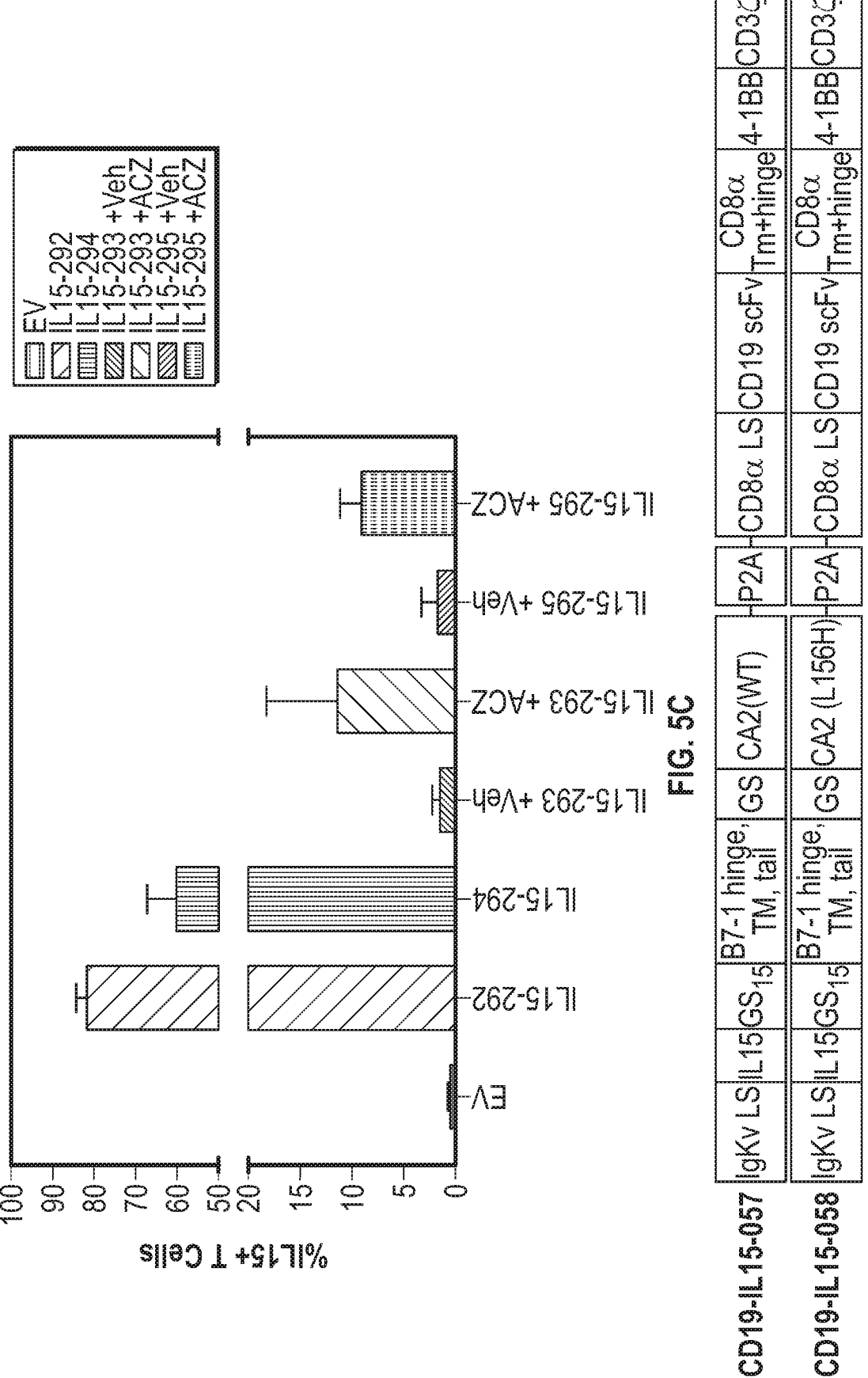
FIG. 6 depicts schematic representations of tandem CD19 CAR and mbIL15 constructs encoding a constitutively expressed mbIL15 (CD19-IL15-057) or a regulated mbIL15 (CD19-IL15-058). Each construct comprises polynucleotide sequences encoding a regulated or constitutive mbIL15 that comprises an IgKv leader sequence (IgKv LS), an IL15 polypeptide component, a GS linker, a B7-1 hinge, a transmembrane domain (TM), and a tail. The constitutive construct encodes the mbIL15 operably linked to a CA2 wild-type sequence (CA2 (WT)). The regulated construct encodes the mbIL15 operably linked to a CA2(L156H) DRD. Each construct also comprises a P2A sequence and polynucleotide sequences encoding an anti-CD19 CAR that comprises a CD8$\alpha$ leader sequence (CD8$\alpha$ LS), a CD19 scFv, a CD8$\alpha$ transmembrane domain and hinge, a costimulatory domain derived from 4-1BB and a CD3$\zeta$ signaling domain.

IL15 expression on T cells in vivo on day 25 was analyzed by flow cytometry (FIG. 5C). T cells transduced with constitutive constructs IL15-292 and IL15-294 expressed high levels of IL15 (82% and 61%). IL15 expression was <1.5% in vehicle-treated IL15-293 and IL15-295 as well as EV groups. IL15 expression levels were 11% and 9% on T cells transduced with IL15-293 and IL15-295 in groups treated with ACZ.

Example 4: In Vivo Analysis of Efficacy and Expansion in CART Cells Expressing Constitutive and Regulated mbIL15

The present example demonstrates that regulated mbIL15 coupled to ACZ dosing enhances anti-tumor efficacy and expansion of CD19 CART cells in the presence of CD19-positive tumors.

Generation of Tandem CD19 CAR and mbIL15 Constructs and Lentivirus Stocks

Lentiviral vector constructs and lentivirus stocks that co-express CD19 CAR and mbIL15 were generated essentially as described in Example 1. A CD19 CAR sequence (AA sequence: SEQ ID NO: 38; NA sequence: SEQ ID NO: 39) was constructed consisting of a CD8a leader sequence (aa1-21 in Uniprot ID P01732), FMC63 (anti-CD19) single chain variable fragment (scFv), a hinge and transmembrane domain derived from CD8 (aa138-206 in Uniprot ID P01732), a costimulatory domain derived from 4-1BB (aa214-255 in Uniprot ID Q07011) and CD3zeta signaling domains (aa52-164 in Uniprot IDP20963).

The bicistronic transgene expression cassette (5' to 3' as described) was comprised of a regulated or constitutive mbIL15, a P2A sequence (AA sequence: SEQ ID NO: 40; NA sequence: SEQ ID NO: 41), and the anti-CD19 CAR downstream from the P2A (see FIG. 6). For the regulated construct (CD19-IL15-058; AA Sequence: SEQ ID NO: 42; NA Sequence: SEQ ID NO: 43), the IL15-293 construct comprising mbIL15 operably linked to the CA2(L156H) DRD was used (AA sequence: SEQ ID NO: 24, NA sequence: SEQ ID NO: 25). For the constitutive construct (CD19-IL15-057; AA Sequence: SEQ ID NO: 45; NA Sequence: SEQ ID NO: 46), a construct comprising mbIL15 operably linked to the CA2 wildtype sequence was used (See FIG. 6). The nucleotide sequence of lentivirus OT-CD19-IL15-058 is SEQ ID NO:44; the nucleotide sequence of lentivirus OT-CD19-IL15-057 is SEQ ID NO:45.

Expression of mbIL15-CAR Constructs in Peripheral Blood T Cells

Figure 7A:
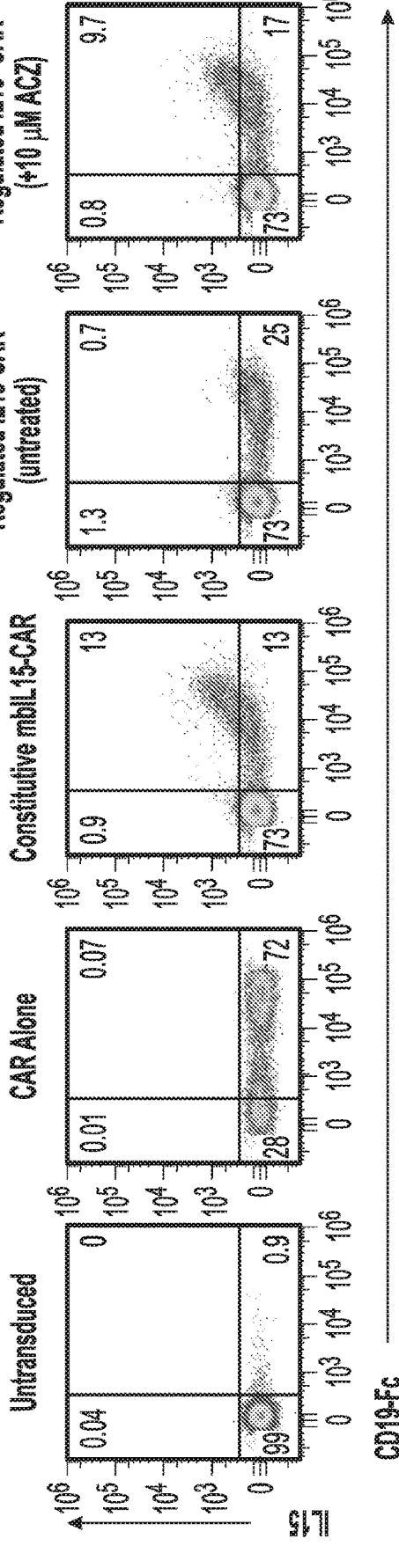
FIG. 7A-FIG. 7E show T cells transduced with tandem CD19 CAR and mbIL15 constructs evaluated for regulated mbIL15 expression and anti-tumor effects in vivo.

Peripheral blood T cells were activated, transduced, expanded for up to 10 days, and frozen in cell freezing medium essentially as described in Example 1 to be used in the in vivo human Nalm6-Luc xenograft tumor model. mbIL15 and CAR expression were analyzed by flow cytometry using anti-IL15 antibody and recombinant protein comprised of the extracellular domain of human CD19 fused to human IgG1 Fc domain (CD19-Fc), respectively. CD19 CAR-only transduced cell or untransduced cells were used as controls. 72% of cells transduced with control CD19 CAR construct were CAR+mbIL15– (FIG. 7A). For cells transduced with lentiviral vector expressing constitutive mbIL15 and CAR (CD19-IL15-057), 26% of the cells were CAR+ and 13% were double positive for CAR+mbIL15+. For cells transduced with vector expressing regulated mbIL15 and CAR (CD19-IL15-058), 25% were CAR+mbIL15– in the absence of ACZ and 9.7% were CAR+mbIL15+ double positive after a 24-hr exposure to 10 µM ACZ. These results confirmed expression of both CAR and mbIL15 after transduction of T cells with lentiviral vector expressing CD19CAR in combination with constitutive or regulated mbIL15.

Evaluation of mbIL15-CART Cells in Nalm6-Luc Xenograft Model

To evaluate the effect of mbIL15 on anti-tumor activity of CART cells, T cells that were transduced with lentiviral vectors expressing CD19 CAR with or without constitutive or regulated mbIL15 were infused into mice after implantation of CD19+ Nalm6-Luc tumors. CD19+ Nalm6 cells expressing luciferase (Nalm6-Luc) were injected by intravenous route (1×10⁶/mouse) into NSG mice and tumor growth was measured once or twice per week by bioluminescence imaging measurement (total flux units in photons per second (p/s)) after intraperitoneal injections of D-luciferin. On day 6, animals were randomized into new cages (N=8 for each group) when average tumor size reached approximately 10⁶ total p/s. CD19 CART cells (engineered with or without constitutive or regulated mbIL15) were thawed for infusion into tumor bearing mice. CAR expression in T cells was determined post-thaw and after 24-hr restimulation with anti-CD3/CD28 beads. CART cells across different groups were normalized based on % CAR+ cells. Each mouse received 0.3×10⁶ CAR+ cells and the total number of T cells in the infusion product was adjusted to 7×10⁶ T cells by addition of EV-transduced T cells.

The first group received T cells engineered with EV as a negative control, the second group received control CART cells without mbIL15 (CD19-063; AA Sequence: SEQ ID NO: 48; NA Sequence: SEQ ID NO: 49; vector sequence: SEQ ID NO: 50) and the third group received CART cells expressing constitutive mbIL5 (CD19-IL15-057). Groups 4 and 5 received CART cells that co-expressed regulated mbIL15 (CD19-IL15-058), and while one group was treated daily PO with 200 mg/kg ACZ, the other group was treated daily with vehicle until the end of the study (~50 days). To monitor T cell expansion, additional animals were included in each group (n=4 for blood, and n=4 for bone marrow). Blood (50 µL) was withdrawn from submandibular veins on days 7, 14, and 21, and bone marrow (from femur) was harvested on day 14 after T cell infusion. Red blood cells were lysed, stained with fluorochrome-conjugated antibodies against human CD45, CD3 and mouse CD45, and cells were analyzed by flow cytometry. Tumor growth was measured up to 55 days after tumor implantation; endpoints included 10¹⁰ total flux units as well as effects on animal health such as hind-limb paralysis and decrease in body weight.

Figure 7B:
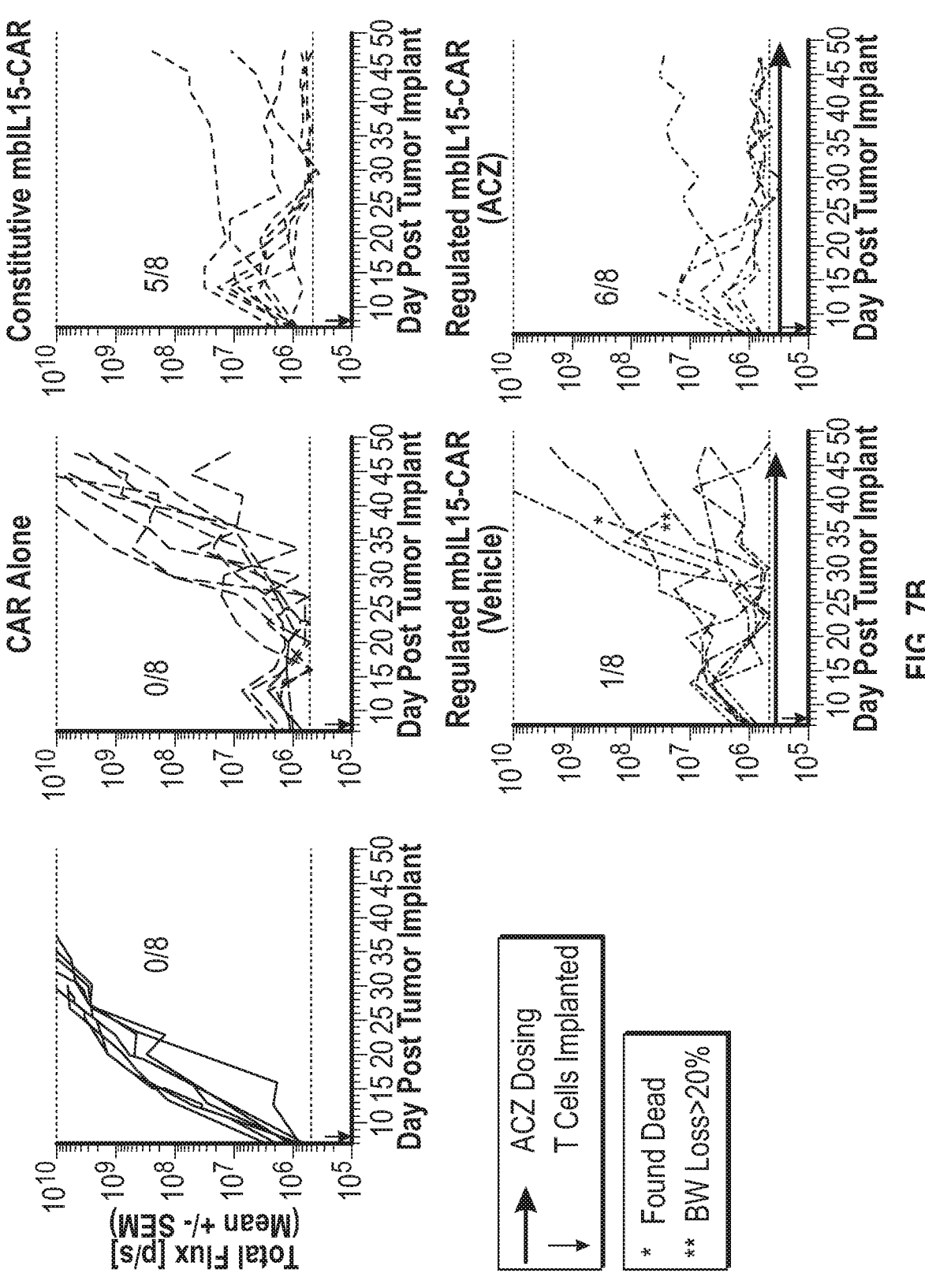
Figure 7C:
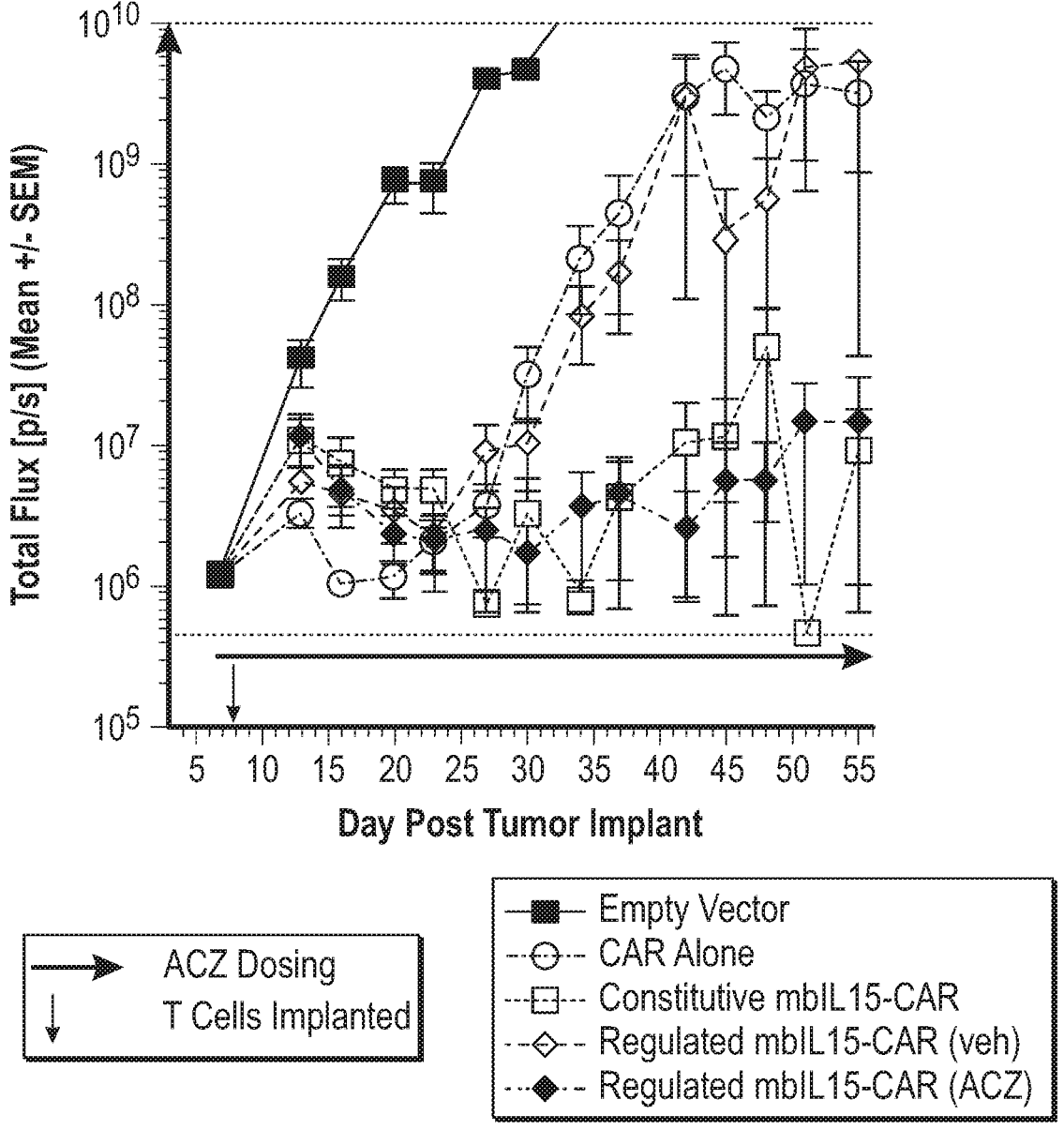
Figure 7D:
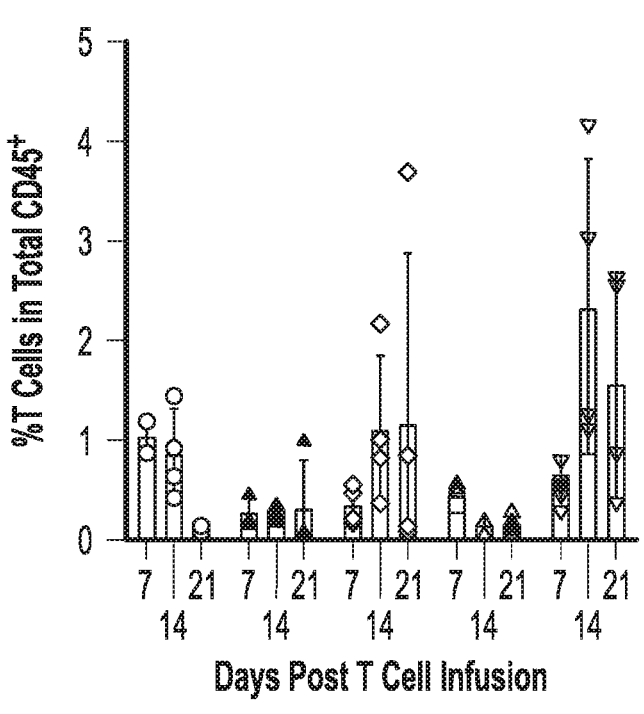
Figure 7E:
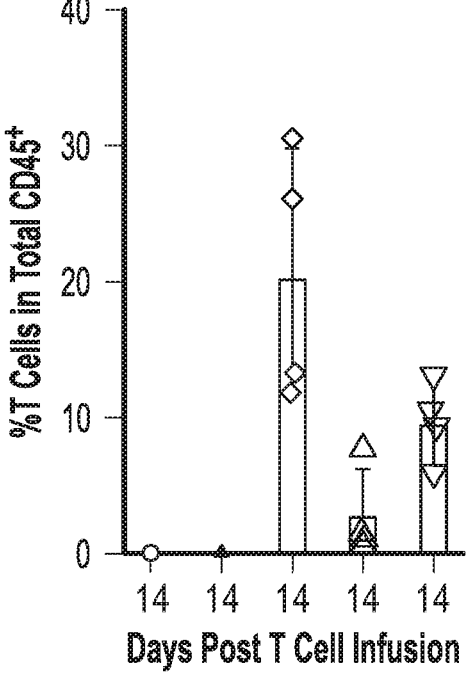

Tumor growth in individual mice in each group is shown in FIG. 7B and group averages are shown in FIG. 7C. Rapid tumor growth was observed in all animals in group 2 treated with EV-transduced T cells, and tumor growth was delayed up to ~25 days upon treatment with control CART cells with no complete response. Tumor growth rate in mice treated with CART cells expressing regulated mbIL15 and vehicle treatment were similar to control CART group. In contrast, tumors regressed to background levels in 5 and 6 of 8 animals in groups treated with CART cells expressing constitutive mbIL15 and CART cells expressing regulated mbIL15 plus ACZ, respectively. T cells numbers were reduced over time in blood (<0.2% on day 21, FIG. 7D) and were low in bone marrow (<1% on day 14, FIG. 7E) from mice treated with control T cells, control CART, and CART expressing regulated mbIL15 with vehicle treatment. In contrast, in mice treated with CART expressing constitutive mbIL15 or regulated mbIL15 with ACZ, T cell numbers increased in blood over time (>1% on day 21, FIG. 7D) and were high in bone marrow (20% for constitutive, 10% for regulated plus ACZ, FIG. 7E). These results demonstrate that regulated mbIL15 coupled to ACZ treatment enhanced CART anti-tumor responses compared to T cells expressing CAR alone after infusion of a suboptimal CART cell dose, and promoted CAR engineered T cell expansion post-tumor clearance.

Example 5: Isolation of TIL From Patient Tumor Samples

Head and neck tumor samples were obtained from Cooperative Human Tissue Network. Tumor samples were cut into 1-3 mm fragments in Hanks' Balanced Salt Solution (HBSS) buffer and fragments were placed in 24-well plates at 1 fragment/well in 2 ml of culture media (RPMI-1640 supplemented with 1× Penicillin/Streptomycin, 1 mM Sodium Pyruvate, 1× HEPES, 50 µM 2-Mercaptoethanol (Invitrogen) and 10% heat-inactivated human AB serum (Valley Bio)) containing 6000 IU/mL IL2. Half of the media was replaced with fresh media containing IL2 starting on day 5 and cells were split into multiple wells as they became confluent for a duration of 3 weeks. This culture process is referred to as pre-rapid expansion protocol (REP). TIL from other tumor types have been isolated using essentially the same process.

Figure 8A:
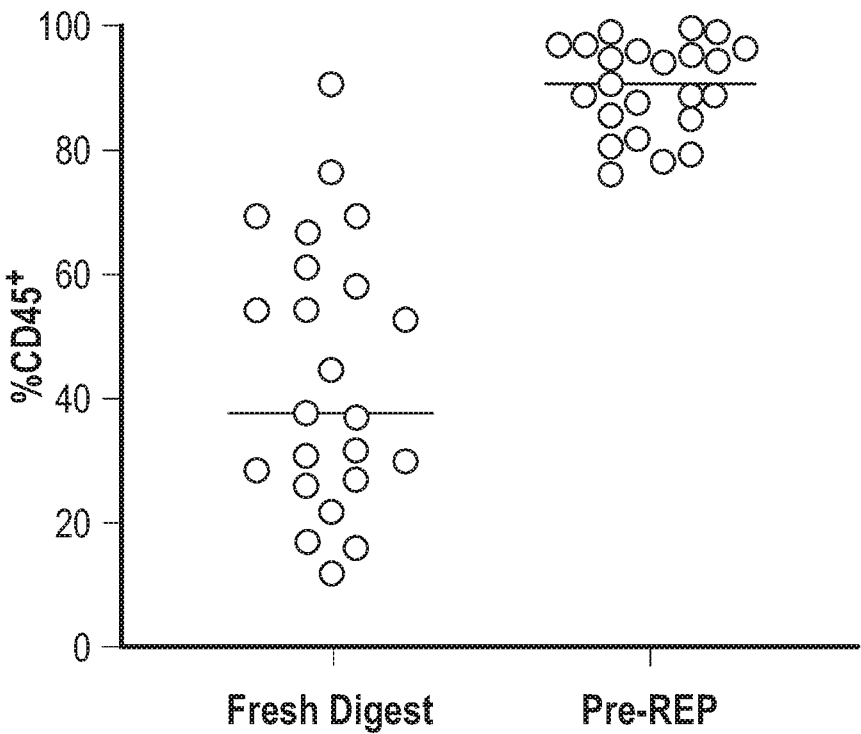
FIG. 8A shows frequency of CD45$^+$ cells (top) and CD3$^+$ T cells within CD45$^+$ cells (bottom) in fresh tumor digest and after 3 weeks of pre-REP TIL culture.
Figure 8A:
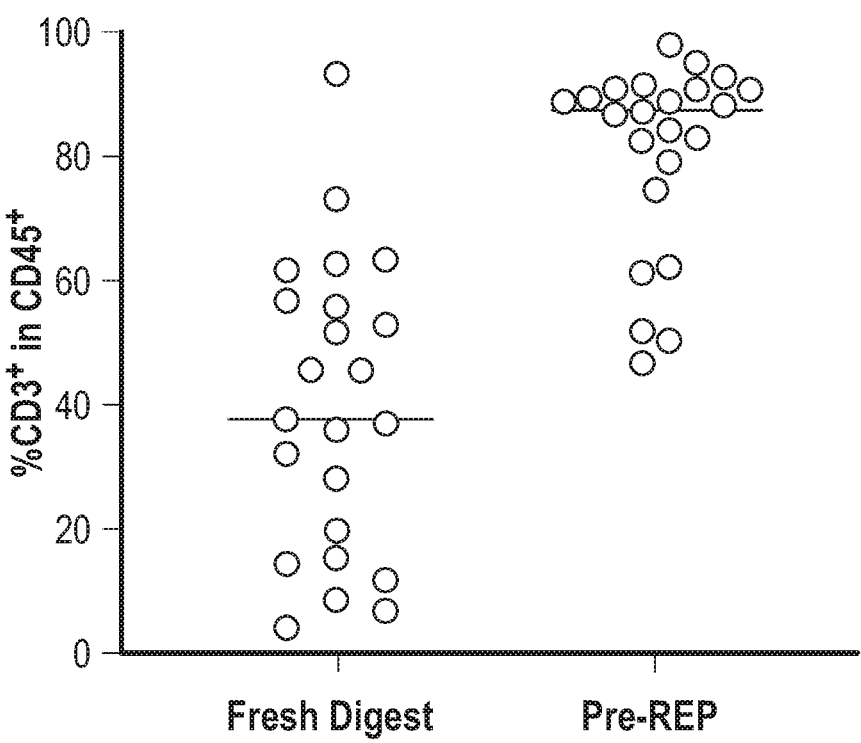

In order to determine the change in frequency of T cells before and after pre-REP culture, a portion of tumor fragments were digested with collagenase and DNase I to generate single cell suspension prior to the pre-REP culture and compared to cells obtained after the pre-REP culture. Frequency of T cells were analyzed by flow cytometry using fluorochrome conjugated anti-CD45 and anti-CD3 antibodies. As shown in FIG. 8A, nearly half of the cells (44.29±21.67%) in the pre-culture tumor cell suspension were CD45+ and among these only ~39.85±23.69% were CD3+ T cells. After 3 weeks of culture in the presence of IL2 (pre-REP), the majority of the cells were CD45+ (90.35±7.28%), indicating an enrichment of hematopoietic cells, and CD3+(80.64±15.19%), indicating an enrichment of T cells.

TIL from numerous other human tumor types, including melanoma tumors and malignant tumors from breast, lung, kidney, endometrium, liver, pancreas and ovary, have been isolated in the same manner.

Figure 8B:
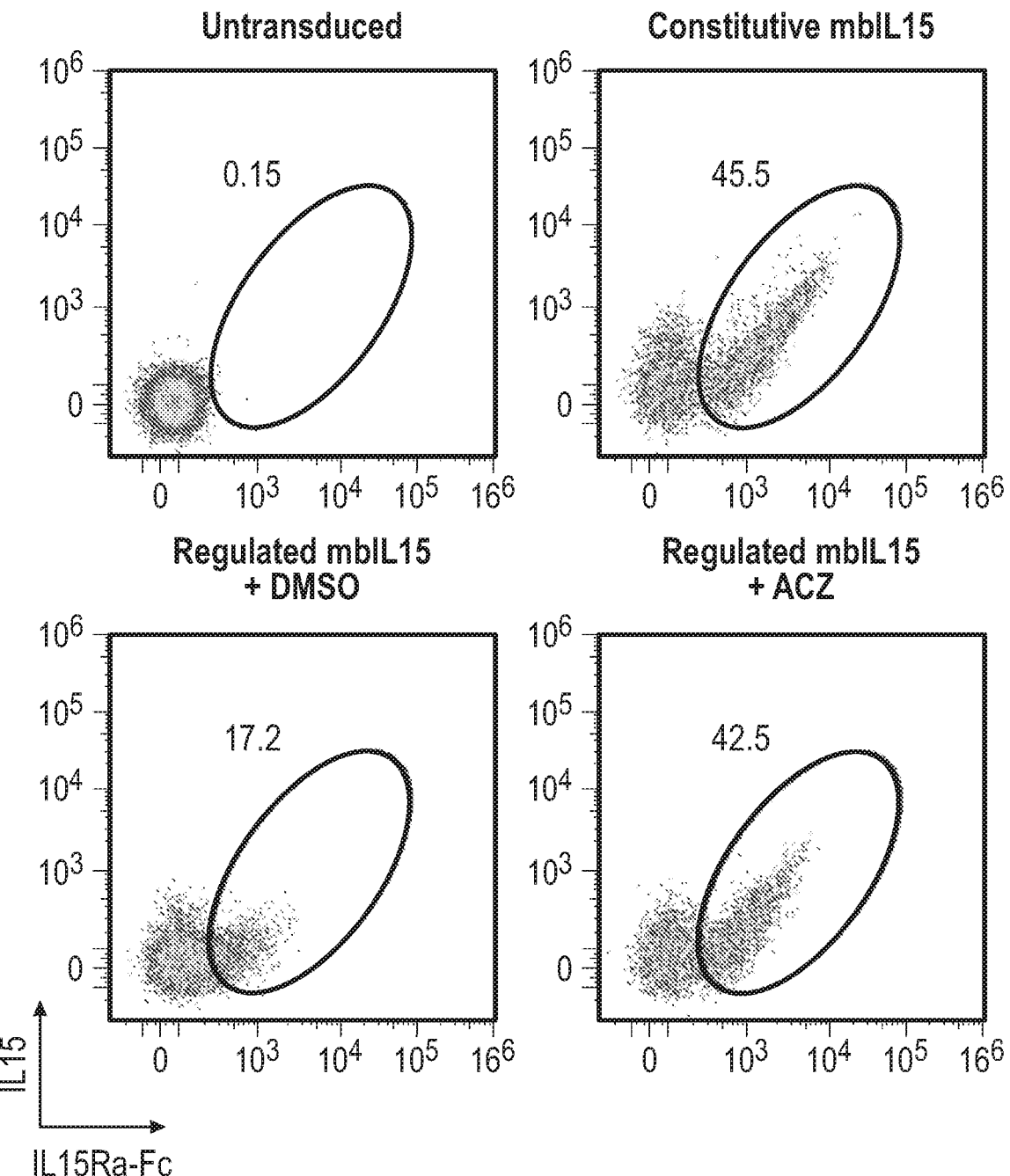
FIG. 8B shows mbIL15 expression determined by flow cytometry for TILs transduced with constitutive or regulated mbIL15 constructs. TILs transduced with the regulated mbIL15 construct were treated with 10 $\mu$M ACZ or DMSO for 24 hrs. Untransduced cells were evaluated as a negative control.

Example 6. In Vitro Analysis of Regulated mbIL15 Expression by ACZ in TIL BaEV-Pseudotyped Lentivirus Production HEK293T cells were seeded on collagen coated tissue culture plates until 70% confluent. Cells were transfected with pELNS transfer vector carrying constitutive (IL15-292) or regulated (IL15-293) IL15 constructs, as well as packaging plasmids (pRSV.REV, pMDLg/pRRE and OT-BaEVg-002 (SEQ ID NO: 51)) using Lipofectamine 3000 transfection reagent in Opti-MEM media. Media was replaced 6-8 hrs post-transfection with serum-free media. Supernatants containing virus were harvested 24 hr post-transfection, fresh media was added, and supernatants were harvested again at 48 hr post-transfection. Viral supernatants were filtered to remove debris and concentrated by low speed ultracentrifugation. Virus were resuspended, aliquoted and stored at −80 C freezer.
Transduction of TIL with Lentivirus 96-well non-coated tissue culture plates were incubated with 35 µg per mL RetroNectin (Takara Bio) in PBS for 2 h at 37° C. or overnight at 4° C. RetroNectin was removed and the plates washed with PBS. BaEV-pseudotyped lentivirus, prepared as described above, and TIL cell media, at a total volume of 50 µL per well, were added to each well and the plates were centrifuged at low speed for 2 hours at 32° C. TIL generated from a head and neck tumor sample prepared as described in Example 5 were engineered after 3 weeks in the pre-REP culture. TIL were activated for 24 hrs in 24-well plates with anti-CD3/CD28 beads at 3:1 bead to T cell ratio. Activated TIL were placed in virus-coated plates and centrifuged at 800 g for 2 hrs and incubated at 37° C. for 4 days in culture media. One well of cells was processed similarly without virus addition and used as negative control ("untransduced"). Cells that were transduced with the regulated mbIL15 construct were treated either with 10 µM ACZ or DMSO for 24 hrs.
Expression of Regulated mbIL15 in TIL in Response to ACZ mbIL15 expression was determined by flow cytometry using two staining reagents: fluorochrome-conjugated anti-IL15 antibody as well as a recombinant protein comprised of extracellular domain of IL15Ra fused to human IgG1 Fc domain (IL15Ra-Fc). mbIL15+ cell frequency was determined based on co-staining with anti-IL15 and IL15Ra-Fc (identified as the IL15+IL15Ra-Fc+ double positive population). As shown in FIG. 8B, 45.5% of TIL expressed constitutive mbIL15 (IL15-292). In the presence of DMSO, regulated mbIL15 (IL15-293) expression was 17.1% with low MFI. In contrast, in the presence of ACZ, regulated mbIL15 expression increased to 42.5% with high MFI. These data indicate that ACZ induces CA2 DRD-regulated mbIL15 in transduced TIL.

Example 7: In Vivo Analysis of TIL Expressing Constitutive and Regulated mbIL15

To evaluate the effect of regulated mbIL15 on the antitumor activity of tumor infiltrating lymphocytes (TIL), a human PDX (hPDX) model is used. TIL are isolated from a patient tumor sample, for example, a head and neck tumor sample, as described in Example 6. TIL are transduced with BaEV-pseudotyped lentiviral vectors containing either the IL15-292 construct or the IL15-293 construct, as described in Example 6, or with BaEV-pseudotyped lentiviral empty vector (EV), and then optionally frozen. TIL-matched patient-derived xenografts (hPDX) from the tumor sample are established via subcutaneous implant into the right flank of NSG mice. Tumor growth is measured once or twice per week using calipers. On study start, tumors are measured, and mice are randomized and placed in cohorts based on similar mean tumor volume across all groups into new cages (N=8 for each group). The engineered matched TIL are thawed if necessary, stimulated with PMA, and then infused into the tumor-bearing mice. Each mouse receives an equal number of engineered TIL.

Group 1 receives untransduced TIL supplemented with recombinant human IL2 (hIL2) as benchmark control, and group 2 receives TIL transduced with constitutive mbIL15 (IL15-292). Groups 3 and 4 receive TIL transduced with regulated mbIL15 (IL15-293). Group 3 is treated daily PO with 200 mg/kg ACZ, and group 4 is treated daily with vehicle until the end of the study. To monitor TIL persistence, additional animals are included in each group (n=4 for blood). Blood (50 µL) was withdrawn from submandibular veins on pre-determined days. Red blood cells are lysed, stained with fluorochrome-conjugated antibodies against human CD45, CD3 and mouse CD45, and cells are analyzed by flow cytometry. Tumor growth is measured for up to approximately 90 days; endpoints include maximal caliper measurements as well as effects on animal health, such as tumor necrosis and decrease in body weight.

Tumor growth in individual mice in each group is followed and group averages are collected. Delayed tumor growth is expected in animals in group 1 treated with untransduced TIL plus hIL2. No tumor growth inhibition will be observed in group 4 because little or no mbIL15 will be expressed by the TIL. In contrast, tumors will substantially regress, in some cases to baseline, in groups 2 and 3 because both groups have TIL expressing mbIL15, which will enhance their persistence and correlated anti-tumor activity.

Example 8: Isolation of NK Cells from Cord Blood

Cryopreserved mononuclear cell-fractionated cord blood units were obtained from BioBridge Global. Cord blood was diluted 1:1 with phosphate-buffered saline (PBS) and centrifuged over a cushion of Ficoll-Paque+(Sigma Cat. No. GE17-1440-02). The buffy coat comprising mononuclear cells (MNC) was collected, and the MNC were washed and counted. NK cells were isolated from MNC using EasySep Human NK Cell Isolation Kit (Stemcell Technologies Cat.

No. 17955). NK cells were counted and checked for purity by FACS using CD56, CD16, CD3 and viability stain.

Example 9: In Vitro Analysis of Regulated mbIL15 Expression by ACZ in NK Cells NK Cell Expansion One day prior to NK cell isolation as described in Example 8, feeder cells (K562 cells expressing 4-1BBL and mbIL-21) were thawed in complete NK cell media (RPMI with Glutamax (ThermoFisher), 10% heat-inactivated fetal bovine serum (Gibco), 1× Penicillin/Streptomycin, 1 mM Sodium Pyruvate, 1×HEPES, 50 μM 2-Mercaptoethanol). On the day of NK cell isolation, $10×10^6$ feeder cells were treated with mitomycin C to inhibit their proliferation and washed to remove excess drug. NK cells were added to the feeder cells at a 1:2 effector to target ratio in NK cell media with 200 U/mL recombinant human IL2 (rhIL2; PeproTech). NK cell cultures were expanded by replenishing cell cultures with NK cell media and rhIL2 every two days, and analyzed by FACS for NK cell expansion.

Transduction of NK Cells with Lentivirus 96-well non-coated tissue culture plates were incubated with 35 μg per mL RetroNectin (Takara Bio) in PBS for 2 h at 37° C. or overnight at 4° C. RetroNectin was removed and the plates washed with PBS. BaEV-pseudotyped lentivirus, prepared as described in Example 6, and NK cell media, at a total volume of 50 μL per well, were added to each well and the plates were centrifuged at low speed for 2 hours at 32° C. $1×10^5$ NK cells in 100 μL NK cell transduction media (NK cell media with 1 mg/mL Synperonic F 108 (Sigma-Aldrich) and 200 U/mL rhIL2) were added to each well and the cells were expanded for four days in NK cell media.

Regulation of mbIL15 Construct with ACZ

Figure 9:
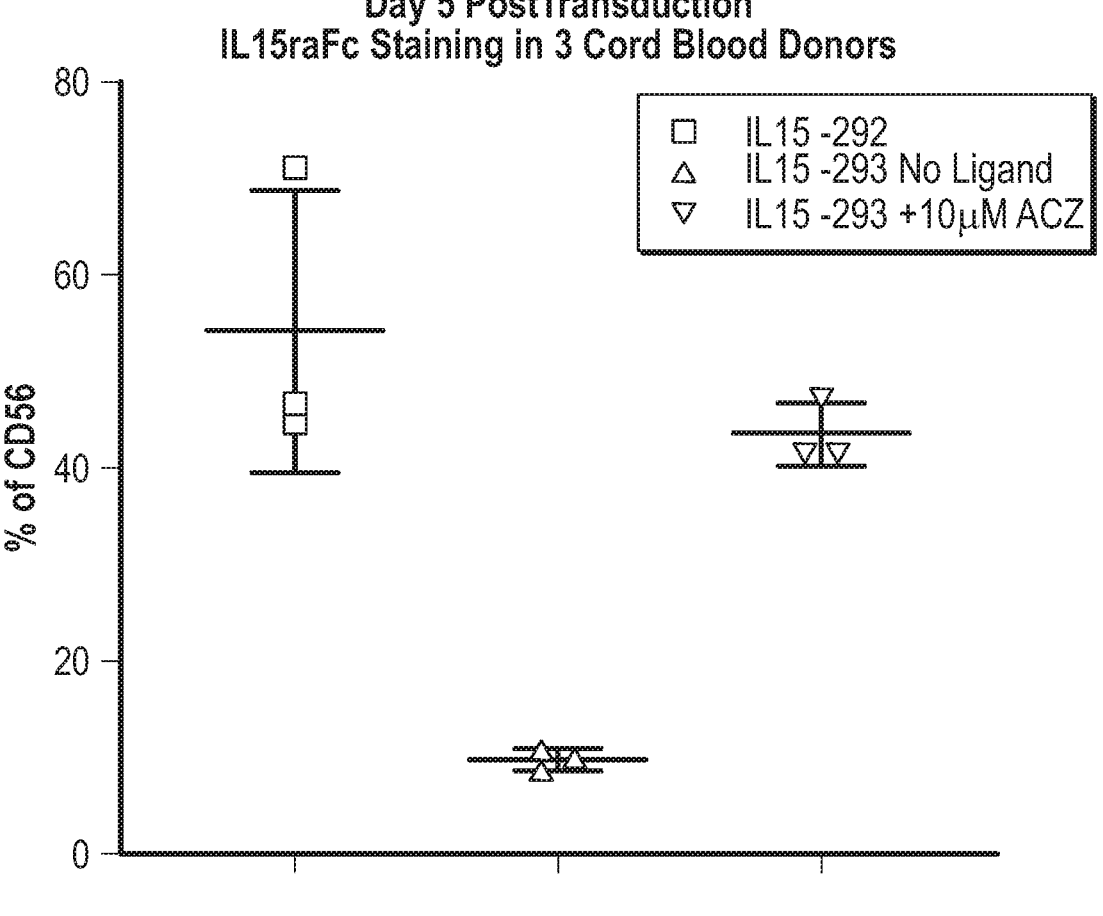
FIG. 9 shows expression of constitutive and regulated mbIL15 in NK cells. Each symbol on the graph (squares and triangles) represents one of three donors. Error bars represent standard deviation for the three donors for each indicated transduction/treatment group.

NK cells from three different donors were isolated, expanded and transduced with BaEV-pseudotyped lentivirus containing either the IL15-292 construct or the IL15-293 construct. The titer of the IL15-292 lentivirus was $2.38×10^8$ TU/mL while the titer for the IL15-293 lentivirus was $6.51×10^8$ TU/mL (as measured by a Jurkat qPCR titer), and 4 μL lentivirus and 46 μL NK cell media were added to each well. After cells were expanded for four days, 10 ACZ or vehicle (DMSO) was added and the cells were incubated overnight. Expression of mbIL15 was anayzed via FACS the following day (five days post-transduction).

mbIL15 expression was determined by flow cytometry using two staining reagents: IL15Ra-Fc and an anti-CD56 antibody. mbIL15+ cell frequency was determined relative to the number of NK cells as determined by the anti-CD56 antibody. As shown in FIG. 9, greater than 40% of cord blood-derived NK cells from two of the three donors expressed mbIL15, and approximately 70% of cord blood-derived NK cells from one of the three donors expressed mbIL15. In the presence of DMSO, regulated mbIL15 expression was 10% or less in NK cells regardless of donor. In contrast, in the presence of ACZ, regulated mbIL15 expression increased to greater than 40% in NK cells regardless of donor. These data indicate that ACZ induces CA2 DRD-regulated mbIL15 in transduced NK.

Example 10: In Vivo Analysis of NK Cells Expressing Constitutive and Regulated mbIL15

To evaluate the effect of regulated mbIL15 on the anti-tumor activity of NK cells, an HL-60 animal model of acute myeloid leukemia is used. Cord blood NK cells are transduced with BaEV-pseudotyped lentiviral vectors containing either the IL15-292 construct or the IL15-293 construct, as described in Example 9, or with BaEV-pseudotyped lentiviral empty vector (EV), and optionally frozen after transduction. HL-60 cells expressing luciferase (HL-60-luc) are injected intravenously ($1×10^6$/mouse) into NSG mice and tumor growth is measured once or twice per week by bioluminescence imaging measurement (total flux units in photons per second (p/s) after intraperitoneal injections of D-luciferin). On day 6, animals are randomized into new cages (N=8 for each group) when average tumor size reaches approximately $10^6$ total p/s. The engineered NK cells are thawed if necessary and infused into the HL-60 tumor-bearing mice. Each mouse receives an equal number of mbIL15+ cells and the total number of NK cells in the infusion product is adjusted by addition of EV-transduced NK cells.

Group 1 receives NK cells engineered with EV as a negative control, and group 2 receives NK cells transduced with constitutive mbIL5 (construct IL15-292). Groups 3 and 4 receive NK cells transduced with regulated mbIL15 (construct IL15-293). Group 3 is treated daily PO with 200 mg/kg ACZ, and group 4 is treated daily with vehicle until the end of the study. To monitor NK expansion, additional animals are included in each group (n=4 for blood analyses). Blood (50 μL) is withdrawn from submandibular veins on days 7, 14, and 21. Red blood cells are lysed, stained with fluorochrome-conjugated antibodies against human CD45, CD3 and mouse CD45, and cells are analyzed by flow cytometry. Tumor growth is measured up to approximately 30 days; endpoints include maximal total flux units ($10^{10}$) as well as effects on animal health such as hind-limb paralysis and decrease in body weight.

Tumor growth in individual mice in each group is measured and group averages are collected. Rapid tumor growth is expected in all animals in group 1 infused with EV-transduced NK cells. Tumor growth rate in group 4 mice will be similar to the control EV group because little or no mbIL15 will be expressed. In contrast, tumors will regress substantially in groups 2 and 3 because both groups of mice express mbIL15 on NK cells such that these cells will exhibit higher expansion and persistence compared to NK cells from groups 1 and 4. This example will demonstrate that ACZ can induce expression in vivo of mbIL15 in transduced NK cells, leading to enhanced NK anti-tumor responses, compared to transduced vehicle-treated NK cells that express little or no mbIL15.

In the foregoing detailed description, the invention has been described with reference to specific embodiments. However, it may be appreciated that various modifications and changes can be made without departing from the scope of the invention as set forth in the appended claims.

The following Items are illustrative of various embodiments of the present disclosure.

Item 1. A nucleic acid molecule comprising a polynucleotide encoding a recombinant protein comprising a drug responsive domain (DRD) operably linked to an IL15 payload, wherein said DRD is derived from human carbonic anhydrase II (CA2) and comprises one, two, three, four or more mutations relative to SEQ ID NO:1 or SEQ ID NO:2.

Item 2. The nucleic acid molecule of Item 1, wherein the DRD comprises one, two, three or four amino acid additions, substitutions and/or deletions relative to SEQ ID NO:1 or SEQ ID NO:2.

Item 3. The nucleic acid molecule of Item 2, wherein the DRD comprises the amino acid sequence of SEQ ID NO:4.

Item 4. The nucleic acid molecule of Item 3, wherein the DRD consists of the amino acid sequence of SEQ ID NO:4.

Item 5. The nucleic acid molecule of any of Items 1-4, wherein the IL15 payload comprises the amino acid sequence of SEQ ID NO:8.

Item 6. The nucleic acid molecule of any one of Items 1-5, wherein the IL15 payload is N-terminal to the DRD.

Item 7. The nucleic acid molecule of Item 6, wherein the IL15 payload is a membrane-bound IL15 polypeptide.

Item 8. The nucleic acid molecule of Item 7, wherein the membrane-bound IL15 polypeptide comprises an IL15 polypeptide component comprising the amino acid sequence of SEQ ID NO:8, a transmembrane domain and an intracellular tail, wherein the transmembrane domain is C-terminal to the IL15 polypeptide component and the intracellular tail is C-terminal to the transmembrane domain.

Item 9. The nucleic acid molecule of Item 8, wherein the membrane-bound IL15 polypeptide further comprises a linker between the IL15 polypeptide component and the transmembrane domain.

Item 10. The nucleic acid molecule of any one of Items 1-7, wherein the IL15 payload further comprises one or more components selected from the group consisting of: (a) a leader sequence; (b) a GS linker; (c) a hinge domain; (d) a transmembrane domain; and (e) an intracellular tail.

Item 11. The nucleic acid molecule of any one of Items 1-7, wherein the IL15 payload further comprises: (a) a leader sequence; (b) a GS linker; (c) a hinge domain; (d) a transmembrane domain; and (e) an intracellular tail.

Item 12. The nucleic acid molecule of Item 11, wherein the polynucleotide encodes the amino acid sequence of SEQ ID NO:24.

Item 13. The nucleic acid molecule of Item 12, wherein the polynucleotide comprises the nucleic acid sequence of SEQ ID NO:25.

Item 14. The nucleic acid molecule of Item 11, wherein the polynucleotide encodes the amino acid sequence of SEQ ID NO:28.

Item 15. The nucleic acid molecule of Item 14, wherein the polynucleotide comprises the nucleic acid sequence of SEQ ID NO:29.

Item 16. The nucleic acid molecule of any one of Items 1-15, wherein the nucleic acid molecule further comprises a second polynucleotide encoding a chimeric antigen receptor (CAR) or T cell receptor (TCR), wherein the CAR or TCR comprises an antigen-binding domain specific to an antigen of interest.

Item 17. The nucleic acid molecule of Item 16, wherein the second polynucleotide encodes a CAR comprising an antigen-binding domain specific to an antigen of interest.

Item 18. The nucleic acid molecule of Item 17, wherein the CAR comprises an antigen-binding domain specific to CD19.

Item 19. A vector comprising the nucleic acid molecule of any one of Items 1-19.

Item 20. The vector of Item 19, wherein the vector is a plasmid or a viral vector.

Item 21. The vector of Item 20, wherein the vector is a viral vector derived from an adenovirus, adeno-associated virus (AAV), alphavirus, flavivirus, herpes virus, measles virus, rhabdovirus, retrovirus, lentivirus, Newcastle disease virus (NDV), poxvirus, or picornavirus.

Item 22. The vector of Item 21, wherein the viral vector is selected from a lentiviral vector, adenoviral vector, AAV vector, herpes simplex viral vector, retroviral vector or oncolytic viral vector.

Item 23. The vector of Item 22, wherein the viral vector is selected from a lentiviral vector or a gamma retroviral vector.

Item 24. A recombinant protein encoded by the nucleic acid molecule of any one of Items 1-15.

Item 25. A cell comprising the nucleic acid molecule of any one of Items 1-18, the vector of any one of Items 18-23, or the recombinant protein of Item 24.

Item 26. The cell of Item 25, wherein the cell is a bacterial cell.

Item 27. The cell of Item 25, wherein the cell is a mammalian cell.

Item 28. The cell of Item 27, wherein the mammalian cell is a human cell.

Item 29. The cell of Item 28, wherein the human cell is a T cell, natural killer (NK) cell, or tumor infiltrating lymphocyte (TIL).

Item 30. The cell of Item 29, wherein the cell is a CD4+ or CD8+ T cell.

Item 31. The cell of Item 29, wherein the cell is isolated.

Item 32. The cell of Item 29, wherein the human cell is a T cell or an NK cell, and wherein the human T cell or the human NK cell further comprises a second polynucleotide encoding a chimeric antigen receptor (CAR) or T cell receptor (TCR), wherein the CAR or TCR comprises an antigen-binding domain specific to an antigen of interest.

Item 33. The cell of Item 32, wherein the second polynucleotide encodes a CAR comprising an antigen-binding domain specific to an antigen of interest.

Item 34. The cell of Item 33, wherein the CAR comprises an antigen-binding domain specific to CD19.

Item 35. A pharmaceutical composition comprising the cell of any one of Items 25-34 and a pharmaceutically acceptable carrier.

Item 36. The pharmaceutical composition of Item 35, wherein the cell is a human T cell, human NK cell or human TIL.

Item 37. A method of modulating the expression, function, and/or level of IL15 in the cell of any one of Items 25-34, said method comprising administering to the cell a stimulus to which the DRD is responsive, wherein the stimulus is administered in an amount sufficient to modulate the expression, function and/or level of IL15.

Item 38. The method of Item 37, wherein the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide.

Item 39. The method of Item 38, wherein the stimulus is acetazolamide.

Item 40. The method of Item 37, wherein the cell is a human T cell or a human NK cell, and wherein the human T cell or the human NK cell further comprises a second polynucleotide encoding a chimeric antigen receptor (CAR) or T cell receptor (TCR), wherein the CAR or TCR comprises an antigen-binding domain specific to an antigen of interest.

Item 41. The method of Item 40, wherein the second polynucleotide encodes a CAR comprising an antigen-binding domain specific to an antigen of interest.

Item 42. The method of Item 41, wherein the CAR comprises an antigen-binding domain specific to CD19.

Item 43. A method of treating a disease or disorder responsive to regulated IL15 in a subject in need thereof, said method comprising: (a) administering to the subject a therapeutically effective amount of the nucleic acid molecule of any one of Items 1-18, the vector of any one of Items 19-23, the recombinant protein of Item 24, the cell of any one of Items 25-34 or the pharmaceutical composition of any one of Items 35-36; and (b) administering a therapeutically effective amount of a stimulus to the subject, wherein the DRD is responsive to the stimulus and wherein expression of the IL15 payload is modulated in response to the stimulus.

Item 44. The method of Item 43, wherein the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide.

Item 45. The method of Item 44, wherein the stimulus is acetazolamide.

Item 46. The method of any of Items 43-45, wherein the disease or disorder is cancer.

Item 47. A method of treating a malignant tumor in a subject in need thereof, wherein said tumor expresses a tumor-associated antigen, said method comprising: (a) administering to the subject a therapeutically effective amount of the human T cell or the human NK cell of any one of Items 32-34, or a pharmaceutical composition thereof, wherein the CAR or TCR comprises an antigen-binding domain specific to the tumor-associated antigen; and (b) administering a therapeutically effective amount of a stimulus to the subject, wherein the DRD is responsive to the stimulus and wherein expression of the IL15 payload is modulated in response to the stimulus.

Item 48. The method according to Item 48, wherein the subject is administered a therapeutically effective amount of the human T cell comprising a CAR, or a pharmaceutical composition thereof.

Item 49. The method according to either of Items 47 or 48, wherein the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide.

Item 50. The method of Item 49, wherein the stimulus is acetazolamide.

Item 51. A method of producing a genetically engineered T cell, natural killer (NK) cell or tumor infiltrating lymphocyte (TIL), comprising introducing into the T cell, NK cell or TIL a polynucleotide encoding a protein comprising a drug responsive domain (DRD) operably linked to an IL15 payload, wherein the polynucleotide encodes an amino acid sequence of SEQ ID NOS:24 or 28.

Item 52. The method of Item 51, wherein the polynucleotide comprises a nucleotide sequence of SEQ ID NOS:25 or 29.

Item 53. The method of Item 52, wherein the polynucleotide is introduced into the T cell, NK cell or TIL by lentiviral transduction.

Item 54. The method of Item 52, wherein the polynucleotide is introduced into the T cell, NK cell or TIL by a non-viral vector delivery method.

Item 55. A modified cell comprising a recombinant protein, said recombinant protein comprising: (i) an effector module, wherein said effector module comprises a stimulus response element (SRE) that comprises a drug responsive domain (DRD), wherein said DRD is derived from a parent protein or a mutant protein having one or more amino acid mutations in the amino acid sequence of human carbonic anhydrase 2 (CA2) (SEQ ID NO: 1) and comprises the amino acid sequence of SEQ ID NO:4; and (ii) a recombinant IL15 linked to the SRE.

Item 56. The cell of Item 55, wherein the recombinant IL15 comprises the amino acid sequence of SEQ ID NO:8.

Item 57. The cell of Item 55 or 56, wherein the recombinant IL15 can be expressed on the cell surface.

Item 58. The cell of Item 55 or 56, wherein the recombinant IL15 is a membrane bound IL15 (mbIL15).

Item 59. The cell of any of Items 55-58, wherein the recombinant protein comprises the whole or a portion of SEQ ID NO: 16.

Item 60. The cell of any of Items 55-59, wherein the recombinant protein comprises the whole or a portion of SEQ ID NO: 18.

Item 61. The cell of Item 55, wherein the recombinant protein further comprises one or more components selected from the group consisting of: (a) a leader sequence; (b) a GS linker; (c) a hinge domain; (d) a transmembrane domain; and (e) a cytoplasmic tail domain.

Item 62. The cell of Item 55, wherein the recombinant protein comprises the amino acid sequence of SEQ ID NO:24.

Item 63. The cell of Item 55, wherein the recombinant protein comprises the amino acid sequence of SEQ ID NO:28.

Item 64. The cell of any one of Items 55-63, wherein the recombinant IL15 is further linked to at least one of: (a) a leader sequence; (b) a signal peptide; (c) a linker; (d) a spacer; (e) a cleavage site; (f) a tag; (g) a co-stimulatory domain; (h) a fluorescence protein; and (i) a hinge.

Item 65. The cell of any of Items 55-64, wherein the SRE is responsive to or interacts with Acetazolamide (ACZ).

Item 66. The cell of Item 55, wherein the cell is a T cell, a natural killer cell (NK cell), or a tumor infiltrating lymphocyte (TIL).

Item 67. A nucleic acid molecule, comprising: a polynucleotide, optionally a first expression cassette, encoding a first recombinant protein comprising a stimulus response element (SRE) linked to an IL15 polypeptide; wherein the SRE comprises a DRD, wherein said DRD comprises an amino acid sequence of SEQ ID NO:4.

Item 68. The nucleic acid molecule of Item 67, wherein the IL15 is under control of the SRE.

Item 69. The nucleic acid molecule of Item 67, wherein the polynucleotide further encodes: (a) a leader sequence; (b) a GS linker; (c) a hinge domain; (d) a transmembrane domain; and (e) a cytoplasmic tail domain.

Item 70. The nucleic acid molecule of Item 67, wherein the polynucleotide comprises the nucleic acid sequence of SEQ ID NO:25.

Item 71. The nucleic acid molecule of Item 67, wherein the polynucleotide comprises the nucleic acid sequence of SEQ ID NO:29.

Item 72. The nucleic acid molecule of any of Items 67-71 that is isolated.

Item 73. A recombinant protein encoded by a nucleic acid molecule of any one of Items 67-72.

Item 74. The recombinant protein of Item 73, wherein the recombinant protein comprises an amino acid sequence of SEQ ID NO:24 or 28.

Item 75. A vector comprising a nucleic acid molecule of any one of Items 67-72.

Item 76. The vector of Item 75, wherein the vector is a plasmid, or lentiviral vector.

Item 77. The vector of Item 76 that is integrase defective.

Item 78. A T cell, NK cell or TIL, comprising the nucleic acid molecule of any one of Items 67-72, a recombinant protein of Items 73-74, or a vector of any one of Items 75-77.

Item 79. The T cell of Item 78 that is a CD4+ or CD8+ T cell.

Item 80. The T cell of Item 79 or Item 42 that is a human T cell.

Item 81. The T cell of any of Items 78-80 that is isolated.

Item 82. A pharmaceutical composition, comprising the cell, T cell, NK cell or TIL of any one of Items 55-66 or 78-81 and a pharmaceutically acceptable carrier.

Item 83. A method of producing a genetically engineered T cell, NK cell or TIL, comprising: introducing into a T cell, NK cell or TIL: a first polynucleotide encoding a stimulus response element comprising a CA2 DRD linked to an IL15 polypeptide payload, wherein the first polynucleotide has a nucleotide sequence of SEQ ID NO:25 or 29.

Item 84. The method of Item 83, wherein the first poly-nucleotide is introduced into the T cell, NK cell or TIL via a lentiviral virus transfection of said T cell, NK cell or TIL.

While the present disclosure has been described at some length and with some particularity with respect to the several described embodiments, it is not intended that it should be limited to any such particulars or embodiments or any particular embodiment, but it is to be construed with refer-ences to the appended claims so as to provide the broadest possible interpretation of such claims in view of the prior art and, therefore, to effectively encompass the intended scope of the disclosure.

All publications, patent applications, patents, and other references mentioned herein are incorporated by reference in their entirety. In case of conflict, the present specification, including definitions, will control. In addition, section head-ings, the materials, methods, and examples are illustrative only and not intended to be limiting.

What is claimed is:

1. A method of treating a disease or disorder responsive to regulated IL 15 in a subject in need thereof, said method comprising:
(a) administering to the subject a therapeutically effective amount of a cell comprising a nucleic acid molecule comprising a polynucleotide encoding a recombinant protein comprising a drug responsive domain (DRD) operably linked to an IL15 payload, wherein the DRD is derived from human carbonic anhydrase II (CA2) and comprises the amino acid sequence of SEQ ID NO:4 and wherein the IL15 payload is a membrane-bound IL15 polypeptide, wherein the cell is a tumor infiltrating lymphocyte (TIL), a human T cell or a human NK cell; and
(b) administering a therapeutically effective amount of a stimulus to the subject, wherein the DRD is stabilized by the stimulus to enable expression of the IL15 payload, wherein the stimulus is acetazolamide, and wherein the disease or disorder is a cancer.

2. The method of claim 1, wherein the TIL or human T cell is a CD4+ or CD8+ T cell.

3. The method of claim 1, wherein the membrane-bound IL 15 polypeptide comprises the amino acid sequence of SEQ ID NO:8.

4. The method of claim 1, wherein the membrane-bound IL15 polypeptide is N-terminal to the DRD.

5. The method of claim 3, wherein the recombinant protein further comprises a transmembrane domain and an intracellular tail.

6. The method of claim 5, wherein the transmembrane domain is C-terminal to the amino acid sequence of SEQ ID NO:8 and the intracellular tail is C-terminal to the transmembrane domain.

7. The method of claim 5, wherein the recombinant protein further comprises a linker between the amino acid sequence of SEQ ID NO:8 and the transmembrane domain and a leader sequence N-terminal to the amino acid sequence of SEQ ID NO:8.

8. The method of claim 1, wherein the polynucleotide encodes the amino acid sequence of SEQ ID NO:24.

9. The method of claim 1, wherein the polynucleotide comprises the nucleic acid sequence of SEQ ID NO:25.

10. The method of claim 1, wherein the cell further comprises a second polynucleotide encoding a chimeric antigen receptor (CAR) or T cell receptor (TCR).

11. The method of claim 10, wherein the CAR or TCR comprises an antigen-binding domain specific to an antigen of interest.

12. The method of claim 10, wherein the second poly-nucleotide encodes a CAR comprising an antigen-binding domain specific to an antigen of interest.

13. The method of claim 12, wherein the CAR comprises an antigen-binding domain specific to CD19.

14. The method of claim 1, wherein the polynucleotide is introduced into the cell by viral transduction.

15. The method of claim 14, wherein the viral transduc-tion comprises using a lentiviral vector comprising the polynucleotide.

\* \* \* \* \*

SEQUENCE LISTING

```
<160> NUMBER OF SEQ ID NOS: 51

<210> SEQ ID NO 1
<211> LENGTH: 260
<212> TYPE: PRT
<213> ORGANISM: Homo sapiens

<400> SEQUENCE: 1

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
            115                 120                 125

Asp Phe Gly Lys Ala Val Gln Gln Pro Asp Gly Leu Ala Val Leu Gly
        130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190
```

```
Tyr Pro Gly Ser Leu Thr Thr Pro Pro Leu Leu Glu Cys Val Thr Trp
        195             200             205

Ile Val Leu Lys Glu Pro Ile Ser Val Ser Ser Glu Gln Val Leu Lys
        210             215             220

Phe Arg Lys Leu Asn Phe Asn Gly Glu Gly Glu Pro Glu Glu Leu Met
225             230             235             240

Val Asp Asn Trp Arg Pro Ala Gln Pro Leu Lys Asn Arg Gln Ile Lys
                245             250             255

Ala Ser Phe Lys
        260

<210> SEQ ID NO 2
<211> LENGTH: 259
<212> TYPE: PRT
<213> ORGANISM: Homo sapiens

<400> SEQUENCE: 2

Ser His His Trp Gly Tyr Gly Lys His Asn Gly Pro Glu His Trp His
1               5               10              15

Lys Asp Phe Pro Ile Ala Lys Gly Glu Arg Gln Ser Pro Val Asp Ile
        20              25              30

Asp Thr His Thr Ala Lys Tyr Asp Pro Ser Leu Lys Pro Leu Ser Val
        35              40              45

Ser Tyr Asp Gln Ala Thr Ser Leu Arg Ile Leu Asn Asn Gly His Ala
        50              55              60

Phe Asn Val Glu Phe Asp Asp Ser Gln Asp Lys Ala Val Leu Lys Gly
65              70              75              80

Gly Pro Leu Asp Gly Thr Tyr Arg Leu Ile Gln Phe His Phe His Trp
                85              90              95

Gly Ser Leu Asp Gly Gln Gly Ser Glu His Thr Val Asp Lys Lys Lys
        100             105             110

Tyr Ala Ala Glu Leu His Leu Val His Trp Asn Thr Lys Tyr Gly Asp
        115             120             125

Phe Gly Lys Ala Val Gln Gln Pro Asp Gly Leu Ala Val Leu Gly Ile
        130             135             140

Phe Leu Lys Val Gly Ser Ala Lys Pro Gly Leu Gln Lys Val Val Asp
145             150             155             160

Val Leu Asp Ser Ile Lys Thr Lys Gly Lys Ser Ala Asp Phe Thr Asn
                165             170             175

Phe Asp Pro Arg Gly Leu Leu Pro Glu Ser Leu Asp Tyr Trp Thr Tyr
                180             185             190

Pro Gly Ser Leu Thr Thr Pro Pro Leu Leu Glu Cys Val Thr Trp Ile
        195             200             205

Val Leu Lys Glu Pro Ile Ser Val Ser Ser Glu Gln Val Leu Lys Phe
        210             215             220

Arg Lys Leu Asn Phe Asn Gly Glu Gly Glu Pro Glu Glu Leu Met Val
225             230             235             240

Asp Asn Trp Arg Pro Ala Gln Pro Leu Lys Asn Arg Gln Ile Lys Ala
                245             250             255

Ser Phe Lys

<210> SEQ ID NO 3
<211> LENGTH: 780
<212> TYPE: DNA
<213> ORGANISM: Homo sapiens
```

<400> SEQUENCE: 3
atgtcccatc actgggggta cggcaaacac aacggacctg agcactggca taaggacttc        60
cccattgcca agggagagcg ccagtcccct gttgacatcg acactcatac agccaagtat       120
gacccttccc tgaagcccct gtctgtttcc tatgatcaag caacttccct gaggatcctc       180
aacaatggtc atgctttcaa cgtggagttt gatgactctc aggacaaagc agtgctcaag       240
ggaggacccc tggatggcac ttacagattg attcagtttc actttcactg gggttcactt       300
gatggacaag gttcagagca tactgtggat aaaaagaaat atgctgcaga acttcacttg       360
gttcactgga acaccaaata tggggatttt gggaaagctg tgcagcaacc tgatggactg       420
gccgttctag gtattttttt gaaggttggc agcgctaaac cgggccttca gaaagttgtt       480
gatgtgctgg attccattaa aacaaagggc aagagtgctg acttcactaa cttcgatcct       540
cgtggcctcc ttcctgaatc cctggattac tggacctacc caggctcact gaccacccct       600
cctcttctgg aatgtgtgac ctggattgtg ctcaaggaac ccatcagcgt cagcagcgag       660
caggtgttga aattccgtaa acttaacttc aatggggagg gtgaacccga agaactgatg       720
gtggacaact ggcgcccagc tcagccactg aagaacaggc aaatcaaagc ttccttcaaa       780

<210> SEQ ID NO 4
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser His His Trp Gly Tyr Gly Lys His Asn Gly Pro Glu His Trp His
1               5                   10                  15

Lys Asp Phe Pro Ile Ala Lys Gly Glu Arg Gln Ser Pro Val Asp Ile
                20                  25                  30

Asp Thr His Thr Ala Lys Tyr Asp Pro Ser Leu Lys Pro Leu Ser Val
            35                  40                  45

Ser Tyr Asp Gln Ala Thr Ser Leu Arg Ile Leu Asn Asn Gly His Ala
        50                  55                  60

Phe Asn Val Glu Phe Asp Asp Ser Gln Asp Lys Ala Val Leu Lys Gly
65                  70                  75                  80

Gly Pro Leu Asp Gly Thr Tyr Arg Leu Ile Gln Phe His Phe His Trp
                85                  90                  95

Gly Ser Leu Asp Gly Gln Gly Ser Glu His Thr Val Asp Lys Lys Lys
            100                 105                 110

Tyr Ala Ala Glu Leu His Leu Val His Trp Asn Thr Lys Tyr Gly Asp
        115                 120                 125

Phe Gly Lys Ala Val Gln Gln Pro Asp Gly Leu Ala Val Leu Gly Ile
    130                 135                 140

Phe Leu Lys Val Gly Ser Ala Lys Pro Gly His Gln Lys Val Val Asp
145                 150                 155                 160

Val Leu Asp Ser Ile Lys Thr Lys Gly Lys Ser Ala Asp Phe Thr Asn
                165                 170                 175

Phe Asp Pro Arg Gly Leu Leu Pro Glu Ser Leu Asp Tyr Trp Thr Tyr
            180                 185                 190

Pro Gly Ser Leu Thr Thr Pro Pro Leu Leu Glu Cys Val Thr Trp Ile
        195                 200                 205

```
Val Leu Lys Glu Pro Ile Ser Val Ser Ser Glu Gln Val Leu Lys Phe
    210             215             220

Arg Lys Leu Asn Phe Asn Gly Glu Gly Glu Pro Glu Glu Leu Met Val
225             230             235             240

Asp Asn Trp Arg Pro Ala Gln Pro Leu Lys Asn Arg Gln Ile Lys Ala
                245             250             255

Ser Phe Lys
```

```
<210> SEQ ID NO 5
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
tcccatcact gggggtacgg caaacacaac ggacctgagc actggcataa ggacttcccc      60
attgccaagg gagagcgcca gtccctgtt gacatcgaca ctcatacagc caagtatgac     120
ccttccctga agcccctgtc tgtttcctat gatcaagcaa cttccctgag aatcctcaac     180
aatggtcatg ctttcaacgt ggagtttgat gactctcagg acaaagcagt gctcaaggga     240
ggacccctgg atggcactta cagattgatt cagtttcact ttcactgggg ttcacttgat     300
ggacaaggtt cagagcatac tgtggataaa aagaaatatg ctgcagaact tcacttggtt     360
cactggaaca ccaaatatgg ggattttggg aaagctgtgc agcaacctga tggactggcc     420
gttctaggta ttttttttgaa ggttggcagc gctaaaccgg gccatcagaa agttgttgat     480
gtgctggatt ccattaaaac aaagggcaag agtgctgact tcactaactt cgatcctcgt     540
ggcctccttc ctgaatccct ggattactgg acctacccag gctcactgac caccctcct      600 cttctggaat gtgtgacctg gattgtgctc aaggaaccca tcagcgtcag cagcgagcag     660
gtgttgaaat tccgtaaact taacttcaat ggggagggtg aacccgaaga actgatggtg     720
gacaactggc gcccagctca gccactgaag aacaggcaaa tcaaagcttc cttcaaa       777
```

```
<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asp Met Arg Val Pro Ala Gln Leu Leu Gly Leu Leu Leu Leu Trp
1               5               10              15

Leu Ser Gly Ala Arg Cys
            20
```

```
<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atggacatgc gggtgcctgc acaacttctg ggcctgctgt tgttgtggct gtctggagcc      60
cggtgt                                                                  66
```

-continued

```
<210> SEQ ID NO 8
<211> LENGTH: 114
<212> TYPE: PRT
<213> ORGANISM: Homo sapiens

<400> SEQUENCE: 8

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 9
<211> LENGTH: 342
<212> TYPE: DNA
<213> ORGANISM: Homo sapiens

<400> SEQUENCE: 9
aattgggtaa atgttatcag tgatctcaag aagatagagg atctcatcca gtccatgcat        60
attgatgcca cgctgtacac agaaagcgat gtgcatccta gctgtaaggt gacagcgatg       120
aagtgttttc ttttggagct gcaggtaatt agtcttgagt ccggcgatgc cagcattcat       180
gataccgtag aaaacttgat tatcctggcc aacaattctc tgtcctcaaa cggaaacgta       240
accgagagcg gttgtaaaga atgtgaagaa ctggaagaaa agaacatcaa ggagtttctg       300
caatcattcg ttcacatcgt acaaatgttc ataaatacgt ca                         342

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

<210> SEQ ID NO 11
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```

```
ggatctggtt ctggttccgg aagtggatct ggttcagggt ccggtagtgg atctgggtca        60
ggaagtggaa gcggtagtgg gtctggatct                                          90

<210> SEQ ID NO 12
<211> LENGTH: 8
<212> TYPE: PRT
<213> ORGANISM: Homo sapiens

<400> SEQUENCE: 12

Lys Gln Glu His Phe Pro Asp Asn
1               5

<210> SEQ ID NO 13
<211> LENGTH: 24
<212> TYPE: DNA
<213> ORGANISM: Homo sapiens

<400> SEQUENCE: 13
aaacaagagc actttcctga taac                                                24

<210> SEQ ID NO 14
<211> LENGTH: 21
<212> TYPE: PRT
<213> ORGANISM: Homo sapiens

<400> SEQUENCE: 14

Leu Leu Pro Ser Trp Ala Ile Thr Leu Ile Ser Val Asn Gly Ile Phe
1               5                   10                  15

Val Ile Cys Cys Leu
            20

<210> SEQ ID NO 15
<211> LENGTH: 63
<212> TYPE: DNA
<213> ORGANISM: Homo sapiens

<400> SEQUENCE: 15
ctgttgccga gctgggcgat tacgcttatc agtgtaaacg gcatctttgt aatatgctgt        60
ctg                                                                       63

<210> SEQ ID NO 16
<211> LENGTH: 25
<212> TYPE: PRT
<213> ORGANISM: Homo sapiens

<400> SEQUENCE: 16

Thr Tyr Cys Phe Ala Pro Arg Cys Arg Glu Arg Arg Arg Asn Glu Arg
1               5                   10                  15

Leu Arg Arg Glu Ser Val Arg Pro Val
            20                  25

<210> SEQ ID NO 17
<211> LENGTH: 75
<212> TYPE: DNA
<213> ORGANISM: Homo sapiens

<400> SEQUENCE: 17
acctactgct tcgcaccaag gtgccgggag agaaggagaa atgaaagact gagaagggag        60
agcgtgagac ctgtg                                                          75
```

```
<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Tyr Cys Phe Ala Pro Arg Cys Arg Glu Arg Ala Arg Asn Glu Arg
1               5                   10                  15

Leu Arg Arg Glu Thr Val Arg Pro Val
            20                  25

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acctactgct tcgcaccaag gtgccgggag agagcaagaa atgaaagact gagaagggag      60
accgtgagac ctgtg                                                       75

<210> SEQ ID NO 20
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser
1

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 ggatcc                                                                  6

<210> SEQ ID NO 22
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
```

```
           50              55              60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
                100                 105                 110

Leu Glu Glu Lys Asn Ile Lys Glu Phe Leu Gln Ser Phe Val His Ile
            115                 120                 125

Val Gln Met Phe Ile Asn Thr Ser Gly Ser Gly Ser Gly Ser Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
                180                 185                 190

Cys Cys Leu Thr Tyr Cys Phe Ala Pro Arg Cys Arg Glu Arg Arg Arg
            195                 200                 205

Asn Glu Arg Leu Arg Arg Glu Ser Val Arg Pro Val Gly Ser
    210                 215                 220
```

<210> SEQ ID NO 23
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggacatgc gggtgcctgc acaacttctg ggcctgctgt tgttgtggct gtctggagcc    60
cggtgtaatt gggtaaatgt tatcagtgat ctcaagaaga tagaggatct catccagtcc   120
atgcatattg atgccacgct gtacacagaa agcgatgtgc atcctagctg taaggtgaca   180
gcgatgaagt gttttctttt ggagctgcag gtaattagtc ttgagtccgg cgatgccagc   240
attcatgata ccgtagaaaa cttgattatc ctggccaaca attctctgtc ctcaaacgga   300
aacgtaaccg agagcggttg taaagaatgt gaagaactgg aagaaagaa catcaaggag   360 tttctgcaat cattcgttca catcgtacaa atgttcataa atacgtcagg atctggttct   420
ggttccggaa gtggatctgg ttcagggtcc ggtagtggat ctgggtcagg aagtggaagc   480
ggtagtgggt ctggatctaa acaagagcac tttcctgata acctgttgcc gagctgggcg   540
attacgctta tcagtgtaaa cggcatcttt gtaatatgct gtctgaccta ctgcttcgca   600
ccaaggtgcc gggagagaag gagaaatgaa agactgagaa gggagagcgt gagacctgtg   660
ggatcc                                                             666
```

<210> SEQ ID NO 24
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Asp Met Arg Val Pro Ala Gln Leu Leu Gly Leu Leu Leu Leu Trp
```

```
1               5                    10                   15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
            35                  40                  45

Thr Glu Ser Asp Val His Pro Ser Cys Lys Val Thr Ala Met Lys Cys
        50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
            115                 120                 125

Val Gln Met Phe Ile Asn Thr Ser Gly Ser Gly Ser Gly Ser Gly Ser
        130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Arg Arg
            195                 200                 205

Asn Glu Arg Leu Arg Arg Glu Ser Val Arg Pro Val Gly Ser Ser His
        210                 215                 220

His Trp Gly Tyr Gly Lys His Asn Gly Pro Glu His Trp His Lys Asp
225                 230                 235                 240

Phe Pro Ile Ala Lys Gly Glu Arg Gln Ser Pro Val Asp Ile Asp Thr
                245                 250                 255

His Thr Ala Lys Tyr Asp Pro Ser Leu Lys Pro Leu Ser Val Ser Tyr
            260                 265                 270

Asp Gln Ala Thr Ser Leu Arg Ile Leu Asn Asn Gly His Ala Phe Asn
        275                 280                 285

Val Glu Phe Asp Asp Ser Gln Asp Lys Ala Val Leu Lys Gly Gly Pro
        290                 295                 300

Leu Asp Gly Thr Tyr Arg Leu Ile Gln Phe His Phe His Trp Gly Ser
305                 310                 315                 320

Leu Asp Gly Gln Gly Ser Glu His Thr Val Asp Lys Lys Tyr Ala
            325                 330                 335

Ala Glu Leu His Leu Val His Trp Asn Thr Lys Tyr Gly Asp Phe Gly
            340                 345                 350

Lys Ala Val Gln Gln Pro Asp Gly Leu Ala Val Leu Gly Ile Phe Leu
            355                 360                 365

Lys Val Gly Ser Ala Lys Pro Gly His Gln Lys Val Val Asp Val Leu
            370                 375                 380

Asp Ser Ile Lys Thr Lys Gly Lys Ser Ala Asp Phe Thr Asn Phe Asp
385                 390                 395                 400

Pro Arg Gly Leu Leu Pro Glu Ser Leu Asp Tyr Trp Thr Tyr Pro Gly
                405                 410                 415

Ser Leu Thr Thr Pro Pro Leu Leu Glu Cys Val Thr Trp Ile Val Leu
            420                 425                 430
```

```
Lys Glu Pro Ile Ser Val Ser Ser Glu Gln Val Leu Lys Phe Arg Lys
        435                 440                 445

Leu Asn Phe Asn Gly Glu Gly Glu Pro Glu Glu Leu Met Val Asp Asn
    450                 455                 460

Trp Arg Pro Ala Gln Pro Leu Lys Asn Arg Gln Ile Lys Ala Ser Phe
465                 470                 475                 480

Lys
```

```
<210> SEQ ID NO 25
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gttttctttt ggagctgcag gtaattagtc ttgagtccgg cgatgccagc     240
attcatgata ccgtagaaaa cttgattatc ctggccaaca attctctgtc ctcaaacgga     300
aacgtaaccg agagcggttg taaagaatgt gaagaactgg aagaaagaa catcaaggag     360 tttctgcaat cattcgttca catcgtacaa atgttcataa atacgtcagg atctggttct     420
ggttccggaa gtggatctgg ttcagggtcc ggtagtggat ctgggtcagg aagtggaagc     480
ggtagtgggt ctggatctaa acaagagcac tttcctgata acctgttgcc gagctgggcg     540
attacgctta tcagtgtaaa cggcatcttt gtaatatgct gtctgaccta ctgcttcgca     600
ccaaggtgcc gggagagaag gagaaatgaa agactgagaa gggagagcgt gagacctgtg     660
ggatcctccc atcactgggg gtacggcaaa cacaacggac ctgagcactg gcataaggac     720
ttccccattg ccaagggaga gcgccagtcc cctgttgaca tcgacactca tacagccaag     780
tatgaccctt ccctgaagcc cctgtctgtt tcctatgatc aagcaacttc cctgagaatc     840
ctcaacaatg tcatgctttt caacgtggag tttgatgact ctcaggacaa agcagtgctc     900
aagggaggac ccctggatgg cacttacaga ttgattcagt ttcactttca ctgggggttca     960 cttgatggac aaggttcaga gcatactgtg gataaaaaga aatatgctgc agaacttcac    1020
ttggttcact ggaacaccaa atatggggat tttgggaaag ctgtgcagca acctgatgga    1080
ctggccgttc taggtatttt tttgaaggtt ggcagcgcta aaccgggcca tcagaaagtt    1140
gttgatgtgc tggattccat taaaacaaag ggcaagagtg ctgacttcac taacttcgat    1200
cctcgtggcc tccttcctga atccctggat tactggacct acccaggctc actgaccacc    1260
cctcctcttc tggaatgtgt gacctggatt gtgctcaagg aacccatcag cgtcagcagc    1320
gagcaggtgt tgaaattccg taaacttaac ttcaatgggg agggtgaacc cgaagaactg    1380
atggtggaca actggcgccc agctcagcca ctgaagaaca ggcaaatcaa agcttccttc    1440
aaa                                                                  1443
```

```
<210> SEQ ID NO 26
<211> LENGTH: 222
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 26

```
Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
            115                 120                 125

Val Gln Met Phe Ile Asn Thr Ser Gly Ser Gly Ser Gly Ser Gly Ser
        130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
            165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Ala Arg
        195                 200                 205

Asn Glu Arg Leu Arg Arg Glu Thr Val Arg Pro Val Gly Ser
    210                 215                 220
```

<210> SEQ ID NO 27
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gttttctttt ggagctgcag gtaattagtc ttgagtccgg cgatgccagc     240
attcatgata ccgtagaaaa cttgattatc ctggccaaca attctctgtc ctcaaacgga     300
aacgtaaccg agagcggttg taaagaatgt gaagaactgg aagaaaagaa catcaaggag     360
tttctgcaat cattcgttca catcgtacaa atgttcataa atacgtcagg atctggttct     420
ggttccggaa gtggatctgg ttcagggtcc ggtagtggat ctgggtcagg aagtggaagc     480
ggtagtgggt ctggatctaa acaagagcac tttcctgata acctgttgcc gagctgggcg     540
attacgctta tcagtgtaaa cggcatcttt gtaatatgct gtctgaccta ctgcttcgca     600
ccaaggtgcc gggagagagc aagaaatgaa agactgagaa gggagaccgt gagacctgtg     660
``` ggatcc                                                                      666

<210> SEQ ID NO 28
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
                20                  25                  30

Lys Ile Glu Asp Leu Ile Gln Ser Met His Ile Asp Ala Thr Leu Tyr
            35                  40                  45

Thr Glu Ser Asp Val His Pro Ser Cys Lys Val Thr Ala Met Lys Cys
        50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
            115                 120                 125

Val Gln Met Phe Ile Asn Thr Ser Gly Ser Gly Ser Gly Ser Gly Ser
        130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
                180                 185                 190

Cys Cys Leu Thr Tyr Cys Phe Ala Pro Arg Cys Arg Glu Arg Ala Arg
            195                 200                 205

Asn Glu Arg Leu Arg Arg Glu Thr Val Arg Pro Val Gly Ser Ser His
        210                 215                 220

His Trp Gly Tyr Gly Lys His Asn Gly Pro Glu His Trp His Lys Asp
225                 230                 235                 240

Phe Pro Ile Ala Lys Gly Glu Arg Gln Ser Pro Val Asp Ile Asp Thr
                245                 250                 255

His Thr Ala Lys Tyr Asp Pro Ser Leu Lys Pro Leu Ser Val Ser Tyr
                260                 265                 270

Asp Gln Ala Thr Ser Leu Arg Ile Leu Asn Asn Gly His Ala Phe Asn
            275                 280                 285

Val Glu Phe Asp Asp Ser Gln Asp Lys Ala Val Leu Lys Gly Gly Pro
        290                 295                 300

Leu Asp Gly Thr Tyr Arg Leu Ile Gln Phe His Phe His Trp Gly Ser
305                 310                 315                 320

Leu Asp Gly Gln Gly Ser Glu His Thr Val Asp Lys Lys Lys Tyr Ala
            325                 330                 335

Ala Glu Leu His Leu Val His Trp Asn Thr Lys Tyr Gly Asp Phe Gly
            340                 345                 350

```
Lys Ala Val Gln Gln Pro Asp Gly Leu Ala Val Leu Gly Ile Phe Leu
        355                 360                 365

Lys Val Gly Ser Ala Lys Pro Gly His Gln Lys Val Val Asp Val Leu
        370                 375                 380

Asp Ser Ile Lys Thr Lys Gly Lys Ser Ala Asp Phe Thr Asn Phe Asp
385                 390                 395                 400

Pro Arg Gly Leu Leu Pro Glu Ser Leu Asp Tyr Trp Thr Tyr Pro Gly
                405                 410                 415

Ser Leu Thr Thr Pro Pro Leu Leu Glu Cys Val Thr Trp Ile Val Leu
                420                 425                 430

Lys Glu Pro Ile Ser Val Ser Ser Glu Gln Val Leu Lys Phe Arg Lys
        435                 440                 445

Leu Asn Phe Asn Gly Glu Gly Glu Pro Glu Glu Leu Met Val Asp Asn
        450                 455                 460

Trp Arg Pro Ala Gln Pro Leu Lys Asn Arg Gln Ile Lys Ala Ser Phe
465                 470                 475                 480

Lys
```

```
<210> SEQ ID NO 29
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gttttctttt ggagctgcag gtaattagtc ttgagtccgg cgatgccagc     240
attcatgata ccgtagaaaa cttgattatc ctggccaaca attctctgtc ctcaaacgga     300
aacgtaaccg agagcggttg taaagaatgt gaagaactgg aagaaagaa catcaaggag      360 tttctgcaat cattcgttca catcgtacaa atgttcataa atacgtcagg atctggttct     420
ggttccggaa gtggatctgg ttcagggtcc ggtagtggat ctgggtcagg aagtggaagc     480
ggtagtgggt ctggatctaa acaagagcac tttcctgata acctgttgcc gagctgggcg     540
attacgctta tcagtgtaaa cggcatcttt gtaatatgct gtctgaccta ctgcttcgca     600
ccaaggtgcc gggagagagc aagaaatgaa agactgagaa gggagaccgt gagacctgtg     660
ggatcctccc atcactgggg gtacggcaaa cacaacggac ctgagcactg gcataaggac     720
ttccccattg ccaagggaga gcgccagtcc cctgttgaca tcgacactca tacagccaag     780
tatgacccct ccctgaagcc cctgtctgtt tcctatgatc aagcaacttc cctgagaatc     840
ctcaacaatg gtcatgcttt caacgtggag tttgatgact ctcaggacaa agcagtgctc     900
aagggaggac ccctggatgg cacttacaga ttgattcagt ttcactttca ctggggttca     960
cttgatggac aaggttcaga gcatactgtg gataaaaaga aatatgctgc agaacttcac    1020
ttggttcact ggaacaccaa atatgggga tttgggaaag ctgtgcagca acctgatgga     1080
ctggccgttc taggtatttt tttgaaggtt ggcagcgcta aaccgggcca tcagaaagtt    1140
gttgatgtgt ggattccat aaaacaaag ggcaagagtg ctgacttcac taacttcgat      1200
cctcgtggcc tccttcctga atccctggat tactggacct acccaggctc actgaccacc    1260
```

-continued

```
cctcctcttc tggaatgtgt gacctggatt gtgctcaagg aacccatcag cgtcagcagc   1320
gagcaggtgt tgaaattccg taaacttaac ttcaatgggg agggtgaacc cgaagaactg   1380
atggtggaca actggcgccc agctcagcca ctgaagaaca ggcaaatcaa agcttccttc   1440
aaa                                                                  1443
```

<210> SEQ ID NO 30
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser Gly Ser Gly Ser Gly Ser Gly Ser Gly Ser Gly Ser Gly Ser
            115                 120                 125

Gly Ser Gly Ser Gly Ser Gly Ser Gly Ser Gly Ser Gly Ser Gly Ser
    130                 135                 140

Lys Gln Glu His Phe Pro Asp Asn Leu Leu Pro Ser Trp Ala Ile Thr
145                 150                 155                 160

Leu Ile Ser Val Asn Gly Ile Phe Val Ile Cys Cys Leu Thr Tyr Cys
            165                 170                 175

Phe Ala Pro Arg Cys Arg Glu Arg Arg Arg Asn Glu Arg Leu Arg Arg
            180                 185                 190

Glu Ser Val Arg Pro Val Gly Ser
            195                 200
```

<210> SEQ ID NO 31
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45
```

```
Val Ile Ser Leu Glu Ser Gly Asp Ala Ser Ile His Asp Thr Val Glu
    50              55                  60

Asn Leu Ile Ile Leu Ala Asn Asn Ser Leu Ser Ser Asn Gly Asn Val
65              70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Ser Gly Ser Gly Ser Gly Ser Gly Ser Gly Ser Gly Ser
            115                 120                 125

Gly Ser Gly Ser Gly Ser Gly Ser Gly Ser Gly Ser Gly Ser Gly Ser
    130                 135                 140

Lys Gln Glu His Phe Pro Asp Asn Leu Leu Pro Ser Trp Ala Ile Thr
145             150                 155                 160

Leu Ile Ser Val Asn Gly Ile Phe Val Ile Cys Cys Leu Thr Tyr Cys
                165                 170                 175

Phe Ala Pro Arg Cys Arg Glu Arg Arg Arg Asn Glu Arg Leu Arg Arg
            180                 185                 190

Glu Ser Val Arg Pro Val Gly Ser Ser His His Trp Gly Tyr Gly Lys
            195                 200                 205

His Asn Gly Pro Glu His Trp His Lys Asp Phe Pro Ile Ala Lys Gly
    210                 215                 220

Glu Arg Gln Ser Pro Val Asp Ile Asp Thr His Thr Ala Lys Tyr Asp
225                 230                 235                 240

Pro Ser Leu Lys Pro Leu Ser Val Ser Tyr Asp Gln Ala Thr Ser Leu
            245                 250                 255

Arg Ile Leu Asn Asn Gly His Ala Phe Asn Val Glu Phe Asp Asp Ser
            260                 265                 270

Gln Asp Lys Ala Val Leu Lys Gly Gly Pro Leu Asp Gly Thr Tyr Arg
            275                 280                 285

Leu Ile Gln Phe His Phe His Trp Gly Ser Leu Asp Gly Gln Gly Ser
    290                 295                 300

Glu His Thr Val Asp Lys Lys Lys Tyr Ala Ala Glu Leu His Leu Val
305                 310                 315                 320

His Trp Asn Thr Lys Tyr Gly Asp Phe Gly Lys Ala Val Gln Gln Pro
            325                 330                 335

Asp Gly Leu Ala Val Leu Gly Ile Phe Leu Lys Val Gly Ser Ala Lys
            340                 345                 350

Pro Gly His Gln Lys Val Val Asp Val Leu Asp Ser Ile Lys Thr Lys
    355                 360                 365

Gly Lys Ser Ala Asp Phe Thr Asn Phe Asp Pro Arg Gly Leu Leu Pro
    370                 375                 380

Glu Ser Leu Asp Tyr Trp Thr Tyr Pro Gly Ser Leu Thr Thr Pro Pro
385                 390                 395                 400

Leu Leu Glu Cys Val Thr Trp Ile Val Leu Lys Glu Pro Ile Ser Val
            405                 410                 415

Ser Ser Glu Gln Val Leu Lys Phe Arg Lys Leu Asn Phe Asn Gly Glu
            420                 425                 430

Gly Glu Pro Glu Glu Leu Met Val Asp Asn Trp Arg Pro Ala Gln Pro
            435                 440                 445

Leu Lys Asn Arg Gln Ile Lys Ala Ser Phe Lys
    450                 455
```

```
<210> SEQ ID NO 32
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser Gly Ser Gly Ser Gly Ser Gly Ser Gly Ser Gly Ser Gly Ser
            115                 120                 125

Gly Ser Gly Ser Gly Ser Gly Ser Gly Ser Gly Ser Gly Ser Gly Ser
    130                 135                 140

Lys Gln Glu His Phe Pro Asp Asn Leu Leu Pro Ser Trp Ala Ile Thr
145                 150                 155                 160

Leu Ile Ser Val Asn Gly Ile Phe Val Ile Cys Cys Leu Thr Tyr Cys
            165                 170                 175

Phe Ala Pro Arg Cys Arg Glu Arg Ala Arg Asn Glu Arg Leu Arg Arg
            180                 185                 190

Glu Thr Val Arg Pro Val Gly Ser
            195                 200

<210> SEQ ID NO 33
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
```

-continued

```
              100             105             110
Thr Ser Gly Ser Gly Ser Gly Ser Gly Ser Gly Ser Gly Ser Gly Ser
        115             120             125

Gly Ser Gly Ser Gly Ser Gly Ser Gly Ser Gly Ser Gly Ser Gly Ser
    130             135             140

Lys Gln Glu His Phe Pro Asp Asn Leu Leu Pro Ser Trp Ala Ile Thr
145             150             155             160

Leu Ile Ser Val Asn Gly Ile Phe Val Ile Cys Cys Leu Thr Tyr Cys
            165             170             175

Phe Ala Pro Arg Cys Arg Glu Arg Ala Arg Asn Glu Arg Leu Arg Arg
            180             185             190

Glu Thr Val Arg Pro Val Gly Ser Ser His His Trp Gly Tyr Gly Lys
            195             200             205

His Asn Gly Pro Glu His Trp His Lys Asp Phe Pro Ile Ala Lys Gly
    210             215             220

Glu Arg Gln Ser Pro Val Asp Ile Asp Thr His Thr Ala Lys Tyr Asp
225             230             235             240

Pro Ser Leu Lys Pro Leu Ser Val Ser Tyr Asp Gln Ala Thr Ser Leu
            245             250             255

Arg Ile Leu Asn Asn Gly His Ala Phe Asn Val Glu Phe Asp Asp Ser
            260             265             270

Gln Asp Lys Ala Val Leu Lys Gly Gly Pro Leu Asp Gly Thr Tyr Arg
            275             280             285

Leu Ile Gln Phe His Phe His Trp Gly Ser Leu Asp Gly Gln Gly Ser
    290             295             300

Glu His Thr Val Asp Lys Lys Lys Tyr Ala Ala Glu Leu His Leu Val
305             310             315             320

His Trp Asn Thr Lys Tyr Gly Asp Phe Gly Lys Ala Val Gln Gln Pro
            325             330             335

Asp Gly Leu Ala Val Leu Gly Ile Phe Leu Lys Val Gly Ser Ala Lys
            340             345             350

Pro Gly His Gln Lys Val Val Asp Val Leu Asp Ser Ile Lys Thr Lys
            355             360             365

Gly Lys Ser Ala Asp Phe Thr Asn Phe Asp Pro Arg Gly Leu Leu Pro
    370             375             380

Glu Ser Leu Asp Tyr Trp Thr Tyr Pro Gly Ser Leu Thr Thr Pro Pro
385             390             395             400

Leu Leu Glu Cys Val Thr Trp Ile Val Leu Lys Glu Pro Ile Ser Val
            405             410             415

Ser Ser Glu Gln Val Leu Lys Phe Arg Lys Leu Asn Phe Asn Gly Glu
            420             425             430

Gly Glu Pro Glu Glu Leu Met Val Asp Asn Trp Arg Pro Ala Gln Pro
            435             440             445

Leu Lys Asn Arg Gln Ile Lys Ala Ser Phe Lys
    450             455
```

<210> SEQ ID NO 34
<211> LENGTH: 8384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

-continued

```
tttgagtgag ctgataccgc tcgccgcagc cgaacgaccg agcgcagcga gtcagtgagc      60
gaggaagcgg aagagcgccc aatacgcaaa ccgcctctcc ccgcgcgttg gccgattcat     120
taatgcagct ggcacgacag gtttcccgac tggaaagcgg gcagtgagcg caacgcaatt     180
aatgtgagtt agctcactca ttaggcaccc caggctttac actttatgct tccggctcgt     240
atgttgtgtg gaattgtgag cggataacaa tttcacacag gaaacagcta tgaccatgat     300
tacgccaagc gcgcaattaa ccctcactaa agggaacaaa agctggagct gcaagcttaa     360
tgtagtctta tgcaatactc ttgtagtctt gcaacatggt aacgatgagt tagcaacatg     420
ccttacaagg agagaaaaag caccgtgcat gccgattggt ggaagtaagg tggtacgatc     480
gtgccttatt aggaaggcaa cagacgggtc tgacatggat tggacgaacc actgaattgc     540
cgcattgcag agatattgta tttaagtgcc tagctcgata caataaacgg tctctctgg      600 ttagaccaga tctgagcctg ggagctctct ggctaactag ggaacccact gcttaagcct     660
caataaagct tgccttgagt gcttcaagta gtgtgtgccc gtctgttgtg tgactctggt     720
aactagagat ccctcagacc cttttagtca gtgtggaaaa tctctagcag tggcgcccga     780
acagggacct gaaagcgaaa gggaaaccag agctctctcg acgcaggact cggcttgctg     840
aagcgcgcac ggcaagaggc gaggggcggc gactggtgag tacgccaaaa attttgacta     900
gcggaggcta aaggagaga gatgggtgcg agagcgtcag tattaagcgg gggagaatta     960
gatcgcgatg ggaaaaaatt cggttaaggc caggggggaa gaaaaaatat aaattaaaac    1020
atatagtatg ggcaagcagg gagctagaac gattcgcagt taatcctggc ctgttagaaa    1080
catcagaagg ctgtagacaa atactgggac agctacaacc atcccttcag acaggatcag    1140
aagaacttag atcattatat aatacagtag caaccctcta ttgtgtgcat caaaggatag    1200
agataaaaga caccaaggaa gctttagaca agatagagga gagcaaaac aaaagtaaga    1260 ccaccgcaca gcaagcggcc gctgatcttc agacctggag gaggagatat gagggacaat    1320
tggagaagtg aattatataa atataaagta gtaaaaattg aaccattagg agtagcaccc    1380
accaaggcaa agagaagagt ggtgcagaga gaaaaaagag cagtgggaat aggagctttg    1440
ttccttgggt tcttgggagc agcaggaagc actatgggcg cagcctcaat gacgctgacg    1500
gtacaggcca gacaattatt gtctggtata gtgcagcagc agaacaattt gctgagggct    1560
attgaggcgc aacagcatct gttgcaactc acagtctggg gcatcaagca gctccaggca    1620
agaatcctgg ctgtggaaag atacctaaag gatcaacagc tcctggggat ttggggttgc    1680
tctggaaaac tcatttgcac cactgctgtg ccttggaatg ctagttggag taataaatct    1740
ctggaacaga ttggaatcac acgacctgga tggagtggga cagagaaatt aacaattaca    1800
caagcttaat acactcctta attgaagaat cgcaaaacca gcaagaaaag aatgaacaag    1860
aattattgga attagataaa tgggcaagtt tgtggaattg gtttaacata acaaattggc    1920
tgtggtatat aaaattattc ataatgatag taggaggctt ggtaggttta agaatagttt    1980
ttgctgtact ttctatagtg aatagagtta ggcaggata ttcaccatta tcgtttcaga    2040
cccacctccc aaccccgagg ggacccgaca ggcccgaagg aatagaagaa gaaggtggag    2100
agagagacag agacagatcc attcgattag tgaacggatc tcgacggtat cgattagact    2160
gtagcccagg aatatggcag ctagattgta cacatttaga aggaaaagtt atcttggtag    2220
cagttcatgt agccagtgga tatatagaag cagaagtaat tccagcagag acagggcaag    2280
aaacagcata cttcctctta aaattagcag gaagatggcc agtaaaaaca gtacatacag    2340
acaatggcag caatttcacc agtactacag ttaaggccgc ctgttggtgg gcggggatca    2400
```

-continued

```
agcaggaatt tggcattccc tacaatcccc aaagtcaagg agtaatagaa tctatgaata    2460
aagaattaaa gaaaattata ggacaggtaa gagatcaggc tgaacatctt aagacagcag    2520
tacaaatggc agtattcatc cacaatttta aaagaaaagg ggggattggg gggtacagtg    2580 cagggaaag aatagtagac ataatagcaa cagacataca aactaaagaa ttacaaaaac     2640
aaattacaaa aattcaaaat tttcgggttt attacaggga cagcagagat ccagtttggc    2700
tgcatacgcg tcgtgaggct ccggtgcccg tcagtgggca gagcgcacat cgcccacagt    2760
ccccgagaag ttggggggag gggtcggcaa ttgaaccggt gcctagagaa ggtggcgcgg    2820
ggtaaactgg gaaagtgatg tcgtgtactg gctccgcctt tttcccgagg gtgggggaga    2880
accgtatata agtgcagtag tcgccgtgaa cgttcttttt cgcaacgggt ttgccgccag    2940
aacacaggta agtgccgtgt gtggttcccg cgggcctggc ctctttacgg gttatggccc    3000
ttgcgtgcct tgaattactt ccacctggct gcagtacgtg attcttgatc ccgagcttcg    3060
ggttggaagt gggtgggaga gttcgaggcc ttgcgcttaa ggagcccctt cgcctcgtgc    3120
ttgagttgag gcctggcctg ggcgctgggg ccgccgcgtg cgaatctggt ggcaccttcg    3180
cgcctgtctc gctgctttcg ataagtctct agccatttaa aatttttgat gacctgctgc    3240
gacgcttttt ttctggcaag atagtcttgt aaatgcgggc caagatctgc acactggtat    3300
ttcggttttt ggggccgcgg gcggcgacgg ggcccgtgcg tcccagcgca catgttcggc    3360
gaggcggggc ctgcgagcgc ggccaccgag aatcggacgg gggtagtctc aagctggccg    3420
gcctgctctg gtgcctggcc tcgcgccgcc gtgtatcgcc ccgccctggg cggcaaggct    3480
ggcccggtcg gcaccagttg cgtgagcgga aagatggccg cttcccggcc ctgctgcagg    3540
gagctcaaaa tggaggacgc ggcgctcggg agagcgggcg ggtgagtcac ccacacaaag    3600
gaaaagggcc tttccgtcct cagccgtcgc ttcatgtgac tccactgagt accgggcgcc    3660
gtccaggcac ctcgattagt tctcgtgctt ttggagtacg tcgtctttag gttgggggga    3720
ggggttttat gcgatggagt ttccccacac tgagtgggtg gagactgaag ttaggccagc    3780
ttggcacttg atgtaattct ccttggaatt tgccctttttt gagtttggat cttggttcat    3840
tctcaagcct cagacagtgg ttcaaagttt ttttcttcca tttcaggtgt cgtgagctag    3900
actagtacca tggacatgcg ggtgcctgca caacttctgg gcctgctgtt gttgtggctg    3960
tctggagccc ggtgtaattg ggtaaatgtt atcagtgatc tcaagaagat agaggatctc    4020
atccagtcca tgcatattga tgccacgctg tacacagaaa gcgatgtgca tcctagctgt    4080
aaggtgacag cgatgaagtg ttttcttttg gagctgcagg taattagtct tgagtccggc    4140
gatgccagca ttcatgatac cgtagaaaac ttgattatcc tggccaacaa ttctctgtcc    4200
tcaaacggaa acgtaaccga gagcggttgt aaagaatgtg aagaactgga agaaaagaac    4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg gggagagaagg agaaatgaaa gactgagaag ggagagcgtg    4560
agacctgtgg gatcctaagc tagcgtcggc aatcaacctc tggattacaa aatttgtgaa    4620
agattgactg gtattcttaa ctatgttgct ccttttacgc tatgtggata cgctgcttta    4680
atgcctttgt atcatgctat tgcttcccgt atggctttca ttttctcctc cttgtataaa    4740
```

```
tcctggttgc tgtctcttta tgaggagttg tggcccgttg tcaggcaacg tggcgtggtg      4800
tgcactgtgt ttgctgacgc aaccccact ggttgggggca ttgccaccac ctgtcagctc      4860
ctttccggga cttttcgcttt cccctccct attgccacgg cggaactcat cgccgcctgc      4920
cttgcccgct gctggacagg ggctcggctg ttgggcactg acaattccgt ggtgttgtcg      4980
gggaagctga cgtcctttcc atggctgctc gcctgtgttg ccacctggat tctgcgcggg      5040
acgtccttct gctacgtccc ttcggccctc aatccagcgg accttccttc ccgcggcctg      5100
ctgccggctc tgcggcctct tccgcgtctt cgccttcgcc ctcagacgag tcggatctcc      5160
ctttgggccg cctccccgcc tggaattcga gctcggtacc tttaagacca atgacttaca      5220
aggcagctgt agatcttagc cacttttttaa aagaaaaggg gggactggaa gggctaattc      5280
actcccaacg aagacaagat ctgctttttg cttgtactgg gtctctctgg ttagaccaga      5340
tctgagcctg ggagctctct ggctaactag ggaacccact gcttaagcct caataaagct      5400
tgccttgagt gcttcaagta gtgtgtgccc gtctgttgtg tgactctggt aactagagat      5460
ccctcagacc cttttagtca gtgtggaaaa tctctagcag tagtagttca tgtcatctta      5520
ttattcagta tttataactt gcaaagaaat gaatatcaga gagtgagagg aacttgttta      5580
ttgcagctta taatggttac aaataaagca atagcatcac aaatttcaca aataaagcat      5640 tttttttcact gcattctagt tgtggtttgt ccaaactcat caatgtatct tatcatgtct      5700
ggctctagct atcccgcccc taactccgcc cagttccgcc cattctccgc cccatggctg      5760 actaatttttt tttatttatg cagaggccga ggccgcctcg gcctctgagc tattccagaa      5820
gtagtgagga ggctttttttg gaggcctagg cttttgcgtc gagacgtacc caattcgccc      5880
tatagtgagt cgtattacgc gcgctcactg gccgtcgttt tacaacgtcg tgactgggaa      5940
aaccctggcg ttacccaact taatcgcctt gcagcacatc cccctttcgc cagctggcgt      6000
aatagcgaag aggcccgcac cgatcgccct tcccaacagt tgcgcagcct gaatggcgaa      6060
tggcgcgacg cgccctgtag cggcgcatta agcgcggcgg gtgtggtggt tacgcgcagc      6120
gtgaccgcta cacttgccag cgccctagcg cccgctcctt tcgctttctt cccttccttt      6180
ctcgccacgt tcgccggctt tccccgtcaa gctctaaatc gggggctccc tttagggttc      6240
cgatttagtg ctttacggca cctcgacccc aaaaaacttg attagggtga tggttcacgt      6300
agtgggccat cgccctgata gacggttttt cgccctttga cgttggagtc cacgttcttt      6360
aatagtggac tcttgttcca aactggaaca acactcaacc ctatctcggt ctattctttt      6420
gatttataag ggattttgcc gatttcggcc tattggttaa aaaatgagct gatttaacaa      6480
aaatttaacg cgaattttaa caaaatatta acgtttacaa tttcccaggt ggcacttttc      6540
ggggaaatgt gcgcggaacc cctatttgtt tattttttcta aatacattca aatatgtatc      6600
cgctcatgag acaataaccc tgataaatgc ttcaataata ttgaaaaagg aagagtatga      6660
gtattcaaca tttccgtgtc gcccttattc ccttttttgc ggcattttgc cttcctgttt      6720
ttgctcaccc agaaacgctg gtgaaagtaa aagatgctga gatcagttg ggtgcacgag      6780 tgggttacat cgaactggat ctcaacagcg gtaagatcct tgagagtttt cgccccgaag      6840
aacgttttcc aatgatgagc acttttaaag ttctgctatg tggcgcggta ttatcccgta      6900
ttgacgccgg gcaagagcaa ctcggtcgcc gcatacacta ttctcagaat gacttggttg      6960
agtactcacc agtcacagaa aagcatctta cggatggcat gacagtaaga gaattatgca      7020
gtgctgccat aaccatgagt gataacactg cggccaactt acttctgaca acgatcggag      7080
gaccgaagga gctaaccgct tttttgcaca acatggggga tcatgtaact cgccttgatc      7140
```

-continued

```
gttgggaacc ggagctgaat gaagccatac caaacgacga gcgtgacacc acgatgcctg      7200
tagcaatggc aacaacgttg cgcaaactat taactggcga actacttact ctagcttccc      7260
ggcaacaatt aatagactgg atggaggcgg ataaagttgc aggaccactt ctgcgctcgg      7320
cccttccggc tggctggttt attgctgata aatctggagc cggtgagcgt gggtctcgcg      7380
gtatcattgc agcactgggg ccagatggta agccctcccg tatcgtagtt atctacacga      7440
cggggagtca ggcaactatg gatgaacgaa atagacagat cgctgagata ggtgcctcac      7500
tgattaagca ttggtaactg tcagaccaag tttactcata tatactttag attgatttaa      7560
aacttcattt ttaatttaaa aggatctagg tgaagatcct ttttgataat ctcatgacca      7620
aaatccctta acgtgagttt tcgttccact gagcgtcaga ccccgtagaa aagatcaaag      7680
gatcttcttg agatcctttt tttctgcgcg taatctgctg cttgcaaaca aaaaaaccac      7740
cgctaccagc ggtggtttgt ttgccggatc aagagctacc aactcttttt ccgaaggtaa      7800
ctggcttcag cagagcgcag ataccaaata ctgtccttct agtgtagccg tagttaggcc      7860
accacttcaa gaactctgta gcaccgccta catacctcgc tctgctaatc ctgttaccag      7920
tggctgctgc cagtggcgat aagtcgtgtc ttaccgggtt ggactcaaga cgatagttac      7980
cggataaggc gcagcggtcg ggctgaacgg ggggttcgtg cacacagccc agcttggagc      8040
gaacgaccta caccgaactg agatacctac agcgtgagct atgagaaagc gccacgcttc      8100
ccgaagggag aaaggcggac aggtatccgg taagcggcag ggtcggaaca ggagagcgca      8160
cgagggagct tccaggggga aacgcctggt atctttatag tcctgtcggg tttcgccacc      8220
tctgacttga gcgtcgattt ttgtgatgct cgtcaggggg gcggagccta tggaaaaacg      8280
ccagcaacgc ggccttttta cggttcctgg ccttttgctg gcctttttgct cacatgttct      8340 ttcctgcgtt atcccctgat tctgtggata accgtattac cgcc      8384
```

<210> SEQ ID NO 35
<211> LENGTH: 9161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
tttgagtgag ctgataccgc tcgccgcagc cgaacgaccg agcgcagcga gtcagtgagc        60
gaggaagcgg aagagcgccc aatacgcaaa ccgcctctcc ccgcgcgttg gccgattcat       120
taatgcagct ggcacgacag gtttcccgac tggaaagcgg gcagtgagcg caacgcaatt       180
aatgtgagtt agctcactca ttaggcaccc caggctttac actttatgct tccggctcgt       240
atgttgtgtg gaattgtgag cggataacaa tttcacacag gaaacagcta tgaccatgat       300
tacgccaagc gcgcaattaa ccctcactaa agggaacaaa agctggagct gcaagcttaa       360
tgtagtctta tgcaatactc ttgtagtctt gcaacatggt aacgatgagt tagcaacatg       420
ccttacaagg agagaaaaag caccgtgcat gccgattggt ggaagtaagg tggtacgatc       480
gtgccttatt aggaaggcaa cagacgggtc tgacatggat tggacgaacc actgaattgc       540
cgcattgcag agatattgta tttaagtgcc tagctcgata caataaacgg tctctctgg        600 ttagaccaga tctgagcctg ggagctctct ggctaactag ggaacccact gcttaagcct       660
caataaagct tgccttgagt gcttcaagta gtgtgtgccc gtctgttgtg tgactctggt       720
aactagagat ccctcagacc cttttagtca gtgtggaaaa tctctagcag tggcgcccga       780
```

```
acagggacct gaaagcgaaa gggaaaccag agctctctcg acgcaggact cggcttgctg     840
aagcgcgcac ggcaagaggc gaggggcggc gactggtgag tacgccaaaa attttgacta     900
gcggaggcta gaaggagaga gatgggtgcg agagcgtcag tattaagcgg gggagaatta     960
gatcgcgatg ggaaaaaatt cggttaaggc caggggggaaa gaaaaaatat aaattaaaac    1020
atatagtatg ggcaagcagg gagctagaac gattcgcagt taatcctggc ctgttagaaa    1080
catcagaagg ctgtagacaa atactgggac agctacaacc atcccttcag acaggatcag    1140
aagaacttag atcattatat aatacagtag caaccctcta ttgtgtgcat caaaggatag    1200
agataaaaga caccaaggaa gctttagaca agatagagga agagcaaaac aaaagtaaga    1260
ccaccgcaca gcaagcggcc gctgatcttc agacctggag gaggagatat gagggacaat    1320
tggagaagtg aattatataa atataaagta gtaaaaattg aaccattagg agtagcaccc    1380
accaaggcaa agagaagagt ggtgcagaga gaaaaaagag cagtgggaat aggagctttg    1440
ttccttgggt tcttgggagc agcaggaagc actatgggcg cagcctcaat gacgctgacg    1500
gtacaggcca gacaattatt gtctggtata gtgcagcagc agaacaattt gctgagggct    1560
attgaggcgc aacagcatct gttgcaactc acagtctggg gcatcaagca gctccaggca    1620
agaatcctgg ctgtggaaag atacctaaag gatcaacagc tcctggggat ttggggttgc    1680
tctggaaaac tcatttgcac cactgctgtg ccttggaatg ctagttggag taataaatct    1740
ctggaacaga ttggaatcac acgacctgga tggagtggga cagagaaatt aacaattaca    1800
caagcttaat acactcctta attgaagaat cgcaaaacca gcaagaaaag aatgaacaag    1860
aattattgga attagataaa tgggcaagtt tgtggaattg gtttaacata acaaattggc    1920
tgtggtatat aaaattattc ataatgatag taggaggctt ggtaggttta agaatagttt    1980
ttgctgtact ttctatagtg aatagagtta ggcagggata ttcaccatta tcgtttcaga    2040
cccacctccc aaccccgagg ggacccgaca ggcccgaagg aatagaagaa gaaggtggag    2100
agagagacag agacagatcc attcgattag tgaacggatc tcgacggtat cgattagact    2160
gtagcccagg aatatggcag ctagattgta cacatttaga aggaaaagtt atcttggtag    2220
cagttcatgt agccagtgga tatatagaag cagaagtaat tccagcagag acagggcaag    2280
aaacagcata cttcctctta aaattagcag gaagatggcc agtaaaaaca gtacatacag    2340
acaatggcag caatttcacc agtactacag ttaaggccgc ctgttggtgg gcggggatca    2400
agcaggaatt tggcattccc tacaatcccc aaagtcaagg agtaatagaa tctatgaata    2460
aagaattaaa gaaaattata ggacaggtaa gagatcaggc tgaacatctt aagacagcag    2520
tacaaatggc agtattcatc cacaatttta aaagaaaagg ggggattggg gggtacagtg    2580
caggggaaag aatagtagac ataatagcaa cagacataca aactaaagaa ttacaaaaac    2640
aaattacaaa aattcaaaat tttcgggttt attacaggga cagcagagat ccagtttggc    2700
tgcatacgcg tcgtgaggct ccggtgcccg tcagtgggca gagcgcacat cgcccacagt    2760
ccccgagaag ttgggggggag gggtcggcaa ttgaaccggt gcctagagaa ggtggcgcgg    2820
ggtaaactgg gaaagtgatg tcgtgtactg gctccgcctt tttccgagg gtgggggaga    2880 accgtatata agtgcagtag tcgccgtgaa cgttcttttt cgcaacgggt ttgccgccag    2940
aacacaggta agtgccgtgt gtggttcccg cgggcctggc ctctttacgg gttatggccc    3000
ttgcgtgcct tgaattactt ccacctggct gcagtacgtg attcttgatc ccgagcttcg    3060
ggttggaagt gggtgggaga gttcgaggcc ttgcgcttaa ggagcccctt cgcctcgtgc    3120
```

-continued

```
ttgagttgag gcctggcctg ggcgctgggg ccgccgcgtg cgaatctggt ggcaccttcg    3180
cgcctgtctc gctgctttcg ataagtctct agccatttaa aatttttgat gacctgctgc    3240
gacgcttttt ttctggcaag atagtcttgt aaatgcgggc caagatctgc acactggtat    3300
ttcggttttt ggggccgcgg gcggcgacgg ggccgtgcg tcccagcgca catgttcggc     3360
gaggcggggc ctgcgagcgc ggccaccgag aatcggacgg gggtagtctc aagctggccg    3420
gcctgctctg gtgcctggcc tcgcgccgcc gtgtatcgcc ccgccctggg cggcaaggct    3480
ggcccggtcg gcaccagttg cgtgagcgga aagatggccg cttccggcc ctgctgcagg     3540 gagctcaaaa tggaggacgc ggcgctcggg agagcgggcg ggtgagtcac ccacacaaag    3600
gaaaagggcc tttccgtcct cagccgtcgc ttcatgtgac tccactgagt accgggcgcc    3660
gtccaggcac ctcgattagt tctcgtgctt ttggagtacg tcgtctttag gttggggggga  3720 ggggtttttat gcgatggagt ttccccacac tgagtgggtg gagactgaag ttaggccagc    3780
ttggcacttg atgtaattct ccttggaatt tgccctttttt gagtttggat cttggttcat    3840
tctcaagcct cagacagtgg ttcaaagttt ttttcttcca tttcaggtgt cgtgagctag    3900
actagtacca tggacatgcg ggtgcctgca caacttctgg gcctgctgtt gttgtggctg     3960
tctggagccc ggtgtaattg ggtaaatgtt atcagtgatc tcaagaagat agaggatctc     4020
atccagtcca tgcatattga tgccacgctg tacacagaaa gcgatgtgca tcctagctgt     4080
aaggtgacag cgatgaagtg ttttcttttg gagctgcagg taattagtct tgagtccggc    4140
gatgccagca ttcatgatac cgtagaaaac ttgattatcc tggccaacaa ttctctgtcc    4200
tcaaacggaa acgtaaccga gagcggttgt aaagaatgtg aagaactgga agaaaagaac    4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg ggagagaagg agaaatgaaa gactgagaag ggagagcgtg    4560
agacctgtgg gatcctccca tcactggggg tacggcaaac acaacggacc tgagcactgg    4620
cataaggact tccccattgc caagggagag cgccagtccc ctgttgacat cgacactcat    4680
acagccaagt atgacccttc cctgaagccc ctgtctgttt cctatgatca agcaacttcc    4740
ctgagaatcc tcaacaatgg tcatgctttc aacgtggagt ttgatgactc tcaggacaaa    4800
gcagtgctca agggaggacc cctggatggc acttacagat tgattcagtt tcactttcac    4860
tggggttcac ttgatggaca aggttcagag catactgtgg ataaaaagaa atatgctgca    4920
gaacttcact tggttcactg gaacaccaaa tatggggatt ttgggaaagc tgtgcagcaa    4980
cctgatggac tggccgttct aggtattttt ttgaaggttg gcagcgctaa accgggccat    5040
cagaaagttg ttgatgtgct ggattccatt aaaacaaagg gcaagagtgc tgacttcact    5100
aacttcgatc ctcgtggcct ccttcctgaa tccctggatt actggaccta cccaggctca    5160
ctgaccaccc ctcctcttct ggaatgtgtg acctggattg tgctcaagga acccatcagc    5220
gtcagcagcg agcaggtgtt gaaattccgt aaacttaact tcaatgggga gggtgaaccc    5280
gaagaactga tggtggacaa ctggcgccca gctcagccac tgaagaacag gcaaatcaaa    5340
gcttccttca aataagctag cgtcgacaat caacctctgg attacaaaat ttgtgaaaga    5400
ttgactggta ttcttaacta tgttgctcct tttacgctat gtggatacgc tgctttaatg    5460
cctttgtatc atgctattgc ttcccgtatg gctttcattt tctcctcctt gtataaatcc    5520
```

```
tggttgctgt ctctttatga ggagttgtgg cccgttgtca ggcaacgtgg cgtggtgtgc    5580
actgtgtttg ctgacgcaac ccccactggt tggggcattg ccaccacctg tcagctcctt    5640
tccgggactt tcgctttccc cctccctatt gccacggcgg aactcatcgc cgcctgcctt    5700
gcccgctgct ggacaggggc tcggctgttg ggcactgaca attccgtggt gttgtcgggg    5760
aagctgacgt cctttccatg gctgctcgcc tgtgttgcca cctggattct gcgcgggacg    5820
tccttctgct acgtcccttc ggccctcaat ccagcggacc ttccttcccg cggcctgctg    5880
ccggctctgc ggcctcttcc gcgtcttcgc cttcgccctc agacgagtcg gatctccctt    5940
tgggccgcct ccccgcctgg aattcgagct cggtaccttt aagaccaatg acttacaagg    6000
cagctgtaga tcttagccac tttttaaaag aaaaggggg actggaaggg ctaattcact    6060
cccaacgaag acaagatctg cttttttgctt gtactgggtc tctctggtta gaccagatct    6120
gagcctggga gctctctggc taactaggga acccactgct taagcctcaa taaagcttgc    6180
cttgagtgct tcaagtagtg tgtgcccgtc tgttgtgtga ctctggtaac tagagatccc    6240
tcagacccct ttagtcagtg tggaaaatct ctagcagtag tagttcatgt catcttatta    6300
ttcagtattt ataacttgca aagaaatgaa tatcagagag tgagaggaac ttgtttattg    6360
cagcttataa tggttacaaa taaagcaata gcatcacaaa tttcacaaat aaagcatttt    6420
tttcactgca ttctagttgt ggtttgtcca aactcatcaa tgtatcttat catgtctggc    6480
tctagctatc ccgcccctaa ctccgcccag ttccgcccat tctccgcccc atggctgact    6540
aatttttttt atttatgcag aggccgaggc cgcctcggcc tctgagctat tccagaagta    6600
gtgaggaggc ttttttggag gcctaggctt ttgcgtcgag acgtacccaa ttcgccctat    6660
agtgagtcgt attacgcgcg ctcactggcc gtcgttttac aacgtcgtga ctgggaaaac    6720
cctggcgtta cccaacttaa tcgccttgca gcacatcccc ctttcgccag ctggcgtaat    6780
agcgaagagg cccgcaccga tcgcccttcc caacagttgc gcagcctgaa tggcgaatgg    6840
cgcgacgcgc cctgtagcgg cgcattaagc gcggcgggtg tggtggttac gcgcagcgtg    6900
accgctacac ttgccagcgc cctagcgccc gctcctttcg ctttcttccc ttcctttctc    6960
gccacgttcg ccggctttcc ccgtcaagct ctaaatcggg ggctcccttt agggttccga    7020
tttagtgctt tacggcacct cgaccccaaa aaacttgatt agggtgatgg ttcacgtagt    7080
gggccatcgc cctgatagac ggtttttcgc cctttgacgt tggagtccac gttctttaat    7140
agtggactct tgttccaaac tggaacaaca ctcaacccta tctcggtcta ttcttttgat    7200
ttataaggga ttttgccgat ttcggcctat tggttaaaaa atgagctgat ttaacaaaaa    7260
tttaacgcga attttaacaa aatattaacg tttacaattt cccaggtggc actttccggg    7320
gaaatgtgcg cggaacccct atttgtttat ttttctaaat acattcaaat atgtatccgc    7380
tcatgagaca ataaccctga taaatgcttc aataatattg aaaaaggaag agtatgagta    7440
ttcaacattt ccgtgtcgcc cttattccct tttttgcggc attttgcctt cctgtttttg    7500
ctcacccaga aacgctggtg aaagtaaaag atgctgaaga tcagttgggt gcacgagtgg    7560
gttacatcga actggatctc aacagcggta agatccttga gttttcgc cccgaagaac    7620 gttttccaat gatgagcact tttaaagttc tgctatgtgg cgcggtatta tcccgtattg    7680
acgccgggca agagcaactc ggtcgccgca tacactattc tcagaatgac ttggttgagt    7740
actcaccagt cacagaaaag catcttacgg atggcatgac agtaagagaa ttatgcagtg    7800
ctgccataac catgagtgat aacactgcgg ccaacttact tctgacaacg atcggaggac    7860
```

-continued

```
cgaaggagct aaccgctttt ttgcacaaca tgggggatca tgtaactcgc cttgatcgtt      7920
gggaaccgga gctgaatgaa gccataccaa acgacgagcg tgacaccacg atgcctgtag      7980
caatggcaac aacgttgcgc aaactattaa ctggcgaact acttactcta gcttcccggc      8040
aacaattaat agactggatg gaggcggata aagttgcagg accacttctg cgctcggccc      8100
ttccggctgg ctggtttatt gctgataaat ctggagccgg tgagcgtggg tctcgcggta      8160
tcattgcagc actggggcca gatggtaagc cctcccgtat cgtagttatc tacacgacgg      8220
ggagtcaggc aactatggat gaacgaaata gacagatcgc tgagataggt gcctcactga      8280
ttaagcattg gtaactgtca gaccaagttt actcatatat actttagatt gatttaaaac      8340 ttcatttta atttaaaagg atctaggtga agatcctttt tgataatctc atgaccaaaa      8400
tcccttaacg tgagttttcg ttccactgag cgtcagaccc cgtagaaaag atcaaaggat      8460
cttcttgaga tcctttttttt ctgcgcgtaa tctgctgctt gcaaacaaaa aaaccaccgc      8520
taccagcggt ggtttgtttg ccggatcaag agctaccaac tctttttccg aaggtaactg      8580
gcttcagcag agcgcagata ccaaatactg tccttctagt gtagccgtag ttaggccacc      8640
acttcaagaa ctctgtagca ccgcctacat acctcgctct gctaatcctg ttaccagtgg      8700
ctgctgccag tggcgataag tcgtgtctta ccgggttgga ctcaagacga tagttaccgg      8760
ataaggcgca gcggtcgggc tgaacggggg gttcgtgcac acagcccagc ttggagcgaa      8820
cgacctacac cgaactgaga tacctacagc gtgagctatg agaaagcgcc acgcttcccg      8880
aagggagaaa ggcggacagg tatccggtaa gcggcagggt cggaacagga gagcgcacga      8940
gggagcttcc agggggaaac gcctggtatc tttatagtcc tgtcgggttt cgccacctct      9000
gacttgagcg tcgatttttg tgatgctcgt caggggggcg gagcctatgg aaaaacgcca      9060
gcaacgcggc cttttttacgg ttcctggcct tttgctggcc ttttgctcac atgttctttc      9120
ctgcgttatc ccctgattct gtggataacc gtattaccgc c                          9161
```

<210> SEQ ID NO 36
<211> LENGTH: 8384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
tttgagtgag ctgataccgc tcgccgcagc cgaacgaccg agcgcagcga gtcagtgagc        60
gaggaagcgg aagagcgccc aatacgcaaa ccgcctctcc ccgcgcgttg gccgattcat       120
taatgcagct ggcacgacag gtttcccgac tggaaagcgg gcagtgagcg caacgcaatt       180
aatgtgagtt agctcactca ttaggcaccc caggctttac actttatgct tccggctcgt       240
atgttgtgtg gaattgtgag cggataacaa tttcacacag gaaacagcta tgaccatgat       300
tacgccaagc gcgcaattaa ccctcactaa agggaacaaa agctggagct gcaagcttaa       360
tgtagtctta tgcaatactc ttgtagtctt gcaacatggt aacgatgagt tagcaacatg       420
ccttacaagg agagaaaaag caccgtgcat gccgattggt ggaagtaagg tggtacgatc       480
gtgccttatt aggaaggcaa cagacgggtc tgacatggat tggacgaacc actgaattgc       540
cgcattgcag agatattgta tttaagtgcc tagctcgata caataaacgg tctctctgg        600 ttagaccaga tctgagcctg ggagctctct ggctaactag ggaacccact gcttaagcct       660
caataaagct tgccttgagt gcttcaagta gtgtgtgccc gtctgttgtg tgactctggt       720
```

-continued

```
aactagagat ccctcagacc cttttagtca gtgtggaaaa tctctagcag tggcgcccga      780
acagggacct gaaagcgaaa gggaaaccag agctctctcg acgcaggact cggcttgctg      840
aagcgcgcac ggcaagaggc gaggggcggc gactggtgag tacgccaaaa attttgacta      900
gcggaggcta gaaggagaga gatgggtgcg agagcgtcag tattaagcgg gggagaatta      960
gatcgcgatg ggaaaaaatt cggttaaggc cagggggaaa gaaaaaatat aaattaaaac     1020
atatagtatg ggcaagcagg gagctagaac gattcgcagt taatcctggc ctgttagaaa     1080
catcagaagg ctgtagacaa atactgggac agctacaacc atcccttcag acaggatcag     1140
aagaacttag atcattatat aatacagtag caaccctcta ttgtgtgcat caaaggatag     1200
agataaaaga caccaaggaa gctttagaca agatagagga agagcaaaac aaaagtaaga     1260
ccaccgcaca gcaagcggcc gctgatcttc agacctggag gaggagatat gagggacaat     1320
tggagaagtg aattatataa atataaagta gtaaaaattg aaccattagg agtagcaccc     1380
accaaggcaa agagaagagt ggtgcagaga gaaaaaagag cagtgggaat aggagctttg     1440
ttccttgggt tcttgggagc agcaggaagc actatgggcg cagcctcaat gacgctgacg     1500
gtacaggcca gacaattatt gtctggtata gtgcagcagc agaacaattt gctgagggct     1560
attgaggcgc aacagcatct gttgcaactc acagtctggg gcatcaagca gctccaggca     1620
agaatcctgg ctgtggaaag atacctaaag gatcaacagc tcctggggat ttggggttgc     1680
tctggaaaac tcatttgcac cactgctgtg ccttggaatg ctagttggag taataaatct     1740
ctggaacaga ttggaatcac acgacctgga tggagtggga cagagaaatt aacaattaca     1800
caagcttaat acactcctta attgaagaat cgcaaaacca gcaagaaaag aatgaacaag     1860
aattattgga attagataaa tgggcaagtt tgtggaattg gtttaacata acaaattggc     1920
tgtggtatat aaaattattc ataatgatag taggaggctt ggtaggttta agaatagttt     1980
ttgctgtact ttctatagtg aatagagtta ggcagggata ttcaccatta tcgtttcaga     2040
cccacctccc aaccccgagg ggacccgaca ggcccgaagg aatagaagaa gaaggtggag     2100
agagagacag agacagatcc attcgattag tgaacggatc tcgacggtat cgattagact     2160
gtagcccagg aatatggcag ctagattgta cacatttaga aggaaaagtt atcttggtag     2220
cagttcatgt agccagtgga tatatagaag cagaagtaat tccagcagag acagggcaag     2280
aaacagcata cttcctctta aaattagcag gaagatggcc agtaaaaaca gtacatacag     2340
acaatggcag caatttcacc agtactacag ttaaggccgc ctgttggtgg gcggggatca     2400
agcaggaatt tggcattccc tacaatcccc aaagtcaagg agtaatagaa tctatgaata     2460
aagaattaaa gaaaattata ggacaggtaa gagatcaggc tgaacatctt aagacagcag     2520
tacaaatggc agtattcatc cacaatttta aaagaaaagg ggggattggg gggtacagtg     2580
caggggaaag aatagtagac ataatagcaa cagacataca aactaaagaa ttacaaaaac     2640
aaattacaaa aattcaaaat tttcgggttt attacaggga cagcagagat ccagtttggc     2700
tgcatacgcg tcgtgaggct ccggtgcccg tcagtgggca gagcgcacat cgcccacagt     2760
ccccgagaag ttggggggag gggtcggcaa ttgaaccggt gcctagagaa ggtggcgcgg     2820
ggtaaactgg gaaagtgatg tcgtgtactg gctccgcctt tttccgagg gtgggggaga     2880 accgtatata agtgcagtag tcgccgtgaa cgttcttttt cgcaacgggt ttgccgccag     2940
aacacaggta agtgccgtgt gtggttcccg cgggcctggc ctctttacgg gttatggccc     3000
ttgcgtgcct tgaattactt ccacctggct gcagtacgtg attcttgatc ccgagcttcg     3060
ggttggaagt gggtgggaga gttcgaggcc ttgcgcttaa ggagcccctt cgcctcgtgc     3120
```

-continued

```
ttgagttgag gcctggcctg ggcgctgggg ccgccgcgtg cgaatctggt ggcaccttcg   3180
cgcctgtctc gctgctttcg ataagtctct agccatttaa aatttttgat gacctgctgc   3240
gacgcttttt ttctggcaag atagtcttgt aaatgcgggc caagatctgc acactggtat   3300
ttcggttttt ggggccgcgg gcggcgacgg ggcccgtgcg tcccagcgca catgttcggc   3360
gaggcggggc ctgcgagcgc ggccaccgag aatcggacgg gggtagtctc aagctggccg   3420
gcctgctctg gtgcctggcc tcgcgccgcc gtgtatcgcc ccgccctggg cggcaaggct   3480
ggcccggtcg gcaccagttg cgtgagcgga aagatggccg cttcccggcc ctgctgcagg   3540
gagctcaaaa tggaggacgc ggcgctcggg agagcgggcg ggtgagtcac ccacacaaag   3600
gaaaagggcc tttccgtcct cagccgtcgc ttcatgtgac tccactgagt accgggcgcc   3660
gtccaggcac ctcgattagt tctcgtgctt ttggagtacg tcgtctttag gttgggggga   3720
ggggttttat gcgatggagt ttccccacac tgagtgggtg gagactgaag ttaggccagc   3780
ttggcacttg atgtaattct ccttggaatt tgcccttttt gagtttggat cttggttcat   3840
tctcaagcct cagacagtgg ttcaaagttt ttttcttcca tttcaggtgt cgtgagctag   3900
actagtacca tggacatgcg ggtgcctgca caacttctgg gcctgctgtt gttgtggctg   3960
tctggagccc ggtgtaattg ggtaaatgtt atcagtgatc tcaagaagat agaggatctc   4020
atccagtcca tgcatattga tgccacgctg tacacagaaa gcgatgtgca tcctagctgt   4080
aaggtgacag cgatgaagtg ttttctttg gagctgcagg taattagtct tgagtccggc   4140
gatgccagca ttcatgatac cgtagaaaac ttgattatcc tggccaacaa ttctctgtcc   4200
tcaaacggaa acgtaaccga gagcggttgt aaagaatgtg aagaactgga agaaaagaac   4260
atcaaggagt ttctgcaatc attcgttcac atcgtacaaa tgttcataaa tacgtcagga   4320
tctggttctg gttccggaag tggatctggt tcagggtccg gtagtggatc tgggtcagga   4380
agtggaagcg gtagtgggtc tggatctaaa caagagcact ttcctgataa cctgttgccg   4440
agctgggcga ttacgcttat cagtgtaaac ggcatctttg taatatgctg tctgacctac   4500
tgcttcgcac caaggtgccg ggagagagca agaaatgaaa gactgagaag ggagaccgtg   4560
agacctgtgg gatcctaagc tagcgtcgac aatcaacctc tggattacaa aatttgtgaa   4620
agattgactg gtattcttaa ctatgttgct ccttttacgc tatgtggata cgctgcttta   4680
atgcctttgt atcatgctat tgcttcccgt atggctttca ttttctcctc cttgtataaa   4740
tcctggttgc tgtctcttta tgaggagttg tggcccgttg tcaggcaacg tggcgtggtg   4800
tgcactgtgt ttgctgacgc aaccccccact ggttggggca ttgccaccac ctgtcagctc   4860
ctttccggga ctttcgcttt ccccctccct attgccacgg cggaactcat cgccgcctgc   4920
cttgcccgct gctggacagg ggctcggctg ttgggcactg acaattccgt ggtgttgtcg   4980
gggaagctga cgtcctttcc atggctgctc gcctgtgttg ccacctggat tctgcgcggg   5040
acgtccttct gctacgtccc ttcggccctc aatccagcgg accttccttc ccgcggcctg   5100
ctgccggctc tgcggcctct tccgcgtctt cgccttcgcc ctcagacgag tcggatctcc   5160
ctttgggccg cctccccgcc tggaattcga gctcggtacc tttaagacca atgacttaca   5220
aggcagctgt agatcttagc cactttttaa aagaaaaggg gggactggaa gggctaattc   5280
actcccaacg aagacaagat ctgcttttg cttgtactgg gtctctctgg ttagaccaga   5340
tctgagcctg ggagctctct ggctaactag ggaacccact gcttaagcct caataaagct   5400
tgccttgagt gcttcaagta gtgtgtgccc gtctgttgtg tgactctggt aactagagat   5460
```

-continued

```
ccctcagacc cttttagtca gtgtggaaaa tctctagcag tagtagttca tgtcatctta   5520
ttattcagta tttataactt gcaaagaaat gaatatcaga gagtgagagg aacttgttta   5580
ttgcagctta taatggttac aaataaagca atagcatcac aaatttcaca aataaagcat   5640 tttttttcact gcattctagt tgtggtttgt ccaaactcat caatgtatct tatcatgtct   5700
ggctctagct atcccgcccc taactccgcc cagttccgcc cattctccgc cccatggctg   5760 actaatttt tttatttatg cagaggccga ggccgcctcg gcctctgagc tattccagaa   5820
gtagtgagga ggcttttttg gaggcctagg cttttgcgtc gagacgtacc caattcgccc   5880
tatagtgagt cgtattacgc gcgctcactg gccgtcgttt tacaacgtcg tgactgggaa   5940
aaccctggcg ttacccaact taatcgcctt gcagcacatc ccccttttcgc cagctggcgt   6000 aatagcgaag aggcccgcac cgatcgccct tcccaacagt tgcgcagcct gaatggcgaa   6060
tggcgcgacg cgccctgtag cggcgcatta agcgcggcgg gtgtggtggt tacgcgcagc   6120
gtgaccgcta cacttgccag cgccctagcg cccgctcctt tcgctttctt cccttccttt   6180
ctcgccacgt tcgccggctt tccccgtcaa gctctaaatc gggggctccc tttagggttc   6240
cgatttagtg ctttacggca cctcgacccc aaaaaacttg attagggtga tggttcacgt   6300
agtgggccat cgccctgata gacggttttt cgccctttga cgttggagtc cacgttcttt   6360
aatagtggac tcttgttcca aactggaaca cactcaacc ctatctcggt ctattctttt   6420
gatttataag ggattttgcc gatttcggcc tattggttaa aaaatgagct gatttaacaa   6480
aaatttaacg cgaattttaa caaaatatta cgtttacaa tttcccaggt ggcacttttc   6540
ggggaaatgt gcgcggaacc cctatttgtt tattttttcta aatacattca aatatgtatc   6600
cgctcatgag acaataaccc tgataaatgc ttcaataata ttgaaaaagg aagagtatga   6660
gtattcaaca tttccgtgtc gcccttattc cctttttttgc ggcattttgc cttcctgttt   6720
ttgctcaccc agaaacgctg gtgaaagtaa aagatgctga agatcagttg ggtgcacgag   6780
tgggttacat cgaactggat ctcaacagcg gtaagatcct tgagagtttt cgccccgaag   6840
aacgttttcc aatgatgagc acttttaaag ttctgctatg tggcgcggta ttatcccgta   6900
ttgacgccgg gcaagagcaa ctcggtcgcc gcatacacta ttctcagaat gacttggttg   6960
agtactcacc agtcacagaa aagcatctta cggatggcat gacagtaaga gaattatgca   7020
gtgctgccat aaccatgagt gataacactg cggccaactt acttctgaca acgatcggag   7080
gaccgaagga gctaaccgct tttttgcaca acatggggga tcatgtaact cgccttgatc   7140
gttgggaacc ggagctgaat gaagccatac caaacgacga gcgtgacacc acgatgcctg   7200
tagcaatggc aacaacgttg cgcaaactat taactggcga actacttact ctagcttccc   7260
ggcaacaatt aatagactgg atggaggcgg ataaagttgc aggaccactt ctgcgctcgg   7320
cccttccggc tggctggttt attgctgata atctggagc cggtgagcgt gggtctcgcg   7380
gtatcattgc agcactgggg ccagatggta agccctccg tatcgtagtt atctacacga   7440
cggggagtca ggcaactatg gatgaacgaa atagacagat cgctgagata ggtgcctcac   7500
tgattaagca ttggtaactg tcagaccaag tttactcata tatactttag attgatttaa   7560
aacttcattt ttaatttaaa aggatctagg tgaagatcct ttttgataat ctcatgacca   7620
aaatccctta acgtgagttt tcgttccact gagcgtcaga ccccgtagaa aagatcaaag   7680
gatcttcttg agatcctttt tttctgcgcg taatctgctg cttgcaaaca aaaaaaccac   7740
cgctaccagc ggtggtttgt ttgccggatc aagagctacc aactcttttt ccgaaggtaa   7800
ctggcttcag cagagcgcag ataccaaata ctgtccttct agtgtagccg tagttaggcc   7860
```

-continued

```
accacttcaa gaactctgta gcaccgccta catacctcgc tctgctaatc ctgttaccag    7920
tggctgctgc cagtggcgat aagtcgtgtc ttaccgggtt ggactcaaga cgatagttac    7980
cggataaggc gcagcggtcg ggctgaacgg ggggttcgtg cacacagccc agcttggagc    8040
gaacgaccta caccgaactg agatacctac agcgtgagct atgagaaagc gccacgcttc    8100
ccgaagggag aaaggcggac aggtatccgg taagcggcag ggtcggaaca ggagagcgca    8160
cgagggagct tccaggggga aacgcctggt atctttatag tcctgtcggg tttcgccacc    8220
tctgacttga gcgtcgattt ttgtgatgct cgtcaggggg cggagccta tggaaaaacg    8280 ccagcaacgc ggcctttta cggttcctgg ccttttgctg gccttttgct cacatgttct    8340
ttcctgcgtt atcccctgat tctgtggata accgtattac cgcc                     8384
```

<210> SEQ ID NO 37
<211> LENGTH: 9161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
tttgagtgag ctgataccgc tcgccgcagc cgaacgaccg agcgcagcga gtcagtgagc      60
gaggaagcgg aagagcgccc aatacgcaaa ccgcctctcc ccgcgcgttg gccgattcat     120
taatgcagct ggcacgacag gtttcccgac tggaaagcgg gcagtgagcg caacgcaatt     180
aatgtgagtt agctcactca ttaggcaccc caggctttac actttatgct tccggctcgt     240
atgttgtgtg gaattgtgag cggataacaa tttcacacag gaaacagcta tgaccatgat     300
tacgccaagc gcgcaattaa ccctcactaa agggaacaaa agctggagct gcaagcttaa     360
tgtagtctta tgcaatactc ttgtagtctt gcaacatggt aacgatgagt tagcaacatg     420
ccttacaaga gagaaaaag caccgtgcat gccgattggt ggaagtaagg tggtacgatc     480
gtgccttatt aggaaggcaa cagacgggtc tgacatggat tggacgaacc actgaattgc     540
cgcattgcag agatattgta tttaagtgcc tagctcgata caataaacgg tctctctgg     600 ttagaccaga tctgagcctg ggagctctct ggctaactag ggaacccact gcttaagcct     660
caataaagct tgccttgagt gcttcaagta gtgtgtgccc gtctgttgtg tgactctggt     720
aactagagat ccctcagacc cttttagtca gtgtggaaaa tctctagcag tggcgcccga     780
acagggacct gaaagcgaaa gggaaaccag agctctctcg acgcaggact cggcttgctg     840
aagcgcgcac ggcaagaggc gaggggcggc gactggtgag tacgccaaaa attttgacta     900
gcggaggcta gaaggagaga gatgggtgcg agagcgtcag tattaagcgg gggagaatta     960
gatcgcgatg ggaaaaaatt cggttaaggc caggggaaa gaaaaaatat aaattaaaac    1020
atatagtatg ggcaagcagg gagctagaac gattcgcagt taatcctggc ctgttagaaa    1080
catcagaagg ctgtagacaa atactgggac agctacaacc atcccttcag acaggatcag    1140
aagaacttag atcattatat aatacagtag caaccctcta ttgtgtgcat caaaggatag    1200
agataaaaga caccaaggaa gctttagaca agatagagga gagcaaaac aaaagtaaga    1260 ccaccgcaca gcaagcggcc gctgatcttc agacctggag gaggagatat gagggacaat    1320
tggagaagtg aattatataa atataaagta gtaaaaattg aaccattagg agtagcaccc    1380
accaaggcaa agagaagagt ggtgcagaga gaaaaaagag cagtgggaat aggagctttg    1440
ttccttgggt tcttgggagc agcaggaagc actatgggcg cagcctcaat gacgctgacg    1500
```

-continued

```
gtacaggcca gacaattatt gtctggtata gtgcagcagc agaacaattt gctgagggct    1560
attgaggcgc aacagcatct gttgcaactc acagtctggg gcatcaagca gctccaggca    1620
agaatcctgg ctgtggaaag atacctaaag gatcaacagc tcctggggat ttggggttgc    1680
tctggaaaac tcatttgcac cactgctgtg ccttggaatg ctagttggag taataaatct    1740
ctggaacaga ttggaatcac acgacctgga tggagtggga cagagaaatt aacaattaca    1800
caagcttaat acactcctta attgaagaat cgcaaaacca gcaagaaaag aatgaacaag    1860
aattattgga attagataaa tgggcaagtt tgtggaattg gtttaacata acaaattggc    1920
tgtggtatat aaaattattc ataatgatag taggaggctt ggtaggttta agaatagttt    1980
ttgctgtact ttctatagtg aatagagtta ggcagggata ttcaccatta tcgtttcaga    2040
cccacctccc aaccccgagg ggacccgaca ggcccgaagg aatagaagaa gaaggtggag    2100
agagagacag agacagatcc attcgattag tgaacggatc tcgacggtat cgattagact    2160
gtagcccagg aatatggcag ctagattgta cacatttaga aggaaaagtt atcttggtag    2220
cagttcatgt agccagtgga tatatagaag cagaagtaat tccagcagag acagggcaag    2280
aaacagcata cttcctctta aaattagcag gaagatggcc agtaaaaaca gtacatacag    2340
acaatggcag caatttcacc agtactacag ttaaggccgc ctgttggtgg gcggggatca    2400
agcaggaatt tggcattccc tacaatcccc aaagtcaagg agtaatagaa tctatgaata    2460
aagaattaaa gaaaattata ggacaggtaa gagatcaggc tgaacatctt aagacagcag    2520
tacaaatggc agtattcatc cacaatttta aaagaaaagg ggggattggg gggtacagtg    2580 cagggggaaag aatagtagac ataatagcaa cagacataca aactaaagaa ttacaaaaac    2640
aaattacaaa aattcaaaat tttcgggttt attacaggga cagcagagat ccagtttggc    2700
tgcatacgcg tcgtgaggct ccggtgcccg tcagtgggca gagcgcacat cgcccacagt    2760
ccccgagaag ttggggggag gggtcggcaa ttgaaccggt gcctagagaa ggtggcgcgg    2820
ggtaaactgg gaaagtgatg tcgtgtactg gctccgcctt tttcccgagg gtgggggaga    2880
accgtatata agtgcagtag tcgccgtgaa cgttcttttt cgcaacgggt ttgccgccag    2940
aacacaggta agtgccgtgt gtggttcccg cgggcctggc ctctttacgg gttatggccc    3000
ttgcgtgcct tgaattactt ccacctggct gcagtacgtg attcttgatc ccgagcttcg    3060
ggttggaagt gggtgggaga gttcgaggcc ttgcgcttaa ggagcccctt cgcctcgtgc    3120
ttgagttgag gcctggcctg ggcgctgggg ccgccgcgtg cgaatctggt ggcaccttcg    3180
cgcctgtctc gctgctttcg ataagtctct agccatttaa aattttttgat gacctgctgc    3240 gacgcttttt ttctggcaag atagtcttgt aaatgcgggc caagatctgc acactggtat    3300
ttcggttttt ggggccgcgg gcggcgacgg ggcccgtgcg tcccagcgca catgttcggc    3360
gaggcggggc ctgcgagcgc ggccaccgag aatcggacgg gggtagtctc aagctggccg    3420
gcctgctctg gtgcctggcc tcgcgccgcc gtgtatcgcc ccgccctggg cggcaaggct    3480
ggcccggtcg gcaccagttg cgtgagcgga aagatggccg cttcccggcc ctgctgcagg    3540
gagctcaaaa tggaggacgc ggcgctcggg agagcgggcg ggtgagtcac ccacacaaag    3600
gaaaagggcc tttccgtcct cagccgtcgc ttcatgtgac tccactgagt accgggcgcc    3660
gtccaggcac ctcgattagt tctcgtgctt ttggagtacg tcgtctttag gttggggga    3720 ggggtttttat gcgatggagt ttccccacac tgagtgggtg gagactgaag ttaggccagc    3780
ttggcacttg atgtaattct ccttggaatt tgccctttt gagtttggat cttggttcat    3840
```

-continued

```
tctcaagcct cagacagtgg ttcaaagttt ttttcttcca tttcaggtgt cgtgagctag    3900
actagtacca tggacatgcg ggtgcctgca caacttctgg gcctgctgtt gttgtggctg    3960
tctggagccc ggtgtaattg ggtaaatgtt atcagtgatc tcaagaagat agaggatctc    4020
atccagtcca tgcatattga tgccacgctg tacacagaaa gcgatgtgca tcctagctgt    4080
aaggtgacag cgatgaagtg ttttcttttg gagctgcagg taattagtct tgagtccggc    4140
gatgccagca ttcatgatac cgtagaaaac ttgattatcc tggccaacaa ttctctgtcc    4200
tcaaacggaa acgtaaccga gagcggttgt aaagaatgtg aagaactgga agaaaagaac    4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg ggagagagca agaaatgaaa gactgagaag ggagaccgtg    4560
agacctgtgg gatcctccca tcactggggg tacggcaaac acaacggacc tgagcactgg    4620
cataaggact tccccattgc caagggagag cgccagtccc ctgttgacat cgacactcat    4680
acagccaagt atgacccttc cctgaagccc ctgtctgttt cctatgatca agcaacttcc    4740
ctgagaatcc tcaacaatgg tcatgctttc aacgtggagt ttgatgactc tcaggacaaa    4800
gcagtgctca agggaggacc cctggatggc acttacagat tgattcagtt tcactttcac    4860
tggggttcac ttgatggaca aggttcagag catactgtgg ataaaaagaa atatgctgca    4920
gaacttcact tggttcactg gaacaccaaa tatgggggatt ttgggaaagc tgtgcagcaa    4980
cctgatggac tggccgttct aggtattttt ttgaaggttg gcagcgctaa accgggccat    5040
cagaaagttg ttgatgtgct ggattccatt aaaacaaagg gcaagagtgc tgacttcact    5100
aacttcgatc ctcgtggcct ccttcctgaa tccctggatt actggaccta cccaggctca    5160
ctgaccaccc ctcctcttct ggaatgtgtg acctggattg tgctcaagga acccatcagc    5220
gtcagcagcg agcaggtgtt gaaattccgt aaacttaact tcaatgggga gggtgaaccc    5280
gaagaactga tggtggacaa ctggcgccca gctcagccac tgaagaacag gcaaatcaaa    5340
gcttccttca ataagctag cgtcgacaat caacctctgg attacaaaat ttgtgaaaga    5400
ttgactggta ttcttaacta tgttgctcct tttacgctat gtggatacgc tgctttaatg    5460
cctttgtatc atgctattgc ttcccgtatg gctttcattt tctcctcctt gtataaatcc    5520
tggttgctgt ctctttatga ggagttgtgg cccgttgtca ggcaacgtgg cgtggtgtgc    5580
actgtgtttg ctgacgcaac ccccactggt tggggcattg ccaccacctg tcagctcctt    5640
tccgggactt tcgctttccc cctccctatt gccacggcgg aactcatcgc cgcctgcctt    5700
gcccgctgct ggacaggggc tcggctgttg ggcactgaca attccgtggt gttgtcgggg    5760
aagctgacgt cctttccatg gctgctcgcc tgtgttgcca cctggattct gcgcgggacg    5820
tccttctgct acgtcccttc ggccctcaat ccagcggacc ttccttcccg cggcctgctg    5880
ccggctctgc ggcctcttcc gcgtcttcgc cttcgccctc agacgagtcg gatctccctt    5940
tgggccgcct ccccgcctgg aattcgagct cggtaccttt aagaccaatg acttacaagg    6000
cagctgtaga tcttagccac ttttttaaaag aaaaggggg actggaaggg ctaattcact    6060
cccaacgaag acaagatctg cttttttgctt gtactgggtc tctctggtta gaccagatct    6120
gagcctggga gctctctggc taactaggga acccactgct taagcctcaa taaagcttgc    6180
cttgagtgct tcaagtagtg tgtgcccgtc tgttgtgtga ctctggtaac tagagatccc    6240
```

-continued

```
tcagaccctt ttagtcagtg tggaaaatct ctagcagtag tagttcatgt catcttatta    6300
ttcagtattt ataacttgca aagaaatgaa tatcagagag tgagaggaac ttgtttattg    6360
cagcttataa tggttacaaa taaagcaata gcatcacaaa tttcacaaat aaagcatttt    6420
tttcactgca ttctagttgt ggtttgtcca aactcatcaa tgtatcttat catgtctggc    6480
tctagctatc ccgcccctaa ctccgcccag ttccgcccat tctccgcccc atggctgact    6540
aatttttttt atttatgcag aggccgaggc cgcctcggcc tctgagctat tccagaagta    6600
gtgaggaggc ttttttggag gcctaggctt ttgcgtcgag acgtacccaa ttcgccctat    6660
agtgagtcgt attacgcgcg ctcactggcc gtcgttttac aacgtcgtga ctgggaaaac    6720
cctggcgtta cccaacttaa tcgccttgca gcacatcccc ctttcgccag ctggcgtaat    6780
agcgaagagg cccgcaccga tcgcccttcc caacagttgc gcagcctgaa tggcgaatgg    6840
cgcgacgcgc cctgtagcgg cgcattaagc gcggcgggtg tggtggttac gcgcagcgtg    6900
accgctacac ttgccagcgc cctagcgccc gctcctttcg ctttcttccc ttcctttctc    6960
gccacgttcg ccggctttcc ccgtcaagct ctaaatcggg ggctcccttt agggttccga    7020
tttagtgctt tacggcacct cgaccccaaa aaacttgatt agggtgatgg ttcacgtagt    7080
gggccatcgc cctgatagac ggtttttcgc cctttgacgt tggagtccac gttctttaat    7140
agtggactct tgttccaaac tggaacaaca ctcaacccta tctcggtcta ttcttttgat    7200
ttataaggga ttttgccgat ttcggcctat tggttaaaaa atgagctgat ttaacaaaaa    7260
tttaacgcga attttaacaa aatattaacg tttacaattt cccaggtggc acttttcggg    7320
gaaatgtgcg cggaacccct atttgtttat ttttctaaat acattcaaat atgtatccgc    7380
tcatgagaca ataaccctga taaatgcttc aataatattg aaaaaggaag agtatgagta    7440
ttcaacattt ccgtgtcgcc cttattccct ttttttgcggc attttgcctt cctgtttttg    7500
ctcacccaga aacgctggtg aaagtaaaag atgctgaaga tcagttgggt gcacgagtgg    7560
gttacatcga actggatctc aacagcggta agatccttga gttttttcgc cccgaagaac    7620
gttttccaat gatgagcact tttaaagttc tgctatgtgg cgcggtatta tcccgtattg    7680
acgccgggca agagcaactc ggtcgccgca tacactattc tcagaatgac ttggttgagt    7740
actcaccagt cacagaaaag catcttacgg atggcatgac agtaagagaa ttatgcagtg    7800
ctgccataac catgagtgat aacactgcgg ccaacttact tctgacaacg atcggaggac    7860
cgaaggagct aaccgctttt ttgcacaaca tgggggatca tgtaactcgc cttgatcgtt    7920
gggaaccgga gctgaatgaa gccataccaa acgacgagcg tgacaccacg atgcctgtag    7980
caatggcaac aacgttgcgc aaactattaa ctggcgaact acttactcta gcttcccggc    8040
aacaattaat agactggatg gaggcggata aagttgcagg accacttctg cgctcggccc    8100
ttccggctgg ctggtttatt gctgataaat ctggagccgg tgagcgtggg tctcgcggta    8160
tcattgcagc actggggcca gatggtaagc cctcccgtat cgtagttatc tacacgacgg    8220
ggagtcaggc aactatggat gaacgaaata gacagatcgc tgagataggt gcctcactga    8280
ttaagcattg gtaactgtca gaccaagttt actcatatat actttagatt gatttaaaac    8340 ttcatttta atttaaaagg atctaggtga agatcctttt tgataatctc atgaccaaaa    8400
tcccttaacg tgagttttcg ttccactgag cgtcagaccc cgtagaaaag atcaaaggat    8460
cttcttgaga tccttttttt ctgcgcgtaa tctgctgctt gcaaacaaaa aaaccaccgc    8520
taccagcggt ggtttgtttg ccggatcaag agctaccaac tctttttccg aaggtaactg    8580
```

-continued

```
gcttcagcag agcgcagata ccaaatactg tccttctagt gtagccgtag ttaggccacc    8640
acttcaagaa ctctgtagca ccgcctacat acctcgctct gctaatcctg ttaccagtgg    8700
ctgctgccag tggcgataag tcgtgtctta ccgggttgga ctcaagacga tagttaccgg    8760
ataaggcgca gcggtcgggc tgaacggggg gttcgtgcac acagcccagc ttggagcgaa    8820
cgacctacac cgaactgaga tacctacagc gtgagctatg agaaagcgcc acgcttcccg    8880
aagggagaaa ggcggacagg tatccggtaa gcggcagggt cggaacagga gagcgcacga    8940
gggagcttcc aggggggaaac gcctggtatc tttatagtcc tgtcgggttt cgccacctct    9000
gacttgagcg tcgatttttg tgatgctcgt caggggggcg gagcctatgg aaaaacgcca    9060
gcaacgcggc ctttttacgg ttcctggcct tttgctggcc ttttgctcac atgttctttc    9120
ctgcgttatc ccctgattct gtggataacc gtattaccgc c                        9161
```

```
<210> SEQ ID NO 38
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Leu Pro Val Thr Ala Leu Leu Pro Leu Ala Leu Leu Leu His
1               5                   10                  15

Ala Ala Arg Pro Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Gly Ser Gly Gly Gly Gly Ser Glu Val
        130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
                180                 185                 190

Ile Trp Gly Ser Glu Thr Thr Tyr Tyr Asn Ser Ala Leu Lys Ser Arg
            195                 200                 205

Leu Thr Ile Ile Lys Asp Asn Ser Lys Ser Gln Val Phe Leu Lys Met
        210                 215                 220

Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
                245                 250                 255
```

```
Ser Val Thr Val Ser Ser Thr Thr Thr Pro Ala Pro Arg Pro Pro Thr
            260             265                 270

Pro Ala Pro Thr Ile Ala Ser Gln Pro Leu Ser Leu Arg Pro Glu Ala
        275             280             285

Cys Arg Pro Ala Ala Gly Gly Ala Val His Thr Arg Gly Leu Asp Phe
    290             295             300

Ala Cys Asp Ile Tyr Ile Trp Ala Pro Leu Ala Gly Thr Cys Gly Val
305             310             315                 320

Leu Leu Leu Ser Leu Val Ile Thr Leu Tyr Cys Lys Arg Gly Arg Lys
                325             330                 335

Lys Leu Leu Tyr Ile Phe Lys Gln Pro Phe Met Arg Pro Val Gln Thr
            340             345                 350

Thr Gln Glu Glu Asp Gly Cys Ser Cys Arg Phe Pro Glu Glu Glu Glu
        355             360             365

Gly Gly Cys Glu Leu Arg Val Lys Phe Ser Arg Ser Ala Asp Ala Pro
    370             375             380

Ala Tyr Lys Gln Gly Gln Asn Gln Leu Tyr Asn Glu Leu Asn Leu Gly
385             390             395                 400

Arg Arg Glu Glu Tyr Asp Val Leu Asp Lys Arg Arg Gly Arg Asp Pro
            405             410             415

Glu Met Gly Gly Lys Pro Arg Arg Lys Asn Pro Gln Glu Gly Leu Tyr
            420             425             430

Asn Glu Leu Gln Lys Asp Lys Met Ala Glu Ala Tyr Ser Glu Ile Gly
        435             440             445

Met Lys Gly Glu Arg Arg Arg Gly Lys Gly His Asp Gly Leu Tyr Gln
    450             455             460

Gly Leu Ser Thr Ala Thr Lys Asp Thr Tyr Asp Ala Leu His Met Gln
465             470             475                 480

Ala Leu Pro Pro Arg
            485
```

<210> SEQ ID NO 39
<211> LENGTH: 1455
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 39

```
gccttaccag tgaccgcctt gctcctgccg ctggccttgc tgctccacgc cgccaggccg      60
gacatccaga tgacacagac tacatcctcc ctgtctgcct ctctgggaga cagagtcacc     120
atcagttgca gggcaagtca ggacattagt aaatatttaa attggtatca gcagaaacca     180
gatggaactg ttaaactcct gatctaccat acatcaagat tacactcagg agtcccatca     240
aggttcagtg gcagtgggtc tggaacagat tattctctca ccattagcaa cctggagcaa     300
gaagatattg ccacttactt ttgccaacag ggtaatacgc ttccgtacac gttcggaggg     360
gggaccaagc tggagatcac aggtggcggt ggctcgggcg gtggtgggtc gggtggcggc     420
ggatctgagg tgaaactgca ggagtcagga cctggcctgg tggcgccctc acagagcctg     480
tccgtcacat gcactgtctc aggggtctca ttacccgact atggtgtaag ctggattcgc     540
cagcctccac gaaagggtct ggagtggctg ggagtaatat ggggtagtga aaccacatac     600
tataattcag ctctcaaatc cagactgacc atcatcaagg acaactccaa gagccaagtt     660
ttcttaaaaa tgaacagtct gcaaactgat gacacagcca tttactactg tgccaaacat     720
```

-continued

```
tattactacg gtggtagcta tgctatggac tactggggcc aaggaacctc agtcaccgtc     780
tcctcaacca cgacgccagc gccgcgacca ccaacaccgg cgcccaccat cgcgtcgcag     840
cccctgtccc tgcgcccaga ggcgtgccgg ccagcggcgg ggggcgcagt gcacacgagg     900
gggctggact cgcctgtga tatctacatc tgggcgccct tggccgggac ttgtggggtc      960
cttctcctgt cactggttat caccctttac tgcaaacggg gcagaaagaa actcctgtat    1020
atattcaaac aaccatttat gagaccagta caaactactc aagaggaaga tggctgtagc    1080
tgccgatttc agaagaaga agaaggagga tgtgaactga gagtgaagtt cagcaggagc    1140
gcagacgccc ccgcgtacaa gcagggccag aaccagctct ataacgagct caatctagga   1200
cgaagagagg agtacgatgt tttggacaag agacgtggcc gggaccctga gatggggggga  1260 aagccgagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgc                                                     1455
```

```
<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Thr Asn Phe Ser Leu Leu Lys Gln Ala Gly Asp Val Glu Glu Asn
1               5                   10                  15

Pro Gly Pro
```

```
<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctactaact tcagcctgct gaagcaggct ggagacgtgg aggagaaccc tggacct     57
```

```
<210> SEQ ID NO 42
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
            35                  40                  45

Thr Glu Ser Asp Val His Pro Ser Cys Lys Val Thr Ala Met Lys Cys
        50                  55                  60
```

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
                100                 105                 110

Leu Glu Glu Lys Asn Ile Lys Glu Phe Leu Gln Ser Phe Val His Ile
                115                 120                 125

Val Gln Met Phe Ile Asn Thr Ser Gly Ser Gly Ser Gly Ser Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
                180                 185                 190

Cys Cys Leu Thr Tyr Cys Phe Ala Pro Arg Cys Arg Glu Arg Arg Arg
                195                 200                 205

Asn Glu Arg Leu Arg Arg Glu Ser Val Arg Pro Val Gly Ser Ser His
    210                 215                 220

His Trp Gly Tyr Gly Lys His Asn Gly Pro Glu His Trp His Lys Asp
225                 230                 235                 240

Phe Pro Ile Ala Lys Gly Glu Arg Gln Ser Pro Val Asp Ile Asp Thr
                245                 250                 255

His Thr Ala Lys Tyr Asp Pro Ser Leu Lys Pro Leu Ser Val Ser Tyr
                260                 265                 270

Asp Gln Ala Thr Ser Leu Arg Ile Leu Asn Asn Gly His Ala Phe Asn
                275                 280                 285

Val Glu Phe Asp Asp Ser Gln Asp Lys Ala Val Leu Lys Gly Gly Pro
    290                 295                 300

Leu Asp Gly Thr Tyr Arg Leu Ile Gln Phe His Phe His Trp Gly Ser
305                 310                 315                 320

Leu Asp Gly Gln Gly Ser Glu His Thr Val Asp Lys Lys Lys Tyr Ala
                325                 330                 335

Ala Glu Leu His Leu Val His Trp Asn Thr Lys Tyr Gly Asp Phe Gly
                340                 345                 350

Lys Ala Val Gln Gln Pro Asp Gly Leu Ala Val Leu Gly Ile Phe Leu
                355                 360                 365

Lys Val Gly Ser Ala Lys Pro Gly His Gln Lys Val Val Asp Val Leu
    370                 375                 380

Asp Ser Ile Lys Thr Lys Gly Lys Ser Ala Asp Phe Thr Asn Phe Asp
385                 390                 395                 400

Pro Arg Gly Leu Leu Pro Glu Ser Leu Asp Tyr Trp Thr Tyr Pro Gly
                405                 410                 415

Ser Leu Thr Thr Pro Pro Leu Leu Glu Cys Val Thr Trp Ile Val Leu
                420                 425                 430

Lys Glu Pro Ile Ser Val Ser Ser Glu Gln Val Leu Lys Phe Arg Lys
    435                 440                 445

Leu Asn Phe Asn Gly Glu Gly Glu Pro Glu Glu Leu Met Val Asp Asn
    450                 455                 460

Trp Arg Pro Ala Gln Pro Leu Lys Asn Arg Gln Ile Lys Ala Ser Phe
465                 470                 475                 480

Lys Gly Ser Gly Ala Thr Asn Phe Ser Leu Leu Lys Gln Ala Gly Asp

-continued

```
                    485               490               495

Val Glu Glu Asn Pro Gly Pro Met Ala Leu Pro Val Thr Ala Leu Leu
            500               505               510

Leu Pro Leu Ala Leu Leu Leu His Ala Ala Arg Pro Asp Ile Gln Met
            515               520               525

Thr Gln Thr Thr Ser Ser Leu Ser Ala Ser Leu Gly Asp Arg Val Thr
    530               535               540

Ile Ser Cys Arg Ala Ser Gln Asp Ile Ser Lys Tyr Leu Asn Trp Tyr
545               550               555               560

Gln Gln Lys Pro Asp Gly Thr Val Lys Leu Leu Ile Tyr His Thr Ser
            565               570               575

Arg Leu His Ser Gly Val Pro Ser Arg Phe Ser Gly Ser Gly Ser Gly
            580               585               590

Thr Asp Tyr Ser Leu Thr Ile Ser Asn Leu Glu Gln Glu Asp Ile Ala
            595               600               605

Thr Tyr Phe Cys Gln Gln Gly Asn Thr Leu Pro Tyr Thr Phe Gly Gly
    610               615               620

Gly Thr Lys Leu Glu Ile Thr Gly Gly Gly Ser Gly Gly Gly Gly
625               630               635               640

Ser Gly Gly Gly Ser Glu Val Lys Leu Gln Glu Ser Gly Pro Gly
            645               650               655

Leu Val Ala Pro Ser Gln Ser Leu Ser Val Thr Cys Thr Val Ser Gly
            660               665               670

Val Ser Leu Pro Asp Tyr Gly Val Ser Trp Ile Arg Gln Pro Pro Arg
            675               680               685

Lys Gly Leu Glu Trp Leu Gly Val Ile Trp Gly Ser Glu Thr Thr Tyr
    690               695               700

Tyr Asn Ser Ala Leu Lys Ser Arg Leu Thr Ile Ile Lys Asp Asn Ser
705               710               715               720

Lys Ser Gln Val Phe Leu Lys Met Asn Ser Leu Gln Thr Asp Asp Thr
            725               730               735

Ala Ile Tyr Tyr Cys Ala Lys His Tyr Tyr Tyr Gly Gly Ser Tyr Ala
            740               745               750

Met Asp Tyr Trp Gly Gln Gly Thr Ser Val Thr Val Ser Ser Thr Thr
            755               760               765

Thr Pro Ala Pro Arg Pro Pro Thr Pro Ala Pro Thr Ile Ala Ser Gln
    770               775               780

Pro Leu Ser Leu Arg Pro Glu Ala Cys Arg Pro Ala Ala Gly Gly Ala
785               790               795               800

Val His Thr Arg Gly Leu Asp Phe Ala Cys Asp Ile Tyr Ile Trp Ala
            805               810               815

Pro Leu Ala Gly Thr Cys Gly Val Leu Leu Leu Ser Leu Val Ile Thr
            820               825               830

Leu Tyr Cys Lys Arg Gly Arg Lys Lys Leu Leu Tyr Ile Phe Lys Gln
            835               840               845

Pro Phe Met Arg Pro Val Gln Thr Thr Gln Glu Glu Asp Gly Cys Ser
    850               855               860

Cys Arg Phe Pro Glu Glu Glu Glu Gly Gly Cys Glu Leu Arg Val Lys
865               870               875               880

Phe Ser Arg Ser Ala Asp Ala Pro Ala Tyr Lys Gln Gly Gln Asn Gln
            885               890               895

Leu Tyr Asn Glu Leu Asn Leu Gly Arg Arg Glu Glu Tyr Asp Val Leu
            900               905               910
```

```
Asp Lys Arg Arg Gly Arg Asp Pro Glu Met Gly Gly Lys Pro Arg Arg
        915                 920                 925

Lys Asn Pro Gln Glu Gly Leu Tyr Asn Glu Leu Gln Lys Asp Lys Met
        930                 935                 940

Ala Glu Ala Tyr Ser Glu Ile Gly Met Lys Gly Glu Arg Arg Arg Gly
945                 950                 955                 960

Lys Gly His Asp Gly Leu Tyr Gln Gly Leu Ser Thr Ala Thr Lys Asp
                965                 970                 975

Thr Tyr Asp Ala Leu His Met Gln Ala Leu Pro Pro Arg
                980                 985
```

```
<210> SEQ ID NO 43
<211> LENGTH: 2970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gtttttcttt ggagctgcag gtaattagtc ttgagtccgg cgatgccagc     240
attcatgata ccgtagaaaa cttgattatc ctggccaaca attctctgtc ctcaaacgga     300
aacgtaaccg agagcggttg taaagaatgt gaagaactgg aagaaagaa catcaaggag     360 tttctgcaat cattcgttca catcgtacaa atgttcataa atacgtcagg atctggttct     420
ggttccggaa gtggatctgg ttcagggtcc ggtagtggat ctgggtcagg aagtggaagc     480
ggtagtgggt ctggatctaa acaagagcac tttcctgata acctgttgcc gagctgggcg     540
attacgctta tcagtgtaaa cggcatcttt gtaatatgct gtctgaccta ctgcttcgca     600
ccaaggtgcc gggagagaag gagaaatgaa agactgagaa gggagagcgt gagacctgtg     660
ggatcctccc atcactgggg gtacggcaaa cacaacggac ctgagcactg gcataaggac     720
ttccccattg ccaagggaga gcgccagtcc cctgttgaca tcgacactca tacagccaag     780 tatgacccctt ccctgaagcc cctgtctgtt tcctatgatc aagcaacttc cctgagaatc     840
ctcaacaatg gtcatgcttt caacgtggag tttgatgact ctcaggacaa agcagtgctc     900
aagggaggac ccctggatgg cacttacaga ttgattcagt ttcactttca ctggggttca     960
cttgatggac aaggttcaga gcatactgtg gataaaaaga aatatgctgc agaacttcac    1020
ttggttcact ggaacaccaa atatgggat tttgggaaag ctgtgcagca acctgatgga    1080
ctggccgttc taggtatttt tttgaaggtt ggcagcgcta aaccgggcca tcagaaagtt    1140
gttgatgtgc tggattccat taaaacaaag ggcaagagtg ctgacttcac taacttcgat    1200
cctcgtggcc tccttcctga atccctggat tactggacct acccaggctc actgaccacc    1260
cctcctcttc tggaatgtgt gacctggatt gtgctcaagg aacccatcag cgtcagcagc    1320
gagcaggtgt tgaaattccg taaacttaac ttcaatgggg agggtgaacc cgaagaactg    1380
atggtggaca actggcgccc agctcagcca ctgaagaaca ggcaaatcaa agcttccttc    1440
aaaggatccg gagctactaa cttcagcctg ctgaagcagg ctggagacgt ggaggagaac    1500
cctggaccta tggccttacc agtgaccgcc ttgctcctgc cgctggcctt gctgctccac    1560
```

```
gccgccaggc cggacatcca gatgacacag actacatcct ccctgtctgc ctctctggga   1620
gacagagtca ccatcagttg cagggcaagt caggacatta gtaaatattt aaattggtat   1680
cagcagaaac cagatggaac tgttaaactc ctgatctacc atacatcaag attacactca   1740
ggagtcccat caaggttcag tggcagtggg tctggaacag attattctct caccattagc   1800
aacctggagc aagaagatat tgccacttac ttttgccaac agggtaatac gcttccgtac   1860
acgttcggag gggggaccaa gctggagatc acaggtggcg gtggctcggg cggtggtggg   1920
tcgggtggcg gcggatctga ggtgaaactg caggagtcag gacctggcct ggtggcgccc   1980 tcacagagctc tgtccgtcac atgcactgtc tcagggggtct cattacccga ctatggtgta   2040
agctggattc gccagcctcc acgaaagggt ctggagtggc tgggagtaat atggggtagt   2100
gaaaccacat actataattc agctctcaaa tccagactga ccatcatcaa ggacaactcc   2160
aagagccaag ttttcttaaa aatgaacagt ctgcaaactg atgacacagc catttactac   2220
tgtgccaaac attattacta cggtggtagc tatgctatgg actactgggg ccaaggaacc   2280
tcagtcaccg tctcctcaac cacgacgcca gcgccgcgac caccaacacc ggcgcccacc   2340
atcgcgtcgc agcccctgtc cctgcgccca gaggcgtgcc ggccagcggc ggggggcgca   2400
gtgcacacga gggggctgga cttcgcctgt gatatctaca tctgggcgcc cttggccggg   2460
acttgtgggg tccttctcct gtcactggtt atcacccttt actgcaaacg gggcagaaag   2520
aaactcctgt atatattcaa acaaccattt atgagaccag tacaaactac tcaagaggaa   2580
gatggctgta gctgccgatt tccagaagaa gaagaggag gatgtgaact gagagtgaag   2640
ttcagcagga gcgcagacgc ccccgcgtac aagcagggcc agaaccagct ctataacag   2700 ctcaatctag gacgaagaga ggagtacgat gttttggaca agagacgtgg ccgggaccct   2760
gagatggggg gaaagccgag aaggaagaac cctcaggaag gcctgtacaa tgaactgcag   2820
aaagataaga tggcggaggc ctacagtgag attgggatga aaggcgagcg ccggaggggc   2880 aagggggcacg atggccttta ccagggtctc agtacagcca ccaaggacac ctacgacgcc   2940
cttcacatgc aggccctgcc ccctcgctaa                                    2970
```

```
<210> SEQ ID NO 44
<211> LENGTH: 10685
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
```

```
tttgagtgag ctgataccgc tcgccgcagc cgaacgaccg agcgcagcga gtcagtgagc     60
gaggaagcgg aagagcgccc aatacgcaaa ccgcctctcc ccgcgcgttg gccgattcat    120
taatgcagct ggcacgacag gtttcccgac tggaaagcgg gcagtgagcg caacgcaatt    180
aatgtgagtt agctcactca ttaggcaccc caggctttac actttatgct ccggctcgt     240 atgttgtgtg gaattgtgag cggataacaa tttcacacag gaaacagcta tgaccatgat    300
tacgccaagc gcgcaattaa ccctcactaa agggaacaaa agctggagct gcaagcttaa    360
tgtagtctta tgcaatactc ttgtagtctt gcaacatggt aacgatgagt tagcaacatg    420
ccttacaagg agagaaaaag caccgtgcat gccgattggt ggaagtaagg tggtacgatc    480
gtgccttatt aggaaggcaa cagacgggtc tgacatggat tggacgaacc actgaattgc    540
cgcattgcag agatattgta tttaagtgcc tagctcgata cataaacggg tctctctggt    600
```

-continued

```
tagaccagat ctgagcctgg gagctctctg gctaactagg gaacccactg cttaagcctc   660
aataaagctt gccttgagtg cttcaagtag tgtgtgcccg tctgttgtgt gactctggta   720
actagagatc cctcagaccc ttttagtcag tgtggaaaat ctctagcagt ggcgcccgaa   780
cagggacttg aaagcgaaag ggaaaccaga ggagctctct cgacgcagga ctcggcttgc   840
tgaagcgcgc acggcaagag gcgaggggcg gcgactggtg agtacgccaa aaattttgac   900
tagcggaggc tagaaggaga gagatgggtg cgagagcgtc agtattaagc gggggagaat   960
tagatcgcga tgggaaaaaa ttcggttaag gccaggggga aagaaaaaat ataaattaaa   1020
acatatagta tgggcaagca gggagctaga acgattcgca gttaatcctg gcctgttaga   1080
aacatcagaa ggctgtagac aaatactggg acagctacaa ccatcccttc agacaggatc   1140
agaagaactt agatcattat ataatacagt agcaaccctc tattgtgtgc atcaaaggat   1200
agagataaaa gacaccaagg aagctttaga caagatagag gaagagcaaa acaaaagtaa   1260
gaccaccgca cagcaagcgg ccgctgatct tcagacctgg aggaggagat atgagggaca   1320
attggagaag tgaattatat aaatataaag tagtaaaaat tgaaccatta ggagtagcac   1380
ccaccaaggc aaagagaaga gtggtgcaga gagaaaaaag agcagtggga ataggagctt   1440
tgttccttgg gttcttggga gcagcaggaa gcactatggg cgcagcgtca atgacgctga   1500
cggtacaggc cagacaatta ttgtctggta tagtgcagca gcagaacaat ttgctgaggg   1560
ctattgaggc gcaacagcat ctgttgcaac tcacagtctg gggcatcaag cagctccagg   1620
caagaatcct ggctgtggaa agatacctaa aggatcaaca gctcctgggg atttggggtt   1680
gctctggaaa actcatttgc accactgctg tgccttggaa tgctagttgg agtaataaat   1740
ctctggaaca gatttggaat cacacgacct ggatggagtg ggacagagaa attaacaatt   1800
acacaagctt aatacactcc ttaattgaag aatcgcaaaa ccagcaagaa aagaatgaac   1860
aagaattatt ggaattagat aaatgggcaa gtttgtggaa ttggtttaac ataacaaatt   1920
ggctgtggta tataaaatta ttcataatga tagtaggagg cttggtaggt ttaagaatag   1980
tttttgctgt actttctata gtgaatagag ttaggcaggg atattcacca ttatcgtttc   2040
agacccacct cccaaccccg aggggacccg acaggcccga aggaatagaa gaagaaggtg   2100
gagagagaga cagagacaga tccattcgat tagtgaacgg atctcgacgg tatcgattag   2160
actgtagccc aggaatatgg cagctagatt gtacacattt agaaggaaaa gttatcttgg   2220
tagcagttca tgtagccagt ggatatatag aagcagaagt aattccagca gagacagggc   2280
aagaaacagc atacttcctc ttaaaattag caggaagatg gccagtaaaa acagtacata   2340
cagacaatgg cagcaatttc accagtacta cagttaaggc cgcctgttgg tgggcgggga   2400
tcaagcagga atttggcatt ccctacaatc cccaaagtca aggagtaata gaatctatga   2460
ataaagaatt aaagaaaatt ataggacagg taagagatca ggctgaacat cttaagacag   2520
cagtacaaat ggcagtattc atccacaatt ttaaaagaaa aggggggatt ggggggtaca   2580
gtgcagggga agaatagta gacataatag caacagacat acaaactaaa gaattacaaa   2640
aacaaattac aaaaattcaa aattttcggg tttattacag ggacagcaga gatccagttt   2700
ggctgcattg atcacgtgag gctccggtgc ccgtcagtgg gcagagcgca catcgcccac   2760
agtccccgag aagttggggg gaggggtcgg caattgaacc ggtgcctaga gaaggtggcg   2820
cggggtaaac tgggaaagtg atgtcgtgta ctggctccgc cttttcccg agggtggggg   2880 agaaccgtat ataagtgcag tagtcgccgt gaacgttctt tttcgcaacg ggtttgccgc   2940
cagaacacag gtaagtgccg tgtgtggttc ccgcgggcct ggcctcttta cgggttatgg   3000
```

```
cccttgcgtg ccttgaatta cttccacctg gctgcagtac gtgattcttg atcccgagct      3060
tcgggttgga agtgggtggg agagttcgag gccttgcgct taaggagccc cttcgcctcg      3120
tgcttgagtt gaggcctggc ctgggcgctg gggccgccgc gtgcgaatct ggtggcacct      3180
tcgcgcctgt ctcgctgctt tcgataagtc tctagccatt taaaattttt gatgacctgc      3240
tgcgacgctt tttttctggc aagatagtct tgtaaatgcg ggccaagatc tgcacactgg      3300
tatttcggtt tttggggccg cgggcggcga cggggcccgt gcgtcccagc gcacatgttc      3360
ggcgaggcgg ggcctgcgag cgcggccacc gagaatcgga cgggggtagt ctcaagctgg      3420
ccggcctgct ctggtgcctg gcctcgcgcc gccgtgtatc gccccgccct gggcggcaag      3480
gctggcccgg tcggcaccag ttgcgtgagc ggaaagatgg ccgcttcccg gccctgctgc      3540
agggagctca aaatggagga cgcggcgctc gggagagcgg gcgggtgagt cacccacaca      3600
aaggaaaagg gcctttccgt cctcagccgt cgcttcatgt gactccactg agtaccgggc      3660
gccgtccagg cacctcgatt agttctcgag cttttggagt acgtcgtctt taggttgggg      3720
ggaggggttt tatgcgatgg agtttcccca cactgagtgg gtggagactg aagttaggcc      3780
agcttggcac ttgatgtaat tctccttgga atttgccctt tttgagtttg gatcttggtt      3840
cattctcaag cctcagacag tggttcaaag ttttttttctt ccatttcagg tgtcgtgagc      3900
tagactagta ccatggacat gcgggtgcct gcacaacttc tgggcctgct gttgttgtgg      3960
ctgtctggag cccggtgtaa ttgggtaaat gttatcagtg atctcaagaa gatagaggat      4020
ctcatccagt ccatgcatat tgatgccacg ctgtacacag aaagcgatgt gcatcctagc      4080
tgtaaggtga cagcgatgaa gtgttttctt ttggagctgc aggtaattag tcttgagtcc      4140
ggcgatgcca gcattcatga taccgtagaa aacttgatta tcctggccaa caattctctg      4200
tcctcaaacg gaaacgtaac cgagagcggt tgtaaagaat gtgaagaact ggaagaaaag      4260
aacatcaagg agtttctgca atcattcgtt cacatcgtac aaatgttcat aaatacgtca      4320
ggatctggtt ctggttccgg aagtggatct ggttcagggt ccggtagtgg atctgggtca      4380
ggaagtggaa gcggtagtgg gtctggatct aaacaagagc actttcctga taacctgttg      4440
ccgagctggg cgattacgct tatcagtgta aacggcatct ttgtaatatg ctgtctgacc      4500
tactgcttcg caccaaggtg ccgggagaga aggagaaatg aaagactgag aagggagagc      4560
gtgagacctg tgggatcctc ccatcactgg gggtacggca aacacaacgg acctgagcac      4620
tggcataagg acttccccat tgccaaggga gagcgccagt cccctgttga catcgacact      4680
catacagcca agtatgaccc ttccctgaag cccctgtctg tttcctatga tcaagcaact      4740
tccctgagaa tcctcaacaa tggtcatgct ttcaacgtgg agtttgatga ctctcaggac      4800
aaagcagtgc tcaagggagg acccctggat ggcacttaca gattgattca gtttcacttt      4860
cactggggtt cacttgatgg acaaggttca gagcatactg tggataaaaa gaaatatgct      4920
gcagaacttc acttggttca ctggaacacc aaatatgggg attttgggaa agctgtgcag      4980
caacctgatg gactggccgt tctaggtatt tttttgaagg ttggcagcgc taaaccgggc      5040
catcagaaag ttgttgatgt gctggattcc attaaaacaa agggcaagag tgctgacttc      5100
actaacttcg atcctcgtgg cctccttcct gaatccctgg attactggac ctacccaggc      5160
tcactgacca cccctcctct tctggaatgt gtgacctgga ttgtgctcaa ggaacccatc      5220
agcgtcagca gcgagcaggt gttgaaattc cgtaaactta acttcaatgg ggagggtgaa      5280
cccgaagaac tgatggtgga caactggcgc ccagctcagc cactgaagaa caggcaaatc      5340
```

-continued

```
aaagcttcct tcaaaggatc cggagctact aacttcagcc tgctgaagca ggctggagac   5400
gtggaggaga accctggacc tatggcctta ccagtgaccg ccttgctcct gccgctggcc   5460
ttgctgctcc acgccgccag gccggacatc cagatgacac agactacatc ctccctgtct   5520
gcctctctgg gagacagagt caccatcagt tgcagggcaa gtcaggacat tagtaaatat   5580
ttaaattggt atcagcagaa accagatgga actgttaaac tcctgatcta ccatacatca   5640
agattacact caggagtccc atcaaggttc agtggcagtg ggtctggaac agattattct   5700
ctcaccatta gcaacctgga gcaagaagat attgccactt acttttgcca acagggtaat   5760
acgcttccgt acacgttcgg aggggggacc aagctggaga tcacaggtgg cggtggctcg   5820
ggcggtggtg ggtcgggtgg cggcggatct gaggtgaaac tgcaggagtc aggacctggc   5880
ctggtggcgc cctcacagag cctgtccgtc acatgcactg tctcaggggt ctcattaccc   5940
gactatggtg taagctggat tcgccagcct ccacgaaagg gtctggagtg ctgggagta   6000 atatggggta gtgaaaccac atactataat tcagctctca aatccagact gaccatcatc   6060
aaggacaact ccaagagcca agttttctta aaaatgaaca gtctgcaaac tgatgacaca   6120
gccatttact actgtgccaa acattattac tacggtggta gctatgctat ggactactgg   6180
ggccaaggaa cctcagtcac cgtctcctca accacgacgc cagcgccgcg accaccaaca   6240
ccggcgccca ccatcgcgtc gcagcccctg tccctgcgcc cagaggcgtg ccggccagcg   6300
gcggggggcg cagtgcacac gaggggggctg gacttcgcct gtgatatcta catctgggcg   6360
cccttggccg ggacttgtgg ggtccttctc ctgtcactgg ttatcaccct ttactgcaaa   6420
cggggcagaa agaaactcct gtatatattc aaacaaccat ttatgagacc agtacaaact   6480
actcaagagg aagatggctg tagctgccga tttccagaag aagaagaagg aggatgtgaa   6540
ctgagagtga agttcagcag gagcgcagac gcccccgcgt acaagcaggg ccagaaccag   6600
ctctataacg agctcaatct aggacgaaga gaggagtacg atgtttggga caagagacgt   6660
ggccgggacc ctgagatggg gggaaagccg agaaggaaga accctcagga aggcctgtac   6720
aatgaactgc agaaagataa gatggcggag gcctacagtg agattgggat gaaaggcgag   6780
cgccggaggg gcaaggggca cgatggcctt taccagggtc tcagtacagc caccaaggac   6840
acctacgacg cccttcacat gcaggccctg cccctcgct aagtcgacaa tcaacctctg   6900
gattacaaaa tttgtgaaag attgactggt attcttaact atgttgctcc ttttacgcta   6960
tgtggatacg ctgctttaat gcctttgtat catgctattg cttcccgtat ggctttcatt   7020
ttctcctcct tgtataaatc ctggttgctg tctctttatg aggagttgtg gcccgttgtc   7080
aggcaacgtg gcgtggtgtg cactgtgttt gctgacgcaa ccccccactgg ttggggcatt   7140 gccaccacct gtcagctcct ttccgggact ttcgctttcc ccctccctat gccacggcg   7200 gaactcatcg ccgcctgcct tgcccgctgc tggacagggg ctcggctgtt gggcactgac   7260
aattccgtgg tgttgtcggg gaagctgacg tcctttccat ggctgctcgc ctgtgttgcc   7320
acctggattc tgcgcgggac gtccttctgc tacgtccctt cggccctcaa tccagcggac   7380
cttccttccc gcggcctgct gccggctctg cggcctcttc cgcgtcttcg ccttcgccct   7440
cagacgagtc ggatctccct ttgggccgcc tccccgcctg gaattcgagc tcggtacctt   7500
taagaccaat gacttacaag gcagctgtag atcttagcca ctttttaaaa gaaaaggggg   7560
gactggaagg gctaattcac tcccaacgaa gacaagatct gctttttgct tgtactgggt   7620
ctctctggtt agaccagatc tgagcctggg agctctctgg ctaactaggg aacccactgc   7680
ttaagcctca ataaagcttg ccttgagtgc ttcaagtagt gtgtgcccgt ctgttgtgtg   7740
```

-continued

```
actctggtaa ctagagatcc ctcagaccct tttagtcagt gtggaaaatc tctagcagta    7800
gtagttcatg tcatcttatt attcagtatt tataacttgc aaagaaatga atatcagaga    7860
gtgagaggaa cttgtttatt gcagcttata atggttacaa ataaagcaat agcatcacaa    7920
atttcacaaa taaagcattt ttttcactgc attctagttg tggtttgtcc aaactcatca    7980
atgtatctta tcatgtctgg ctctagctat cccgcccta actccgccca tcccgcccct      8040
aactccgccc agtccgccc attctccgcc ccatggctga ctaatttttt ttatttatgc      8100
agaggccgag gccgcctcgg cctctgagct attccagaag tagtgaggag gcttttttgg    8160
aggcctaggg acgtacccaa ttcgccctat agtgagtcgt attacgcgcg ctcactggcc    8220
gtcgttttac aacgtcgtga ctgggaaaac cctggcgtta cccaacttaa tcgccttgca    8280
gcacatcccc ctttcgccag ctggcgtaat agcgaagagg cccgcaccga tcgcccttcc    8340
caacagttgc gcagcctgaa tggcgaatgg gacgcgccct gtagcggcgc attaagcgcg    8400
gcgggtgtgg tggttacgcg cagcgtgacc gctacacttg ccagcgccct agcgcccgct    8460
cctttcgctt tcttccctc ctttctcgcc acgttcgccg gctttccccg tcaagctcta     8520
aatcgggggc tccctttagg gttccgattt agtgctttac ggcacctcga ccccaaaaaa    8580
cttgattagg gtgatggttc acgtagtggg ccatcgccct gatagacggt ttttcgccct    8640
ttgacgttgg agtccacgtt ctttaatagt ggactcttgt tccaaactgg aacaacactc    8700
aaccctatct cggtctattc ttttgattta taagggattt tgccgatttc ggcctattgg    8760
ttaaaaaatg agctgattta acaaaaattt aacgcgaatt ttaacaaaat attaacgctt    8820
acaatttagg tggcactttt cggggaaatg tgcgcggaac ccctatttgt ttattttct    8880 aaatacattc aaatatgtat ccgctcatga dacaataacc ctgataaatg cttcaataat    8940
attgaaaaag gaagagtatg agtattcaac atttccgtgt cgcccttatt ccctttttg     9000 cggcattttg ccttcctgtt tttgctcacc cagaaacgct ggtgaaagta aaagatgctg    9060
aagatcagtt gggtgcacga gtgggttaca tcgaactgga tctcaacagc ggtaagatcc    9120
ttgagagttt tcgccccgaa gaacgttttc caatgatgag cacttttaaa gttctgctat    9180
gtggcgcggt attatcccgt attgacgccg ggcaagagca actcggtcgc cgcatacact    9240
attctcagaa tgacttggtt gagtactcac cagtcacaga aaagcatctt acggatggca    9300
tgacagtaag agaattatgc agtgctgcca taaccatgag tgataacact gcggccaact    9360
tacttctgac aacgatcgga ggaccgaagg agctaaccgc ttttttgcac aacatggggg    9420
atcatgtaac tcgccttgat cgttgggaac cggagctgaa tgaagccata ccaaacgacg    9480
agcgtgacac cacgatgcct gtagcaatgg caacaacgtt gcgcaaacta ttaactggcg    9540
aactacttac tctagcttcc cggcaacaat taatagactg gatggaggcg gataaagttg    9600
caggaccact tctgcgctcg gcccttccgg ctggctggtt tattgctgat aaatctggag    9660
ccggtgagcg tgggtctcgc ggtatcattg cagcactggg gccagatggt aagccctccc    9720
gtatcgtagt tatctacacg acggggagtc aggcaactat ggatgaacga aatagacaga    9780
tcgctgagat aggtgcctca ctgattaagc attggtaact gtcagaccaa gtttactcat    9840
atatacttta gattgattta aaacttcatt tttaatttaa aaggatctag gtgaagatcc    9900
tttttgataa tctcatgacc aaaatccctt aacgtgagtt ttcgttccac tgagcgtcag    9960
accccgtaga aaagatcaaa ggatcttctt gagatccttt ttttctgcgc gtaatctgct    10020
gcttgcaaac aaaaaaacca ccgctaccag cggtggtttg tttgccggat caagagctac    10080
```

```
caactctttt tccgaaggta actggcttca gcagagcgca gataccaaat actgttcttc    10140
tagtgtagcc gtagttaggc caccacttca agaactctgt agcaccgcct acatacctcg    10200
ctctgctaat cctgttacca gtggctgctg ccagtggcga taagtcgtgt cttaccgggt    10260
tggactcaag acgatagtta ccggataagg cgcagcggtc gggctgaacg gggggttcgt    10320
gcacacagcc cagcttggag cgaacgacct acaccgaact gagataccta cagcgtgagc    10380
tatgagaaag cgccacgctt cccgaaggga gaaaggcgga caggtatccg gtaagcggca    10440
gggtcggaac aggagagcgc acgagggagc ttccagggggg aaacgcctgg tatctttata    10500
gtcctgtcgg gtttcgccac ctctgacttg agcgtcgatt tttgtgatgc tcgtcagggg    10560
ggcggagcct atggaaaaac gccagcaacg cggcctttttt acggttcctg gcctttttgct    10620 ggcctttttgc tcacatgttc tttcctgcgt tatcccctga ttctgtggat aaccgtatta    10680
ccgcc                                                               10685
```

<210> SEQ ID NO 45
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Asp Met Arg Val Pro Ala Gln Leu Leu Gly Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Ser Gly Ser Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Arg Arg
            195                 200                 205

Asn Glu Arg Leu Arg Arg Glu Ser Val Arg Pro Val Gly Ser Ser His
        210                 215                 220

His Trp Gly Tyr Gly Lys His Asn Gly Pro Glu His Trp His Lys Asp
225                 230                 235                 240

Phe Pro Ile Ala Lys Gly Glu Arg Gln Ser Pro Val Asp Ile Asp Thr
```

-continued

```
                  245                   250                   255

His Thr Ala Lys Tyr Asp Pro Ser Leu Lys Pro Leu Ser Val Ser Tyr
              260                   265                   270

Asp Gln Ala Thr Ser Leu Arg Ile Leu Asn Asn Gly His Ala Phe Asn
          275                   280                   285

Val Glu Phe Asp Asp Ser Gln Asp Lys Ala Val Leu Lys Gly Gly Pro
      290                   295                   300

Leu Asp Gly Thr Tyr Arg Leu Ile Gln Phe His Phe His Trp Gly Ser
  305                   310                   315                   320

Leu Asp Gly Gln Gly Ser Glu His Thr Val Asp Lys Lys Tyr Ala
              325                   330                   335

Ala Glu Leu His Leu Val His Trp Asn Thr Lys Tyr Gly Asp Phe Gly
              340                   345                   350

Lys Ala Val Gln Gln Pro Asp Gly Leu Ala Val Leu Gly Ile Phe Leu
          355                   360                   365

Lys Val Gly Ser Ala Lys Pro Gly Leu Gln Lys Val Val Asp Val Leu
      370                   375                   380

Asp Ser Ile Lys Thr Lys Gly Lys Ser Ala Asp Phe Thr Asn Phe Asp
  385                   390                   395                   400

Pro Arg Gly Leu Leu Pro Glu Ser Leu Asp Tyr Trp Thr Tyr Pro Gly
              405                   410                   415

Ser Leu Thr Thr Pro Pro Leu Leu Glu Cys Val Thr Trp Ile Val Leu
              420                   425                   430

Lys Glu Pro Ile Ser Val Ser Ser Glu Gln Val Leu Lys Phe Arg Lys
          435                   440                   445

Leu Asn Phe Asn Gly Glu Gly Glu Pro Glu Glu Leu Met Val Asp Asn
      450                   455                   460

Trp Arg Pro Ala Gln Pro Leu Lys Asn Arg Gln Ile Lys Ala Ser Phe
  465                   470                   475                   480

Lys Gly Ser Gly Ala Thr Asn Phe Ser Leu Leu Lys Gln Ala Gly Asp
              485                   490                   495

Val Glu Glu Asn Pro Gly Pro Met Ala Leu Pro Val Thr Ala Leu Leu
              500                   505                   510

Leu Pro Leu Ala Leu Leu Leu His Ala Ala Arg Pro Asp Ile Gln Met
          515                   520                   525

Thr Gln Thr Thr Ser Ser Leu Ser Ala Ser Leu Gly Asp Arg Val Thr
      530                   535                   540

Ile Ser Cys Arg Ala Ser Gln Asp Ile Ser Lys Tyr Leu Asn Trp Tyr
  545                   550                   555                   560

Gln Gln Lys Pro Asp Gly Thr Val Lys Leu Leu Ile Tyr His Thr Ser
              565                   570                   575

Arg Leu His Ser Gly Val Pro Ser Arg Phe Ser Gly Ser Gly Ser Gly
              580                   585                   590

Thr Asp Tyr Ser Leu Thr Ile Ser Asn Leu Glu Gln Glu Asp Ile Ala
          595                   600                   605

Thr Tyr Phe Cys Gln Gln Gly Asn Thr Leu Pro Tyr Thr Phe Gly Gly
      610                   615                   620

Gly Thr Lys Leu Glu Ile Thr Gly Gly Gly Ser Gly Gly Gly Gly
  625                   630                   635                   640

Ser Gly Gly Gly Gly Ser Glu Val Lys Leu Gln Glu Ser Gly Pro Gly
              645                   650                   655

Leu Val Ala Pro Ser Gln Ser Leu Ser Val Thr Cys Thr Val Ser Gly
              660                   665                   670
```

```
Val Ser Leu Pro Asp Tyr Gly Val Ser Trp Ile Arg Gln Pro Pro Arg
        675                 680                 685

Lys Gly Leu Glu Trp Leu Gly Val Ile Trp Gly Ser Glu Thr Thr Tyr
        690                 695                 700

Tyr Asn Ser Ala Leu Lys Ser Arg Leu Thr Ile Ile Lys Asp Asn Ser
705                 710                 715                 720

Lys Ser Gln Val Phe Leu Lys Met Asn Ser Leu Gln Thr Asp Asp Thr
                725                 730                 735

Ala Ile Tyr Tyr Cys Ala Lys His Tyr Tyr Tyr Gly Gly Ser Tyr Ala
                740                 745                 750

Met Asp Tyr Trp Gly Gln Gly Thr Ser Val Thr Val Ser Ser Thr Thr
                755                 760                 765

Thr Pro Ala Pro Arg Pro Pro Thr Pro Ala Pro Thr Ile Ala Ser Gln
        770                 775                 780

Pro Leu Ser Leu Arg Pro Glu Ala Cys Arg Pro Ala Ala Gly Gly Ala
785                 790                 795                 800

Val His Thr Arg Gly Leu Asp Phe Ala Cys Asp Ile Tyr Ile Trp Ala
                805                 810                 815

Pro Leu Ala Gly Thr Cys Gly Val Leu Leu Leu Ser Leu Val Ile Thr
                820                 825                 830

Leu Tyr Cys Lys Arg Gly Arg Lys Lys Leu Leu Tyr Ile Phe Lys Gln
        835                 840                 845

Pro Phe Met Arg Pro Val Gln Thr Thr Gln Glu Glu Asp Gly Cys Ser
        850                 855                 860

Cys Arg Phe Pro Glu Glu Glu Glu Gly Gly Cys Glu Leu Arg Val Lys
865                 870                 875                 880

Phe Ser Arg Ser Ala Asp Ala Pro Ala Tyr Lys Gln Gly Gln Asn Gln
                885                 890                 895

Leu Tyr Asn Glu Leu Asn Leu Gly Arg Arg Glu Glu Tyr Asp Val Leu
                900                 905                 910

Asp Lys Arg Arg Gly Arg Asp Pro Glu Met Gly Gly Lys Pro Arg Arg
        915                 920                 925

Lys Asn Pro Gln Glu Gly Leu Tyr Asn Glu Leu Gln Lys Asp Lys Met
        930                 935                 940

Ala Glu Ala Tyr Ser Glu Ile Gly Met Lys Gly Glu Arg Arg Arg Gly
945                 950                 955                 960

Lys Gly His Asp Gly Leu Tyr Gln Gly Leu Ser Thr Ala Thr Lys Asp
                965                 970                 975

Thr Tyr Asp Ala Leu His Met Gln Ala Leu Pro Pro Arg
                980                 985
```

```
<210> SEQ ID NO 46
<211> LENGTH: 2970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gttttctttt ggagctgcag gtaattagtc ttgagtccgg cgatgccagc     240
```

-continued

```
attcatgata ccgtagaaaa cttgattatc ctggccaaca attctctgtc ctcaaacgga      300
aacgtaaccg agagcggttg taaagaatgt gaagaactgg aagaaaagaa catcaaggag      360
tttctgcaat cattcgttca catcgtacaa atgttcataa atacgtcagg atctggttct      420
ggttccggaa gtggatctgg ttcagggtcc ggtagtggat ctgggtcagg aagtggaagc      480
ggtagtgggt ctggatctaa acaagagcac tttcctgata acctgttgcc gagctgggcg      540
attacgctta tcagtgtaaa cggcatcttt gtaatatgct gtctgaccta ctgcttcgca      600
ccaaggtgcc gggagagaag gagaaatgaa agactgagaa gggagagcgt gagacctgtg      660
ggatcctccc atcactgggg gtacggcaaa cacaacggac ctgagcactg gcataaggac      720
ttccccattg ccaagggaga gcgccagtcc cctgttgaca tcgacactca tacagccaag      780
tatgaccctt ccctgaagcc cctgtctgtt tcctatgatc aagcaacttc cctgagaatc      840
ctcaacaatg gtcatgcttt caacgtggag tttgatgact ctcaggacaa agcagtgctc      900
aagggaggac ccctggatgg cacttacaga ttgattcagt ttcactttca ctggggttca      960
cttgatggac aaggttcaga gcatactgtg gataaaaaga aatatgctgc agaacttcac     1020
ttggttcact ggaacaccaa atatgggat tttgggaaag ctgtgcagca acctgatgga      1080
ctggccgttc taggtatttt tttgaaggtt ggcagcgcta aaccgggcct tcagaaagtt     1140
gttgatgtgc tggattccat taaaacaaag ggcaagagtg ctgacttcac taacttcgat     1200
cctcgtggcc tccttcctga atccctggat tactggacct acccaggctc actgaccacc     1260
cctcctcttc tggaatgtgt gacctggatt gtgctcaagg aacccatcag cgtcagcagc     1320
gagcaggtgt tgaaattccg taaacttaac ttcaatgggg agggtgaacc cgaagaactg     1380
atggtggaca actggcgccc agctcagcca ctgaagaaca ggcaaatcaa agcttccttc     1440
aaaggatccg gagctactaa cttcagcctg ctgaagcagg ctggagacgt ggaggagaac     1500
cctggaccta tggccttacc agtgaccgcc ttgctcctgc cgctggcctt gctgctccac     1560
gccgccaggc cggacatcca gatgacacag actacatcct ccctgtctgc ctctctggga     1620
gacagagtca ccatcagttg cagggcaagt caggacatta gtaaatattt aaattggtat     1680
cagcagaaac cagatggaac tgttaaactc ctgatctacc atacatcaag attacactca     1740
ggagtcccat caaggttcag tggcagtggg tctggaacag attattctct caccattagc     1800
aacctggagc aagaagatat tgccacttac ttttgccaac agggtaatac gcttccgtac     1860
acgttcggag gggggaccaa gctggagatc acaggtggcg gtggctcggg cggtggtggg     1920
tcgggtggcg gcggatctga ggtgaaactg caggagtcag gacctggcct ggtggcgccc     1980
tcacagagcc tgtccgtcac atgcactgtc tcaggggtct cattacccga ctatggtgta     2040
agctggattc gccagcctcc acgaaagggt ctggagtggc tgggagtaat atgggggagt     2100
gaaaccacat actataattc agctctcaaa tccagactga ccatcatcaa ggacaactcc     2160
aagagccaag ttttcttaaa aatgaacagt ctgcaaactg atgacacagc catttactac     2220
tgtgccaaac attattacta cggtggtagc tatgctatgg actactgggg ccaaggaacc     2280
tcagtcaccg tctcctcaac cacgacgcca gcgccgcgac caccaacacc ggcgcccacc     2340
atcgcgtcgc agcccctgtc cctgcgccca gaggcgtgcc ggccagcggc ggggggcgca     2400
gtgcacacga gggggctgga cttcgcctgt gatatctaca tctgggcgcc cttggccggg     2460
acttgtgggg tccttctcct gtcactggtt atcacccttt actgcaaacg gggcagaaag     2520
aaactcctgt atatattcaa acaaccattt atgagaccag tacaaactac tcaagaggaa     2580
```

-continued

```
gatggctgta gctgccgatt tccagaagaa gaagaaggag gatgtgaact gagagtgaag    2640
ttcagcagga gcgcagacgc ccccgcgtac aagcagggcc agaaccagct ctataacgag    2700
ctcaatctag gacgaagaga ggagtacgat gtttttggaca agagacgtgg ccgggaccct   2760
gagatggggg gaaagccgag aaggaagaac cctcaggaag gcctgtacaa tgaactgcag    2820
aaagataaga tggcggaggc ctacagtgag attgggatga aaggcgagcg ccggagggggc   2880 aaggggcacg atggccttta ccagggtctc agtacagcca ccaaggacac ctacgacgcc    2940
cttcacatgc aggccctgcc ccctcgctaa                                     2970
```

```
<210> SEQ ID NO 47
<211> LENGTH: 10685
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
```

```
tttgagtgag ctgataccgc tcgccgcagc cgaacgaccg agcgcagcga gtcagtgagc      60
gaggaagcgg aagagcgccc aatacgcaaa ccgcctctcc ccgcgcgttg gccgattcat     120
taatgcagct ggcacgacag gtttcccgac tggaaagcgg gcagtgagcg caacgcaatt     180
aatgtgagtt agctcactca ttaggcaccc caggctttac actttatgct tccggctcgt     240
atgttgtgtg gaattgtgag cggataacaa tttcacacag gaaacagcta tgaccatgat     300
tacgccaagc gcgcaattaa ccctcactaa agggaacaaa agctggagct gcaagcttaa     360
tgtagtctta tgcaatactc ttgtagtctt gcaacatggt aacgatgagt tagcaacatg     420
ccttacaagg agagaaaaag caccgtgcat gccgattggt ggaagtaagg tggtacgatc     480
gtgccttatt aggaaggcaa cagacgggtc tgacatggat tggacgaacc actgaattgc     540
cgcattgcag agatattgta tttaagtgcc tagctcgata cataaacggg tctctctggt     600
tagaccagat ctgagcctgg gagctctctg gctaactagg gaacccactg cttaagcctc     660
aataaagctt gccttgagtg cttcaagtag tgtgtgcccg tctgttgtgt gactctggta     720
actagagatc cctcagaccc ttttagtcag tgtggaaaat ctctagcagt ggcgcccgaa     780
cagggacttg aaagcgaaag ggaaaccaga ggagctctct cgacgcagga ctcggcttgc     840
tgaagcgcgc acggcaagag gcgaggggcg cgactggtg agtacgccaa aaattttgac       900
tagcggaggc tagaaggaga gagatgggtg cgagagcgtc agtattaagc gggggagaat     960
tagatcgcga tgggaaaaaa ttcggttaag gccagggggga aagaaaaaat ataaattaaa    1020
acatatagta tgggcaagca gggagctaga acgattcgca gttaatcctg gcctgttaga    1080
aacatcagaa ggctgtagac aaatactggg acagctacaa ccatcccttc agacaggatc    1140
agaagaactt agatcattat ataatacagt agcaaccctc tattgtgtgc atcaaaggat    1200
agagataaaa gacaccaagg aagctttaga caagatagag gaagagcaaa acaaaagtaa    1260
gaccaccgca cagcaagcgg ccgctgatct tcagacctgg aggaggagat atgagggaca    1320
attggagaag tgaattatat aaatataaag tagtaaaaat tgaaccatta ggagtagcac    1380
ccaccaaggc aaagagaaga gtggtgcaga gagaaaaaag agcagtggga ataggagctt    1440
tgttccttgg gttcttggga gcagcaggaa gcactatggg cgcagcgtca atgacgctga    1500
cggtacaggc cagacaatta ttgtctggta tagtgcagca gcagaacaat ttgctgaggg    1560
ctattgaggc gcaacagcat ctgttgcaac tcacagtctg gggcatcaag cagctccagg    1620
```

-continued

```
caagaatcct ggctgtggaa agatacctaa aggatcaaca gctcctgggg atttggggtt    1680
gctctggaaa actcatttgc accactgctg tgccttggaa tgctagttgg agtaataaat    1740
ctctggaaca gatttggaat cacacgacct ggatggagtg ggacagagaa attaacaatt    1800
acacaagctt aatacactcc ttaattgaag aatcgcaaaa ccagcaagaa aagaatgaac    1860
aagaattatt ggaattagat aaatgggcaa gtttgtggaa ttggtttaac ataacaaatt    1920
ggctgtggta tataaaatta ttcataatga tagtaggagg cttggtaggt ttaagaatag    1980
tttttgctgt actttctata gtgaatagag ttaggcaggg atattcacca ttatcgtttc    2040
agacccacct cccaaccccg aggggaccceg acaggcccga aggaatagaa gaagaaggtg    2100
gagagagaga cagagacaga tccattcgat tagtgaacgg atctcgacgg tatcgattag    2160
actgtagccc aggaatatgg cagctagatt gtacacattt agaaggaaaa gttatcttgg    2220
tagcagttca tgtagccagt ggatatatag aagcagaagt aattccagca gagacagggc    2280
aagaaacagc atacttcctc ttaaaattag caggaagatg gccagtaaaa acagtacata    2340
cagacaatgg cagcaatttc accagtacta cagttaaggc cgcctgttgg tgggcgggga    2400
tcaagcagga atttggcatt ccctacaatc cccaaagtca aggagtaata gaatctatga    2460
ataaagaatt aaagaaaatt ataggacagg taagagatca ggctgaacat cttaagacag    2520
cagtacaaat ggcagtattc atccacaatt ttaaaagaaa aggggggatt ggggggtaca    2580
gtgcagggga aagaatagta gacataatag caacagacat acaaactaaa gaattacaaa    2640
aacaaattac aaaaattcaa aattttcggg tttattacag ggacagcaga gatccagttt    2700
ggctgcattg atcacgtgag gctccggtgc ccgtcagtgg gcagagcgca catcgcccac    2760
agtccccgag aagttggggg gaggggtcgg caattgaacc ggtgcctaga gaaggtggcg    2820
cggggtaaac tgggaaagtg atgtcgtgta ctggctccgc cttttttcccg agggtggggg    2880 agaaccgtat ataagtgcag tagtcgccgt gaacgttctt tttcgcaacg ggtttgccgc    2940
cagaacacag gtaagtgccg tgtgtggttc ccgcgggcct ggcctcttta cgggttatgg    3000
cccttgcgtg ccttgaatta cttccacctg gctgcagtac gtgattcttg atcccgagct    3060
tcgggttgga agtgggtggg agagttcgag gccttgcgct taaggagccc cttcgcctcg    3120
tgcttgagtt gaggcctggc ctgggcgctg gggccgccgc gtgcgaatct ggtggcacct    3180
tcgcgcctgt ctcgctgctt tcgataagtc tctagccatt taaaattttt gatgacctgc    3240
tgcgacgctt tttttctggc aagatagtct tgtaaatgcg ggccaagatc tgcacactgg    3300
tatttcggtt tttggggccg cgggcggcga cggggcccgt gcgtcccagc gcacatgttc    3360
ggcgaggcgg ggcctgcgag cgcggccacc gagaatcgga cgggggtagt ctcaagctgg    3420
ccggcctgct ctggtgcctg gcctcgcgcc gccgtgtatc gccccgccct gggcggcaag    3480
gctggcccgg tcggcaccag ttgcgtgagc ggaaagatgg ccgcttcccg gccctgctgc    3540
agggagctca aaatggagga cgcggcgctc gggagagcgg gcgggtgagt cacccacaca    3600
aaggaaaagg gcctttccgt cctcagccgt cgcttcatgt gactccactg agtaccgggc    3660
gccgtccagg cacctcgatt agttctcgag ctttttggagt acgtcgtctt taggttgggg    3720
ggaggggttt tatgcgatgg agtttcccca cactgagtgg gtggagactg aagttaggcc    3780
agcttggcac ttgatgtaat tctccttgga atttgccctt tttgagtttg gatcttggtt    3840
cattctcaag cctcagacag tggttcaaag ttttttttctt ccatttcagg tgtcgtgagc    3900
tagactagta ccatggacat gcgggtgcct gcacaacttc tgggcctgct gttgttgtgb    3960
ctgtctggag cccggtgtaa ttgggtaaat gttatcagtg atctcaagaa gatagaggat    4020
```

```
ctcatccagt ccatgcatat tgatgccacg ctgtacacag aaagcgatgt gcatcctagc      4080
tgtaaggtga cagcgatgaa gtgttttctt ttggagctgc aggtaattag tcttgagtcc      4140
ggcgatgcca gcattcatga taccgtagaa aacttgatta tcctggccaa caattctctg      4200
tcctcaaacg gaaacgtaac cgagagcggt tgtaaagaat gtgaagaact ggaagaaaag      4260
aacatcaagg agtttctgca atcattcgtt cacatcgtac aaatgttcat aaatacgtca      4320
ggatctggtt ctggttccgg aagtggatct ggttcagggt ccggtagtgg atctgggtca      4380
ggaagtggaa gcggtagtgg gtctggatct aaacaagagc actttcctga taacctgttg      4440
ccgagctggg cgattacgct tatcagtgta aacggcatct ttgtaatatg ctgtctgacc      4500
tactgcttcg caccaaggtg ccgggagaga aggagaaatg aaagactgag aagggagagc      4560
gtgagacctg tgggatcctc ccatcactgg gggtacggca aacacaacgg acctgagcac      4620
tggcataagg acttccccat tgccaaggga gagcgccagt cccctgttga catcgacact      4680
catacagcca agtatgaccc ttccctgaag cccctgtctg tttcctatga tcaagcaact      4740
tccctgagaa tcctcaacaa tggtcatgct ttcaacgtgg agtttgatga ctctcaggac      4800
aaagcagtgc tcaagggagg acccctggat ggcacttaca gattgattca gtttcacttt      4860
cactggggtt cacttgatgg acaaggttca gagcatactg tggataaaaa gaaatatgct      4920
gcagaacttc acttggttca ctggaacacc aaatatgggg attttgggaa agctgtgcag      4980
caacctgatg gactggccgt tctaggtatt tttttgaagg ttggcagcgc taaaccgggc      5040
cttcagaaag ttgttgatgt gctggattcc attaaaacaa agggcaagag tgctgacttc      5100
actaacttcg atcctcgtgg cctccttcct gaatccctgg attactggac ctacccaggc      5160
tcactgacca cccctcctct tctggaatgt gtgacctgga ttgtgctcaa ggaacccatc      5220
agcgtcagca gcgagcaggt gttgaaattc cgtaaactta acttcaatgg ggagggtgaa      5280
cccgaagaac tgatggtgga caactggcgc ccagctcagc cactgaagaa caggcaaatc      5340
aaagcttcct tcaaaggatc cggagctact aacttcagcc tgctgaagca ggctggagac      5400
gtggaggaga accctggacc tatggcctta ccagtgaccg ccttgctcct gccgctggcc      5460
ttgctgctcc acgccgccag gccggacatc cagatgacac agactacatc ctccctgtct      5520
gcctctctgg gagacagagt caccatcagt tgcagggcaa gtcaggacat tagtaaatat      5580
ttaaattggt atcagcagaa accagatgga actgttaaac tcctgatcta ccatacatca      5640
agattacact caggagtccc atcaaggttc agtggcagtg ggtctggaac agattattct      5700
ctcaccatta gcaacctgga gcaagaagat attgccactt acttttgcca acagggtaat      5760
acgcttccgt acacgttcgg aggggggacc aagctggaga tcacaggtgg cggtggctcg      5820
ggcggtggtg gtcgggtgg cggcggatct gaggtgaaac tgcaggagtc aggacctggc      5880
ctggtggcgc cctcacagag cctgtccgtc acatgcactg tctcagggt ctcattaccc      5940 gactatggtg taagctggat tcgccagcct ccacgaaagg gtctggagtg ctgggagta      6000 atatgggta gtgaaaccac atactataat tcagctctca aatccagact gaccatcatc      6060
aaggacaact ccaagagcca agttttctta aaaatgaaca gtctgcaaac tgatgacaca      6120
gccatttact actgtgccaa acattattac tacggtggta gctatgctat ggactactgg      6180
ggccaaggaa cctcagtcac cgtctcctca accacgacgc cagcgccgcg accaccaaca      6240
ccggcgccca ccatcgcgtc gcagcccctg tccctgcgcc cagaggcgtg ccggccagcg      6300
gcggggggcg cagtgcacac gagggggctg gacttcgcct gtgatatcta catctgggcg      6360
```

```
cccttggccg ggacttgtgg ggtccttctc ctgtcactgg ttatcaccct ttactgcaaa      6420
cggggcagaa agaaactcct gtatatattc aaacaaccat ttatgagacc agtacaaact      6480
actcaagagg aagatggctg tagctgccga tttccagaag aagaagaagg aggatgtgaa      6540
ctgagagtga agttcagcag gagcgcagac gcccccgcgt acaagcaggg ccagaaccag      6600
ctctataacg agctcaatct aggacgaaga gaggagtacg atgtttttgga caagagacgt      6660 ggccgggacc ctgagatggg gggaaagccg agaaggaaga accctcagga aggcctgtac      6720
aatgaactgc agaaagataa gatggcggag gcctacagtg agattgggat gaaaggcgag      6780
cgccggaggg gcaaggggca cgatggcctt taccagggtc tcagtacagc caccaaggac      6840
acctacgacg cccttcacat gcaggccctg cccctcgct aagtcgacaa tcaacctctg       6900
gattacaaaa tttgtgaaag attgactggt attcttaact atgttgctcc ttttacgcta      6960
tgtggatacg ctgctttaat gcctttgtat catgctattg cttcccgtat ggctttcatt      7020
ttctcctcct tgtataaatc ctggttgctg tctctttatg aggagttgtg gcccgttgtc      7080
aggcaacgtg gcgtggtgtg cactgtgttt gctgacgcaa ccccactgg ttggggcatt       7140 gccaccacct gtcagctcct ttccgggact ttcgctttcc ccctccctat gccacggcg       7200 gaactcatcg ccgcctgcct tgcccgctgc tggacagggg ctcggctgtt gggcactgac      7260
aattccgtgg tgttgtcggg gaagctgacg tcctttccat ggctgctcgc ctgtgttgcc      7320
acctggattc tgcgcgggac gtccttctgc tacgtccctt cggccctcaa tccagcggac      7380
cttccttccc gcggcctgct gccggctctg cggcctcttc cgcgtcttcg ccttcgccct      7440
cagacgagtc ggatctccct ttgggccgcc tccccgcctg gaattcgagc tcggtacctt      7500
taagaccaat gacttacaag gcagctgtag atcttagcca ctttttaaaa gaaaaggggg      7560
gactggaagg gctaattcac tcccaacgaa gacaagatct gctttttgct tgtactgggt      7620
ctctctggtt agaccagatc tgagcctggg agctctctgg ctaactaggg aacccactgc      7680
ttaagcctca ataaagcttg ccttgagtgc ttcaagtagt gtgtgcccgt ctgttgtgtg      7740
actctggtaa ctagagatcc ctcagaccct tttagtcagt gtggaaaatc tctagcagta      7800
gtagttcatg tcatcttatt attcagtatt tataacttgc aaagaaatga atatcagaga      7860
gtgagaggaa cttgtttatt gcagcttata atggttacaa ataaagcaat agcatcacaa      7920
atttcacaaa taaagcattt ttttcactgc attctagttg tggtttgtcc aaactcatca      7980
atgtatctta tcatgtctgg ctctagctat cccgcccta actccgccca tcccgcccct       8040
aactccgccc agtccgccc attctccgcc ccatggctga ctaattttt ttatttatgc        8100 agaggccgag gccgcctcgg cctctgagct attccagaag tagtgaggag gcttttttgg      8160
aggcctaggg acgtacccaa ttcgccctat agtgagtcgt attacgcgcg ctcactggcc      8220
gtcgttttac aacgtcgtga ctgggaaaac cctggcgtta cccaacttaa tcgccttgca      8280
gcacatcccc ctttcgccag ctggcgtaat agcgaagagg cccgcaccga tcgcccttcc      8340
caacagttgc gcagcctgaa tggcgaatgg gacgcgccct gtagcggcgc attaagcgcg      8400
gcgggtgtgg tggttacgcg cagcgtgacc gctacacttg ccagcgccct agcgcccgct      8460
cctttcgctt tcttcccttc ctttctcgcc acgttcgccg gctttccccg tcaagctcta      8520 aatcggggc tccctttagg gttccgattt agtgctttac ggcacctcga ccccaaaaaa       8580
cttgattagg gtgatggttc acgtagtggg ccatcgccct gatagacggt ttttcgccct      8640
ttgacgttgg agtccacgtt ctttaatagt ggactcttgt tccaaactgg aacaacactc      8700
aaccctatct cggtctattc ttttgattta taagggattt tgccgatttc ggcctattgg      8760
```

```
ttaaaaaatg agctgattta acaaaaattt aacgcgaatt ttaacaaaat attaacgctt    8820
acaatttagg tggcactttt cggggaaatg tgcgcggaac ccctatttgt ttattttct    8880 aaatacattc aaatatgtat ccgctcatga gacaataacc ctgataaatg cttcaataat    8940
attgaaaaag gaagagtatg agtattcaac atttccgtgt cgcccttatt cccttttttg    9000
cggcattttg ccttcctgtt tttgctcacc cagaaacgct ggtgaaagta aaagatgctg    9060
aagatcagtt gggtgcacga gtgggttaca tcgaactgga tctcaacagc ggtaagatcc    9120
ttgagagttt tcgccccgaa gaacgttttc caatgatgag cactttttaaa gttctgctat    9180 gtggcgcggt attatcccgt attgacgccg ggcaagagca actcggtcgc cgcatacact    9240
attctcagaa tgacttggtt gagtactcac cagtcacaga aaagcatctt acggatggca    9300
tgacagtaag agaattatgc agtgctgcca taaccatgag tgataacact gcggccaact    9360
tacttctgac aacgatcgga ggaccgaagg agctaaccgc ttttttgcac aacatggggg    9420
atcatgtaac tcgccttgat cgttgggaac cggagctgaa tgaagccata ccaaacgacg    9480
agcgtgacac cacgatgcct gtagcaatgg caacaacgtt gcgcaaacta ttaactggcg    9540
aactacttac tctagcttcc cggcaacaat taatagactg gatggaggcg gataaagttg    9600
caggaccact tctgcgctcg gcccttccgg ctggctggtt tattgctgat aaatctggag    9660
ccggtgagcg tgggtctcgc ggtatcattg cagcactggg gccagatggt aagccctccc    9720
gtatcgtagt tatctacacg acggggagtc aggcaactat ggatgaacga aatagacaga    9780
tcgctgagat aggtgcctca ctgattaagc attggtaact gtcagaccaa gtttactcat    9840
atatacttta gattgattta aaacttcatt tttaatttaa aaggatctag gtgaagatcc    9900
tttttgataa tctcatgacc aaaatccctt aacgtgagtt ttcgttccac tgagcgtcag    9960
accccgtaga aaagatcaaa ggatcttctt gagatccttt ttttctgcgc gtaatctgct   10020
gcttgcaaac aaaaaaacca ccgctaccag cggtggtttg tttgccggat caagagctac   10080
caactctttt tccgaaggta actggcttca gcagagcgca gataccaaat actgttcttc   10140
tagtgtagcc gtagttaggc caccacttca agaactctgt agcaccgcct acatacctcg   10200
ctctgctaat cctgttacca gtggctgctg ccagtggcga taagtcgtgt cttaccgggt   10260
tggactcaag acgatagtta ccggataagg cgcagcggtc gggctgaacg ggggggttcgt   10320 gcacacagcc cagcttggag cgaacgacct acaccgaact gagataccta cagcgtgagc   10380
tatgagaaag cgccacgctt cccgaaggga gaaaggcgga caggtatccg gtaagcggca   10440
gggtcggaac aggagagcgc acgagggagc ttccaggggg aaacgcctgg tatctttata   10500
gtcctgtcgg gtttcgccac ctctgacttg agcgtcgatt tttgtgatgc tcgtcagggg   10560
ggcggagcct atgaaaaac gccagcaacg cggccttttt acggttcctg gccttttgct   10620 ggcctttttgc tcacatgttc tttcctgcgt tatcccctga ttctgtggat aaccgtatta   10680
ccgcc                                                                10685
```

<210> SEQ ID NO 48
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Ala Leu Pro Val Thr Ala Leu Leu Leu Pro Leu Ala Leu Leu Leu

```
1               5                    10                   15

His Ala Ala Arg Pro Asp Ile Gln Met Thr Gln Thr Thr Ser Ser Leu
            20                   25                   30

Ser Ala Ser Leu Gly Asp Arg Val Thr Ile Ser Cys Arg Ala Ser Gln
            35                   40                   45

Asp Ile Ser Lys Tyr Leu Asn Trp Tyr Gln Gln Lys Pro Asp Gly Thr
        50                   55                   60

Val Lys Leu Leu Ile Tyr His Thr Ser Arg Leu His Ser Gly Val Pro
65                   70                   75                   80

Ser Arg Phe Ser Gly Ser Gly Ser Gly Thr Asp Tyr Ser Leu Thr Ile
                85                   90                   95

Ser Asn Leu Glu Gln Glu Asp Ile Ala Thr Tyr Phe Cys Gln Gln Gly
            100                  105                  110

Asn Thr Leu Pro Tyr Thr Phe Gly Gly Gly Thr Lys Leu Glu Ile Thr
            115                  120                  125

Gly Gly Gly Gly Ser Gly Gly Gly Gly Ser Gly Gly Gly Gly Ser Glu
        130                  135                  140

Val Lys Leu Gln Glu Ser Gly Pro Gly Leu Val Ala Pro Ser Gln Ser
145                  150                  155                  160

Leu Ser Val Thr Cys Thr Val Ser Gly Val Ser Leu Pro Asp Tyr Gly
                165                  170                  175

Val Ser Trp Ile Arg Gln Pro Pro Arg Lys Gly Leu Glu Trp Leu Gly
            180                  185                  190

Val Ile Trp Gly Ser Glu Thr Thr Tyr Tyr Asn Ser Ala Leu Lys Ser
            195                  200                  205

Arg Leu Thr Ile Ile Lys Asp Asn Ser Lys Ser Gln Val Phe Leu Lys
        210                  215                  220

Met Asn Ser Leu Gln Thr Asp Asp Thr Ala Ile Tyr Tyr Cys Ala Lys
225                  230                  235                  240

His Tyr Tyr Tyr Gly Gly Ser Tyr Ala Met Asp Tyr Trp Gly Gln Gly
                245                  250                  255

Thr Ser Val Thr Val Ser Ser Thr Thr Thr Pro Ala Pro Arg Pro Pro
            260                  265                  270

Thr Pro Ala Pro Thr Ile Ala Ser Gln Pro Leu Ser Leu Arg Pro Glu
            275                  280                  285

Ala Cys Arg Pro Ala Ala Gly Gly Ala Val His Thr Arg Gly Leu Asp
        290                  295                  300

Phe Ala Cys Asp Ile Tyr Ile Trp Ala Pro Leu Ala Gly Thr Cys Gly
305                  310                  315                  320

Val Leu Leu Leu Ser Leu Val Ile Thr Leu Tyr Cys Lys Arg Gly Arg
                325                  330                  335

Lys Lys Leu Leu Tyr Ile Phe Lys Gln Pro Phe Met Arg Pro Val Gln
            340                  345                  350

Thr Thr Gln Glu Glu Asp Gly Cys Ser Cys Arg Phe Pro Glu Glu Glu
            355                  360                  365

Glu Gly Gly Cys Glu Leu Arg Val Lys Phe Ser Arg Ser Ala Asp Ala
        370                  375                  380

Pro Ala Tyr Lys Gln Gly Gln Asn Gln Leu Tyr Asn Glu Leu Asn Leu
385                  390                  395                  400

Gly Arg Arg Glu Glu Tyr Asp Val Leu Asp Lys Arg Arg Gly Arg Asp
                405                  410                  415

Pro Glu Met Gly Gly Lys Pro Arg Arg Lys Asn Pro Gln Glu Gly Leu
            420                  425                  430
```

-continued

```
Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 49
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atggccttac cagtgaccgc cttgctcctg ccgctggcct tgctgctcca cgccgccagg        60
ccggacatcc agatgacaca gactacatcc tccctgtctg cctctctggg agacagagtc       120
accatcagtt gcagggcaag tcaggacatt agtaaatatt taaattggta tcagcagaaa       180
ccagatggaa ctgttaaact cctgatctac catacatcaa gattacactc aggagtccca       240
tcaaggttca gtggcagtgg gtctggaaca gattattctc tcaccattag caacctggag       300
caagaagata ttgccactta cttttgccaa cagggtaata cgcttccgta cacgttcgga       360
ggggggacca agctggagat cacaggtggc ggtggctcgg cggtggtggg gtcgggtggc       420
ggcggatctg aggtgaaact gcaggagtca ggacctggcc tggtggcgcc ctcacagagc       480
ctgtccgtca catgcactgt ctcaggggtc tcattacccg actatggtgt aagctggatt       540
cgccagcctc cacgaaaggg tctggagtgg ctgggagtaa tatggggtag tgaaaccaca       600
tactataatt cagctctcaa atccagactg accatcatca aggacaactc caagagccaa       660
gttttcttaa aaatgaacag tctgcaaact gatgacacag ccatttacta ctgtgccaaa       720
cattattact acggtggtag ctatgctatg gactactggg gccaaggaac ctcagtcacc       780
gtctcctcaa ccacgacgcc agcgccgcga ccaccaacac cggcgcccac catcgcgtcg       840
cagcccctgt ccctgcgccc agaggcgtgc cggccagcgg cggggggcgc agtgcacacg       900 aggggggctgg acttcgcctg tgatatctac atctgggcgc ccttggccgg gacttgtggg       960
gtccttctcc tgtcactggt tatcaccctt tactgcaaac ggggcagaaa gaaactcctg      1020
tatatattca acaaccatt tatgagacca gtacaaacta ctcaagagga agatggctgt       1080
agctgccgat ttccagaaga agaagaagga ggatgtgaac tgagagtgaa gttcagcagg      1140
agcgcagacg cccccgcgta caagcagggc cagaaccagc tctataacga gctcaatcta      1200
ggacgaagag aggagtacga tgtttttggac aagagacgtg gccgggaccc tgagatgggg      1260
ggaaagccga gaaggaagaa ccctcaggaa ggcctgtaca tgaactgca gaaagataag        1320 atggcggagg cctacagtga gattgggatg aaaggcgagc gccggagggg caaggggcac      1380
gatggccttt accaggatct cagtacagcc accaaggaca cctacgacgc ccttcacatg      1440 caggcccctgc cccctcgcta a                                               1461

<210> SEQ ID NO 50
<211> LENGTH: 9174
<212> TYPE: DNA
<213> ORGANISM: Artificial Sequence
```

-continued

```
<220> FEATURE:
<223> OTHER INFORMATION: Description of Artificial Sequence: Synthetic
      polynucleotide

<400> SEQUENCE: 50
gcgcgctcac tggccgtcgt tttacaacgt cgtgactggg aaaaccctgg cgttacccaa      60
cttaatcgcc ttgcagcaca tcccccttc gccagctggc gtaatagcga agaggcccgc      120
accgatcgcc cttcccaaca gttgcgcagc ctgaatggcg aatgggacgc gccctgtagc     180
ggcgcattaa gcgcggcggg tgtggtggtt acgcgcagcg tgaccgctac acttgccagc     240
gccctagcgc ccgctccttt cgctttcttc ccttcctttc tcgccacgtt cgccggcttt     300
ccccgtcaag ctctaaatcg ggggctccct ttagggttcc gatttagtgc tttacggcac     360
ctcgacccca aaaaacttga ttagggtgat ggttcacgta gtgggccatc gccctgatag     420
acggtttttc gccctttgac gttggagtcc acgttcttta atagtggact cttgttccaa     480
actggaacaa cactcaaccc tatctcggtc tattcttttg atttataagg gattttgccg     540
atttcggcct attggttaaa aaatgagctg atttaacaaa aatttaacgc gaattttaac     600
aaaatattaa cgcttacaat ttaggtggca cttttcgggg aaatgtgcgc ggaaccccta     660
tttgtttatt tttctaaata cattcaaata tgtatccgct catgagacaa taaccctgat     720
aaatgcttca ataatattga aaaaggaaga gtatgagtat tcaacatttc cgtgtcgccc     780
ttattccctt ttttgcggca ttttgccttc ctgttttgc tcacccagaa acgctggtga     840
aagtaaaaga tgctgaagat cagttgggtg cacgagtggg ttacatcgaa ctggatctca     900
acagcggtaa gatccttgag agttttcgcc ccgaagaacg ttttccaatg atgagcactt     960
ttaaagttct gctatgtggc gcggtattat cccgtattga cgccgggcaa gagcaactcg     1020
gtcgccgcat acactattct cagaatgact tggttgagta ctcaccagtc acagaaaagc     1080
atcttacgga tggcatgaca gtaagagaat tatgcagtgc tgccataacc atgagtgata     1140
acactgcggc caacttactt ctgacaacga tcggaggacc gaaggagcta accgcttttt     1200
tgcacaacat gggggatcat gtaactcgcc ttgatcgttg ggaaccggag ctgaatgaag     1260
ccataccaaa cgacgagcgt gacaccacga tgcctgtagc aatggcaaca cgttgcgca     1320 aactattaac tggcgaacta cttactctag cttcccggca acaattaata gactggatgg     1380
aggcggataa agttgcagga ccacttctgc gctcggccct tccggctggc tggtttattg     1440
ctgataaatc tggagccggt gagcgtgggt ctcgcggtat cattgcagca ctggggccag     1500
atggtaagcc ctcccgtatc gtagttatct acacgacggg gagtcaggca actatggatg     1560
aacgaaatag acagatcgct gagataggtg cctcactgat taagcattgg taactgtcag     1620
accaagttta ctcatatata ctttagattg atttaaaact tcattttaa tttaaaagga     1680 tctaggtgaa gatcctttt gataatctca tgaccaaaat cccttaacgt gagttttcgt     1740
tccactgagc gtcagacccc gtagaaaaga tcaaaggatc ttcttgagat ccttttttc     1800 tgcgcgtaat ctgctgcttg caaacaaaaa aaccaccgct accagcggtg gtttgtttgc     1860
cggatcaaga gctaccaact cttttttccga aggtaactgg cttcagcaga gcgcagatac     1920
caaatactgt tcttctagtg tagccgtagt taggccacca cttcaagaac tctgtagcac     1980
cgcctacata cctcgctctg ctaatcctgt taccagtggc tgctgccagt ggcgataagt     2040
cgtgtcttac cgggttggac tcaagacgat agttaccgga taaggcgcag cggtcgggct     2100
gaacgggggg ttcgtgcaca cagcccagct tggagcgaac gacctacacc gaactgagat     2160
acctacagcg tgagctatga gaaagcgcca cgcttcccga agggagaaag gcggacaggt     2220
```

```
atccggtaag cggcagggtc ggaacaggag agcgcacgag ggagcttcca gggggaaacg      2280
cctggtatct ttatagtcct gtcgggtttc gccacctctg acttgagcgt cgattttgt      2340 gatgctcgtc agggggcgg agcctatgga aaaacgccag caacgcggcc tttttacggt      2400
tcctggcctt ttgctggcct tttgctcaca tgttctttcc tgcgttatcc cctgattctg      2460
tggataaccg tattaccgcc tttgagtgag ctgataccgc tcgccgcagc cgaacgaccg      2520
agcgcagcga gtcagtgagc gaggaagcgg aagagcgccc aatacgcaaa ccgcctctcc      2580
ccgcgcgttg gccgattcat taatgcagct ggcacgacag gtttcccgac tggaaagcgg      2640
gcagtgagcg caacgcaatt aatgtgagtt agctcactca ttaggcaccc caggctttac      2700
actttatgct tccggctcgt atgttgtgtg gaattgtgag cggataacaa tttcacacag      2760
gaaacagcta tgaccatgat tacgccaagc gcgcaattaa ccctcactaa agggaacaaa      2820
agctggagct gcaagcttaa tgtagtctta tgcaatactc ttgtagtctt gcaacatggt      2880
aacgatgagt tagcaacatg ccttacaagg agagaaaaag caccgtgcat gccgattggt      2940
ggaagtaagg tggtacgatc gtgccttatt aggaaggcaa cagacgggtc tgacatggat      3000
tggacgaacc actgaattgc cgcattgcag agatattgta tttaagtgcc tagctcgata      3060
cataaacggg tctctctggt tagaccagat ctgagcctgg gagctctctg gctaactagg      3120
gaacccactg cttaagcctc aataaagctt gccttgagtg cttcaagtag tgtgtgcccg      3180
tctgttgtgt gactctggta actagagatc cctcagaccc ttttagtcag tgtggaaaat      3240
ctctagcagt ggcgcccgaa cagggacttg aaagcgaaag ggaaaccaga ggagctctct      3300
cgacgcagga ctcggcttgc tgaagcgcgc acggcaagag gcgaggggcg cgactggtg      3360 agtacgccaa aaattttgac tagcggaggc tagaaggaga gagatgggtg cgagagcgtc      3420
agtattaagc gggggagaat tagatcgcga tgggaaaaaa ttcggttaag gccagggggca      3480 aagaaaaat ataaattaaa acatatagta tgggcaagca gggagctaga acgattcgca      3540
gttaatcctg gcctgttaga aacatcagaa ggctgtagac aaatactggg acagctacaa      3600
ccatcccttc agacaggatc agaagaactt agatcattat ataatacagt agcaaccctc      3660
tattgtgtgc atcaaaggat agagataaaa gacaccaagg aagctttaga caagatagag      3720
gaagagcaaa acaaaagtaa gaccaccgca cagcaagcgg ccgctgatct tcagacctgg      3780
aggaggagat atgagggaca attggagaag tgaattatat aaatataaag tagtaaaaat      3840
tgaaccatta ggagtagcac ccaccaaggc aaagagaaga gtggtgcaga gagaaaaaag      3900
agcagtggga ataggagctt tgttccttgg gttcttggga gcagcaggaa gcactatggg      3960
cgcagcgtca atgacgctga cggtacaggc cagacaatta ttgtctggta tagtgcagca      4020
gcagaacaat ttgctgaggg ctattgaggc gcaacagcat ctgttgcaac tcacagtctg      4080
gggcatcaag cagctccagg caagaatcct ggctgtggaa agatacctaa aggatcaaca      4140
gctcctgggg atttggggtt gctctggaaa actcatttgc accactgctg tgccttggaa      4200
tgctagttgg agtaataaat ctctggaaca gatttggaat cacacgacct ggatggagtg      4260
ggacagagaa attaacaatt acacaagctt aatacactcc ttaattgaag aatcgcaaaa      4320
ccagcaagaa aagaatgaac aagaattatt ggaattagat aaatgggcaa gtttgtggaa      4380
ttggtttaac ataacaaatt ggctgtggta tataaaatta ttcataatga tagtaggagg      4440
cttggtaggt ttaagaatag tttttgctgt actttctata gtgaatagag ttaggcaggg      4500
atattcacca ttatcgtttc agacccacct cccaaccccg aggggacccg acaggcccga      4560
```

-continued

```
aggaatagaa gaagaaggtg gagagagaga cagagacaga tccattcgat tagtgaacgg    4620
atctcgacgg tatcgattag actgtagccc aggaatatgg cagctagatt gtacacattt    4680
agaaggaaaa gttatcttgg tagcagttca tgtagccagt ggatatatag aagcagaagt    4740
aattccagca gagacagggc aagaaacagc atacttcctc ttaaaattag caggaagatg    4800
gccagtaaaa acagtacata cagacaatgg cagcaatttc accagtacta cagttaaggc    4860
cgcctgttgg tgggcgggga tcaagcagga atttggcatt ccctacaatc cccaaagtca    4920
aggagtaata gaatctatga ataaagaatt aaagaaaatt ataggacagg taagagatca    4980
ggctgaacat cttaagacag cagtacaaat ggcagtattc atccacaatt ttaaaagaaa    5040 agggggggatt ggggggtaca gtgcagggga agaatagta gacataatag caacagacat    5100
acaaactaaa gaattacaaa aacaaattac aaaaattcaa aattttcggg tttattacag    5160
ggacagcaga gatccagttt ggctgcattg atcacgtgag gctccggtgc ccgtcagtgg    5220
gcagagcgca catcgcccac agtccccgag aagttggggg gaggggtcgg caattgaacc    5280
ggtgcctaga gaaggtggcg cggggtaaac tgggaaagtg atgtcgtgta ctggctccgc    5340
cttttttccg agggtggggg agaaccgtat ataagtgcag tagtcgccgt gaacgttctt    5400
tttcgcaacg ggtttgccgc cagaacacag gtaagtgccg tgtgtggttc ccgcgggcct    5460
ggcctcttta cgggttatgg cccttgcgtg ccttgaatta cttccacctg gctgcagtac    5520
gtgattcttg atcccgagct tcgggttgga agtgggtggg agagttcgag gccttgcgct    5580
taaggagccc cttcgcctcg tgcttgagtt gaggcctggc ctgggcgctg gggccgccgc    5640
gtgcgaatct ggtggcacct tcgcgcctgt ctcgctgctt tcgataagtc tctagccatt    5700 taaaatttt gatgacctgc tgcgacgctt tttttctggc aagatagtct tgtaaatgcg    5760
ggccaagatc tgcacactgg tatttcggtt tttggggccg cgggcggcga cggggcccgt    5820
gcgtcccagc gcacatgttc ggcgaggcgg ggcctgcgag cgcggccacc gagaatcgga    5880 cggggggtagt ctcaagctgg ccggcctgct ctggtgcctg gcctcgcgcc gccgtgtatc    5940
gccccgccct gggcggcaag gctggcccgg tcggcaccag ttgcgtgagc ggaaagatgg    6000
ccgcttcccg gccctgctgc agggagctca aaatggagga cgcggcgctc gggagagcgg    6060
gcgggtgagt cacccacaca aaggaaaagg gcctttccgt cctcagccgt cgcttcatgt    6120
gactccactg agtaccgggc gccgtccagg cacctcgatt agttctcgag cttttggagt    6180
acgtcgtctt taggttgggg ggaggggttt tatgcgatgg agtttcccca cactgagtgg    6240
gtggagactg aagttaggcc agcttggcac ttgatgtaat tctccttgga atttgccctt    6300
tttgagtttg gatcttggtt cattctcaag cctcagacag tggttcaaag ttttttttctt    6360 ccatttcagg tgtcgtgatc tagaggatcc atggccttac cagtgaccgc cttgctcctg    6420
ccgctggcct tgctgctcca cgccgccagg ccggacatcc agatgacaca gactacatcc    6480
tccctgtctg cctctctggg agacagagtc accatcagtt gcaggcaag tcaggacatt    6540 agtaaatatt taaattggta tcagcagaaa ccagatggaa ctgttaaact cctgatctac    6600
catacatcaa gattacactc aggagtccca tcaaggttca gtggcagtgg gtctggaaca    6660
gattattctc tcaccattag caacctggag caagaagata ttgccactta cttttgccaa    6720
cagggtaata cgcttccgta cacgttcgga ggggggacca agctggagat cacaggtggc    6780
ggtggctcgg gcggtggtgg gtcgggtggc ggcggatctg aggtgaaact gcaggagtca    6840
ggacctggcc tggtggcgcc ctcacagagc ctgtccgtca catgcactgt ctcagggggtc    6900 tcattacccg actatggtgt aagctggatt cgccagcctc cacgaaaggg tctggagtgg    6960
```

```
ctgggagtaa tatggggtag tgaaaccaca tactataatt cagctctcaa atccagactg     7020
accatcatca aggacaactc caagagccaa gttttcttaa aaatgaacag tctgcaaact     7080
gatgacacag ccatttacta ctgtgccaaa cattattact acggtggtag ctatgctatg     7140
gactactggg gccaaggaac ctcagtcacc gtctcctcaa ccacgacgcc agcgccgcga     7200
ccaccaacac cggcgcccac catcgcgtcg cagcccctgt ccctgcgccc agaggcgtgc     7260
cggccagcgg cggggggcgc agtgcacacg aggggggctgg acttcgcctg tgatatctac     7320
atctgggcgc ccttggccgg gacttgtggg gtccttctcc tgtcactggt tatcaccctt     7380
tactgcaaac ggggcagaaa gaaactcctg tatatattca aacaaccatt tatgagacca     7440
gtacaaacta ctcaagagga agatggctgt agctgccgat ttccagaaga agaagaagga     7500
ggatgtgaac tgagagtgaa gttcagcagg agcgcagacg cccccgcgta caagcagggc     7560
cagaaccagc tctataacga gctcaatcta ggacgaagag aggagtacga tgttttggac     7620
aagagacgtg gccgggaccc tgagatgggg ggaaagccga gaaggaagaa ccctcaggaa     7680
ggcctgtaca atgaactgca gaaagataag atggcggagg cctacagtga gattgggatg     7740
aaaggcgagc gccggagggg caaggggcac gatggccttt accagggtct cagtacagcc     7800
accaaggaca cctacgacgc ccttcacatg caggccctgc cccctcgcta agtcgacaat     7860
caacctctgg attacaaaat ttgtgaaaga ttgactggta ttcttaacta tgttgctcct     7920
tttacgctat gtggatacgc tgctttaatg cctttgtatc atgctattgc ttcccgtatg     7980
gctttcattt tctcctcctt gtataaatcc tggttgctgt ctctttatga ggagttgtgg     8040
cccgttgtca ggcaacgtgg cgtggtgtgc actgtgtttg ctgacgcaac ccccactggt     8100
tggggcattg ccaccacctg tcagctcctt tccgggactt tcgctttccc cctccctatt     8160
gccacggcgg aactcatcgc cgcctgcctt gcccgctgct ggacaggggc tcggctgttg     8220
ggcactgaca attccgtggt gttgtcgggg aagctgacgt cctttccatg gctgctcgcc     8280
tgtgttgcca cctggattct gcgcgggacg tccttctgct acgtcccttc ggccctcaat     8340
ccagcggacc ttccttcccg cggcctgctg ccggctctgc ggcctcttcc gcgtcttcgc     8400
cttcgccctc agacgagtcg gatctccctt tgggccgcct ccccgcctgg aattcgagct     8460
cggtaccttt aagaccaatg acttacaagg cagctgtaga tcttagccac ttttttaaaag     8520 aaaaggggggg actggaaggg ctaattcact cccaacgaag acaagatctg cttttttgctt     8580 gtactgggtc tctctggtta gaccagatct gagcctggga gctctctggc taactaggga     8640
acccactgct taagcctcaa taaagcttgc cttgagtgct tcaagtagtg tgtgcccgtc     8700
tgttgtgtga ctctggtaac tagagatccc tcagacccctt ttagtcagtg tggaaaatct     8760
ctagcagtag tagttcatgt catcttatta ttcagtattt ataacttgca aagaaatgaa     8820
tatcagagag tgagaggaac ttgtttattg cagcttataa tggttacaaa taaagcaata     8880
gcatcacaaa tttcacaaat aaagcatttt tttcactgca ttctagttgt ggtttgtcca     8940
aactcatcaa tgtatcttat catgtctggc tctagctatc ccgcccctaa ctccgcccat     9000 cccgcccta actccgccca gttccgccca ttctccgccc catggctgac taatttttttt     9060 tatttatgca gaggccgagg ccgcctcggc ctctgagcta ttccagaagt agtgaggagg     9120 ctttttttgga ggcctaggga cgtacccaat tcgccctata gtgagtcgta ttac         9174
```

<210> SEQ ID NO 51
<211> LENGTH: 5981
<212> TYPE: DNA

-continued

```
<213> ORGANISM: Artificial Sequence
<220> FEATURE:
<223> OTHER INFORMATION: Description of Artificial Sequence: Synthetic
      polynucleotide

<400> SEQUENCE: 51
ggatcccctg aggggccccc catgggctag aggatccggc ctcggcctct gcataaataa        60
aaaaaattag tcagccatga gcttggccca ttgcatacgt tgtatccata tcataatatg       120
tacatttata ttggctcatg tccaacatta ccgccatgtt gacattgatt attgactagt       180
tattaatagt aatcaattac ggggtcatta gttcatagcc catatatgga gttccgcgtt       240
acataactta cggtaaatgg cccgcctggc tgaccgccca acgacccccg cccattgacg       300
tcaataatga cgtatgttcc catagtaacg ccaatagggga ctttccattg acgtcaatgg       360
gtggagtatt tacggtaaac tgcccacttg gcagtacatc aagtgtatca tatgccaagt       420
acgcccccta ttgacgtcaa tgacggtaaa tggcccgcct ggcattatgc ccagtacatg       480
accttatggg actttcctac ttggcagtac atctacgtat tagtcatcgc tattaccatg       540
gtgatgcggt tttggcagta catcaatggg cgtggatagc ggtttgactc acggggattt       600
ccaagtctcc accccattga cgtcaatggg agtttgtttt ggcaccaaaa tcaacgggac       660
tttccaaaat gtcgtaacaa ctccgcccca ttgacgcaaa tgggcggtag gcgtgtacgg       720
tgggaggtct atataagcag agctcgttta gtgaaccgtc agatcgcctg gagacgccat       780
ccacgctgtt ttgacctcca tagaagacac cgggaccgat ccagcctccc ctcgaagctt       840
acatgtggta ccgagctcgg atcctgagaa cttcagggtg agtctatggg acccttgatg       900
ttttctttcc ccttcttttc tatggttaag ttcatgtcat aggaaggggga gaagtaacag       960 ggtacacata ttgaccaaat cagggtaatt ttgcatttgt aattttaaaa aatgctttct      1020
tcttttaata tactttttg tttatcttat ttctaatact ttccctaatc tctttctttc      1080
agggcaataa tgatacaatg tatcatgcct ctttgcacca ttctaaagaa taacagtgat      1140
aatttctggg ttaaggcaat agcaatattt ctgcatataa atatttctgc atataaattg      1200
taactgatgt aagaggtttc atattgctaa tagcagctac aatccagcta ccattctgct      1260
tttattttat ggttgggata aggctggatt attctgagtc caagctaggc ccttttgcta      1320
atcatgttca tacctcttat cttcctccca cagctcctgg gcaacgtgct ggtctgtgtg      1380
ctggcccatc actttggcaa agcacgtgag atctgaattc aacagagatc gatctgtttc      1440
cttgacacta tgggattcac aacaaagata atcttcttat acaacctagt actggtctac      1500
gcggggtttg acgaccctcg caaagccata gaactagtac aaaagcgata tggccgacca      1560
tgcgattgca gcggaggaca agtgtccgag cctccgtcag acagggtcag tcaagtgact      1620
tgctcaggca agacagctta cttaatgccc gaccaaagat ggaaatgtaa gtcaattcca      1680
aaagacacct ccccaagcgg gccactccaa gagtgcccct gtaattctta ccagtcctca      1740
gtacacagtt cttgttatac ctcataccaa caatgcagat caggcaataa gacatattat      1800
acggctactc tgctaaaaac acaaactggg ggcaccagtg atgtacaagt attaggatcc      1860
accaacaaac ttatacaatc tccctgtaat ggcataaaag ggcagtctat atgctggagc      1920
actacagctc ctatccacgt ctctgatgga ggaggtccta tagacaccac aagaattaaa      1980
agtgttcaga gaaaactgga agaaattcat aaagccctat atcctgaact tcagtatcac      2040
cctttggcca tacctaaggt tagagataac ctcatggtcg atgcccagac tttaaacatt      2100
ctcaatgcca cttacaactt actcctaatg tccaacacga gcctagtgga cgactgttgg      2160
```

-continued

```
ctttgtttaa aattaggtcc ccctactccc ctcgcaatac ctaacttcct attatcctac    2220
gtgactcgct cctcggataa tatctcttgt ttaataattc cccctcttct agttcaaccg    2280
atgcagtttt ccaattcatc ttgcctcttt tccccctcct acaacagtac agaagaaata    2340
gatctaggcc atgttgcctt cagcaactgt acctccataa ccaatgtcac cggtcccata    2400
tgcgctgtaa atggttcggt ctttctctgt ggcaataaca tggcatacac ttatctaccc    2460
acgaactgga cggggctttg cgtcctagca actctcctcc ccgacattga catcattccc    2520
ggagatgaac cggtccccat ccctgctatt gatcatttta tatatagacc taaacgggcc    2580
atacagttta ttcctttact agcagggcta gggatcaccg cagccttcac aacaggagct    2640
acaggcctag gtgtctctgt gacccaatat acaaaattat ctaatcagct aatttctgat    2700
gtacaaatct tatctagcac catacaagat ctgcaagatc aagtagactc attagccgaa    2760
gtggttctcc agaacagaag ggggctagat ctacttacag cagaacaagg aggaatctgt    2820
ttagccctgc aagaaaaatg ctgcttttat gttaacaagt cagggattgt gagagacaaa    2880
ataaaaacct tacaagaaga actagaaaga cgtagaaaag atctagcttc caacccactt    2940
tggactgggc ttcaagggct cctcccttac ctcctgccct ttcttggccc tctacttacc    3000
ctcctgctct tactcaccat tgggccgtgc atttttaaca ggttggtcca gtttgttaaa    3060
gaccgcattt cagttgtgca agcgttggtg ctaacccaac agtatcaggt gctcagaacc    3120
gatgaagaag ctcaagatta actcaaatcc tgcacaacag attcttcatg tttgaccaa     3180 atcaacttgt gataccatgc tcaaagaggc ctcaattata tttgagtttt taatttttat    3240
ggaattcacc ccaccagtgc aggctgccta tcagaaagtg gtggctggtg tggctaatgc    3300
cctggcccac aagtatcact aagctcgctt tcttgctgtc caatttctat taaaggttcc    3360
tttgttccct aagtccaact actaaactgg gggatattat gaagggcctt gagcatctgg    3420
attctgccta ataaaaaaca tttattttca ttgcaatgat gtatttaaat tatttctgaa    3480
tattttacta aaaagggaat gtgggaggtc agtgcattta aaacataaag aaatgaagag    3540
ctagttcaaa ccttgggaaa atacactata tcttaaactc catgaaagaa ggtgaggctg    3600
caaacagcta atgcacattg gcaacagccc ctgatgccta tgccttattc atccctcaga    3660
aaaggattca agtagaggct tgatttggag gttaaagttt tgctatgctg tattttacat    3720
tacttattgt tttagctgtc ctcatgaatg tcttttcact acccatttgc ttatcctgca    3780
tctctcagcc ttgactccac tcagttctct tgcttagaga taccaccttt cccctgaagt    3840
gttccttcca tgttttacgg cgagatggtt tctcctcgcc tggccactca gccttagttg    3900
tctctgttgt cttatagagg tctacttgaa gaaggaaaaa caggggcat ggtttgactg     3960 tcctgtgagc ccttcttccc tgcctccccc actcacagtg accggaatc cctcgacatg      4020 gcagtctagc actagtgcgg ccgcagatct gcttcctcgc tcactgactc gctgcgctcg    4080
gtcgttcggc tgcggcgagc ggtatcagct cactcaaagg cggtaatacg gttatccaca    4140
gaatcagggg ataacgcagg aaagaacatg tgagcaaaag gccagcaaaa ggccaggaac    4200
cgtaaaaagg ccgcgttgct ggcgtttttc cataggctcc gcccccctga cgagcatcac    4260
aaaaatcgac gctcaagtca gaggtggcga aacccgacag gactataaag ataccaggcg    4320
tttccccctg gaagctccct cgtgcgctct cctgttccga ccctgccgct taccggatac    4380
ctgtccgcct ttctcccttc gggaagcgtg gcgctttctc atagctcacg ctgtaggtat    4440
ctcagttcgg tgtaggtcgt tcgctccaag ctgggctgtg tgcacgaacc ccccgttcag    4500
cccgaccgct gcgccttatc cggtaactat cgtcttgagt ccaacccggt aagacacgac    4560
```

-continued

```
ttatcgccac tggcagcagc cactggtaac aggattagca gagcgaggta tgtaggcggt    4620
gctacagagt tcttgaagtg gtggcctaac tacggctaca ctagaagaac agtatttggt    4680
atctgcgctc tgctgaagcc agttaccttc ggaaaaagag ttggtagctc ttgatccggc    4740
aaacaaacca ccgctggtag cggtggtttt tttgtttgca agcagcagat tacgcgcaga    4800
aaaaaaggat ctcaagaaga tcctttgatc ttttctacgg ggtctgacgc tcagtggaac    4860
gaaaactcac gttaagggat tttggtcatg agattatcaa aaaggatctt cacctagatc    4920
cttttaaatt aaaaatgaag ttttaaatca atctaaagta tatatgagta aacttggtct    4980
gacagttacc aatgcttaat cagtgaggca cctatctcag cgatctgtct atttcgttca    5040
tccatagttg cctgactccc cgtcgtgtag ataactacga tacgggaggg cttaccatct    5100
ggccccagtg ctgcaatgat accgcgagac ccacgctcac cggctccaga tttatcagca    5160
ataaaccagc cagccggaag ggccgagcgc agaagtggtc ctgcaacttt atccgcctcc    5220
atccagtcta ttaattgttg ccgggaagct agagtaagta gttcgccagt taatagtttg    5280
cgcaacgttg ttgccattgc tacaggcatc gtggtgtcac gctcgtcgtt tggtatggct    5340
tcattcagct ccggttccca acgatcaagc gagttacat gatcccccat gttgtgcaaa     5400
aaagcggtta gctccttcgg tcctccgatc gttgtcagaa gtaagttggc cgcagtgtta    5460
tcactcatgg ttatggcagc actgcataat tctcttactg tcatgccatc cgtaagatgc    5520
ttttctgtga ctggtgagta ctcaaccaag tcattctgag aatagtgtat gcggcgaccg    5580
agttgctctt gcccggcgtc aatacgggat aataccgcgc cacatagcag aactttaaaa    5640
gtgctcatca ttggaaaacg ttcttcgggg cgaaaactct caaggatctt accgctgttg    5700
agatccagtt cgatgtaacc cactcgtgca cccaactgat cttcagcatc ttttactttc    5760
accagcgttt ctgggtgagc aaaaacagga aggcaaaatg ccgcaaaaaa gggaataagg    5820
gcgacacgga aatgttgaat actcatactc ttcctttttc aatattattg aagcatttat    5880
cagggttatt gtctcatgag cggatacata tttgaatgta tttagaaaaa taaacaaata    5940
ggggttccgc gcacatttcc ccgaaaagtg ccacctgacg t                        5981
```